(12) United States Patent
Short et al.

(10) Patent No.: US 10,189,810 B2
(45) Date of Patent: Jan. 29, 2019

(54) PYRAZOLYL-SUBSTITUTED PYRIDONE COMPOUNDS AS SERINE PROTEASE INHIBITORS

(71) Applicant: VERSEON CORPORATION, Fremont, CA (US)

(72) Inventors: Kevin Michael Short, Fremont, CA (US); David Ben Kita, Fremont, CA (US); Maria de los Angeles Estiarte-Martinez, Fremont, CA (US); Son Minh Pham, Fremont, CA (US)

(73) Assignee: VERSEON CORPORATION, Fremont, CA (US)

( * ) Notice: Subject to any disclaimer, the term of this patent is extended or adjusted under 35 U.S.C. 154(b) by 0 days.

(21) Appl. No.: 15/512,037

(22) PCT Filed: Sep. 17, 2015

(86) PCT No.: PCT/US2015/050809
§ 371 (c)(1),
(2) Date: Mar. 16, 2017

(87) PCT Pub. No.: WO2016/044662
PCT Pub. Date: Mar. 24, 2016

(65) Prior Publication Data
US 2017/0267656 A1 Sep. 21, 2017

Related U.S. Application Data

(60) Provisional application No. 62/051,511, filed on Sep. 17, 2014, provisional application No. 62/051,585, filed on Sep. 17, 2014.

(51) Int. Cl.
*A61K 31/4155* (2006.01)
*C07D 401/04* (2006.01)
*C07D 409/14* (2006.01)
*C07D 413/14* (2006.01)

(52) U.S. Cl.
CPC ......... *C07D 401/04* (2013.01); *C07D 409/14* (2013.01)

(58) Field of Classification Search
CPC .............. A61K 31/4155; C07D 401/04; C07D 409/14; C07D 413/14
USPC ............ 514/236.5, 341; 544/131; 546/275.4
See application file for complete search history.

(56) References Cited

U.S. PATENT DOCUMENTS

| | | |
|---|---|---|
| 3,250,761 A | 5/1966 | Schmidt et al. |
| 3,926,999 A | 12/1975 | Poetsch |
| 4,008,249 A | 2/1977 | Fischer et al. |
| 4,160,452 A | 7/1979 | Theeuwes |
| 4,256,108 A | 3/1981 | Theeuwes |
| 4,265,874 A | 5/1981 | Bonsen et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,466,823 A | 11/1995 | Talley et al. |
| 5,547,978 A | 8/1996 | Christensen et al. |
| 5,739,083 A | 4/1998 | Endo et al. |
| 5,753,688 A | 5/1998 | Talley et al. |
| 5,792,761 A | 8/1998 | Fraley et al. |
| 5,902,852 A | 5/1999 | Schulz et al. |
| 5,916,908 A | 6/1999 | Giese et al. |
| 6,114,358 A | 9/2000 | Baucke et al. |
| 6,589,997 B2 | 7/2003 | Pillarisetti et al. |
| 6,962,905 B1 | 11/2005 | Gustafsson |
| 7,625,944 B2 | 12/2009 | Sinha et al. |
| 8,188,045 B2 | 5/2012 | Blair et al. |
| 9,371,307 B2 | 6/2016 | Freire et al. |
| 2002/0055639 A1 | 5/2002 | Nebel et al. |
| 2002/0091116 A1 | 7/2002 | Zhu et al. |
| 2003/0144309 A1 | 7/2003 | Choon-Moon |
| 2004/0132726 A1 | 7/2004 | Arora et al. |
| 2005/0009827 A1 | 1/2005 | Nazare et al. |
| 2005/0065144 A1 | 3/2005 | Feng et al. |
| 2005/0203127 A1 | 9/2005 | Cezanne et al. |
| 2008/0188527 A1 | 8/2008 | Cashman |
| 2008/0269293 A1 | 10/2008 | Chi et al. |
| 2008/0275070 A1 | 11/2008 | Liu et al. |
| 2009/0105253 A1 | 4/2009 | Kubo et al. |
| 2009/0163545 A1 | 6/2009 | Goldfarb |
| 2010/0016320 A1 | 1/2010 | Dyckman et al. |

(Continued)

FOREIGN PATENT DOCUMENTS

| | | |
|---|---|---|
| CN | 101851207 A | 10/2010 |
| EP | 0246888 A2 | 11/1987 |

(Continued)

OTHER PUBLICATIONS

International Search Report and Written Opinion, dated Dec. 18, 2015, received in International Application No. PCT/US2015/050809.

Olsson et al., "Stroke prevention with the oral direct thrombin inhibitor ximelagatran compared with warfarin in patients with non-valvular atrial fibrillation (SPORTIF III): randomised controlled trial.," Lancet, 362(9397): 1691-1698, Nov. 22, 2003.

(Continued)

*Primary Examiner* — Brenda L Coleman
(74) *Attorney, Agent, or Firm* — Davis Wright Tremaine LLP

(57) ABSTRACT

There are provided inter alia pyrazolyl-substituted pyridone compounds, which exhibit biological activity, e.g., inhibitory action, against serine proteases, including thrombin and various kallikreins. There are additionally provided pharmaceutical compositions. There are additionally provided methods of treating and preventing certain diseases or disorders, which disease or disorder is amenable to treatment or prevention by the inhibition of serine proteases, including thrombin and various kallikreins.

66 Claims, No Drawings

(56) References Cited

U.S. PATENT DOCUMENTS

| | | |
|---|---|---|
| 2010/0210696 A1 | 8/2010 | Nishida et al. |
| 2011/0071182 A1 | 3/2011 | Seefeld et al. |
| 2011/0071289 A1 | 3/2011 | Horiuchi et al. |
| 2012/0110702 A1 | 5/2012 | Yap et al. |
| 2012/0264798 A1 | 10/2012 | Sinha et al. |
| 2013/0040950 A1 | 2/2013 | Short et al. |

FOREIGN PATENT DOCUMENTS

| | | | |
|---|---|---|---|
| EP | 0854723 | A1 | 7/1998 |
| EP | 0788358 | B1 | 3/2004 |
| JP | S50-117936 | A | 9/1975 |
| JP | H01226815 | A | 9/1989 |
| JP | H02300173 | A | 12/1990 |
| JP | H09059113 | A | 3/1997 |
| JP | H10-509708 | A | 9/1998 |
| JP | 2003313103 | A | 11/2003 |
| JP | 2004231528 | A | 8/2004 |
| JP | 2006511608 | A | 4/2006 |
| JP | 2007506741 | A | 3/2007 |
| JP | 2007511485 | A | 5/2007 |
| JP | 2007530459 | A | 11/2007 |
| JP | 2009543818 | A | 12/2009 |
| JP | 2011520967 | A | 7/2011 |
| JP | 2011529944 | A | 12/2011 |
| JP | 2011530548 | A | 12/2011 |
| RU | 2221808 | C2 | 1/2004 |
| WO | 9605309 | A2 | 2/1996 |
| WO | 1996014843 | A2 | 5/1996 |
| WO | 1998018792 | A1 | 5/1998 |
| WO | 1998025930 | A2 | 6/1998 |
| WO | 9828269 | A1 | 7/1998 |
| WO | 2000009500 | A2 | 2/2000 |
| WO | 00041716 | A1 | 7/2000 |
| WO | 2000071536 | A1 | 11/2000 |
| WO | 0112189 | A1 | 2/2001 |
| WO | 2001019798 | A2 | 3/2001 |
| WO | 2001040223 | A2 | 6/2001 |
| WO | 2002000651 | A2 | 1/2002 |
| WO | 02092573 | A2 | 11/2002 |
| WO | 03048155 | A1 | 6/2003 |
| WO | 03061682 | A1 | 7/2003 |
| WO | 03062206 | A2 | 7/2003 |
| WO | 2004000785 | A2 | 12/2003 |
| WO | 2004035564 | A1 | 4/2004 |
| WO | 2004058721 | A2 | 7/2004 |
| WO | 2004058722 | A1 | 7/2004 |
| WO | 2004060890 | A1 | 7/2004 |
| WO | 2004089911 | A1 | 10/2004 |
| WO | 2004098589 | A1 | 11/2004 |
| WO | 2004101555 | A1 | 11/2004 |
| WO | 2005023761 | A2 | 3/2005 |
| WO | 2006074445 | A2 | 7/2006 |
| WO | 2006108643 | A2 | 10/2006 |
| WO | 2007067836 | A2 | 6/2007 |
| WO | 2007129052 | A1 | 11/2007 |
| WO | 2007146712 | A2 | 12/2007 |
| WO | 2008009638 | A2 | 1/2008 |
| WO | 2008016883 | A2 | 2/2008 |
| WO | 2008062739 | A1 | 5/2008 |
| WO | 2008064265 | A2 | 5/2008 |
| WO | 2008079277 | A1 | 7/2008 |
| WO | 2008105383 | A1 | 9/2008 |
| WO | 2009010560 | A1 | 1/2009 |
| WO | 2009041447 | A1 | 4/2009 |
| WO | 2008061796 | A3 | 7/2009 |
| WO | 2009097141 | A1 | 8/2009 |
| WO | 2009100438 | A2 | 8/2009 |
| WO | 2009140621 | A2 | 11/2009 |
| WO | 2010005580 | A2 | 1/2010 |
| WO | 2010020600 | A1 | 2/2010 |
| WO | 2010020601 | A1 | 2/2010 |
| WO | 2010020602 | A1 | 2/2010 |
| WO | 2010127855 | A1 | 11/2010 |
| WO | 2011163518 | A1 | 12/2011 |
| WO | 2012020820 | A1 | 2/2012 |
| WO | 2012065019 | A2 | 5/2012 |
| WO | 2012129258 | A1 | 9/2012 |
| WO | 2012154880 | A1 | 11/2012 |
| WO | 2012158957 | A2 | 11/2012 |
| WO | 2013039985 | A2 | 3/2013 |
| WO | 2013/049591 | | 4/2013 |
| WO | 2013101830 | A1 | 7/2013 |
| WO | 2013111108 | A1 | 8/2013 |
| WO | 2013187462 | A1 | 12/2013 |
| WO | 2014111496 | A1 | 7/2014 |
| WO | 2015087995 | A1 | 6/2015 |
| WO | 2015118342 | A1 | 8/2015 |

OTHER PUBLICATIONS

Pinto et al., "Discovery of 1-[3-(Aminomethyl)phenyl]-N-[3-fluoro-2'-(methylsulfonyl)-[1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa," Journal of Medicinal Chemistry, 44(4). pp. 566-578. Jan. 24, 2001.

Prezelj et al., "Recent Advances in Serine Protease Inhibitors as Anticoagulant Agents," Current Pharmaceutical Design, 13(3):287-312, Jan. 2007.

Ramalakshmi et al., "Synthesis, Characterization and Biological Screening of Some Novel 1,3,5 Trisubstituted 2-Pyrazolines," Rasayan Journal of Chemistry 2(2):393-396, Apr. 2009.

Reiter et al., "On Triazoles. VI. The acylation of 5-amino-1,2,4-triazoles," Journal of Heterocyclic Chemistry, 24(1). pp. 127-142. Jan. 1987.

Renné et al., "Plasma kallikrein: Novel functions for an old protease," Thrombosis and Haemostasis 107(6):1012-1013, Jun. 2012.

Saalfrank et al., "Geminale Vinyldiazide, VI. 4,5-Dihydro-1H-tetrazol-5-ylidene aus 3,3-Diazido-2-cyanacrylsäureestern und Hydrazinen, Hydraziden sowie O-substituierten Hydroxylaminen," Chemische Berichte, 122(3). pp. 519-522. Mar. 1989.

Schepetkin et al., "N-Benzoylpyrazoles are Novel Small-Molecule Inhibitors of Human Neutrophil Elastase," Journal of Medicinal Chemistry, 50(20). pp. 4928-4938. Oct. 4, 2007. Published ahead of print Sep. 12, 2007.

Schmidt et al., "Thrombin Inhibitors Reduce Intrapulmonary Accumulation of Fibrinogen and Procoagulant Activity of Bronchoalveolar Lavage Fluid During Acute Lung Injury Induced by Pulmonary Overdistention in Newborn Piglets1," Pediatric Research 39(5):798-804, May 1, 1996.

Schmitt et al., "The kallikreins: old proteases with new clinical potentials," Thrombosis and Haemostasis, 110(3):396-398, Sep. 1, 2013.

Schneider et al., "Critical role of kallikrein in hereditary angioedema pathogenesis: a clinical trial of ecallantide, a novel kallikrein inhibitor," Journal of Allergy and Clinical Immunology 120(2):416-422, Aug. 2007.

Schulman et al., "Dabigatran versus warfarin in the treatment of acute venous thromboembolism," New England Journal of Medicine 361(24):2342-52, Dec. 10, 2009.

Silver et al., "Dabigatran Etexilate, An Oral Direct Thrombin Inhibitor, Represses Fibrotic Changes in a Murine Model of Pulmonary Fibrosis." American Journal of Respiratory and Critical Care Medicine 181:A6780, May 2010.

Simiti et al., "Kondensation von 3-Merkapto-5-phenyl-1,2,4-triazole mit Monochloracetaldehyd," Archiv Der Pharmazie, 320(1). pp. 528-534. Jan. 1, 1987.

Smorenburg et al., "The effects of unfractionated heparin on survival in patients with malignancy—a systematic review," Thrombosis and Haemostasis 82(6):1600-1604, Dec. 1, 1999.

Sotiropoulou et al., "Targeting the kallikrein-related peptidases for drug development," Trends in Pharmacological Sciences 33(12):623-634, Dec. 2012.

Stella, "Prodrugs: An Overview and Definition." Pro-drugs as Novel Drug Delivery Systems, vol. 14, Chapter 1. 115 pages. American Chemical Society. Jun. 1, 1975.

STN International File caplus [Online], AN 2007:157737, DN 147: 385893, SO: Zhurnal Organichnoi ta Farmatsevtichnoi Kimii 2006,

(56) References Cited

OTHER PUBLICATIONS

4(1), p. 32-37, CAS registration No. RN:882238-17-7, 882238-21-3, 882238-25-7, 882239-13-6, 882239-17-0, 882239-21-6.
STN International File Registry [Online]. CAS registration No. RN: 1189909-54-3, 1007171-70-1, 956442-20-9, 956441-56-8, 956375-74-9, 882239-05-6, 2015.
STN International Registry File [Online] May 14, 2008, CAS Registration No. RN 1020709-18-5.
Syed et al., "Wet AMD market," Nature Reviews Drug Discovery 11:827-828, Nov. 2012.
Telander, "Inflammation and age-related macular degeneration (AMD)," Seminars in Ophthalmology 26(3):192-197, published online May 24, 2011.
The National Formulary, 14th Ed. American Pharmaceutical Association. Washington, D.C. pp. 1-5. Jul. 1, 1975.
The National Formulary, 14th Ed. American Pharmaceutical Association. Washington, D.C. pp. 6-19. Jul. 1, 1975.
Tripathy et al., "Thrombin, a mediator of cerebrovascular inflammation in AD and hypoxia," Frontiers in Aging Neuroscience 5(19):1-9, May 9, 2013.
Van Noorden et al., "Experimental and clinical effects of anticoagulants on cancer progression," Thrombosis Search, 125 Supplement 2:S77-S79, Apr. 2010.
Varnes et al., "Design, structure-activity relationship, and pharmacokinetic profile of pyrazole-based indoline factor Xa inhibitors," Bioorganic & Medicinal Chemistry Letters 17(1):6481-6488, available online Oct. 1, 2007, print publication Dec. 2007.
Varnes et al., "Structure-activity relationship and pharmacokinetic profile of 5-ketopyrazole factor Xa inhibitors," Bioorganic & Medicinal Chemistry Letters 18(2):749-754, available online Nov. 17, 2007, print publication Jan. 15, 2008.
Vaughan et al., "Protease nexin-1, a potent thrombin inhibitor, is reduced around cerebral blood vessels in Alzheimer's disease," Brain Research 668(1-2):160-170, Dec. 30, 1994.
Wardakhan et al., "Synthesis of novel pyrazole, coumarin, and pyridazine derivatives evaluated as potential antimicrobial and antifungal agents," Journal of the Chilean Chemical Society, 52(2). pp. 1145-1149. Jun. 2007.
Weitz et al., "Direct Thrombin Inhibitors in Acute Coronary Syndromes: Present and Future," Circulation 105(8):1004-1011, Feb. 26, 2002.
Wiedermann et al., "The anti-inflammatory actions of antithrombin—a review," Acta Medica Austriaca 29(3):89-92, Jul. 29, 2002.
Wieland et al., "Approaches in anticoagulation: rationales for target positiong," Current Opinion in Investigational Drugs 4(3):264-271, Mar. 2003.
Wolfram et al., "Update on Pharmacologic Approaches to Prevent Thromboembolism in Atrial Fibrillation: Are Thrombin and Factor Xa Inhibitors the Ultimate Answer?," Current Vascular Pharmacology 9(3):350-357, May 2011.
Wong et al., "Nonpeptide Factor Xa Inhibitors III: Effects of DPC423, an Orally-Active Pyrazole Antithrombotic Agent, on Arterial Thrombosis in Rabbits." The Journal of Pharmacolor and Experimental Therapeutics, 303(3). pp. 993-1000. Dec. 1, 2002.
Wåhlander et al., "Pharmacokinetics, pharmacodynamics and clinical effects of the oral direct thrombin inhibitor ximelagatran in acute treatment of patients with pulmonary embolism and deep vein thrombosis," Thrombosis Research 107(3-4):93-99, Aug. 15, 2002.
Xiong et al., "Discovery and Structure-Activity Relationship of 3-Methoxy-N-(3-(1 methyl-1 H-pyrazol-5-y-1)-4-(2-morpholinoethoxy)phenyl)benzamide (APD791): A Highly Selective 5-Hydroxytryptamine 2A Receptor Inverse Agonist for the Treatment of Arterial Thrombosis," Journal of Medicinal Chemistry 53(11):4412-4421, Jun. 10, 2010, ISSN: 0022-2623, DOI: 10.1021/jm100044a.
Yin et al., "Brain endothelial cells synthesize neurotoxic thrombin in Alzheimer's disease," The American Journal of Pathology 176(4):1600-1606, Apr. 2010.

Young et al., "Selective and dual action orally active inhibitors of thrombin and factor Xa" Bioorganic & Medicinal Chemistry Letters, 17(10). pp. 2927-2930. May 15, 2007.
Yu et al., "Synthesis and biological activities of 5-substituted benzamide triazole," Journal of Central China Normal University, Natural Sciences Edition, 37(4). pp. 505-503. 2003. Accessed from Database CAPLUS. Database accession No. 2004:240714.
Zacharski et al., "Heparin as an anticancer therapeutic," Expert Opinion on Investigational Drugs, 17(7):1029-1037, Jun. 12, 2008.
Abdel-Salam et al., "A study of unfractionated and low molecular weight heparins in a model of cholestatic liver injury in the rat," Pharmacological Research 51(1):59-67, Jan. 2005.
Abe et al., "Low molecular weight heparin prevents hepatic fibrogenesis caused by carbon tetrachloride in the rat," Journal of Hepatology, 46(2):286-294, Feb. 2007.
Akerblom et al., "Nitrofuryltriazole derivatives as potential urinary tract antibacterial agents," Journal of Medicinal Chemistry, 16(4). pp. 312-319. Apr. 1973.
Akiyama et al., "Thrombin accumulation in brains of patients with Alzheimer's disease," Neuroscience Letters 146(2):152-154, Nov. 9, 1992.
Akl et al., "Parenteral anticoagulation may prolong the survival of patients with limited small cell lung cancer: a Cochrane systematic review," Journal of Experimental & Clinical Cancer Research 27(4), May 15, 2008, 10 pages.
Albers et al., "Ximelagatran vs warfarin for stroke prevention in patients with nonvalvular atrial fibrillation: a randomized trial," JAMA 293(6):690-8, Feb. 2005.
Albert-Weißenberger et al., "Ischemic stroke and traumatic brain injury: The role of the kallikrein-kinin system," Progress in Neurobiology 101-102:65-82, Feb.-Mar. 2013.
Altinbas et al., "A randomized clinical trial of combination chemotherapy with and without low-molecular-weight heparin in small cell lung cancer," Journal of Thrombosis and Haemostasis 2(8):1266-1271, Aug. 2004.
Assy et al., "The beneficial effect of aspirin and enoxaparin on fibrosis progression and regenerative activity in a rat model of cirrhosis," Digestive Diseases and Sciences 52(5):1187-1193, May 2007.
Bader, "Kallikrein-Kinin System in Neovascularization," Arteriosclerosis, Thombosis, and Vascular Biology 29(5):617-619, May 2009.
Becker et al., "Why Do So Many Drugs for Alzheimer's Disease Fail in Development? Time for New Methods and New Practices?" Journal of Alzheimer's Disease 15(2):303-325, Oct. 2008.
Berge et al. "Pharmaceutical Salts," Journal of Pharmaceutical Sciences 66(1):1-19, Jan. 1977.
Bird et al., "Effects of plasma kallikrein deficiency on haemostasis and thrombosis in mice: Murine Ortholog of the Fletcher Trait," Thrombosis and Haemostasis, 107(6):1141-1150, Jun. 2012.
Bogatkevich et al., "Dabigatran, a direct thrombin inhibitor, demonstrates antifibrotic effects on lung fibroblasts," Arthritis & Rheumatism 60(11):3455-3464, published ahead of print Oct. 29, 2009, print publication Nov. 2009.
Brent et al., "Fomepizole for the treatment of ethylene glycol poisoning," The New England Journal of Medicine, 340(11). pp. 832-838. Mar. 18, 1999.
Caliendo et al., "Kallikrein Protease Activated Receptor (PAR) Axis: An Attractive Target for Drug Development," Journal of Medicinal Chemistry 55(15):6669-6686, May 18, 2012.
Calvaruso et al., "Cogaulation and fibrosis in chronic liver disease," Gut 57(12):1722-1727, Dec. 2008.
Chambers et al., "Coagulation cascade proteases and tissue fibrosis," Biochemical Society Transactions 30(2):194-200, Apr. 2002.
Chambers et al., "Procoagulant signalling mechanisms in lung inflammation and fibrosis: novel opportunities for pharmacological intervention?" British Journal of Pharmacology 153(S1):S367-S378, published ahead of print Jan. 28, 2008, print publication Mar. 2008.
Chang et al., "Synthesis and structure-activity relationships of quaternary ammonium cephalosporins with 3-pyrazolylpyridinium derivatives," Bioorganic & Medicinal Chemistry Letters, 10(11). pp. 1211-1214. Jun. 5, 2000.

(56) References Cited

OTHER PUBLICATIONS

Chelmicka-Szorc et al., "Partial suppression of experimental allergic encephalomyelitis with heparin," Archives of Neurology 27(2):153-158, Aug. 1972.
Chen et al., "Interaction of Novel Positive Allosteric Modulators of Metabotropic Glutamate Receptor 5 with the Negative Allosteric Antagonist Site is Required for Potentiation of Receptor Responses," Molecular Pharmacology, 71(5). pp. 1389-1398. May 2007. Published ahead of print Feb. 15, 2007.
Cherton et al., "Réactivité du nucléophile azoture vis-à-vis de cations hétérocycliques aromatiques. VIII. Réarrangement de ß-tétrazolo-trans-benzalacétophénones," Canadian Journal of Chemistry, 63(10). pp. 2601-2607. Oct. 1985.
Cipens et al., "Aminoguanidine derivatives and their transformations. V. Alkyl- and arylamino substituted 1,2,4-triazoles and," Proceedings of the Academy of Science of Latvian SSR, Chemistry Series, 2. pp. 255-261. 1962. Accessed through CAPLUS. Database accession No. 1963:469125.
Colman et al., "The plasma kallikrein-kinin system in sepsis, inflammatory arthritis, and enterocolitis," Clinical Reviews in Allergy and Immunology 16(4):365-384, Dec. 1998.
Connolly et al., "Dabigatran versus warfarin in patients with atrial fibrillation," New England Journal of Medicine 361(12):1139-51, Sep. 17, 2009.
Defeo et al., "Dabigatran etexilate blocks breast cancer progression in vitro and in a 4T1 breast cancer tumor model in mice," Thrombosis Research, 125, Supplement 2, S188, Apr. 2010.
Defeo et al., "Use of dabigatran etexilate to reduce breast cancer progression," Cancer Biology & Therapy, 10(10):1001-1008, Nov. 15, 2010.
Deng et al., "Development of an oxazolopyridine series of dual thrombin/factor Xa inhibitors via structure-guided lead optimization," Bioorganic & Medicinal Chemistry Letters, 15(20). pp. 4411-4416. Oct. 15, 2005.
Diener et al., "Stroke prevention using the oral direct thrombin inhibitor ximelagatran in patients with non-valvular atrial fibrillation. Pooled analysis from the SPORTIF III and V studies," Cerebrovascular Diseases 21(4):279-293, Mar. 2006.
Dubau et al., "Malonylierungsreaktionen an 4-monosubstituierten Pyrazolidin-3,5-dionen," Chemische Berichte, 108(7). pp. 2189-2201. Jul. 1975.
Duplantier et al., "A role for thrombin in liver fibrosis," Gut, 53(11):1682-1687, Nov. 2004.
Dzygiel et al., "Synthesis, Structure and Properties of N-Acetylated Derivatives of Methyl 5-Amino-1H-[1,2,4] triazole-3-carboxylate," Chemical and Pharaceutical Bulletin, 52(2). pp. 192-198. Feb. 1, 2004.
Eliel et al., Stereochemistry of Organic Compounds, Chapter 1. pp. 1-16. Wiley. Sep. 1994.
Eriksson et al., "A Dose-ranging Study of the Oral Direct Thrombin Inhibitor, Ximelagatran, and Its Subcutaneous Form, Melagatran, Compared with Dalteparin in the Prophylaxis of Thromboembolism after Hip or Knee Replacement: METHRO I," Thrombosis and Haemostasis 87(2):231-237, Feb. 2002.
Eriksson et al., "Dabigatran etexilate versus enoxaparin for prevention of venous thromboembolism after total hip replacement: a randomised, double-blind, non-inferiority trial;" The Lancet 370(9591):949-56, Sep. 21, 2007.
Eriksson et al., "Direct thrombin inhibitor melagatran followed by oral ximelagatran in comparison with enoxaparin for prevention of venous thromboembolism after total hip or knee replacement." Thrombosis and Haemostasis, 89(2):288-296. Feb. 2003.
Eriksson et al., "Oral dabigatran etexilate vs. subcutaneous enoxaparin for the prevention of venous thromboembolism after total knee replacement: the RE-MODEL randomized trial," Journal of Thrombosis and Haemostasis 5(11):2178-85, Nov. 1, 2007.
Eriksson et al., "Oral dabigatran versus enoxaparin for thromboprophylaxis after primary total hip arthroplasty (RE-NOVATE II)," Thrombosis and Haemostasis 105(4):721-729, Apr. 2011.
Eriksson et al., "The direct thrombin inhibitor melagatran followed by oral ximelagatran compared with enoxaparin for the prevention of venous thromboembolism after total hip or knee replacement: the EXPRESS study," Journal of Thrombosis and Haemostasis, 1(12):2490-6, Dec. 1, 2003.
Falanga et al., "Effect of anticoagulant drugs in cancer," Current Opinion in Pulmonary Medicine, 11(5):403-407, Sep. 2005.
Farghaly et al., "Synthesis of some new azoles with antiviral protential," ARKIVOC XI. pp. 76-90. 2006.
Favreau et al., "Anti-thrombin therapy during warm ischemia and cold preservation prevents chronic kidney graft fibrosis in a DCD model," American Journal of Transplantation 10(1):30-39, published ahead of print Dec. 2, 2009, print publication Jan. 2010.
Feener et al., "Plasma Kallikrein and Diabetic Macular Edema," Current Diabetes Reports, 10(4):270-275, published ahead of print Jun. 10, 2010, print publication Aug. 1, 2010.
Feener et al., "Plasma Kallikrein Kinin System and Diabetic Retinopathy," Biological Chemistry 394(3):319-328, published online Feb. 2, 2013, print publication Mar. 1, 2013.
Ferrera, "VEGF: an update on biological and therapeutic aspects," Current Opinion in Biotechnology 11(6):617-624, Dec. 1, 2000.
Fiessinger et al., "Ximelagatran vs low-molecular-weight heparin and warfarin for the treatment of deep vein thrombosis: a randomized trial;" JAMA 293(6):681-9, Feb. 9, 2005.
Francis et al., "Comparison of ximelagatran with warfarin for the prevention of venous thromboembolism after total knee replacement," New England Journal of Medicine, 349(18):1703-12, Oct. 30, 2003.
Francis et al., "Ximelagatran versus warfarin for the prevention of venous thromboembolism after total knee arthroplasty. A randomized, double-blind trial." Annals of Internal Medicine, 137(8):648-655. Oct. 15, 2002.
Freitas et al., "Isomannide derivatives as new class of inhibitors for human kallikrein 7," Bioorganic & Medicinal Chemistry Letters 22(19):6072-6075, Oct. 1, 2012.
U.S. Appl. No. 13/630,201, filed Sep. 28, 2012.
U.S. Appl. No. 14/989,742, filed Jan. 6, 2016.
U.S. Appl. No. 15/004,789, filed Jan. 22, 2016.
U.S. Appl. No. 15/155,954, filed May 16, 2016.
U.S. Appl. No. 14/776,612, filed Sep. 14, 2015.
U.S. Appl. No. 15/354,756, filed Nov. 17, 2016.
U.S. Appl. No. 14/776,641, filed Sep. 14, 2015.
U.S. Appl. No. 15/156,154, filed May 16, 2016.
"Medication Guide: PRADAXA (pra dax' a) (dabigatran etexilate mesylate) capsules," Boehringer Ingelheim Pharmaceuticals, Inc., copyright 2010, FDA approval Sep. 20, 2010, four pages.
Beilin et al., "Increased Thrombin Inhibition in Experimental Automimmune Encephalomyelitis," Journal of Neuroscience Research 79(3):351-359, published online Dec. 16, 2004, print publication Feb. 1, 2005.
Brown, "A New Era of Anticoagulation: Factor Xa and Direct Thrombin Inhibitors," U.S. Pharmacist 32(3):HS-35-HS-48, Mar. 21, 2007, 25 pages.
Galanud et al., "The history and historical treatments of deep vein thrombosis," Journal of Thrombosis and Heamostasis 11(3):402-411, Mar. 13, 2013.
Garcia et al., "The role of thrombin and protease-activated receptors in pain mechanisms," Thrombosis and Haemostasis 103(6):1145-1151, published ahead of print Apr. 29, 2010, print publication Jun. 2010.
Gasparini et al., "Peripheral markers in testing pathophysiological hypotheses and diagnosing Alzheimer's disease," The FASEB Journal 12(1):17-34, Jan. 1998.
Giardino, E. C., et al., "Cooperative antithrombotic effect from the simultaneous inhibition of thrombin and factor Xa", Blood Coagulation and Fibrinolysis, 21(2). pp. 128-134. Mar. 2010.
Ginsberg et al., "Oral Thrombin Inhibitor Dabigatran Etexilate vs North American Enoxaparin Regimen for Prevention of Venous Thromboembolism After Knee Arthroplasty Surgery," The Journal of Arthroplasty 24(1):1-9, Jan. 2009.
Goding, "Monoclonal Antibodies: Prinicples and Practice," Academic Press, p. 104, copyright 1986.

(56) References Cited

OTHER PUBLICATIONS

Greicius et al., "Presenile dementia syndromes: an update on taxonomy and diagnosis," Journal of Neurology, Neurosurgery, and Psychiatry 72(6):691-700, Jun. 2002.
Gross et al., "New anticoagulants for treatment of venous thromboembolism," Arteriosclerosis, Thrombosis, and Vascular Biology 28(3):380-386, Mar. 2008.
Hallet, "Acute Peripheral Arterial Occulusion," Merck Manual, Professional/Cardiovascular Disorders/Peripheral Arterial Disorders, two pages, May 2014.
Han et al., "Proteomic analysis of active multiple sclerosis lesions reveals therapeutic targets," Nature 451 (7182):1076-1081, published ahead of print Feb. 17, 2008, print publication Feb. 28, 2008.
Hankey et al, "Antithrombotic Drugs for Patients with Ischaemic Stroke and Transient Ischaemic Attack to Prevent Recurrent Major Vascular Events," The Lancet Neurology 9(3):273-284, Mar. 2010.
Heit et al., "Comparison of the Oral Direct Thrombin Inhibitor Ximelagatran With Enoxaparin as Prophylaxis Against Venous Thromboembolism After Total Knee Replacement: A Phase 2 Dose-Finding Study," Archives of Internal Medicine 161(18): 2215-2221, Oct. 8, 2001.
Herrera et al., "Regio- and Stereoselectivity of Captodative Olefins in 1,3-Dipolar Cycloadditions. A DFT/HSAB Theory Rationale for the Observed Regiochemistry of Nitrones," The Journal of Organic Chemistry, 66(4). pp. 1252-1263. Feb. 9, 2001 Published ahead of print Jan. 27, 2001.
Hettiarachchi et al., "Do Heparins Do More Than Just Treat Thrombosis? The Influence of Heparins on Cancer Spread," Thrombosis and Haemostasis, 82(2):947-952, Aug. 1, 1999.
Hirsh et al., "New anticoagulants," Blood, 105(2):453-463, published ahead of print Jun. 10, 2004, print publication Jan. 2005.
Howell et al., "Direct thrombin inhibition reduces lung collagen, accumulation, and connective tissue growth factor mRNA levels in bleomycin-induced pulmonary fibrosis.," American Journal of Pathology 159(4):1383-1395, Oct. 2001.
Hu et al., "Role of endogenous thrombin in tumor implantation, seeding, and spontaneous metastasis," Blood, 104(9):2746-2751, Nov. 1, 2004.
Hua et al., "Systemic use of argatroban reduces tumor mass, attenuates neurological deficits and prolongs survival time in rat glioma models," Acta Neurochirurgica Supplement, 95:403-406, date of conference Aug. 2004, print publication 2005.
Hua et al., "The role of thrombin in gliomas," Journal of Thrombosis and Haemostasis, 3(9):1917-1923, published ahead of print Jun. 24, 2005, print publication Sep. 2005.
Hughes, "First oral warfarin alternative approved in the US," Nature Reviews Drug Discovery, 9(12):903-906, published ahead of print Oct. 29, 2010, print publication Dec. 2010.
Inaba et al., "Suppression of experimental autoimmune encephalomyelitis by dermatan sulfate," Cellular Immunology 198(2):96-102, Dec. 15, 1999.
International Search Report and Written Opinion dated Jul. 17, 2014, International Patent Application No. PCT/US2014/030853, filed Mar. 17, 2014.
Kaiser et al., "Synthetic and recombinant antithrombin drugs," Expert Opinion on Investigational Drugs 7(6):963-985, Jun. 1, 1998.
Kakkar et al., "Low Molecular Weight Heparin, Therapy With Dalteparin, and Survival in Advanced Cancer: The Fragmin Advanced Malignancy Outcome Study (FAMOUS)," Journal of Clinical Oncology 22(10):1944-1948, May 15, 2004.
Kantlehner et al., "Orthoamide, XXXII. Umsetzungen von tert-Butoxy-N,N,N',N'-tetramethylmethandiamin mit NH-und CH-aciden Verbindungen," Liebigs Annalen der Chemie, 1980(3). pp. 344-357 Mar. 1980.
Katritzky et al. "Selective Reactivity of sp3 and sp2 Carbanions of 1-Substituted 1,2,4-Triazoles. A Comparative Approach," Journal of Organic Chemsitry, 63(13). pp. 4323-4331. Jun. 5, 1998.
Keel et al., "Pathophysiology of polytrauma," Injury, 36(6):691-709, Jun. 2005.

Klerk et al., "The Effect of Low Molecular Weight Heparin on Survival in Patients With Advanced Malignancy," Journal of Clinical Oncology, 23(10):2130-2135, Apr. 1, 2005.
Kokolis et al., "Anticoagulation strategies for patients undergoing percutaneous coronary intervention: unfractionated heparin, low-molecular-weight heparins, and direct thrombin inhibitors." Progress in Cardiovascular Disease 46(6):506-523, May-Jun. 2004.
Kolte et al., "PF-04886847 (an Inhibitor of Plasma Kallikrein) Attenuates Inflammatory Mediators and Activation of Blood Coagulation in Rat Model of Lipopolysaccharide (LPS)—Induced Sepsis," Cardiovascular & Hematological Agents in Medicinal Chemistry 10(2):154-66, Feb. 2012.
Kranjc et al., "Dual Inhibitors of the Blood Coagulation Enzymes" Current Medicinal Chemistry, 11(19). pp. 2535-2547. Oct. 2004.
Kraut, "Serine Proteases: Structure and Mechanism of Catalysis," Annual Review of Biochemistry 46(1):331-358, Jul. 1977.
Kumar et al., "Efficient Routes to Pyrazolo[3,4-b]indoles and Pyrazolo[1,5-a]benzimidazoles via Palladium- and copper-Catalyzed Intramolecular C—C and C—N. Bond Formation", The Journal of Organic Chemistry, 74(18). pp. 7046-7051. Sep. 18, 2009. Published ahead of print Aug. 11, 2009.
Labanauskas et al., "Synthesis of 3-(3,4-Dimethoxyphenyl)-1H-1,2,4,-Triazole-5-Thiol and 2-Amino-5-(3,4-Dimethoxypheny)-1,3,4-Thiadiazole Derivatives Exhibiting Anti-Inflammatory Activity," Die Pharmazie, 56(8). pp. 617-619. Aug. 2001.
Langer et al., "New methods of drug delivery," Science, 249(4976). pp. 1527-1533. Sep. 28, 1990.
Lee et al., "Randomized comparison of low molecular weight heparin and coumarin derivatives on the survival of patients with cancer and venous thromboembolism," Journal of Clinical Oncology, 23(10):2123-2129, Apr. 1, 2005.
Lehman et al., "Bivalirudin in percutaneous coronary intervention," Vascular Health and Risk Management 2(4):357-363, Dec. 2006.
Lewis et al., "Argatroban anticoagulation during percutaneous coronary intervention in patients with heparin-induced thrombocytopenia." Catheterization & Cardiovascular Interventions 57(2):177-184, published ahead of print Sep. 30, 2002, print publication Oct. 2002.
Lloyd et al., "Benzopyran sulfonamides as Kv1.5 potassium channel blockers," Bioorganic & Medicinal Chemistry Letters, 17(12). pp. 3271-3275. Jun. 15, 2007.
Lopez et al., "Transdifferentiated retinal pigment epithelial cells are immunoreactive for vascular endothelial growth factor in surgically excised age-related macular degeneration-related choroidal neovascular membranes," Investigative Ophthalmology & Visual Science 37(5):855-868, Apr. 1996.
Lottenberg et al., "The action of thrombin on peptide p-Nitroanilide substrates: Substrate selectivity and examination of hydrolysis under different reaction condtions," Biochimica et Biophysica Acta (BBA)—Protein Structure and Molecular Enzymology, 742(3). pp. 539-557. Feb. 15, 1983.
Luo et al., "The Role of Thrombin and Thrombin Receptors in the Brain," Chapter 8 in Thrombin: Physiology and Disease, XII. Maragoudakis et al. (eds.). pp. 133-159. 2009.
Mehta et al., "An update on recent patents on thrombin inhibitors (2010-2013)," Expert Opinion on Therapeutic Patents 24(1):47-67, published online Oct. 8, 2013, print publication Jan. 1, 2014.
Miller Keane et al., Miller-Keane Encyclopedia & Dictionary of Medicine, Nursing & Allied Health, 5th Ed. pp. 1651 and 1708. O'Toole (ed.). W.B. Saunders, Philadephia, PA. 1992.
Miura "Transactivation of KDR/Flk-1 by the B2 receptor induces tube formation in human coronary endothelial cells," Hypertension 41(5):1118-1123, published ahead of print Mar. 24, 2003.
Montoya et al., "Regioselective formation of N-alkyl-3,5-pyrazole derived ligands. A synthetic and computational study," Tetrahedron, 61(52). pp. 12377-12385. Dec. 26, 2005.
Moreau et al., "The kallikrein-kinin system: current and future pharmacological targets," Journal of Pharmacological Sciences 99(1):6-38, Sep. 22, 2005.
Narita et al., "Protease-activated receptor-1 and platelet-derived growth factor in spinal cord neurons are implicated in neuropathic pain after nerve injury," The Journal of Neuroscience 25(43):10000-10009, Oct. 26, 2005.

(56) References Cited

OTHER PUBLICATIONS

Nieman et al., "Oral thrombostatin FM19 inhibits prostate cancer," Thrombosis and Haemostasis, 104(5):1044-1048, published ahead of print Sep. 30, 2010, print publication Nov. 2010.
Nieman et al., "Thrombostatin FM compounds: direct thrombin inhibitors—mechanism of action in vitro and in vivo," Journal of Thrombosis and Haemostasis, 6(5):837-845, published ahead of print Feb. 26, 2008, print publication May 2008.
Database Registry Chemical Abstracts Service, Columbus, Ohio, Accession No. RN 67897-88-5, Entered STN: Nov. 16, 1984.
Surmont et al., "Synthesis of 3-Amino-4-fluoropyrazoles," The Journal of Organic Chemistry 76(10):4105-4111, Apr. 29, 2011.
Wang et al., "Synthesis and biological activity of 1-[2-(2,4-dichlorophenoxyl)acetyl]-5-amino-IH-pyrazole derivatives," Youji Huaxue (Chinese Journal of Organic Chemistry) 24(7):797-801, Jul. 1, 2004.

PYRAZOLYL-SUBSTITUTED PYRIDONE COMPOUNDS AS SERINE PROTEASE INHIBITORS

CROSS-REFERENCE TO RELATED APPLICATIONS

The present application is a U.S. National Stage entry under 35 U.S.C. § 371 of International Application No. PCT/US2015/050809, filed on Sep. 17, 2015, designating the United States of America and published in English on Mar. 24, 2016, which in turn claims priority to U.S. Provisional Application Nos. 62/051,511 and 62/051,585, filed on Sep. 17, 2014, each of which is hereby incorporated by reference in its entirety.

FIELD OF THE INVENTION

The invention disclosed herein generally relates to pyrazolyl-substituted pyridine compounds, their use in treating disorders involving serine proteases, including thrombin and various kallikreins, and methods of treating such disorders involving said compounds.

BACKGROUND

Serine proteases are a large family of enzymes with diverse biological functions, their commonality being the presence and critical function of the active-site serine residue. Their central function is the catalytic scission of peptide bond substrates via a Ser, His, Asp triad within the active site (Kraut, *J. Annual Review of Biochemistry* 1977, 46, 331-358)

The present disclosure relates to compounds, e.g., pyrazolyl-substituted pyridone compounds, which exhibit biological activity, e.g., inhibitory action, against serine proteases, including thrombin and various kallikreins.

Kallikreins are a subgroup of serine proteases, divided into plasma kallikrein and tissue kallikreins. Plasma kallikrein (KLKB1) liberates kinins (bradykinin and kallidin) from the kininogens, peptides responsible for the regulation of blood pressure and activation of inflammation. In the contact activation pathway of the coagulation cascade, plasma kallikrein assists in the conversion of factor XII to factor XIIa (Keel, M.; Trentz, O. *Injury* 2005, 36, 691-709). Factor XIIa converts factor XI into factor XIa, which in turn activates factor IX, which with its co-factor factor VIIIa forms the tenase complex, which finally activates factor X to factor Xa. In the fibrinolysis part of the coagulation cascade, plasma kallikrein serves to convert plasminogen to plasmin. Thus, it has been proposed that plasma kallikrein inhibitors can be useful in the treatment of thrombotic and fibrinolytic diseases and disease conditions (U.S. Pat. No. 7,625,944; Bird et al. *Thrombosis and Hemostasis* 2012, 107, Dhaval Kolte, MD. et al., Cardiology in Review, 2015).

In rodent models, it has been shown that activation of plasma kallikrein in the eye increases retinal vascular permeability; whereas inhibition of the kallikrein-kinin system reduces retinal leakage induced by diabetes and hypertension. These findings suggest that intraocular activation of the plasma kallikrein pathway can contribute to excessive retinal vascular permeability that can lead to diabetic macular edema (DME). Thus, evidence suggests that plasma kallikrein inhibitors can provide a new therapeutic opportunity to reduce retinal vascular permeability (Feener, E. P. *Curr Diab Rep* 2010, 10, 270).

Hyperglycemic and diabetic individuals have an elevated risk of hemorrhage during thrombolytic therapy. In rodent models of intracerebral hemorrhage (ICH), it has been shown that KLKB1 inhibition or knockout reduces this effect. While the mechanism is not fully understood, this evidence suggests that plasma kallikrein inhibitors can be useful in the treatment of cerebral hemorrhage (Feener, E. P. *Curr Diab Rep* 2010, 10, 270).

Plasma kallikrein and Factor XIIa inhibitors have been shown to be neuroprotective in animal models of acute ischemic stroke and traumatic brain injury, reducing edema formation, inflammation, and thrombosis (Albert-Weißenberger C, Siren A L, Kleinschnitz C. *Prog Neurobiol.* 2013, 101-102, 65-82.). Thus, evidence suggests that plasma kallikrein inhibitors can be useful in the treatment of acute ischemic stroke and traumatic brain injury.

Plasma kallikrein can also cleave glucagon-like peptide 1 (GLP-1) and neuropeptide Y (NPY), both substrates for dipeptidyl peptidase-4 (DPP-4), a validated diabetes drug target. In the case of GLP-1, cleavage by KLKB1 reduces both its potency as well as plasma stability. In the case of NPY, cleavage by KLKB1 reduces its affinity to the Y2 and Y5 receptors. Thus, evidence suggests that plasma kallikrein inhibitors can be useful in the modulation of energy homeostasis and in the treatment of diabetes. (Feener, E. P. *Curr Diab Rep* 2010, 10, Feener, E. P. et al., *Biol. Chem.* 2013, 394, 319).

The Kallikrein-kinin system is involved in the regulation of vascular endothelial growth factor (VEGF), endothelial NO synthase, and fibroblast growth factor 2, all of which are involved in angiogenesis (Bader M. 2009, *Arteriosclerosis, Thrombosis, and Vascular Biology,* 29: 617). Tissue kallikrein (KLK1) has been linked to blood vessel growth (Miura S., 2003, *Hypertension,* 41, 1118). Therapies that moderate angiogenesis have been proposed for the treatment of both diabetic macular edema (DME) and age-related macular degeneration (AMD) (Syed, B. A.; Evans, J. B.; Bielory, L., 2012, *Nature Reviews Drug Discovery,* 11, 827). Without further wishing to be bound by any theory, it is therefore reasonable to conclude that kallikrein inhibitors, including KLK1 inhibitors, can be useful in the treatment of diabetic retinopathy, DME, and AMD.

Studies have shown that inflammation plays an important role in the origin and development of AMD, and treatment often includes anti-inflammatories such as corticosteroid (Telander, D., 2011, *Seminars in Ophthalmology,* 26(3), 192). The connection between the kallikrein-kinin system and inflammation is also well established (Duchene, 2011, "Kallikrein-kinin kystem in inflammatory diseases". *Kinins.* De Gruyter. 261). Without further wishing to be bound by any theory, it is reasonable to conclude that the anti-inflammatory nature of kallikrein (e.g. KLK1 and KLKB1) inhibitors can be useful in the treatment of AMD.

Ecallantide (Kalbitor) is a 60-amino acid recombinant protein that acts as a potent reversible inhibitor of plasma kallikrein (Schneider L, et al., *J Allergy Clin Immunol* 2007, 120, 416). Ecallantide has been approved by the FDA for the treatment of acute attacks of hereditary angioedema (HAE). Without further wishing to be bound by any theory, it is reasonable to believe that plasma kallikrein inhibition in general can be a useful treatment for HAE, and thus there is strong interest in the development of plasma kallikrein inhibitors as a therapy for HAE.

Tissue kallikreins (KLKs, for example, KLK1) are subdivided into various types, and have been extensively investigated in cancer and inflammation biology. Various kallikrein KLKs have been found to be up- or down-regulated in various cancer types, such as cervical-, testicular-, and non-small-cell lung adenocarcinoma (Caliendo et al. *J. Med. Chem.*, 2012, 55, 6669). Furthermore, overexpression of various KLKs in the skin has led to the recognition that certain kallikrein inhibitors can be useful for certain dermatological conditions, including atopic dermatitis, psoriasis and rare skin diseases such as Netherton Syndrome (Freitas et al. *Bioorganic & Medicinal Chemistry Letters* 2012, 22, 6072-6075). A thorough discussion of tissue kallikreins, plasma kallikrein, their functions and potential roles in various diseases can be found in a variety of references, including the following which are incorporated herein by reference in their entireties and for all purposes: Renné, T.; Gruber, A. *Thromb Haemost* 2012, 107, 1012-3; Sotiropoulou, G.; Pampalakis, G. *Trends in Pharmacological Sciences* 2012, 33, 623-634; Pampalakis, G.; Sotiropoulou, G. *Chapter 9 Pharmacological Targeting of Human Tissue Kallikrein-Related Peptidases. In Proteinases as Drug Targets*, Dunn, B., Ed. *The Royal Society of Chemistry:* 2012; pp 199-228; Caliendo, G.; Santagada, V.; Perissutti, E.; Severino, B.; Fiorino, F.; Frecentese, F.; Juliano, L. *J Med Chem* 2012, 55, 6669-86.

Daiichi Seiyaku Co Ltd received approval in Japan to market cetraxate for gastritis and peptic ulcers. Cetraxate is reported as a plasma kallikrein inhibitor (WIPO Patent Application WO/2006/108643). Without further wishing to be bound by any theory, it is reasonable to believe that plasma kallikrein inhibition in general can be useful in the treatment of gastritis and peptic ulcers.

Thrombin (fIIa, the active form of prothrombin) is another serine protease that is involved in the coagulation cascade. In mammalian systems, blood vessel injuries result in bleeding events, which are dealt with by the blood coagulation cascade. The cascade includes the extrinsic and intrinsic pathways, involving the activation of at least 13 interconnected factors and a variety of co-factors and other regulatory proteins. Upon vascular injury, plasma factor VII interacts with exposed Tissue Factor (TF), and the resultant TF-fVIIa complex initiates a complex series of events. Factor Xa is produced directly 'downstream' from the TF-fVIIa complex, and amplified manifold via the intrinsic Pathway. FXa then serves as the catalyst for formation of thrombin (fIIa), which in turn is the direct precursor to fibrinolysis. The outcome is a fibrinolytic clot, which stops the bleeding. Fibrinolysis of the polymeric clot into fibrin monomers leads to dissolution and a return of the system to the pre-clot state. The cascade is a complex balance of factors and co-factors and is tightly regulated. In disease states, undesired up- or down-regulation of any factor leads to conditions such as bleeding or thrombosis.

Historically, anticoagulants have been used in patients at risk of suffering from thrombotic complications, such as angina, stroke and heart attack. Warfarin has enjoyed dominance as a first-in-line anticoagulant therapeutic. Developed in the 1940s, it is a Vitamin K antagonist and inhibits factors II, VII, IX and X, amongst others. It is administered orally, but its ease of use is tempered by other effects: it has a very long half-life (>2 days) and has serious drug-drug interactions. Importantly, since Vitamin K is a ubiquitous cofactor within the coagulation cascade, antagonism results in the simultaneous inhibition of many clotting factors and thus can lead to significant bleeding complications.

Much attention has been focused on heparin, the naturally-occurring polysaccharide that activates AT III, the endogenous inhibitor of many of the factors in the coagulation cascade. The need for parenteral administration for the heparin-derived therapeutics, and the inconvenient requirements for close supervision for the orally available warfarin, has resulted in a drive to discover and develop orally available drugs with wide therapeutic windows for safety and efficacy. Indeed, the position of thrombin in the coagulation cascade has made it a popular target for drug discovery. Without wishing to be bound by any theory, it is believed that the ultimate development of direct thrombin inhibitors (DTIs) is usefully based upon the classical D-Phe-Pro-Arg motif, a sequence that mimics fibrinogen, which is a natural substrate of thrombin. Without further wishing to be bound by any theory, it is believed that the use of DTIs is very well precedented, such as with the hirudin-based anticoagulants, and thus there is strong interest in the discovery and development of novel DTIs.

A thorough discussion of thrombin and its roles in the coagulation process can be found in a variety of references, including the following which are incorporated herein by reference in their entireties and for all purposes: Wieland, H. A., et al., 2003, *Curr Opin Investig Drugs*, 4:264-71; Gross, P. L. & Weitz, J. I., 2008, *Arterioscler Thromb Vasc Biol*, 28:380-6; Hirsh, J., et al., 2005, *Blood*, 105:453-63; Prezelj, A., et al., 2007, *Curr Pharm Des*, 13:287-312.

It will be obvious to one who is skilled in the art that plasma and tissue kallikreins and thrombin are only a few of the many serine proteases that are relevant to the treatment or prevention of certain disorders or diseases

SUMMARY OF THE INVENTION

Embodiments of the present invention encompass compounds including a substituted or unsubstituted pyridone ring attached to a substituted or unsubstituted pyrazole ring with structure of Formula (I):

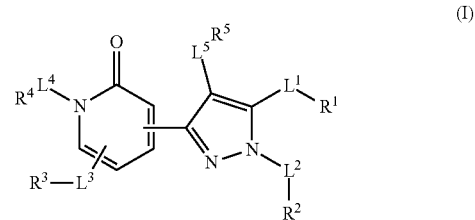

or pharmaceutically acceptable salts, esters, solvates, or prodrugs thereof, wherein $L^1$ can be a bond, substituted or unsubstituted alkylene, substituted or unsubstituted heteroalkylene, —S—, —O—, or —$NR^6$—; $L^2$ and $L^4$ are independently a bond, substituted or unsubstituted alkylene, substituted or unsubstituted heteroalkylene, —S—, —SO—, or —$SO_2$—; $L^3$ and $L^5$ are independently a bond, substituted or unsubstituted alkylene, substituted or unsubstituted heteroalkylene, or —O—; $R^1$ can be hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl; $R^2$ and $R^4$ are independently hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl; $R^3$ and $R^5$ are independently hydrogen, halogen, substituted or unsubstituted alkyl, substituted or unsubstituted heteroalkyl, substituted or unsubstituted aryl, or substituted or unsubstituted heteroaryl; and $R^6$ can be hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted heterocycloalkyl, substituted or unsubstituted aryl, or substituted or unsubstituted heteroaryl; provided that if the compound has a structure according to Formula (IIa), as follows, either $L^3$ is not a bond or $R^3$ is not hydrogen:

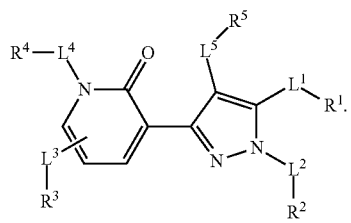

(IIa)

In some embodiments, the compound can have the structure of Formula (IIa), Formula (IIIa), Formula (IVa), or Formula (Va):

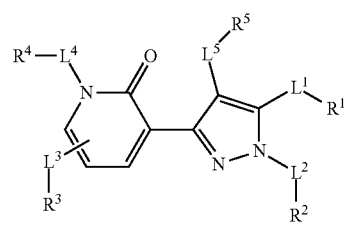

(IIa)

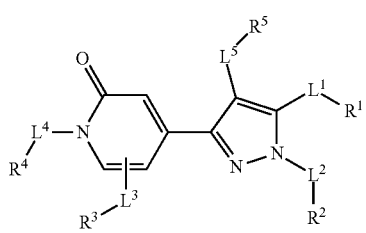

(IIIa)

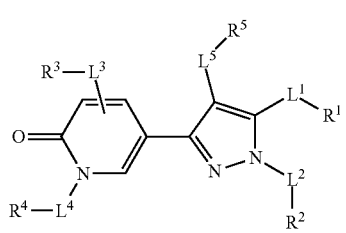

(IVa)

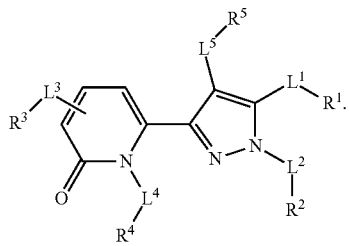

(Va)

In some embodiments, $L^2$ can be a bond, and $R^2$ can be hydrogen.

In some embodiments, the compound can have the structure according to any of Formula (IIIa), Formula (IVa), or Formula (Va) as set forth above, wherein $L^3$ can be a bond, and $R^3$ can be hydrogen.

In some embodiments, $L^4$ can be a bond and $R^4$ can be hydrogen. In some embodiments, $L^5$ can be a bond, and $R^5$ can be hydrogen.

In some embodiments, $L^2$ can be —C(O)—, and $R^2$ can be substituted or unsubstituted alkyl, substituted or unsubstituted cycloalkyl, substituted or unsubstituted cycloalkenyl, substituted or unsubstituted heteroalkyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, $R^2$ can be substituted or unsubstituted aryl or substituted or unsubstituted heteroaryl. In some embodiments, the aryl or heteroaryl can be phenyl, 2-chlorophenyl, 2-methoxyphenyl, phenyl-3-carboxylic acid, phenyl-3-carboxamide, 3-(hydroxymethyl)phenyl, phenyl-4-carboxylic acid, phenyl-4-carboxamide, 4-(hydroxymethyl)phenyl, 2-thienyl, 3-thienyl, 2-furyl, 3-furyl, 1,3-thiazol-2-yl, 1,3-thiazol-4-yl, 1,3-thiazol-5-yl, 1,3-oxazol-2-yl, 1,3-oxazol-4-yl, or 1,3-oxazol-5-yl. In some embodiments, $R^2$ can be substituted or unsubstituted alkyl. In some embodiments, $R^2$ can be tert-butyl, 1,1-dimethyl-2-hydroxy-ethyl, 1,1-dimethyl-2-methoxy-ethyl, or 1,1-dimethyl-2-cyclopropoxy-ethyl.

In some embodiments, $L^1$ can be bond, —S—, —O—, —NR$^6$—, substituted or unsubstituted alkylene, or substituted or unsubstituted heteroalkylene, and $R^1$ can be hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, the aryl or heteroaryl can be phenyl, 4-fluorophenyl, 4-chlorophenyl, 2-thienyl, or 5-chloro-thien-2-yl, 1,3-thiazol-2-yl, 1,3-thiazol-4-yl, 2-chloro-1,3-thiazol-5-yl, or 5-chloro-1,3-thiazol-2-yl.

In some embodiments, $L^4$ can be a bond or substituted or unsubstituted alkylene, and $R^4$ can be substituted or unsubstituted aryl, substituted or unsubstituted fused ring aryl, or substituted or unsubstituted heteroaryl. In some embodiments, the heteroaryl can be pyridyl, pyridazinyl, pyrimidinyl, thienyl, or furyl. In some embodiments, $L^4$ can be substituted or unsubstituted alkylene, and $R^4$ can be substituted or unsubstituted heterocycloalkyl. In some embodiments, the heterocycloalkyl can be morpholinyl, oxanyl, or oxetanyl. In some embodiments, $L^4$ can be a bond, and $R^4$ can be substituted or unsubstituted alkyl or substituted or unsubstituted heteroalkyl In some embodiments, $L^3$ can be bond, and $R^3$ can be halogen, substituted or unsubstituted alkyl, substituted or unsubstituted heteroalkyl, substituted or unsubstituted aryl, or substituted or unsubstituted heteroaryl. In some embodiments, the aryl or heteroaryl can be phenyl, pyridyl, pyridazinyl, pyrimidinyl, thienyl, or furyl. In some embodiments, the alkyl or heteroalkyl can be methyl or cyano.

In some embodiments, $L^5$ can be bond, and $R^5$ can be hydrogen, halogen, substituted or unsubstituted alkyl, substituted or unsubstituted heteroalkyl, substituted or unsubstituted aryl, or substituted or unsubstituted heteroaryl.

In some embodiments, the compound can be selected from any compound listed in Table A. In some embodiments, the compound can be selected from any compound listed in Table B (Appendix A).

Embodiments of the present invention also relate to pharmaceutical compositions including a compound as described above, and a pharmaceutically acceptable excipient.

Embodiments of the present invention also encompass methods for treating a disease or disorder in a subject, including administering a compound or a pharmaceutical composition as described above, to a subject in need thereof in an amount effective to treat or prevent the disease or disorder.

In some embodiments, the disease or disorder can be a thrombotic disorder or a kallikrein-related disorder.

In some embodiments, the thrombotic disorder can be acute coronary syndrome, venous thromboembolism, arterial thromboembolism, cardiogenic thromboembolism, disseminated intravascular coagulation, or a blood clot thrombus. In some embodiments, the compound acts by inhibiting thrombin.

In some embodiments, the kallikrein-related disorder can be a thrombotic disease, a fibrinolytic disease, a type of cancer, an inflammatory condition, a dermatological condition, or an ophthalmic disease. In some embodiments, the ophthalmic disease can be diabetic macular edema, age-related macular degeneration, or diabetic retinopathy. In some embodiments, the type of cancer can be cervical-, testicular-, or non-small-cell lung adenocarcinoma. In some embodiments, the inflammatory condition can be sepsis, inflammatory bowel disease, systemic inflammatory response syndrome, or rheumatoid arthritis. In some embodiments, the compound acts by inhibiting plasma kallikrein. In some embodiments, the compound acts by inhibiting tissue kallikrein.

In some embodiments, the disease or disorder can be fibrosis, Alzheimer's Disease, multiple sclerosis, pain, or cancer.

BRIEF DESCRIPTION OF THE DRAWINGS

Not applicable.

DETAILED DESCRIPTION OF THE INVENTION

I. Definitions

Unless otherwise noted, terms are to be understood according to conventional usage by those of ordinary skill in the relevant art The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the term "attached" signifies a stable covalent bond, certain preferred points of attachment being apparent to those of ordinary skill in the art.

The terms "halogen" or "halo" include fluorine, chlorine, bromine, and iodine. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "alkyl," by itself or as part of another substituent, means, unless otherwise stated, a straight (i.e., unbranched) or branched chain, or combination thereof, which can be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Accordingly, the term "alkyl" can refer to C$_1$-C$_{16}$ straight chain saturated, C$_1$-C$_{16}$ branched saturated, C$_3$-C$_8$ cyclic saturated and C$_1$-C$_{16}$ straight chain or branched saturated aliphatic hydrocarbon groups substituted with C$_3$-C$_8$ cyclic saturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, octyl, nonyl, decyl, undecyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopropylmethyl, and the like.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the compounds disclosed herein. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen, phosphorus, silicon, and sulfur atoms can optionally be oxidized, and the nitrogen heteroatom can optionally be quaternized. The heteroatom(s) O, N, P, S, and Si can be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —S(O)—CH$_3$, —CH$_2$—CH$_2$—S (O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms can be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "alkenyl" includes C$_2$-C$_{16}$ straight chain unsaturated, C$_2$-C$_{11}$ branched unsaturated, C$_5$-C$_8$ unsaturated cyclic, and C$_2$-C$_{16}$ straight chain or branched unsaturated aliphatic hydrocarbon groups substituted with C$_3$-C$_8$ cyclic saturated and unsaturated aliphatic hydrocarbon groups having the specified number of carbon atoms. Double bonds can occur in any stable point along the chain and the carbon-carbon double bonds can have either the cis or trans configuration. For example, this definition shall include but is not limited to ethenyl, propenyl, butenyl, pentenyl, hexenyl, heptenyl, octenyl, nonenyl, decenyl, undecenyl, 1,5-octadienyl, 1,4,7-nonatrienyl, cyclopentenyl, cyclohexenyl, cycloheptenyl, cyclooctenyl, ethylcyclohexenyl, butenylcyclopentyl, 1-pentenyl-3-cyclohexenyl, and the like. Similarly, "heteroalkenyl" refers to heteroalkyl having one or more double bonds.

The term "alkynyl" refers in the customary sense to alkyl additionally having one or more triple bonds. The term "cycloalkenyl" refers to cycloalkyl additionally having one or more double bonds. The term "heterocycloalkenyl" refers to heterocycloalkyl additionally having one or more double bonds.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Each of the above terms (e.g., "alkyl," "heteroalkyl,") and below terms (e.g., "aryl," and "heteroaryl") includes both substituted and unsubstituted forms of the indicated radical. Preferred substituents for each type of radical are provided herein.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, 1\1, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R") =NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", and R'" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound disclosed herein includes more than one R group, for example, each of the R groups is independently selected as are each R', R", and R'" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", and R'" groups when more than one of these groups is present.

Two or more substituents can optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring can optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring can optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed can optionally be replaced with a double bond. Alternatively, two of the substituents on adjacent atoms of the aryl or heteroaryl ring can optionally be replaced with a substituent of the formula —(CRR')$_s$—X'— (C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si). The heteroatom can itself be substituted with an alkyl or aryl group when the heteroatom is N, P, or Si.

The term "alkyloxy" (e.g. methoxy, ethoxy, propyloxy, allyloxy, cyclohexyloxy) represents an alkyl group as defined above having the indicated number of carbon atoms attached through an oxygen bridge (—O—).

The term "alkylthio" (e.g. methylthio, ethylthio, propylthio, cyclohexylthio and the like) represents an alkyl group as defined above having the indicated number of carbon atoms attached through a sulfur bridge (—S—).

The term "alkylamino" represents one or two alkyl groups as defined above having the indicated number of carbon atoms attached through an amine bridge. The two alkyl groups can joined together with the nitrogen to which they are attached, thereby forming a cyclic system containing 3 to 8 carbon atoms with or without one $C_1$-$C_{16}$alkyl, aryl$C_0$-$C_{16}$alkyl, or $C_0$-$C_{16}$alkylaryl substituent.

The term "alkylaminoalkyl" represents an alkylamino group attached through an alkyl group as defined above having the indicated number of carbon atoms.

The term "alkyloxy(alkyl)amino" (e.g. methoxy(methyl) amine, ethoxy(propyl)amine) represents an alkyloxy group as defined above attached through an amino group, the amino group itself having an alkyl substituent.

The term "alkylcarbonyl" (e.g. cyclooctylcarbonyl, pentylcarbonyl, 3-hexylcarbonyl) represents an alkyl group as defined above having the indicated number of carbon atoms attached through a carbonyl group.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen.

The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonylaminomethyl, methylcarbonylaminophenyl) represents an alkylcarbonyl group as defined above wherein the carbonyl is in turn attached through the nitrogen atom of an amino group.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. Likewise, a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, benzodioxan-2-yl, benzodioxan-5-yl, benzodioxan-6-yl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, 1,2,4-oxadiazin-3-yl, 1,2,4-oxadiazin-5-yl, 1,2,4-thiazin-3-yl, and 1,2,4-thiazin-5-yl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Accordingly, the term "aryl" can represent an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e. g. 3-indolyl, 4-imidazolyl). The aryl substituents are independently selected from the group consisting of halo, nitro, cyano, trihalomethyl, $C_{1-16}$alkyl, aryl$C_{1-16}$alkyl, $C_{0-16}$alkyloxy$C_{0-16}$ alkyl, aryl$C_{0-16}$ alkyloxy$C_{0-16}$ alkyl, $C_{0-16}$ alkylthio $C_{0-16}$alkyl, aryl$C_{0-16}$alkylthio$C_{0-16}$alkyl, $C_{0-16}$alkylamino$C_{0-16}$ alkyl, aryl$C_{0-16}$alkylamino$C_{0-16}$alkyl, di(aryl$C_{1-16}$ alkyl)amino $C_{0-16}$alkyl, $C_{1-16}$alkylcarbonyl$C_{0-16}$alkyl, aryl$C_{1-16}$alkylcarbonyl$C_{0-16}$alkyl, $C_{1-16}$alkylcarboxy$C_{0-16}$alkyl, aryl $C_{1-16}$alkylcarboxy$C_{0-16}$alkyl, $C_{1-16}$alkylcarbonylamino$C_{0-16}$alkyl, aryl$C_{1-16}$alkylcarbonylamino$C_{0-16}$alkyl, —$C_{0-16}$alkylCOOR$_4$, —$C_{0-16}$alkylCONR$_5$R$_6$ wherein $R_4$, $R_5$ and $R_6$ are independently selected from hydrogen, $C_1$-$C_{11}$alkyl, aryl$C_0$-$C_{11}$alkyl, or $R_5$ and $R_6$ are taken together with the nitrogen to which they are attached forming a cyclic system containing 3 to 8 carbon atoms with or without one $C_{1-16}$alkyl, aryl$C_0$-$C_{16}$alkyl, or $C_0$-$C_{16}$alkylaryl substituent.

For brevity, the term "aryl" when used in combination with other terms (e.g., aryloxy, arylthioxy, arylalkyl) includes both aryl and heteroaryl rings as defined above. Thus, the terms "arylalkyl," "aralkyl" and the like are meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like), or a sulfur atom. Accordingly, the terms "arylalkyl" and the like (e.g. (4-hydroxyphenyl)ethyl, (2-aminonaphthyl)hexyl, pyridylcyclopentyl) represents an aryl group as defined above attached through an alkyl group as defined above having the indicated number of carbon atoms.

The term "oxo," as used herein, means an oxygen that is double bonded to a carbon atom.

The term "alkylsulfonyl," as used herein, means a moiety having the formula —$S(O_2)$—R', where R' is an alkyl group as defined above. R' can have a specified number of carbons (e.g., "$C_1$-$C_4$ alkylsulfonyl").

The term "carbonyloxy" represents a carbonyl group attached through an oxygen bridge.

In the above definitions, the terms "alkyl" and "alkenyl" can be used interchangeably in so far as a stable chemical entity is formed, as would be apparent to those skilled in the art.

The term "linker" refers to attachment groups interposed between substituents, e.g., R', $R^2$, $R^3$, $R^4$ or $R^5$ described herein, e.g., Formula (I) and generically referred to as R'', and the group which is substituted. In some embodiments, the linker includes amido (—CONH—R'' or —NHCO—R''), thioamido (—CSNH—R'' or —NHCS—R''), carboxyl (—CO$_2$—R'' or —OCOR''), carbonyl (—CO—R''), urea (—NHCONH—R''), thiourea (—NHCSNH—R''), sulfonamido (—NHSO$_2$—R'' or —SO$_2$NH—R''), ether (—O—R''), sulfonyl (—SO$_2$—R''), sulfoxyl (—SO—R''), carbamoyl (—NHCO$_2$—R'' or —OCONH—R''), or amino (—NHR'') linking moieties.

A "substituent group," as used herein, means a group selected from the following moieties:
- (A) —OH, —NH$_2$, —SH, —CN, —CF$_3$, —NO$_2$, oxo, halogen, —COOH, unsubstituted alkyl, unsubstituted heteroalkyl, unsubstituted cycloalkyl, unsubstituted heterocycloalkyl, unsubstituted aryl, unsubstituted heteroaryl, and
- (B) alkyl, heteroalkyl, cycloalkyl, heterocycloalkyl, aryl, and heteroaryl, substituted with at least one substituent selected from:
  - (i) oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and
  - (ii) alkyl, heteroalkyl, cycloalkyl, heterocycloalkyl, aryl, and heteroaryl, substituted with at least one substituent selected from:
    - (a) oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and
    - (b) alkyl, heteroalkyl, cycloalkyl, heterocycloalkyl, aryl, or heteroaryl, substituted with at least one substituent selected from:
      oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2-20-membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4-8-membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2-8-membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5-7-membered heterocycloalkyl The term "about" used in the context of a numeric value indicates a range of +/−10% of the numeric value, unless expressly indicated otherwise.

II. Compounds

In one aspect, there is provided a compound with structure of Formula (I):

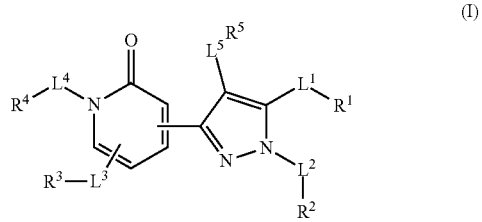

or pharmaceutically acceptable salt, ester, solvate, or prodrug thereof. Compounds of Formula (I) have substituent groups according to the following:

$L^1$ is a bond, substituted or unsubstituted alkylene, substituted or unsubstituted heteroalkylene, —S—, —SO—, —SO$_2$—, —O—, —NHSO$_2$—, or —NR$^6$—;

$R^1$ is hydrogen, a halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl;

$L^2$ is a bond, substituted or unsubstituted alkylene, substituted or unsubstituted heteroalkylene, —S—, —SO—, —SO$_2$—, —O—, —NHSO$_2$—, or —NR$^6$;

$R^2$ is a hydrogen, a halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heterdoaryl;

$L^3$ is a bond, substituted or unsubstituted alkylene, substituted or unsubstituted heteroalkylene, or —O—;

$R^3$ is a hydrogen, a halogen, substituted or unsubstituted alkyl, substituted or unsubstituted heteroalkyl, substituted or unsubstituted aryl, or substituted or unsubstituted heteroaryl;

$L^4$ is a bond, substituted or unsubstituted alkylene, substituted or unsubstituted heteroalkylene, —S—, —SO—, —SO$_2$—, —O—, —NHSO$_2$—, or —NR$^6$;

$R^4$ is hydrogen, a halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl;

$L^5$ is a bond, substituted or unsubstituted alkylene, substituted or unsubstituted heteroalkylene or —O—;

$R^5$ is hydrogen, halogen, substituted or unsubstituted alkyl, substituted or unsubstituted heteroalkyl, substituted or unsubstituted aryl, or substituted or unsubstituted heteroaryl; and $R^6$ is hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl;

provided that if the pyrazole ring is connected to the 3-position of the pyridone ring, either $L^3$ is not a bond or $R^3$ is not hydrogen.

In some embodiments, the compound is a pharmaceutically acceptable salt, ester, solvate, or prodrug of a compound of Formula (I). In some embodiments, the compound is not an ester, not a solvate, and not a prodrug.

Further to any embodiment above wherein the compound has the structure of Formula (I), in some embodiments, $L^1$ is —S—, —NR$^6$—, substituted or unsubstituted alkylene, or substituted or unsubstituted heteroalkylene, where $R^6$ is previously described, and $R^1$ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, $R^1$ is substituted or unsubstituted phenyl. In some embodiments, $R^1$ is unsubstituted phenyl. In some embodiments, $R^1$ is a substituted or unsubstituted pyridyl. In some embodiments, $R^1$ is a substituted or unsubstituted pyridazinyl. In some embodiments, $R^1$ is a substituted or unsubstituted pyrimidinyl. In some embodiments, $R^1$ is a substituted or unsubstituted thienyl. In some embodiments, $R^1$ is a substituted or unsubstituted furyl. In some embodiments, $R^1$ is a substituted or unsubstituted thiazoyl. In some embodiments, $R^1$ is an unsubstituted pyridyl. In some embodiments, $R^1$ is an unsubstituted pyridazinyl. In some embodiments, $R^1$ is an unsubstituted pyrimidinyl. In some embodiments, $R^1$ is an unsubstituted thienyl. In some embodiments, $R^1$ is a chloro-substituted thienyl. In some embodiments, $R^1$ is 5-chloro-thien-2-yl. In some embodiments, $R^1$ is a chloro-substituted thiazoyl. In some embodiments, $R^1$ is an unsubstituted furyl.

Further to any embodiment above wherein the compound has the structure of Formula (I), in some embodiments, $L^2$ is a bond. In some embodiments, $R^2$ is hydrogen. In some embodiments, $L^2$ is a bond, and $R^2$ is hydrogen In some embodiments, $L^2$ is substituted or unsubstituted alkylene or —C(O)—, and $R^2$ is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, $R^2$ is substituted or unsubstituted tert-butyl. In some embodiments, $R^2$ is substituted or unsubstituted cyclopropyl. $R^2$ is substituted or unsubstituted bicycloalkyl. In some embodiments, $R^2$ is substituted or unsubstituted tetrahydropyranyl. In some embodiments, $R^2$ is substituted or unsubstituted piperidinyl. In some embodiments, $R^2$ is a substituted or unsubstituted morpholinyl. In some embodiments, $R^2$ is a substituted or unsubstituted oxanyl. In some embodiments, $R^2$ is a substituted or unsubstituted oxetanyl. In some embodiments, $R^2$ is an unsubstituted morpholinyl. In some embodiments, $R^2$ is an unsubstituted oxanyl. In some embodiments, $R^2$ is an unsubstituted oxetanyl. In some embodiments, $R^2$ is substituted or unsubstituted benzodioxinyl. In some embodiments, $R^2$ is substituted or unsubstituted phenyl. In some embodiments, $R^2$ is a substituted or unsubstituted pyridyl. In some embodiments, $R^2$ is a substituted or unsubstituted pyridazinyl. In some embodiments, $R^2$ is a substituted or unsubstituted pyrimidinyl. In some embodiments, $R^2$ is a substituted or unsubstituted pyrazinyl. In some embodiments, $R^2$ is a substituted or unsubstituted thienyl. In some embodiments, $R^2$ is a substituted or unsubstituted furyl. In some embodiments, $R^2$ is a substituted or unsubstituted thiazole. In some embodiments, $R^2$ is an unsubstituted pyridyl. In some embodiments, $R^2$ is an unsubstituted pyridazinyl. In some embodiments, $R^2$ is an unsubstituted pyrimidinyl. In some embodiments, $R^2$ is an unsubstituted thienyl. In some embodiments, $R^2$ is a chloro-substituted thienyl. In some embodiments, $R^2$ is an unsubstituted furyl. In some embodiments, $R^2$ is a substituted or unsubstituted oxazole. In some embodiments, $R^2$ is a substituted or unsubstituted isothiazole. In some embodiments, $R^2$ is a substituted or unsubstituted isoxazole. In some embodiments, $R^2$ is a substituted or unsubstituted thiadiazole. In some embodiments, $R^2$ is a substituted or unsubstituted oxadiazole. In some embodiments, $R^2$ is an unsubstituted morpholinyl. In some embodiments, $R^2$ is an unsubstituted oxanyl. In some embodiments, $R^2$ is an unsubstituted oxetanyl. In some embodiments, $R^2$ is substituted or unsubstituted benzodioxinyl. In some embodiments, $R^2$ is substituted or unsubstituted naphthyl. In some embodiments, $R^2$ is unsubstituted benzodioxinyl. In some embodiments, $R^2$ is unsubstituted naphthyl.

In some embodiments, $R^2$ is unsubstituted tert-butyl. In some embodiments, $R^2$ is unsubstituted phenyl. In some embodiments, $R^2$ is 2-fluorophenyl. In some embodiments, $R^2$ is 2-chlorophenyl. In some embodiments, $R^2$ is 2-methoxyphenyl. In some embodiments, $R^2$ is 2,4-dimethoxyphenyl. In some embodiments, $R^2$ is 2-cyclopropoxyphenyl. In some embodiments, $R^2$ is 2-aminophenyl. In some embodiments, $R^2$ is phenyl-2-carboxylic acid. In some embodiments, $R^2$ is phenyl-2-carboxamide. In some embodiments, $R^2$ is 3-fluorophenyl. In some embodiments, $R^2$ is 3-chlorophenyl. In some embodiments, $R^2$ is 3-aminophenyl. In some embodiments, $R^2$ is phenyl-3-carboxylic acid. In some embodiments, $R^2$ is phenyl-3-carboxamide. In some embodiments, $R^2$ is 3-(hydroxymethyl)phenyl. In some embodiments, $R^2$ is 4-fluorophenyl. In some embodiments, $R^2$ is 4-chlorophenyl. In some embodiments, $R^2$ is phenyl-4-carboxylic acid. In some embodiments, $R^2$ is phenyl-4-carboxamide. In some embodiments, $R^2$ is 4-(hydroxymethyl)phenyl. In some embodiments, $R^2$ is an unsubstituted pyridyl. In some embodiments, $R^2$ is unsubstituted pyridazinyl. In some embodiments, $R^2$ is unsubstituted pyrimidinyl. In some embodiments, $R^2$ is unsubstituted pyrazinyl. In some embodiments, $R^2$ is unsubstituted thienyl. In some embodiments, $R^2$ is thien-2-yl. In some embodiments, $R^2$ is thien-3-yl. In some embodiments, $R^2$ is unsubstituted furyl. In some embodiments, $R^2$ is fur-2-yl. In some embodiments, $R^2$ is fur-3-yl. In some embodiments, $R^2$ is unsubstituted thiazole. In some embodiments, $R^2$ is 1,3-thiazol-2-yl. In some embodiments, $R^2$ is 1,3-thiazol-4-yl. In some embodiments, $R^2$ is 1,3-thiazol-5-yl. In some embodiments, $R^2$ is unsubstituted oxazole. In some embodiments, $R^2$ is 1,3-oxazol-2-yl. In some embodiments, $R^2$ is 1,3-oxazol-4-yl. In some embodiments, $R^2$ is 1,3-oxazol-5-yl. In some embodiments, $R^2$ is unsubstituted isothiazole. In some embodiments, $R^2$ is unsubstituted isoxazole. In some embodiments, $R^2$ is unsubstituted thiadiazole. In some embodiments, $R^2$ is unsubstituted oxadiazole.

Further to any embodiment above wherein the compound has the structure of Formula (I), in some embodiments, $R^3$ is halogen, and $L^3$ is a bond. In some embodiments, $L^3$ is a bond, and $R^3$ is substituted or unsubstituted alkyl, substituted or unsubstituted heteroalkyl, substituted or unsubstituted aryl, or substituted or unsubstituted heteroaryl. In some embodiments, $L^3$ and $R^3$ are attached to the pyridone nucleus such that there may be single or multiple instances of $L^3$ and $R^3$, wherein the multiple instances of $L^3$ and $R^3$ can be independent of each other, and they can be independently attached at one or more of the three open sites of the pyridone moiety. In some embodiments, there is one instance of $L^3$ and $R^3$. In some embodiments, there are two instances of $L^3$ and $R^3$. In some embodiments, there are three instances of $L^3$ and $R^3$.

Further to any embodiment above wherein the compound has the structure of Formula (I), in some embodiments, $R^4$ is hydrogen and $L^4$ is a bond. In some embodiments, $L^4$ is a bond, or substituted or unsubstituted alkylene, and $R^4$ is substituted or unsubstituted aryl, substituted or unsubstituted fused ring aryl, substituted or unsubstituted heterocycloalkyl. In some embodiments, $R^4$ is substituted or unsubstituted phenyl, or substituted or unsubstituted thienyl. In some embodiments, $R^4$ is unsubstituted phenyl. In some embodiments, $R^4$ is unsubstituted thienyl. In some embodiments, $R^4$ is a chloro-substituted thienyl. In some embodiments, $R^4$ is substituted or unsubstituted pyridyl, or substituted or unsubstituted pyridazinyl. In some embodiments, $R^4$ is unsubstituted pyridyl. In some embodiments, $R^4$ is unsubstituted pyridazinyl. In some embodiments, $R^4$ is substituted or unsubstituted pyrimidinyl, or substituted or unsubstituted furyl. In some embodiments, $R^4$ is unsubstituted pyrimidinyl. In some embodiments, $R^4$ is unsubstituted furyl. In some embodiments, $R^4$ is substituted or unsubstituted morpholinyl, or substituted or unsubstituted oxanyl, or substituted or unsubstituted oxetanyl. In some embodiments, $R^4$ is unsubstituted morpholinyl. In some embodiments, $R^4$ is unsubstituted oxanyl. In some embodiments, $R^4$ is unsubstituted oxetanyl. In some embodiments, $R^4$ is substituted or unsubstituted benzodioxinyl, or substituted or unsubstituted naphthyl. In some embodiments, $R^4$ is unsubstituted benzodioxinyl. In some embodiments, $R^4$ is unsubstituted naphthyl.

Further to any embodiment above wherein the compound has the structure of Formula (I), in some embodiments, $L^5$ is a bond, and $R^5$ is hydrogen or halogen.

The pyridone can be substituted with the pyrazolyl group at any available position, thus leading to the various possible pyridone-pyrazole isomers. Accordingly, in some embodiments, there is provided a compound according to Formula (I), with structures of any of Formulae (IIa), (IIIa), (IVa), or (Va), according to the following:

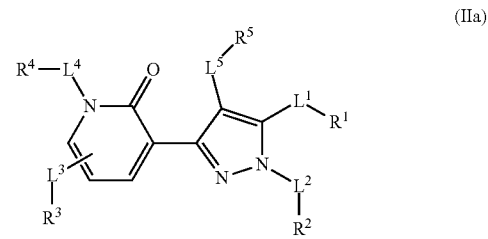

(IIa)

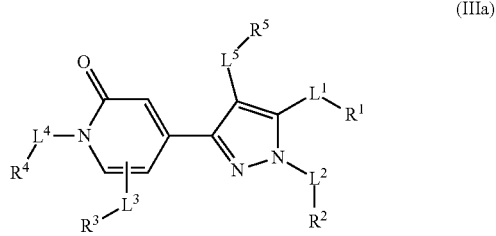

(IIIa)

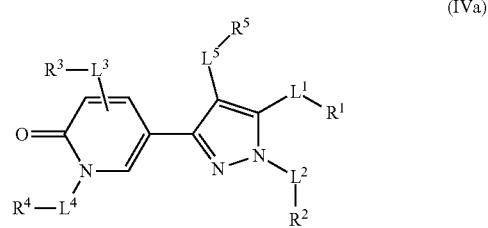

(IVa)

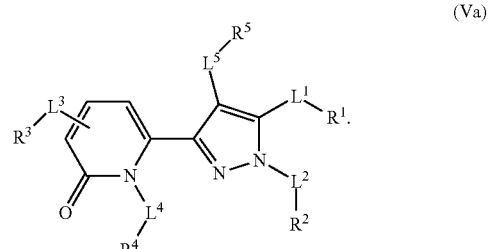

(Va)

In some embodiments, there is provided a compound according to any of Formulae (IIa), (IIIa), (IVa), or (Va) and their embodiments, wherein $L^2$ is a bond and $R^2$ is hydrogen, providing a respective compound with structure of Formulae (IIb), (IIIb), (IVb), or (Vb), according to the following:

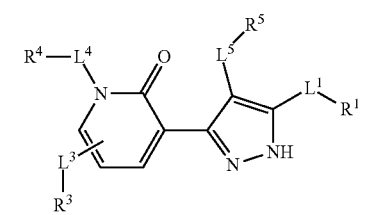 (IIb)

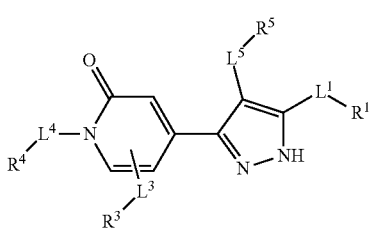 (IIIb)

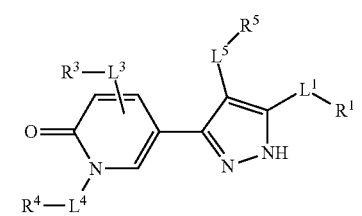 (IVb)

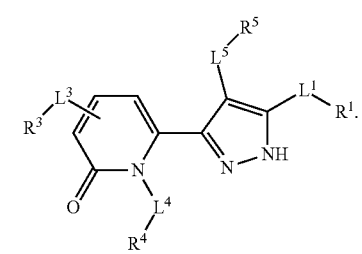 (Vb)

In some embodiments, there is provided a compound according to any of Formulae (IIa), (IIIa), (IVa), or (Va) and their embodiments, wherein $L^2$ is a bond, $R^2$ is hydrogen, $L^4$ is a bond, and $R^4$ is a hydrogen, providing a respective compound with structure of Formulae (IIc), (IIIc), (IVc), or (Vc), according to the following:

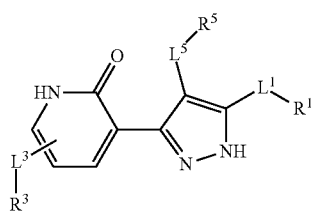 (IIc)

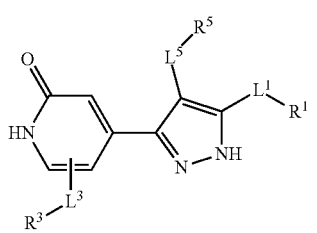 (IIIc)

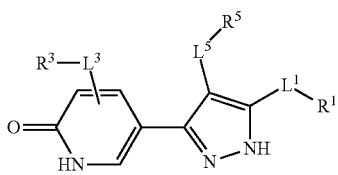 (IVc)

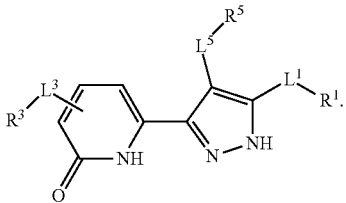 (Vc)

In some embodiments, the pyridone moiety of any of Formulae (IIa), (IIIa), (IVa), or (Va) can be substituted with the $L^3$-$R^3$ groups at any available position, thus leading to the various possible substituted pyridone-pyrazole isomers. Accordingly, in some embodiments, there is provided a compound according to Formula (I), with structures of any of Formulae (VIa), (VIb), (VIc), or (VId), according to the following:

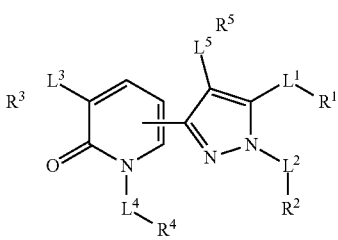 (VIa)

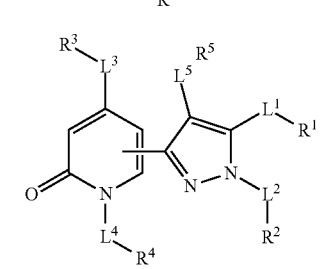 (VIb)

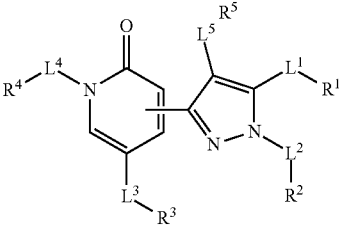 (VIc)

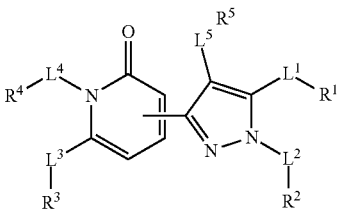 (VId)

Exemplary compounds, e.g., multisubstituted aromatic compounds, in accordance with the present disclosure are provided herein. In Tables A and B following, compound (Cmpd) number, chemical name (i.e., International Union of Pure and Applied Chemistry [IUPAC] name), calculated molecular weight (MW) and biological activity (i.e., inhibition activity in thrombin and KLKB1 assays) are disclosed.

For Table A following, the disclosed compounds were assayed for inhibition of the protease activity of thrombin and KLKB1 as described herein. In Table A, the level of inhibition in the thrombin and KLKB1 assays are indicated as follows: a IC$_{50}$<0.1 µM; b: 0.1 µM<IC$_{50}$<1 µM; c: 1 µM<IC$_{50}$<10 µM; d: 10 µM<IC$_{50}$<100 µM; e: IC$_{50}$ 100 µM. Accordingly, in some embodiments, there is provided a compound as expressly set forth in Table A as follows:

TABLE A

| Entry No. | IUPAC name | MW | Thrombin Activity | KLKB1 Activity |
|---|---|---|---|---|
| 1 | 3-(5-[(5-chlorothiophen-2-yl)methyl]amino-1-(2,2-dimethylpropanoyl)-1H-pyrazol-3-yl)-5-(morpholin-4-yl)-1,2-dihydropyridin-2-one | 476 | a | c |
| 2 | 3-(5-[(5-chlorothiophen-2-yl)methyl]amino-1-(2,2-dimethylpropanoyl)-1H-pyrazol-3-yl)-5-phenyl-1,2-dihydropyridin-2-one | 467 | a | d |
| 3 | 3-(5-[(5-chlorothiophen-2-yl)methyl]amino-1-(2-methoxybenzoyl)-1H-pyrazol-3-yl)-5-(pyridin-3-yl)-1,2-dihydropyridin-2-one | 518 | b | b |
| 4 | 3-(5-[(5-chlorothiophen-2-yl)methyl]amino-1-(furan-3-carbonyl)-1H-pyrazol-3-yl)-5-methyl-1,2-dihydropyridin-2-one | 415 | a | b |
| 5 | 3-bromo-5-(5-[(5-chlorothiophen-2-yl)methyl]amino-1-(2-methoxybenzoyl)-1H-pyrazol-3-yl)-1,2-dihydropyridin-2-one | 520 | b | c |
| 6 | 3-bromo-5-(5-[(5-chlorothiophen-2-yl)methyl]amino-1H-pyrazol-3-yl)-1,2-dihydropyridin-2-one | 386 | e | e |
| 7 | 3-bromo-6-(5-[(5-chlorothiophen-2-yl)methyl]amino-1-(furan-3-carbonyl)-1H-pyrazol-3-yl)-1,2-dihydropyridin-2-one | 480 | b | d |
| 8 | 4-(5-[(5-chlorothiophen-2-yl)methyl]amino-1-(2,2-dimethylpropanoyl)-1H-pyrazol-3-yl)-1,2-dihydropyridin-2-one | 391 | a | c |
| 9 | 4-(5-[(5-chlorothiophen-2-yl)methyl]amino-1-(2,2-dimethylpropanoyl)-1H-pyrazol-3-yl)-1-(2-methoxyethyl)-1,2-dihydropyridin-2-one | 449 | a | c |
| 10 | 4-(5-[(5-chlorothiophen-2-yl)methyl]amino-1-(2,2-dimethylpropanoyl)-1H-pyrazol-3-yl)-1-(pyridin-2-ylmethyl)-1,2-dihydropyridin-2-one | 482 | a | c |
| 11 | 4-(5-[(5-chlorothiophen-2-yl)methyl]amino-1-(2,2-dimethylpropanoyl)-1H-pyrazol-3-yl)-1-(pyridin-3-ylmethyl)-1,2-dihydropyridin-2-one | 482 | a | b |
| 12 | 4-(5-[(5-chlorothiophen-2-yl)methyl]amino-1-(2,2-dimethylpropanoyl)-1H-pyrazol-3-yl)-1-[2-(morpholin-4-yl)-2-oxoethyl]-1,2-dihydropyridin-2-one | 518 | a | d |
| 13 | 4-(5-[(5-chlorothiophen-2-yl)methyl]amino-1-(2,2-dimethylpropanoyl)-1H-pyrazol-3-yl)-6-(morpholin-4-yl)-1,2-dihydropyridin-2-one | 476 | c | e |
| 14 | 4-(5-[(5-chlorothiophen-2-yl)methyl]amino-1-(2-methoxybenzoyl)-1H-pyrazol-3-yl)-6-ethenyl-1,2-dihydropyridin-2-one | 467 | b | d |
| 15 | 4-(5-[(5-chlorothiophen-2-yl)methyl]amino-1-(furan-2-carbonyl)-1H-pyrazol-3-yl)-6-(pyridin-3-yl)-1,2-dihydropyridin-2-one | 478 | c | e |
| 16 | 4-(5-[(5-chlorothiophen-2-yl)methyl]amino-1-(furan-3-carbonyl)-1H-pyrazol-3-yl)-1,2-dihydropyridin-2-one | 401 | a | c |
| 17 | 4-(5-[(5-chlorothiophen-2-yl)methyl]amino-1-(furan-3-carbonyl)-1H-pyrazol-3-yl)-1-(2-methoxy ethyl)-1,2-dihydropyridin-2-one | 459 | a | c |
| 18 | 4-(5-[(5-chlorothiophen-2-yl)methyl]amino-1-(furan-3-carbonyl)-1H-pyrazol-3-yl)-1-(pyridin-2-ylmethyl)-1,2-dihydropyridin-2-one | 492 | a | b |
| 19 | 4-(5-[(5-chlorothiophen-2-yl)methyl]amino-1-(furan-3-carbonyl)-1H-pyrazol-3-yl)-1-(pyridin-3-ylmethyl)-1,2-dihydropyridin-2-one | 492 | a | a |
| 20 | 4-(5-[(5-chlorothiophen-2-yl)methyl]amino-1-(furan-3-carbonyl)-1H-pyrazol-3-yl)-1-[2-(morpholin-4-yl)-2-oxoethyl]-1,2-dihydropyridin-2-one | 528 | b | c |
| 21 | 4-(5-[(5-chlorothiophen-2-yl)methyl]amino-1-(furan-3-carbonyl)-1H-pyrazol-3-yl)-1-[2-(morpholin-4-yl)ethyl]-1,2-dihydropyridin-2-one | 514 | a | b |
| 22 | 4-(5-[(5-chlorothiophen-2-yl)methyl]amino-1-(thiophene-3-carbonyl)-1H-pyrazol-3-yl)-1,2-dihydropyridin-2-one | 417 | a | b |
| 23 | 4-(5-[(5-chlorothiophen-2-yl)methyl]amino-1-(thiophene-3-carbonyl)-1H-pyrazol-3-yl)-1-(2-methoxyethyl)-1,2-dihydropyridin-2-one | 475 | a | b |

TABLE A-continued

| Entry No. | IUPAC name | MW | Thrombin Activity | KLKB1 Activity |
|---|---|---|---|---|
| 24 | 4-(5-[(5-chlorothiophen-2-yl)methyl]amino-1-(thiophene-3-carbonyl)-1H-pyrazol-3-yl)-1-(pyridin-2-ylmethyl)-1,2-dihydropyridin-2-one | 508 | a | a |
| 25 | 4-(5-[(5-chlorothiophen-2-yl)methyl]amino-1-(thiophene-3-carbonyl)-1H-pyrazol-3-yl)-1-(pyridin-3-ylmethyl)-1,2-dihydropyridin-2-one | 508 | a | a |
| 26 | 4-(5-[(5-chlorothiophen-2-yl)methyl]amino-1-(thiophene-3-carbonyl)-1H-pyrazol-3-yl)-1-[2-(morpholin-4-yl)-2-oxoethyl]-1,2-dihydropyridin-2-one | 544 | b | c |
| 27 | 4-(5-[(5-chlorothiophen-2-yl)methyl]amino-1-(thiophene-3-carbonyl)-1H-pyrazol-3-yl)-1-[2-(morpholin-4-yl)ethyl]-1,2-dihydropyridin-2-one | 530 | a | b |
| 28 | 4-(5-[(5-chlorothiophen-2-yl)methyl]amino-1-(thiophene-3-carbonyl)-1H-pyrazol-3-yl)-6-phenyl-1,2-dihydropyridin-2-one | 493 | e | e |
| 29 | 4-(5-[(5-chlorothiophen-2-yl)methyl]amino-1H-pyrazol-3-yl)-1,2-dihydropyridin-2-one | 307 | e | e |
| 30 | 4-(5-[(5-chlorothiophen-2-yl)methyl]amino-1H-pyrazol-3-yl)-1-(pyridin-3-ylmethyl)-1,2-dihydropyridin-2-one | 398 | e | e |
| 31 | 5-(5-[(5-chlorothiophen-2-yl)methyl]amino-1-(2,2-dimethylpropanoyl)-1H-pyrazol-3-yl)-1,2-dihydropyridin-2-one | 391 | b | d |
| 32 | 5-(5-[(5-chlorothiophen-2-yl)methyl]amino-1-(2,2-dimethylpropanoyl)-1H-pyrazol-3-yl)-1-[2-(morpholin-4-yl)-2-oxoethyl]-1,2-dihydropyridin-2-one | 518 | a | e |
| 33 | 5-(5-[(5-chlorothiophen-2-yl)methyl]amino-1-(2,2-dimethylpropanoyl)-1H-pyrazol-3-yl)-3-(pyridin-3-yl)-1,2-dihydropyridin-2-one | 468 | b | d |
| 34 | 5-(5-[(5-chlorothiophen-2-yl)methyl]amino-1-(2,2-dimethylpropanoyl)-1H-pyrazol-3-yl)-3-methyl-1,2-dihydropyridin-2-one | 405 | b | d |
| 35 | 5-(5-[(5-chlorothiophen-2-yl)methyl]amino-1-(2,2-dimethylpropanoyl)-1H-pyrazol-3-yl)-3-phenyl-1,2-dihydropyridin-2-one | 467 | c | d |
| 36 | 5-(5-[(5-chlorothiophen-2-yl)methyl]amino-1-(2-methoxybenzoyl)-1H-pyrazol-3-yl)-6-oxo-1,6-dihydropyridine-3-carbonitrile | 466 | b | b |
| 37 | 5-(5-[(5-chlorothiophen-2-yl)methyl]amino-1-(thiophene-3-carbonyl)-1H-pyrazol-3-yl)-1,2-dihydropyridin-2-one | 417 | b | c |
| 38 | 5-(5-[(5-chlorothiophen-2-yl)methyl]amino-1H-pyrazol-3-yl)-1,2-dihydropyridin-2-one | 307 | e | e |
| 39 | 5-bromo-3-(5-[(5-chlorothiophen-2-yl)methyl]amino-1-(2,2-dimethylpropanoyl)-1H-pyrazol-3-yl)-1,2-dihydropyridin-2-one | 470 | a | d |
| 40 | 5-bromo-3-(5-[(5-chlorothiophen-2-yl)methyl]amino-1-(2,2-dimethylpropanoyl)-1H-pyrazol-3-yl)-1-[2-(morpholin-4-yl)-2-oxoethyl]-1,2-dihydropyridin-2-one | 597 | a | c |
| 41 | 5-bromo-3-(5-[(5-chlorothiophen-2-yl)methyl]amino-1-(thiophene-3-carbonyl)-1H-pyrazol-3-yl)-1,2-dihydropyridin-2-one | 496 | a | b |
| 42 | 5-bromo-3-(5-[(5-chlorothiophen-2-yl)methyl]amino-1H-pyrazol-3-yl)-1,2-dihydropyridin-2-one | 386 | e | d |
| 43 | 6-(5-[(5-chlorothiophen-2-yl)methyl]amino-1-(2,2-dimethylpropanoyl)-1H-pyrazol-3-yl)-1,2-dihydropyridin-2-one | 391 | a | c |
| 44 | 6-(5-[(5-chlorothiophen-2-yl)methyl]amino-1-(2,2-dimethylpropanoyl)-1H-pyrazol-3-yl)-1-(pyridin-2-ylmethyl)-1,2-dihydropyridin-2-one | 482 | a | e |
| 45 | 6-(5-[(5-chlorothiophen-2-yl)methyl]amino-1-(2,2-dimethylpropanoyl)-1H-pyrazol-3-yl)-1-[2-(morpholin-4-yl)-2-oxoethyl]-1,2-dihydropyridin-2-one | 518 | a | e |
| 46 | 6-(5-[(5-chlorothiophen-2-yl)methyl]amino-1-(2,2-dimethylpropanoyl)-1H-pyrazol-3-yl)-3-ethenyl-1,2-dihydropyridin-2-one | 417 | a | d |
| 47 | 6-(5-[(5-chlorothiophen-2-yl)methyl]amino-1H-pyrazol-3-yl)-1,2-dihydropyridin-2-one | 307 | e | e |
| 48 | 6-bromo-4-(5-[(5-chlorothiophen-2-yl)methyl]amino-1-(2,2-dimethylpropanoyl)-1H-pyrazol-3-yl)-1,2-dihydropyridin-2-one | 470 | a | d |

Compounds disclosed herein also include racemic mixtures, stereoisomers and mixtures of the compounds, including isotopically-labeled and radio-labeled compounds. See e.g., Goding, 1986, MONOCLONAL ANTIBODIES PRINCIPLES AND PRACTICE; Academic Press, p. 104. Such isomers can be isolated by standard resolution techniques, including e.g., fractional crystallization, chiral chromatography, and the like. See e.g., Eliel, E. L. & Wilen S. H., 1993, STEREOCHEMISTRY IN ORGANIC COMPOUNDS; John Wiley & Sons, New York.

In some embodiments, compounds disclosed herein have asymmetric centers and can occur as racemates, racemic mixtures, and as individual enantiomers or diastereoisomers, with all isomeric forms as well as mixtures thereof being contemplated for use in the compounds and methods described herein. The compounds contemplated for use in the compounds and methods described herein do not include those that are known in the art to be too unstable to synthesize and/or isolate.

The compounds disclosed herein can also contain unnatural proportions of atomic isotopes at one or more of the atoms that constitute such compounds. For example, the compounds can be radiolabeled with radioactive isotopes, such as for example tritium ($^3$H), iodine-125 ($^{125}$I), or carbon-14 ($^{14}$C). All isotopic variations of the compounds disclosed herein, whether radioactive or not, are encompassed within the contemplated scope.

In some embodiments, metabolites of the compounds disclosed herein are useful for the methods disclosed herein.

In some embodiments, compounds contemplated herein are provided in the form of a prodrug. The term "prodrug" refers to a compound that can be converted into a compound (e.g., a biologically active compound) described herein in vivo. Prodrugs can be useful for a variety of reason known in the art, including e.g., ease of administration due e.g., to enhance bioavailability in oral administration, and the like. The prodrug can also have improved solubility in pharmaceutical compositions over the biologically active compounds. An example, without limitation, of a prodrug is a compound which is administered as an ester (i.e., the "prodrug") to facilitate transmittal across a cell membrane where water solubility is detrimental to mobility but which then is metabolically hydrolyzed to the carboxylic acid, the active entity, once inside the cell where water solubility is beneficial. Conventional procedures for the selection and preparation of suitable prodrug derivatives are described, for example, in DESIGN OF PRODRUGS (ed. H. Bundgaard, Elsevier, 1985), which is hereby incorporated herein by reference for the limited purpose describing procedures and preparation of suitable prodrug derivatives.

Accordingly, in some embodiments, compounds contemplated herein are provided in the form of a prodrug ester. The term "prodrug ester" refers to derivatives of the compounds disclosed herein formed by the addition of any of a variety of ester-forming groups, e.g., groups known in the art, that are hydrolyzed under physiological conditions. Examples of prodrug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in, for example, T. Higuchi and V. Stella, in "Pro-drugs as Novel Delivery Systems", Vol. 14, A.C.S. Symposium Series, American Chemical Society (1975); and BIOREVERSIBLE CARRIERS IN DRUG DESIGN: THEORY AND APPLICATION, edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

In some embodiments, prodrugs can be slowly converted to the compounds described herein useful for the methods described herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope of contemplated compounds. Certain compounds of the present invention can exist in multiple crystalline or amorphous forms. In general, all physical forms are equivalent for the compounds and methods contemplated herein and are intended to be within the scope disclosed herein.

III. Biological Activities

In some embodiments, compounds described herein exhibit inhibitory activity against thrombin with activities ≥1 µM, e.g., about 1, 2, 3, 4, 5, 6, 7, 8, 9, 10, 11, 12, 13, 14, 16, 18, 20, 22, 24, 26, 28, 30, 32, 34, 36, 38, 40, 45, 50, 55, 60, 65, 70, 75, 80, 85, 90, 95, 100 µM, or even greater. In some embodiments, the compounds exhibit inhibitory activity against thrombin with activities between 0.1 µM and 1 µM, e.g., about 0.1, 0.2, 0.3, 0.4, 0.5, 0.6, 0.7, 0.8, 0.9 or 1.0 µM. In some embodiments, compounds described herein exhibit inhibitory activity against thrombin with activities ≤0.1 µM, e.g., about 1, 2, 5, 10, 15, 20, 30, 40, 50, 60, 70, 80, 90, or 100 nM. Ranges of values using a combination of any of the values recited herein as upper and/or lower limits are also contemplated, for example, but not limited to, 1-10 nM, 10-100 nM, 0.1-1 µM, 1-10 µM, 10-100 µM, 100-200 µM, 200-500 µM, or even 500-1000 µM. In some embodiments, the inhibitory activity is in the range of about 1-10 nM, 10-100 nM, 0.1-1 µM, 1-10 µM, 10-100 µM, 100-200 µM, 200-500 µM, or even 500-1000 µM. It is understood that for purposes of quantification, the terms "activity," "inhibitory activity," "biological activity," "thrombin activity" and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

Inhibitory activity against thrombin in turn inhibits the blood coagulation process. Accordingly, compounds disclosed herein are indicated in the treatment or management of thrombotic disorders. In some embodiments, a dose or a therapeutically effective dose of a compound disclosed herein will be that which is sufficient to achieve a plasma concentration of the compound or its active metabolite(s) within a range set forth herein, e.g., about 1-10 nM, 10-100 nM, 0.1-1 µM, 1-10 µM, 10-100 µM, 100-200 µM, 200-500 µM, or even 500-1000 µM, preferably about 1-10 nM, 10-100 nM, or 0.1-1 µM. Without wishing to be bound by any theory, it is believe that such compounds are indicated in the treatment or management of thrombotic disorders.

In some embodiments, compounds described herein exhibit inhibitory activity against KLK1 and/or KLKB1 with activities between 1 µM and 10 µM, e.g., about 1, 2, 3, 4, 5, 6, 7, 8, 9 or 10 µM. In some embodiments, compounds described herein exhibit inhibitory activity against KLK1 and/or KLKB1 with activities 10 µM, e.g., about 10, 20, 50, 100, 150, 200, 300, 400, 500, 600, 700, 800, 900, 1000 µM or even greater. In some embodiments, compounds described herein exhibit inhibitory activity against KLK1 and/or KLKB1 with activities 1 µM, e.g., about 900, 800, 700, 600, 500, 400, 300, 200, 100, 50 nM or even lower. Ranges of values using a combination of any of the values recited herein as upper and/or lower limits are also contemplated, for example, but not limited to, 1-10 nM, 10-100 nM, 0.1-1 µM, 1-10 µM, 10-100 µM, 100-200 µM, 200-500 µM, or even 500-1000 µM. In some embodiments, the inhibitory activity is in the range of about 1-10 nM, 10-100 nM, 0.1-1 µM, 1-10 µM, 10-100 µM, 100-200 µM, 200-500 µM, or even 500-1000 µM. It is understood that for purposes of quantification, the terms "activity," "inhibitory activity," "biological activity," "KLK1 activity", "KLKB1 activity" and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

Inhibitory activity against KLKB1 has an effect on the coagulation cascade and the inflammatory response. Thus, it has been proposed that KLKB1 inhibitors can be useful in the treatment of thrombotic and fibrinolytic diseases and disease conditions.

Accordingly, compounds disclosed herein are indicated in the treatment or management of a variety of diseases or disorders. In some embodiments, a dose or a therapeutically effective dose of a compound disclosed herein will be that which is sufficient to achieve a plasma concentration of the compound or its active metabolite(s) within a range set forth herein, e.g., about 1-10 nM, 10-100 nM, 0.1-1 µM, 1-10 µM, 10-100 µM, 100-200 µM, 200-500 µM, or even 500-1000 µM, preferably about 1-10 nM, 10-100 nM, or 0.1-1 µM. Without wishing to be bound by any theory, it is believe that such compounds are indicated in the treatment or management of diseases associated with thrombin or kallikrein.

IV. Methods of Treating and Preventing Disease

Serine proteases are a large family of enzymes with diverse biological functions, their commonality being the presence and critical function of the active-site serine residue. Their central function is the catalytic scission of peptide bond substrates via a Ser, His, Asp triad within the active site (Kraut, *J. Annual Review of Biochemistry* 1977, 46, 331-358).

The present disclosure relates to compounds, e.g., 3-pyrazolyl-substituted pyridone compounds, which exhibit biological activity, e.g., inhibitory action, against serine proteases, including thrombin and various kallikreins.

Kallikrein-related diseases or disorders are biological conditions associated with or moderated by kallikrein. They include, but are not limited by, those conditions associated with biological pathways that are moderated by tissue and plasma kallikrein. An example of such a pathway is the kallikrein-kinin system (Moreau, M. E. 2005, *Journal of Pharmacological Sciences*, 99, 6). Kallikrein-related diseases or disorders include, but are not limited to, fibrosis, inflammation, thrombosis, hereditary angioedema, skin disorders, cancer, and ophthalmic diseases. Ophthalmic diseases include, but are not limited to, diabetic macular edema, diabetic retinopathy, and age-related macular degeneration.

Diabetic Macular Edema.

In rodent models, it has been shown that activation of KLKB1 in the eye increases retinal vascular permeability; whereas inhibition of the kallikrein-kinin system reduces retinal leakage induced by diabetes and hypertension. These findings suggest that intraocular activation of the KLKB1 pathway can contribute to excessive retinal vascular permeability that can lead to diabetic macular edema. Thus, evidence suggests that KLKB1 inhibitors can provide a new therapeutic opportunity to reduce retinal vascular permeability (Feener, E. P. 2010, *Curr Diab Rep* 10, 270).

Hereditary Angioedema.

Ecallantide (Kalbitor) is a 60-amino acid recombinant protein that acts as a potent reversible inhibitor of KLKB1 (Schneider L, et al. 2007, *J Allergy Clin Immunol*, 120, 416) and has been approved by the FDA for the treatment of acute attacks of hereditary angioedema (HAE). Thus plasma kallikrein inhibition can be a useful treatment for HAE, and there is strong interest in the development of plasma kallikrein inhibitors as a therapy for HAE.

Cerebral Hemorrhage.

Hyperglycemic and diabetic individuals have an elevated risk of hemorrhage during thrombolytic therapy. In rodent models of intracerebral hemorrhage (ICH), it has been shown that KLKB1 inhibition or knockout reduces this effect. While the mechanism is not fully understood, this evidence suggests that plasma kallikrein inhibitors can be useful in the treatment of cerebral hemorrhage (Feener, E. P. *Curr Diab Rep* 2010, 10, 270).

Ischemic Stroke and Traumatic Brain Injury.

Plasma kallikrein and Factor XIIa inhibitors have been shown to be neuroprotective in animal models of acute ischemic stroke and traumatic brain injury, reducing edema formation, inflammation, and thrombosis (Albert-Weiβenberger C, Sirén A L, Kleinschnitz C. *Prog Neurobiol.* 2013, 101-102, 65-82.). Thus, evidence suggests that plasma kallikrein inhibitors can be useful in the treatment of acute ischemic stroke and traumatic brain injury.

Diabetes.

Plasma kallikrein can also cleave glucagon-like peptide 1 (GLP-1) and neuropeptide Y (NPY), both substrates for dipeptidyl peptidase-4 (DPP-4), a validated diabetes drug target. In the case of GLP-1, cleavage by KLKB1 reduces both its potency as well as plasma stability. In the case of NPY, cleavage by KLKB1 reduces its affinity to the Y2 and Y5 receptors. Thus, evidence suggests that plasma kallikrein inhibitors can be useful in the modulation of energy homeostasis and in the treatment of diabetes. (Feener, E. P. *Curr Diab Rep* 2010, 10, Feener, E. P. et al., *Biol. Chem.* 2013, 394, 319).

Gastritis and Peptic Ulcers.

Daiichi Seiyaku Co Ltd received approval in Japan to market cetraxate for gastritis and peptic ulcers. Cetraxate is reported as a plasma kallikrein inhibitor (WIPO Patent Application WO/2006/108643). Without further wishing to be bound by any theory, it is reasonable to believe that plasma kallikrein inhibition in general can be useful in the treatment of gastritis and peptic ulcers.

Skin.

Overexpression of various KLKs in the skin has led to the recognition that certain kallikrein inhibitors can be useful for certain dermatological conditions, including atopic dermatitis, psoriasis and rare skin diseases such as Netherton Syndrome (Freitas et al. *Bioorganic & Medicinal Chemistry Letters* 2012, 22, 6072-6075).

Thrombosis.

Thrombotic diseases are the primary indications for thrombin inhibition, because of thrombin's location in the coagulation cascade and, in turn, the importance of the coagulation cascade in the progression of blood clotting processes. However, without wishing to be bound by any theory, it is believed the coagulation cascade in general, and thrombin in particular, is important in a variety other disease states.

It has been discovered that compounds described herein, e.g., multisubstituted aromatic compounds, exhibit inhibitory action against thrombin (activated blood-coagulation factor II; EC 3.4.21.5). This, in turn inhibits the blood coagulation process.

This inhibitory action is useful in the treatment of a variety of thrombotic disorders, such as, but not limited to, acute vascular diseases such as acute coronary syndromes; venous-, arterial- and cardiogenic thromboembolisms; the prevention of other states such as disseminated intravascular coagulation, or other conditions that involve the presence or the potential formation of a blood clot thrombus. Other indications for methods described herein include the following.

Cancer.

Tissue kallikreins (KLKs) are subdivided into various types, and have been extensively investigated in cancer and inflammation biology. Various kallikrein KLKs have been found to be up- or down-regulated in various cancer types, such as cervical-, testicular-, and non-small-cell lung adenocarcinoma (Caliendo et al. *J. Med. Chem.*, 2012, 55, 6669). It has been proposed that kallikrein inhibitors, including KLK1 inhibitors, can be useful in certain cancers.

It has long been recognized that cancer progression is accompanied by venous thrombosis, but it has not been understood how each disease is related. From several clinical trials studying the treatment of VTE, meta-analyses have shown that low molecular weight heparins (LMWHs) improve overall survival in subgroups of cancer patients. See e.g., Zacharski, L. R. & Lee, A. Y., 2008, *Expert Opin Investig Drugs*, 17:1029-1037; Falanga, A. & Piccioli, A., 2005, *Current Opinion in Pulmonary Medicine*, 11:403-407; Smorenburg, S. M., et al., 1999, *Thromb Haemost*, 82:1600-1604; Hettiarachchi, R. J., et al., 1999, *Thromb Haemost*, 82:947-952. This finding was substantiated in later clinical trials that measured specifically the survival of cancer patients. See e.g., Lee, A. Y. et al., 2005, *J Clin Oncol*, 23:2123-2129; Klerk, C. P. et al., *J Clin Oncol* 2005, 23:2130-2135; Kakkar, A. K., et al., 2004, *J Clin Oncol*, 22:1944-1948; Altinbas, M., et al., 2004, *J Thromb Haemost*, 2:1266-1271.

More recently, researchers have focused on the specific anticancer effect of DTIs. For example, it was shown that heparin significantly prolonged the survival of patients with limited small cell lung cancer. See e.g., Akl, E. A., et al., 2008, *J Exp Clin Cancer Res*, 27:4. Other investigators found that systemic use of argatroban reduced tumor mass and prolonged survival time in rat glioma models leading to the conclusion that argatroban should be considered as a novel therapeutic for glioma, a notoriously difficult to treat cancer type. See e.g., Hua, Y., et al., 2005, *Acta Neurochir*, Suppl 2005, 95:403-406; Hua, Y., et al., 2005, *J Thromb Haemost*, 3:1917-1923. Very recently, it was demonstrated that dabigatran etexilate, a DTI recently FDA-approved (see e.g., Hughes, B., 2010, *Nat Rev Drug Discov*, 9:903-906) for DVT indications, inhibited both the invasion and metastasis of malignant breast tumors. See e.g., DeFeo, K. et al., 2010, *Thrombosis Research*, 125 (Supplement 2): S188-S188; Defeo, K., et al., 2010, *Cancer Biol Ther*, 10:1001-1008. Thus, dabigatran etexilate treatment led to a 50% reduction in tumor volume at 4 weeks with no weight loss in treated mice. Dabigatran etexilate also reduced tumor cells in the blood and liver and liver micrometastases by 50-60%. These investigators concluded that dabigatran etexilate can be beneficial in not only preventing thrombotic events in cancer patients, but also as adjunct therapy to treat malignant tumors.

Further, hirudin and the LMWH nadroparin dramatically reduced the number of lung metastases when administered prior to cancer cell inoculation. See e.g., Hu, L., et al., 2004, *Blood*, 104:2746-51.

The de novo thrombin inhibitor d-Arg-Oic-Pro-d-Ala-Phe (p-Me) has been found to block thrombin-stimulated invasion of prostate cancer cell line PC-3 in a concentration dependent manner. See e.g., Nieman, M. T., et al., 2008, *J Thromb Haemost*, 6:837-845. A reduced rate of tumor growth was observed in mice dosed with the pentapeptide through their drinking water. The mice also showed reduced fold rate in tumor size and reduced overall tumor weight compared to untreated mice. Microscopic examination of treated tumors showed reduced number of large blood vessels thus concluding that the pentapeptide interfered with tumor angiogenesis. Nieman, M. T., et al., *Thromb Haemost*, 104:1044-8.

In view of these and related studies, it is suggested that anticoagulants affect tumor metastasis; that is, angiogenesis, cancer cell adhesion, migration and invasion processes. See e.g., Van Noorden, C. J., et al., 2010, *Thromb Res*, 125 Suppl 2:S77-79.

Fibrosis. Kallikreins are a subgroup of serine proteases, divided into plasma kallikrein (KLKB1) and tissue kallikreins. KLKB1 liberates kinins (bradykinin and kallidin) from the kininogens, peptides responsible for the regulation of blood pressure and activation of inflammation. In the Contact Activation Pathway of the coagulation cascade, KLKB1 assists in the conversion of factor XII to factor XIIa (Keel, M.; Trentz, O. *Injury* 2005, 36, 691-709). Factor XIIa converts FXI into FXIa, which in turn activates FIX, which with its co-factor FVIIIa forms the tenase complex, which finally activates FX to FXa. In the fibrinolysis part of the coagulation cascade, KLKB1 serves to convert plasminogen to plasmin. Thus, it has been proposed that KLKB1 inhibitors can be useful in the treatment of thrombotic and fibrinolytic diseases and disease conditions (U.S. Pat. No. 7,625,944; Bird et al. *Thrombosis and Hemostasis* 2012, 107, 1141).

Several studies have shown the utility of anticoagulant therapy in fibrotic disorders. For example, in a rat model of $CCl_4$-induced chronic liver injury, the DTI SSR182289 decreased liver fibrogenesis significantly after 7 weeks of administration. Similar observations were made in other studies using the LMWHs nadroparin, tinzaparin, enoxaparin, and dalteparin sodium. See e.g., Duplantier, J. G., et al., 2004, *Gut*, 53:1682-1687; Abdel-Salam, O. M., et al., 2005, *Pharmacol Res*, 51:59-67; Assy, N., et al., 2007, *Dig Dis Sci*, 52:1187-1193; Abe, W., et al., 2007, *J Hepatol*, 46:286-294. Thus a thrombin inhibitor as an anticoagulant can be useful in the treatment of fibrinolytic diseases.

In another example, the DTI melagatran greatly reduced ischemia reperfusion injury in a kidney transplant model in the large white pig. This led to a drastically improved kidney graft survival at 3 months. See e.g., Favreau, F., et al., 2010, *Am J Transplant*, 10:30-39.

Recent studies have shown that in a bleomycin-induced mouse model of pulmonary fibrosis, dabigatran etexilate treatment reduced important profibrotic events in lung fibroblasts, including the production of collagen and connective tissue growth factor. See e.g., Silver, R. M., et al., 2010, *Am. J. Respir. Crit. Care Med.*, 181:A6780; Bogatkevich, G. S., et al., 2009, *Arthritis Rheum*, 60:3455-3464.

The above experimental evidence points to a close relationship between thrombin and fibrosis and suggests novel therapeutic opportunities for fibrosis using thrombin inhibitors. See e.g., Calvaruso, V., et al., 2008, *Gut*, 57:1722-1727;

Chambers, R. C., 2008, *Br J Pharmacol*, 153 Suppl 1:S367-378; Chambers, R. C. & Laurent, G. J., 2002, *Biochem Soc Trans*, 30:194-200; Howell, D. C., et al., 2001, *Am J Pathol*, 159:1383-1395.

Kallikrein has long been implicated in inflammation (Clements, J. A. *The Molecular Biology of the Kallikreins and Their Roles in Inflammation*, Academic Press: San Diego, Calif., 1997; Vol. 5). There is experimental evidence that KLKB1 is associated with sepsis and inflammatory arthritis (Colman, R. W., 1998, *Clinical Reviews in Allergy and Immunology*, 16: 365). Thus a KLKB1 inhibitor can be useful in the treatment of inflammatory conditions associated with the kallikrein-kinin system, such as systemic inflammatory response syndrome, sepsis, rheumatoid arthritis, and inflammatory bowel disease.

Age-Related Macular Degeneration.

KLK1 has been linked to blood vessel growth moderated by the VEGF pathway (Miura S., 2003, *Hypertension*, 41, 1118). Age-related macular degeneration (AMD) is associated with the proliferation of abnormal blood vessels and VEGF expression (Lopez, P. F., 1996, *Investigative Ophthalmology & Visual Science*, 37, 855). Thus, kallikrein inhibitors, including KLK1 inhibitors, have been proposed for the treatment of AMD (US Patent #20120264798; Ferrara, N., 2000, *Current Opinion in Biotechnology*, 11, 617).

Alzheimer's Disease.

Very recent experiments confirm higher thrombin levels in brain endothelial cells of patients with Alzheimer's disease. While 'normal' thrombin levels are connected to regulatory CNS functions, thrombin accumulation in the brain is toxic. It has also been found that the neural thrombin inhibitor Protease Nexin 1 (PN-1) is significantly reduced in the Alzheimer's disease brain, despite the fact that PN-1 mRNA levels are unchanged. These observations have led some investigators to suggest that reduction of CNS-resident thrombin will prove useful in Alzheimer's Disease (AD) treatment. See e.g., Vaughan, P. J., et al., 1994, *Brain Res*, 668:160-170; Yin, X., et al., 2010, *Am J Pathol*, 176:1600-1606; Akiyama, H., et al., 1992, *Neurosci Lett*, 146:152-154.

Multiple Sclerosis. Investigators found that hirudin treatment in an animal model of Multiple Sclerosis (MS) showed a dramatic improvement in disease severity. See e.g., Han, M. H., et al., 2008, *Nature*, 451:1076-1081. Similar results were obtained following treatment with heparin (a DTI) and dermatan sulfate, another coagulation inhibitor. See e.g., Chelmicka-Szorc, E. & Arnason, B. G., 1972, *Arch Neurol*, 27:153-158; Inaba, Y., et al., 1999, *Cell Immunol*, 198:96-102. Other evidence shows that naturally occurring antithrombin III has anti-inflammatory effects in diseases such as endotoxemia and other sepsis-related conditions. See e.g., Wiedermann, C. J. & Romisch, J., 2002, *Acta Med Austriaca*, 29:89-92. Naturally occurring thrombin inhibitors are presumably synthesized in situ and have protective roles in CNS inflammation. Therefore, therapeutic thrombin inhibition has been proposed as a potential MS treatment. See e.g., Luo, W., et al., 2009, In: THROMBIN, Maragoudakis, M. E.; Tsopanoglou, N. E., Eds. Springer New York: 2009; pp 133-159.

Pain.

In a rat pain model with partial lesion of the sciatic nerve, intrathecal hirudin prevented the development of neuropathic pain and curbed pain responses for 7 days. The investigators found that following injury, neuropathic pain was mediated by thrombin generation, which in turn activated PAR-1 receptor in the spinal cord. Hirudin inhibited thrombin generation and ultimately led to pain relief. See e.g., Garcia, P. S., et al., 2010, *Thromb Haemost*, 103:1145-1151; Narita, M., et al., 2005, *J Neurosci*, 25:10000-10009. Researchers hypothesize that thrombin and the PARs are involved not just as part of the coagulation cascade, but in inflammation, nociception and neurodevelopment. Development of a DTI to intersect an unexploited pharmacology will lead to pain therapeutics distinct from opioids and NSAIDs, whose shortcomings are well documented. See e.g., Garcia 2010, Id.

Accordingly, in a further aspect, there is provided a method for treating a disease or disorder in a subject in need thereof. The method includes administering a compound of any of Formulae (I), (II) or (III) as disclosed herein, a compound as set forth in Table A, or in Table B (Appendix A) pharmaceutically acceptable salt, ester, solvate, or prodrug thereof, or pharmaceutical composition thereof, to a subject in need thereof in an amount effective to treat the disease or disorder. The terms "therapeutically effective amount," "amount effective to treat," "amount effective to prevent" and the like refer to that amount of drug or pharmaceutical agent (e.g., compound or pharmaceutical composition disclosed herein) that will elicit the biological or medical response of a tissue, system, animal, or human that is being sought by a researcher, veterinarian, medical doctor or other clinician.

Compounds useful for methods disclosed herein include the compounds set forth for Formulae (I), (II) or (III) and for the compounds set forth in Table A above or in Table B (Appendix A).

In some embodiments, the diseases or disorders are thrombotic disorders. In some embodiments, the thrombotic disorder is acute coronary syndrome, venous thromboembolism, arterial thromboembolism, cardiogenic thromboembolism, disseminated intravascular coagulation, or a blood clot thrombus.

In some embodiments, the diseases or disorders are fibrinolytic diseases. In some embodiments the disease is a fibrotic disorder. In some embodiments, the disease is cancer. In some embodiments, the diseases are inflammatory diseases. In some embodiments the disease is sepsis. In some embodiments the disease is inflammatory arthritis. In some embodiments, the disease is diabetic macular edema. In some embodiments, the disease is hereditary angioedema. In some embodiments, the disease is diabetic retinopathy. In some embodiments, the disease is age-related macular degeneration. In some embodiments, the diseases are various skin diseases which include but are not limited to atopic dermatitis, psoriasis and rare skin diseases such as Netherton Syndrome. In some embodiments, the diseases or disorder is Alzheimer's disease. In some embodiments, the disease is multiple sclerosis. In some embodiments, the disease is pain.

In some embodiments, the disease or disorder is cancer. In some embodiments, the cancer is limited small cell lung cancer. In some embodiments, the cancer is a glioma. In some embodiments, the cancer is malignant breast cancer. In some embodiments, the cancer is a micrometastasis. In some embodiments, the micrometastasis is of the blood or liver. In some embodiments, the cancer is a lung metastasis. In some embodiments, the cancer is prostatic cancer.

In another aspect, there is provided a method for preventing a disease or disorder in a subject. The method includes administering a compound of any of Formulae (I), (II) or (III) as disclosed herein, compound as set forth in Table A or in Table B (Appendix A), pharmaceutically acceptable salt, ester, solvate, or prodrug thereof, or pharmaceutical composition thereof, to a subject in need thereof in an amount effective to prevent the disease or disorder.

V. Assays

Compounds described herein can be assayed, by a variety of methods known in the art and described herein, for inhibition of biological activity, e.g., protease activity, of a variety of proteins, e.g., thrombin, KLKB1, and KLK1.

The KLKB1 kallikrein activity reported herein (e.g., Table A) was obtained as follows. Human KLKB1 protein was obtained from Enzyme Research Labs. The chromogenic substrate S-2302 was obtained from DiaPharma. KLKB1 was assayed in buffer containing 0.05 M Tris (pH 7.4), 0.01 M NaCl and 0.2% w/v PEG-8000. The final concentration of enzyme used was 3 nM KLKB1. The final concentration of substrate used was 250 µM S-2302 for KLKB1. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices) Inhibitor $IC_{50}$ values were determined by adding test compound as ten point, three-fold serial dilutions in buffer solution, as known in the art. The plate was read at 10 minutes after substrate addition. The $IC_{50}$ was calculated by plotting the percent (%) inhibition against compound concentration and fitting the data to a constrained four parameter sigmoidal curve, as known in the art.

KLK1 kallikrein activity is obtained as follows. Recombinant human tissue kallikrein (KLK1) is obtained from R&D Systems. Pro-Phe-Arg-AMC (1-1295) substrate is obtained from Bachem. KLK1 enzyme is activated by incubating 0.5 mg/ml KLK1 combined with 0.1 µg/ml thermolysin in a buffer of 0.05 M Tres (pH 7.5), 0.15 M NaCl, and 0.01 M $CaCl_2$ for one hour at 37° C. The thermolysin is then deactivated by the addition of equal parts 20 mM 1, 10 phenanthroline solution in water. The activated KLK1 solution is then added to CHES buffer (0.05 M CHES, 0.15 M NaCl, 0.01 M $CaCl_2$, pH 10) for a final concentration of 5 nM along with the test article and incubated for 10 minutes. Substrate is then added at a concentration of 2.75 µM. Substrate activation is read 10 minutes after substrate addition using a Synergy H1 multi-function plate reader (Biotek) programmed with a 360 nm excitation wavelength and a 480 nm emission wavelength. Inhibitor response is established by adding test compound as ten point, three-fold serial dilutions, as known in the art. The $IC_{50}$ is calculated by plotting the percent (%) inhibition against compound concentration and fitting the data to a constrained four parameter sigmoidal curve, as known in the art.

The thrombin activity reported herein (e.g., Table A) was obtained as follows. Human thrombin was obtained from Haematologic Technologies Inc. The chromogenic substrate S-2238 was obtained from DiaPharma. Thrombin was assayed in buffer containing 0.05 M Tris (pH 7.4), 0.015 M NaCl and 0.01% PEG-8000. The final concentration of enzyme used was 3 nM thrombin. The final concentration of substrate used was 125 µM S-2238 for thrombin. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor $IC_{50}$ values were determined by adding test compound as ten point, three-fold serial dilutions in buffer solution, as known in the art. The plate was read at 10 minutes after substrate addition. The $IC_{50}$ was calculated by plotting the percent (%) inhibition against compound concentration and fitting the data to a constrained four parameter sigmoidal curve, as known in the art.

VI. Pharmaceutical Compositions

In another aspect, there is provided a pharmaceutical composition comprising a compound disclosed herein and a pharmaceutically acceptable excipient. The compound is a compound of any of Formulae (I), (II) or (III) as disclosed herein, a compound as set forth in Table A or in Table B (Appendix A) herein, or pharmaceutically acceptable salt, ester, solvate, or prodrug thereof. In some embodiments, the compound is set forth in Table A or in Table B (Appendix A) herein.

The term "pharmaceutically acceptable salts" is meant to include salts of the active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galacturonic acids and the like (see, for example, Berge et al., "Pharmaceutical Salts", *Journal of Pharmaceutical Science,* 1977, 66, 1-19). Certain specific compounds disclosed herein contain both basic and acidic functionalities that allow the compounds to be converted into either base or acid addition salts.

Compounds disclosed herein can exist as salts, such as with pharmaceutically acceptable acids. Accordingly, the compounds contemplated herein include such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts can be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Pharmaceutically acceptable salts of the compounds above, where a basic or acidic group is present in the structure, are also included within the scope of compounds contemplated herein. When an acidic substituent is present, such as —NHSO$_3$H, —COOH and —P(O)(OH)$_2$, there can be formed the ammonium, sodium, potassium, calcium salt, and the like, for use as the dosage form. Basic groups, such as amino or basic heteroaryl radicals, or pyridyl and acidic salts, such as hydrochloride, hydrobromide, acetate, maleate, palmoate, methanesulfonate, p-toluenesulfonate, and the like, can be used as the dosage form.

Also, in the embodiments in which R—COOH is present, pharmaceutically acceptable esters can be employed, e. g., methyl, ethyl, tert-butyl, pivaloyloxymethyl, and the like, and those esters known in the art for modifying solubility or hydrolysis characteristics for use as sustained release or prodrug formulations.

A. Formulations

The compounds disclosed herein can be prepared and administered in a wide variety of ophthalmic, oral, parenteral, and topical dosage forms. The compounds described herein can be administered by eye drop. Also, compounds described herein can be administered by injection (e.g. intravenously, intramuscularly, intravitreally, intracutaneously, subcutaneously, intraduodenally, or intraperitoneally). As such, compounds described herein can also be administered by intravitreal injection. Also, the compounds described herein can be administered by inhalation, for example, intranasally. Additionally, the compounds disclosed herein can be administered transdermally. It is also envisioned that multiple routes of administration (e.g., intramuscular, oral, ocular) can be used to administer the compounds disclosed herein.

In some embodiments, the compounds disclosed herein can be prepared in liquid pharmaceutical compositions for ocular administration. The composition for ocular use can contain one or more agents selected from the group of buffering agents, solubilizing agents, coloring agents, viscosity enhancing agents, and preservation agents in order to produce pharmaceutically elegant and convenient preparations.

In some embodiments, the composition for ocular use can contain preservatives for protection against microbiological contamination, including but not limited to benzalkodium chloride and/or EDTA. Other possible preservatives include but are not limited to benzyl alcohol, methyl parabens, propyl parabens, and chlorobutanol. Preferably, a preservative, or combination of preservatives, will be employed to impart microbiological protection in addition to protection against oxidation of components.

In some embodiments, the compounds disclosed herein can be administered orally as tablets, aqueous or oily suspensions, lozenges, troches, powders, granules, emulsions, capsules, syrups or elixirs. The composition for oral use can contain one or more agents selected from the group of sweetening agents, flavoring agents, coloring agents and preserving agents in order to produce pharmaceutically elegant and palatable preparations. Accordingly, there are also provided pharmaceutical compositions comprising a pharmaceutically acceptable carrier or excipient and one or more compounds disclosed herein.

In some embodiments, tablets contain the acting ingredient in admixture with non-toxic pharmaceutically acceptable excipients that are suitable for the manufacture of tablets. These excipients can be, for example, (1) inert diluents, such as calcium carbonate, lactose, calcium phosphate, carboxymethylcellulose, or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets can be uncoated or coated by known techniques to delay disintegration and absorption in the gastrointestinal tract and thereby provide a sustained action over a longer period. For example, a time delay material such as glyceryl monostearate or glyceryl distearate can be employed.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substance that can also act as diluents, flavoring agents, binders, preservatives, tablet disintegrating agents, or an encapsulating material.

A compound disclosed herein, in the form of a free compound or a pharmaceutically-acceptable pro-drug, metabolite, analogue, derivative, solvate or salt, can be administered, for in vivo application, parenterally by injection or by gradual perfusion over time. Administration can be intravenously, intraperitoneally, intramuscularly, subcutaneously, intracavity, or transdermally. For in vitro studies the compounds can be added or dissolved in an appropriate biologically acceptable buffer and added to a cell or tissue.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds disclosed herein can also be incorporated into liposomes or administered via transdermal pumps or patches. Pharmaceutical admixtures suitable for use in the pharmaceuticals compositions and methods disclosed herein include those described, for example, in PHARMACEUTICAL SCI- ENCES (17th Ed., Mack Pub. Co., Easton, Pa.) and WO 96/05309, the teachings of both of which are hereby incorporated by reference.

In some embodiments, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, growth factors and inert gases and the like.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation can be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds can have limited solubility in water and therefore can require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions can be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions disclosed herein can additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

By the present, there are provided methods for ameliorating wound healing and for mediating tissue repair (including but not limited to treatment of peripheral and coronary vascular disease). According to these methods, a subject having a wound or in need of tissue repair, is treated at the site of the wound or damaged tissue or treated systemically, with a compound disclosed herein in the form of a free compound or a pharmaceutically-acceptable prodrug, metabolite, analogue, derivative, solvate or salt.

Generally, the terms "treating", "treatment" and the like are used herein to mean affecting a subject, tissue or cell to obtain a desired pharmacologic and/or physiologic effect. The effect can be prophylactic in terms of completely or partially preventing a disease or disorder or sign or symptom thereof, and/or can be therapeutic in terms of a partial or complete cure for a disorder and/or adverse effect attributable to it. "Treating" as used herein covers any treatment of, or prevention of a disease or disorder in a vertebrate, a mammal, particularly a human, and includes: (a) preventing the disease or disorder from occurring in a subject that can be predisposed to the disease or disorder, but has not yet been diagnosed as having it; (b) inhibiting the disease or disorder, i.e., arresting its development; or (c) relieving or ameliorating the disease or disorder, i.e., cause regression of the disease or disorder.

There are provided various pharmaceutical compositions useful for ameliorating certain diseases and disorders. The pharmaceutical compositions according to one embodiment are prepared by formulating a compound disclosed herein in the form of a free compound or a pharmaceutically-acceptable pro-drug, metabolite, analogue, derivative, solvate or salt, either alone or together with other pharmaceutical agents, suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See e.g., Goodman and Gilman (eds.), 1990, THE PHARMACOLOGICAL BASIS FOR THERAPEUTICS (7th ed.).

The pharmaceutical compositions are preferably prepared and administered in dose units. Solid dose units are tablets, capsules and suppositories. For treatment of a subject, depending on activity of the compound, manner of administration, nature and severity of the disease or disorder, age and body weight of the subject, different daily doses can be used.

Under certain circumstances, however, higher or lower daily doses can be appropriate. The administration of the daily dose can be carried out both by single administration in the form of an individual dose unit or else several smaller dose units and also by multiple administrations of subdivided doses at specific intervals.

The pharmaceutical compositions contemplated herein can be administered locally or systemically in a therapeutically effective dose. Amounts effective for this use will, of course, depend on the severity of the disease or disorder and the weight and general state of the subject. Typically, dosages used in vitro can provide useful guidance in the amounts useful for in situ administration of the pharmaceutical composition, and animal models can be used to determine effective dosages for treatment of particular disorders.

Various considerations are described, e. g., in Langer, 1990, *Science,* 249: 1527; Goodman and Gilman's (eds.), 1990, Id., each of which is herein incorporated by reference and for all purposes. Dosages for parenteral administration of active pharmaceutical agents can be converted into corresponding dosages for oral administration by multiplying parenteral dosages by appropriate conversion factors. As to general applications, the parenteral dosage in mg/mL times 1.8=the corresponding oral dosage in milligrams ("mg"). As to oncology applications, the parenteral dosage in mg/mL times 1.6=the corresponding oral dosage in mg. An average adult weighs about 70 kg. See e.g., Miller-Keane, 1992, Encyclopedia & Dictionary of Medicine, Nursing & Allied Health, 5th Ed., (W. B. Saunders Co.), pp. 1708 and 1651.

The method by which the compound disclosed herein can be administered for oral use would be, for example, in a hard gelatin capsule wherein the active ingredient is mixed with an inert solid diluent, or soft gelatin capsule, wherein the active ingredient is mixed with a co-solvent mixture, such as PEG 400 containing Tween-20. A compound disclosed herein can also be administered in the form of a sterile injectable aqueous or oleaginous solution or suspension. The compound can generally be administered intravenously or as an oral dose of 0.1 µg to 20 mg/kg given, for example, every 3-12 hours.

Formulations for oral use can be in the form of hard gelatin capsules wherein the active ingredient is mixed with an inert solid diluent, for example, calcium carbonate, calcium phosphate or kaolin. They can also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients can be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which can be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions can be in the form of a sterile injectable aqueous or oleagenous suspension. This suspension can be formulated according to known methods using those suitable dispersing or wetting agents and suspending agents that have been mentioned above. The sterile injectable preparation can also a sterile injectable solution or suspension in a non-toxic parenterally-acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

A compound disclosed herein can also be administered in the form of ophthalmic compositions applied topically to the eye, preferably in the form of eye drops. A compound disclosed herein can also be administered in the form of intravitreal injection.

A compound disclosed herein can also be administered in the form of suppositories for rectal administration of the drug. These compositions can be prepared by mixing the drug with a suitable non-irritating excipient that is solid at ordinary temperature but liquid at the rectal temperature and will therefore melt in the rectum to release the drug. Such materials include cocoa butter and polyethylene glycols.

The compounds disclosed herein as used in the methods disclosed herein can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds disclosed herein, are employed.

In addition, some of the compounds disclosed herein can form solvates with water or common organic solvents. Such solvates are encompassed within the scope of the methods contemplated herein.

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to inhibition of thrombin and/or KLKB1 and/or KLK1); presence of other diseases or other health-related problems; kind of concurrent treatment; and complications from any disease or treatment regimen. Other therapeutic regimens or agents can be used in conjunction with the methods and compounds disclosed herein.

For any compound described herein, the therapeutically effective amount can be initially determined from a variety of techniques known in the art, e.g., biochemical characterization of inhibition of enzyme (thrombin, KLKB1, or KLK1), cell culture assays, and the like. Target concentrations will be those concentrations of active compound(s) that are capable of decreasing enzymatic activity as measured, for example, using the methods described.

Therapeutically effective amounts for use in humans can be determined from animal models. For example, a dose for humans can be formulated to achieve a concentration that has been found to be effective in animals. The dosage in humans can be adjusted by monitoring enzymatic inhibition and adjusting the dosage upwards or downwards, as described above.

Dosages can be varied depending upon the requirements of the patient and the compound being employed. The dose administered to a patient, in the context of the methods disclosed herein, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments of a method disclosed herein, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Accordingly, in some embodiments, dosage levels of the compounds disclosed herein as used in the present methods are of the order of e.g., about 0.1 mg to about 1 mg, about 1 mg to about 10 mg, about 0.5 mg to about 20 mg per kilogram body weight, an average adult weighing 70 kilograms, with a preferred dosage range between about 0.1 mg to about 20 mg per kilogram body weight per day (from about 7.0 mg to about 1.4 gm per patient per day). The amount of the compound disclosed herein that can be combined with the carrier materials to produce a single dosage will vary depending upon the host treated and the particular mode of administration. For example, a formulation intended for oral administration to humans can contain about 5 µg to 1 g of a compound disclosed herein with an appropriate and convenient amount of carrier material that can vary from about 5 to 95 percent of the total composition. Dosage unit forms will generally contain between from about 0.1 mg to 500 mg of a compound disclosed herein.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from in vitro assays, cell culture assays and/or animal studies can be used in formulating a range of dosages for use in humans. The dosage of such compounds preferably lies within a range of plasma concentrations that include the $ED_{50}$ with little or no toxicity. The dosage can vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual practitioner in view of the patient's condition and the particular method in which the compound is used. For in vitro formulations, the exact formulation and dosage can be chosen by the individual practitioner in view of the patient's condition and the particular method in which the compound is used.

Pharmacokinetics in Mice

In order to test compound exposure in animals, pharmacokinetics in mice is measured. Each compound is administered intravenously (i.v.) as a single dose via tail vein or orally (p.o.) as a single dose via gastric gavage to male CD-1 mice of nominal weights between 20 g and 26 g. Nominal doses are 1 mg/kg and 5 mg/kg for i.v. and p.o., respectively. In some examples (dose type A), both p.o. and i.v. doses are prepared by dissolving the test compound in 5% dimethyl acetamide and diluted in tetraethylene glycol for a final concentration of 0.25 mg/mL. In other examples (dose type B), i.v. doses are prepared by dissolving test compounds in 20% dimethyl acetamide, 40% polyethylene glycol 300 and 40% phosphate buffered saline, and p.o. doses are prepared by dissolving test compounds in carboxymethyl cellulose suspension (1% by weight) in water and 2.5% dimethyl acetamide.

Animals are housed in standard holding cages with food and water available ad libitum except for animals used for p.o. dosing which are fasted overnight prior to dosing. Samples are taken in triplicate via cardiac puncture at times prior to dosing and at 0.083 (i.v. only), 0.25, 0.5, 1, 2, 4, 8, and 24 hours after administration. Plasma is obtained by centrifuge and stored frozen until analyzed by LC-MS/MS using a Shimadzu VP System HPLC coupled to a Applied Biosystems MDS SCIEX API 3000 triple quadrapole MS. Assay results are calibrated using reference samples prepared in a range between 1.5 and 5000 ng/mL.

Pharmacokinetic parameters are calculated from mean concentration values using a non-compartmental analysis as described in the following and as apparent to those of ordinary skill in the art. Half-lives ($t_{1/2}$) and elimination rate constants ($\lambda$) are determined by log linear regression using equal weighting on the last three finite sample time points. Concentration at time zero ($C_0$) for the i.v. data is established by the extrapolation of log linear regression using equal weighting on the first three sample time points. Area under the curve (AUC) values are calculated using linear trapezoidal integration. Systemic clearance (CL) is calculated as the ratio of dosage and AUC. The apparent volume of distribution ($V_d$) is calculated as the ratio of CL and $\lambda$. Percent oral bioavailability (% F) is determined from the ratio of i.v. and p.o. AUC values weighted by dosage Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

General Scheme I. A synthetic scheme useful for synthesis of compounds described herein is disclosed in General Scheme I following, wherein the terms "$R^1$", "$R^2$", "$R^3$", "$R^4$" are as defined above, "$R^m$" and "$R^n$" are substituted or unsubstituted alkyl, and "$R^{3'}$" is a radical defined as the linkage of a methylene group attached to the radical "$R^3$" as defined above.

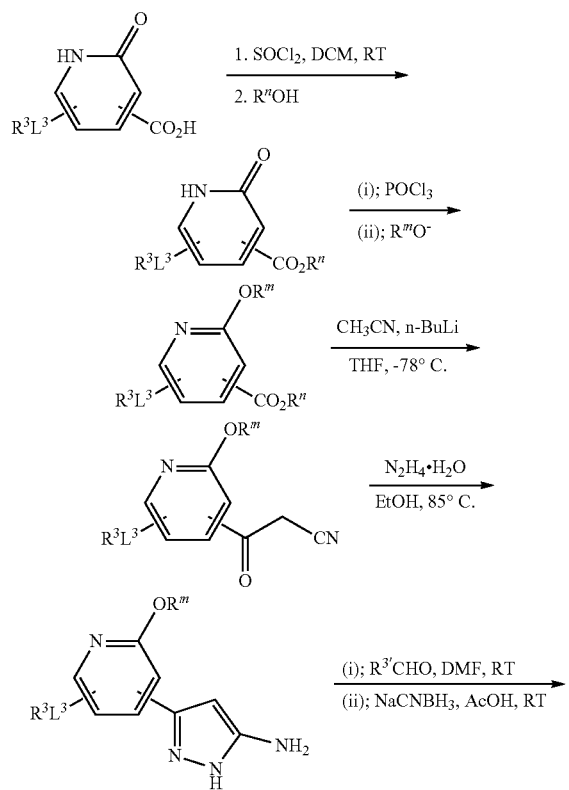

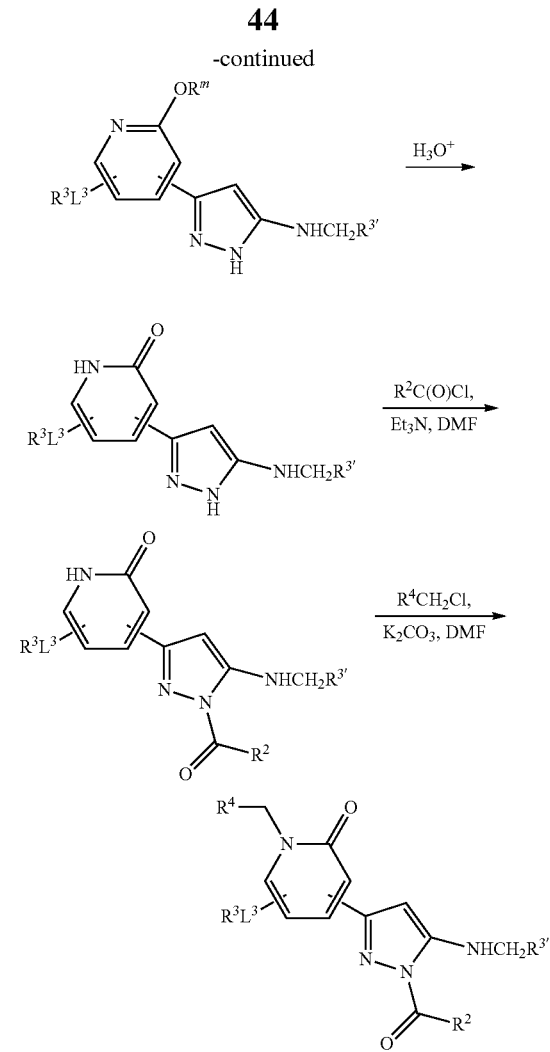

General Scheme II. Further, we describe General Scheme II, synthetically similar to General Scheme I, useful for the introduction of functional groups $R^3L^3$, wherein the terms "$R^1$", "$R^2$", "$R^3$", "$R^4$", "$R^m$" and "$R^n$" are as defined above, and "$R^{3'}$" is a radical defined as the linkage of a methylene group attached to the radical "$R^3$", as defined above.

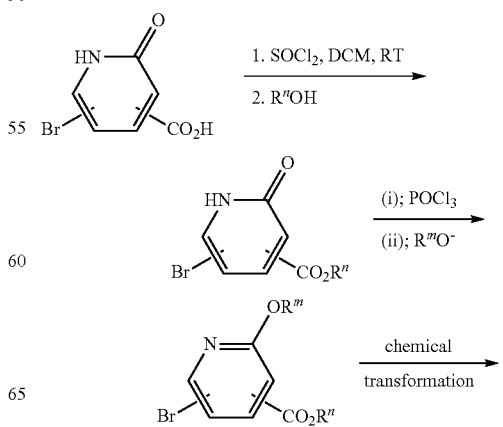

-continued

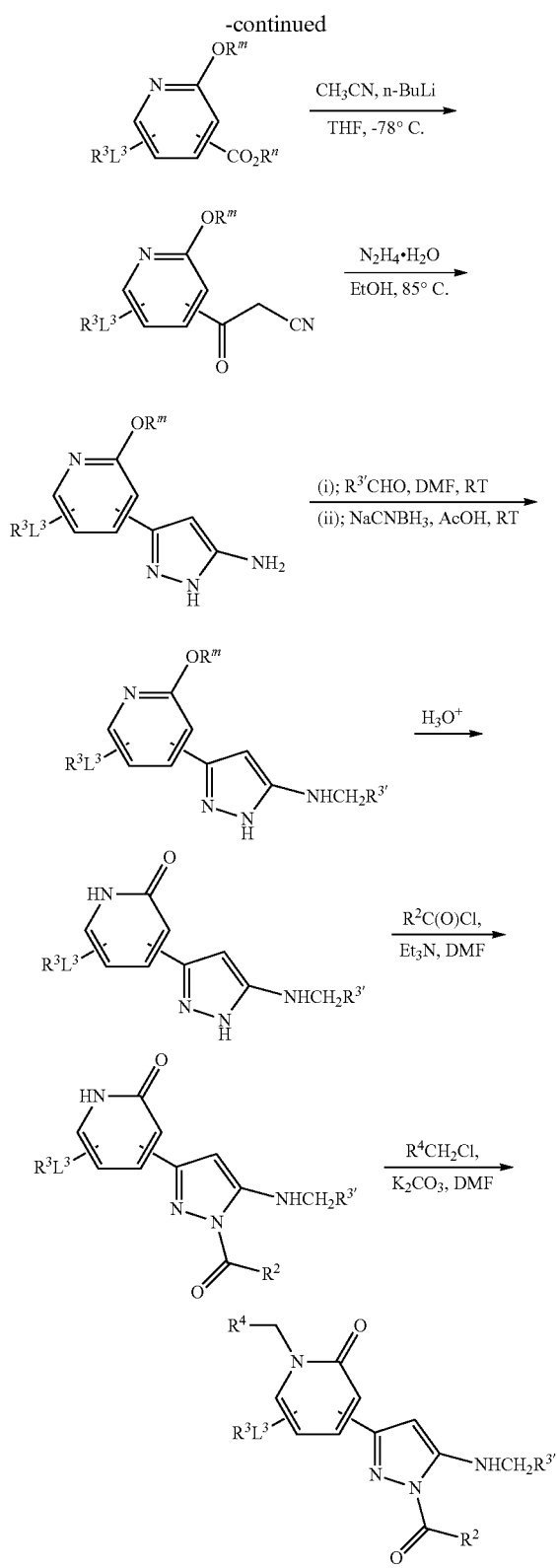

Example 1—Preparation of Intermediate 1

The synthesis of Intermediate 1 followed General Procedure 1 following.

General Procedure 1

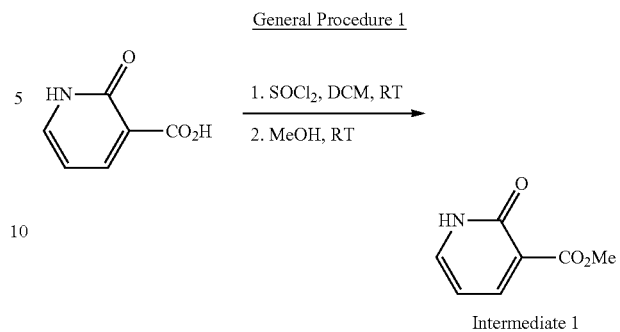

Intermediate 1

To a solution of 2-hydroxynicotinic acid (50.0 g, 0.359 moles, 1.0 eq.) in dichloromethane (500 mL) at 0° C. was added thionyl chloride (133.6 mL, 1.8 moles, 5.0 eq.) dropwise. After 30 min tetrahydrofuran (500 mL) was added and the reaction stirred for 14-15 hours at ambient temperature. The reaction mixture was cooled to 0° C., to it was added methanol (150 mL) dropwise, and the mixture was stirred for a further 30 min at room temperature. The reaction mixture was concentrated under reduced pressure to obtain a solid, which was then neutralized with aqueous sodium bicarbonate (pH 7-8), and again concentrated to obtain solid product. The solid was dissolved in methanol, filtered, and the filtrate concentrated to give desired product 45.0 g, (yield; 81.8%) m/z 153.99 [M+H]$^+$ $^1$H NMR (DMSO-d6, 400 MHz) δ 8.051-074 (1H, q), 7.661-7.682 (1H, q), 6.259-6.292 (1H, m), 3.734 (3H, s) ppm.

Example 2—Preparation of Intermediate 2

The synthesis of Intermediate 2 followed the procedure of General Procedure 2 following.

General Procedure 2

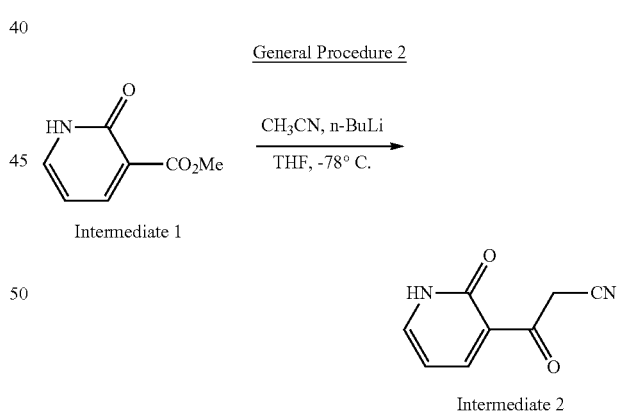

Intermediate 2

To a cold (−78° C.) solution of acetonitrile (8.18 mL, 0.156 moles, 1.2 eq.) in tetrahydrofuran (300 mL) was added n-BuLi (2.5M in Hexane; 62.68 mL, 0.156 moles, 1.2 eq) dropwise over a period of 60 min. After addition, the reaction was stirred for another 60 min, then to it added methyl 2-oxo-1,2-dihydropyridine-3-carboxylate (Intermediate 1, 20.0 g, 130 mmol, 1.0 eq) portionwise to reaction mixture and maintained −78° C. for 3 hrs. The reaction was quenched with water and washed with ethyl acetate. The aqueous layer was evaporated to obtain crude product, which was suspended in methanol and stirred for 30 min at room temperature. The solid was filtered through suction and dried over high vacuum to afford Intermediate 2 (11.5 g, 54%).

Example 3—Preparation of Compound 1

The synthesis of Compound 1 followed the procedure of General Procedure 3 following.

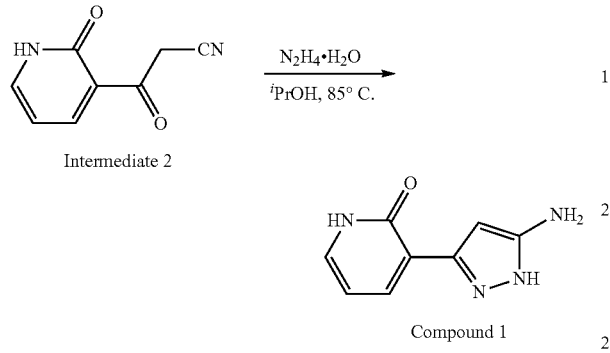

General Procedure 3

Intermediate 2

Compound 1

To a solution of Intermediate 2 (20.0 g, 0.123 moles, 1.0 eq) in isopropanol (600 mL) and acetic acid (22.2 mL) was added hydrazine monohydrate (7.40 mL, 0.148 moles, 1.2 eq) dropwise and the reaction was heated at 85° C. for 4-5 Hrs. After cooling, the reaction mixture was concentrated to give crude product, which was purified by column chromatography using neutral silica gel (60-120 mesh), eluting with 10-25% methanol in dichloromethane as gradient to give the desired product Compound 1 13.25 g (yield–61%) m/z 177.06 [M+H]+ 1H NMR (DMSO-d6, 400 MHz) δ 11.831 (1H, s), 7.857-7.879 (1H, q), 7.383-7.403 (1H, q), 6.303-6.336 (1H, m), 6.048 (1H, s) 4.633 (2H, s) ppm.

Example 4—Preparation of Compound 2

The synthesis of Compound 2 followed the procedure of General Procedure 4 following.

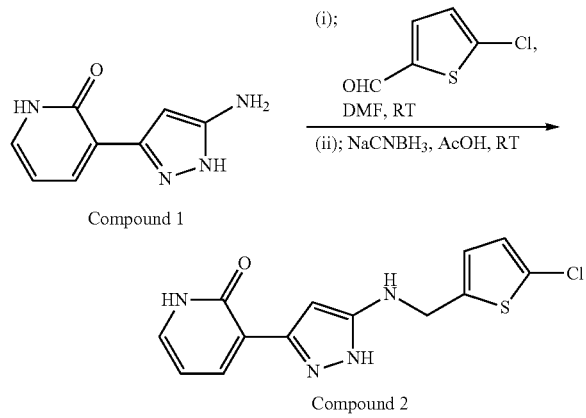

General Procedure 4

Compound 1

Compound 2

To a solution of Compound 1 in dimethylformamide (100 mL) at 10-15° C. was added acetic acid (11.2 mL) dropwise, followed by 5-chlorothiophene-2-carbaldehyde (9.15 g, 0.0624 moles, 1.1 eq) added portionwise. The reaction was stirred for 30-45 min at room temperature. Sodium cyanoborohydride (5.35 g, 0.0851 moles, 1.5 eq.) was added portionwise over a period of 45 min and reaction was stirred for 2 hours. After completion of reaction, the mixture was poured into ice cold water under stirring and the product was extracted with ethyl acetate. The organic layer was dried over sodium sulfate and concentrated under reduced pressure to obtain crude product, which was purified by column chromatography using neutral silica gel and product was eluted with 10-12% methanol in dichloromethane as mobile phase to yield pure desired product Compound 2 (7.3 g, yield: 42.7%) m/z[M+H]+ 307.10 1H NMR (DMSO-d6, 400 MHz) δ 12.034 (1H, s), 11.815 (1H, s), 7.869-7.882 (1H, q), 7.404-7.415 (1H, d), 6.922-6.931 (1H, d), 6.862-6.871 (1H, d), 6.314-6.331 (1H, d), 6.117 (1H, s), 5.867-5.898 (1H, t), 4.348-4.363 (2H, d) ppm.

Example 5—Preparation of Compound 3

The synthesis of Compound 3 followed the procedure of General Procedure 5 following.

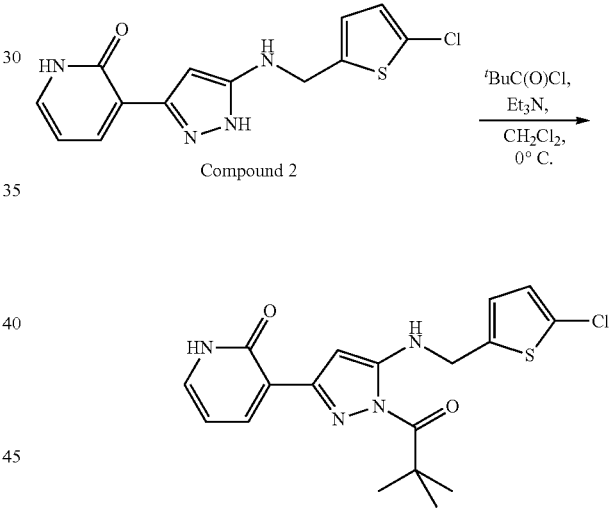

General Procedure 5

Compound 2

Compound 3

To a cooled (0° C.) solution of Compound 2 in triethylamine (2.98 mL, 0.0215 moles, 3.0 eq.) and dichloromethane (40 mL) was added pivaloyl chloride (0.776 g, 0.00647 moles, 0.9 eq) dropwise over a period of 30 minutes. The reaction was stirred for 2-3 hours by maintaining the temperature below 10° C. After completion, the reaction was diluted with ice cold water under stirring and the product was extracted with dichloromethane. The organic phase was dried over sodium sulfate and concentrated under reduced pressure. The resultant crude product was purified by column chromatography using neutral silica gel, eluting with 5-8% methanol in dichloromethane to furnish pure desired product (Compound 3, 0.76 g, yield: 43.6%) m/z[M+H]+ 391.24 1H NMR (DMSO-d6, 400 MHz) δ 11.250 (1H, s), 8.086-8.109 (1H, q), 7.731-7.761 (1H, t), 7.484 (1H, s), 6.974-6.984 (1H, d), 6.934-6.944 (1H, d), 6.317-6.350 (1H, t), 6.213 (1H, s), 4.471-4.486 (2H, d), 1.47 (9H, s) ppm.

Example 6—Preparation of Compound 4

The synthesis of Compound 4 followed the procedure of General Procedure 6 following.

General Procedure 6

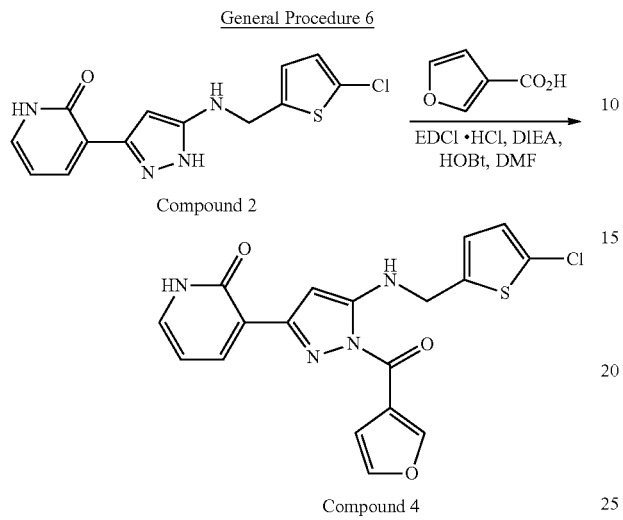

Compound 2

Compound 4

To a solution of furan-3-carboxylic acid (0.338 g, 0.00301 moles, 1.2 eq) in dimethylformamide (5.0 mL) was added EDCI.HCl (0.724 g, 0.00337 moles, 1.5 eq), DIEA (0.811 g, 0.00629 moles, 2.5 eq) and finally HOBt (0.074 g, 0.00048 moles, 0.5 eq). The reaction mixture was stirred at room temperature for 30 min, followed by the addition of Compound 2 (0.770 g, 0.00251 moles, 1.0 eq). The mixture was stirred at 14 hours at room temperature. After checking that the reaction had reached completion by LC-MS, the mixture was poured into ice cold water under stirring. The product was extracted with ethyl acetate. The organic phase was dried over sodium sulfate, concentrated under reduced pressure and purified by column chromatography using neutral silica gel (60-120 mesh), eluting with 15-25% ethyl acetate in n-hexane as gradient to give pure desired Compound 4 (0.45 g, yield: 45%) m/z[M+H]+ 401.84 1H NMR (DMSO-d6, 400 MHz) δ 11.923 (1H, s), 9.024-9.029 (1H, q), 8.274-8.297 (1H, q), 7.888-7.893 (1H, d), 7.833-7.884 (1H, q), 7.500-7.512 (1H, d), 7.085-7.091 (1H, q), 6.965-6.990 (2H, q), 6.313-6.347 (2H, t), 5.771 (1H, s), 4.445-4.560 (1H, d) ppm.

Example 7—Preparation of Compound 5

The synthesis of Compound 5 followed the procedure of General Procedure 7 following.

General Procedure 7

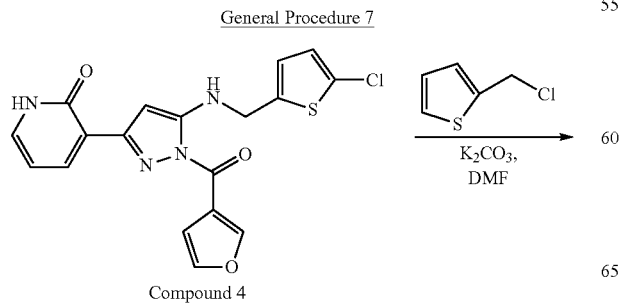

Compound 4

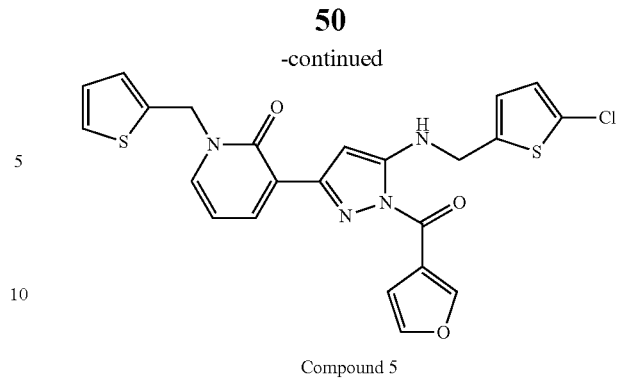

Compound 5

To a solution of Compound 4 (0.150 g, 0.375 mmoles, 1.0 eq) in DMF (5.0 mL) was added anhydrous potassium carbonate (0.129 g, 0.937 mmoles, 2.5 eq) and then stirred for 30 minutes at room temperature. 2-(Chloromethyl)thiophene (0.059 g, 0.45 mmoles, 1.2 eq) was added to the reaction mixture and the reaction stirred for a further 2-3 hours at room temperature. The mixture was monitored by TLC and LCMS. After completion of reaction, the reaction mixture was poured into ice cold water under stirring and extracted with ethyl acetate. The organic phase was dried over sodium sulfate, concentrated under reduced pressure and purified by column chromatography using neutral silica gel. The product was eluted with 1-5% ethyl acetate as gradient in n-hexane to furnish Compound 5 (0.036 g, yield-19.3%) m/z[M+H]+ 497.23. 1H NMR (DMSO-d6, 400 MHz) δ 9.020 (1H, s), 8.274-8.297 (1H, dd), 7.960-7.981 (1H, dd), 7.885-7.893 (1H, t), 7.833-7.864 (1H, t), 7.519-7.539 (1H, dd), 7.430-7.434 (1H, d), 7.117-7.133 (1H, dd), 7.087-7.091 (1H, d), 6.975-6.987 (1H, t), 6.380-6.427 (1H, t), 6.435 (1H, s), 5.189 (2H, s), 4.550-4.565 (2H, d) ppm.

Example 8—Preparation of Compound 6

The synthesis of Compound 6 followed the procedure of General Procedure 8 following.

General Procedure 8

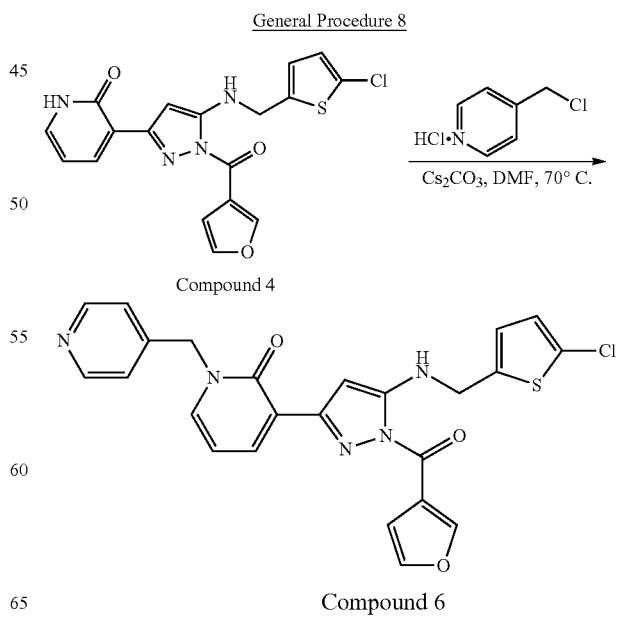

Compound 4

Compound 6

To a solution of Compound 4 (0.150 g, 0.375 mmoles, 1.0 eq.) in DMF (5.0 mL) was added cesium carbonate (0.304 g, 0.937 mmoles, 2.5 eq.). The reaction mixture was stirred for 30 min at room temperature, followed by the addition of 4-(chloromethyl)pyridine hydrochloride (0.073 g, 0.45 mmoles, 1.2 eq). The reaction was stirred for 3-4 hours at 70° C. The reaction was monitored by TLC and LCMS. After completion of the reaction, the mixture was poured into ice cold water under stirring and extracted into ethyl acetate. The organic phase was dried over sodium sulfate, filtered and concentrated under reduced pressure. The crude product was purified by column chromatography using neutral silica gel, eluting with 40-55% ethyl acetate as gradient in n-hexane to furnish Compound 6 (0.032 g, yield: 17.4%) m/z [M+H]+ 491.95. 1H NMR (DMSO-d6, 400 MHz) δ 9.030 (1H, s), 8.541-8.526 (2H, d), 8.379-8.356 (1H, dd), 8.020-7.999 (1H, dd), 7.893-7.836 (2H, m), 7.210-7.195 (2H, d), 7.093-7.089 (1H, d), 6.968-6.948 (2H, t), 6.498-6.463 (1H, t), 6.294 (1H, s), 5.255 (2H, s), 4.542-4.526 (2H, d) ppm.

Example 9—Preparation of Intermediate 3

The synthesis of Intermediate 3 followed General Procedure 1 following.

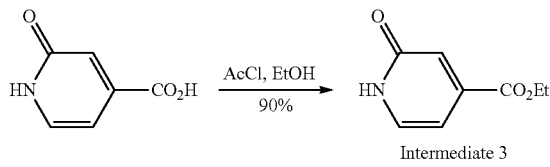 [SMILES: O=C(O)c1cc[nH]c(=O)c1 ; CCOC(=O)c1cc[nH]c(=O)c1]

Intermediate 3

Acetyl Chloride (200 mL) was added slowly to ethanol (800 mL) at room temperature. The clear solution was stirred for 10 minutes and then 4-hydroxynicotinic acid (50.0 g, 0.359 moles, 1.0 eq.) was added as solid. The reaction mixture was heated at reflux for overnight (12 hr). After completion, reaction mixture was concentrated under reduced pressure. The residue was diluted with dichloromethane (300 mL×3) and water (300 mL). The layers were neutralized by NaHCO$_3$. The organic layer was separated and the aqueous layer was extracted further with dichloromethane (300 mL×2). The combined organic layer was dried over sodium sulfate and concentrated to afford the desired product. (5.4 g, yield-90.00%). m/z [M+H]+ 167.8. $^1$H NMR (DMSO-d$_6$, 400 MHz) δ 7.529-7.512 (1H, d), 6.814 (1H, s), 6.505-6.525 (1H, dd), 4.325-4.272 (2H, q), 1.323-1.286 (3H, t) ppm.

Example 10—Preparation of Intermediate 4

The synthesis of Intermediate 4 followed General Procedure 2 following.

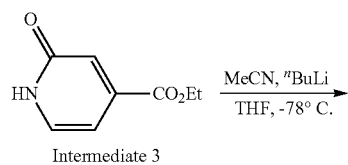

Intermediate 3

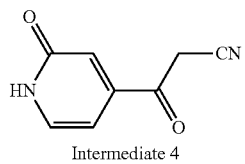

Intermediate 4

Acetonitrile (8.18 mL, 0.156 mol, 1.2 eq) was added in tetrahydrofuran (300 mL) and was then cooled to −78° C. $^n$BuLi (2.5M in hexane, 62.68 mL, 0.156 moles, 1.2 eq) was added dropwise over a period of 60 minutes and the reaction mixture was stirred further for 60 minutes. Intermediate 3 (20.0 g, 0.13 mol, 1.0 eq) was added portionwise to the reaction mixture at −78° C. and maintained for 3 hrs. After completion, the reaction was quenched with saturated ammonium chloride solution and washed with ethyl acetate. The aqueous layer was evaporated to obtain crude product, which was suspended in methanol and stirred for 30 minutes at room temperature. The solid was suction-filtered and dried under high vacuum to obtain desired product. (11.5 g, yield-58%). m/z[M+H]+ 163.05 $^1$H NMR (CD$_3$CN, 400 MHz) δ 9.88 (1H, bs), 7.40-7.38 (1H, d), 6.84 (1H, s), 6.50-6.48 (1H, dd), 4.27 (2H, s) ppm.

Example 11—Preparation of Compound 7

The synthesis of Compound 7 followed the procedure of General Procedure 3 following.

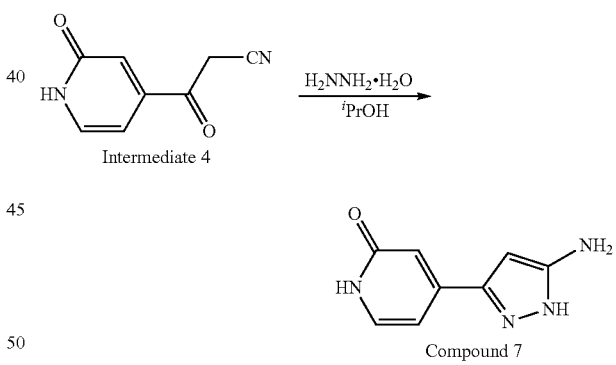

Intermediate 4 (20.0 g, 0.123 mol, 1.0 eq) was added to a mixture of isopropanol (600 mL) and acetic acid (22.2 mL). To this was added hydrazine monohydrate (7.40 mL, 0.148 moles, 1.2 eq) dropwise. The reaction mixture was stirred at 85° C. for 4-5 hours. After completion, the reaction mixture was concentrated to give crude product, which was purified by column chromatography using neutral silica gel (60-120 mesh). The product was eluted with 10-15% methanol in dichloromethane as gradient to give desired product. (13.25 g, yield-61%) m/z[M+H]+ 176.9. $^1$H NMR (DMSO-d$_6$, 400 MHz) δ 11.492 (2H, bs), 7.336-7.318 (1H, d), 6.529-6.515 (2H, d), 5.775 (1H, s), 4.995 (2H, s) ppm.

Example 12—Preparation of Compound 8

The synthesis of Compound 8 followed the procedure of General Procedure 4 following.

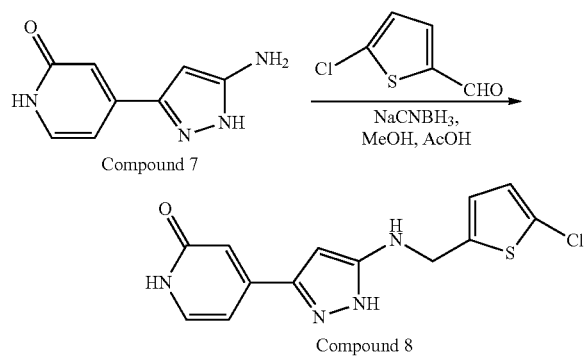

Compound 7 (5.0 g, 28.4 mol, 1.0 eq) was dissolved in methanol (200 mL) at 10-15° C. and to it was added acetic acid (1.7 mL) dropwise. To this solution was added 5-chlorothiophene-2-carbaldehyde (6.22 g, 42.6 mmol, 1.5 eq) dropwise. The reaction was stirred for 30-45 minutes at room temperature. Sodium cyanoborohydride (3.52 g, 56.8 mmol, 2.0 eq) was added portionwise over a period of 45 minutes and reaction was stirred for 2 hours. After completion, the reaction mixture was poured into ice-cold water (200 mL) under stirring and the product was extracted with ethyl acetate (200 mL×3). The organic layer was dried over sodium sulfate and concentrated under reduced pressure. The crude product was purified by column chromatography using neutral silica gel eluting with 10-12% methanol in dichloromethane as mobile phase. (6.9 g, yield-79.3%) m/z[M+H]+ 307.00. $^1$H NMR (DMSO-$d_6$, 400 MHz) δ 12.356 (1H, s), 11.475 (1H, s), 7.370 (1H, s), 6.944-6.936 (2H, d), 6.576-6.487 (2H, m), 6.024 (2H, s), 4.360-4.344 (2H, d) ppm.

Example 13—Preparation of Compound 9

The synthesis of Compound 9 followed the procedure of General Procedure 6 following.

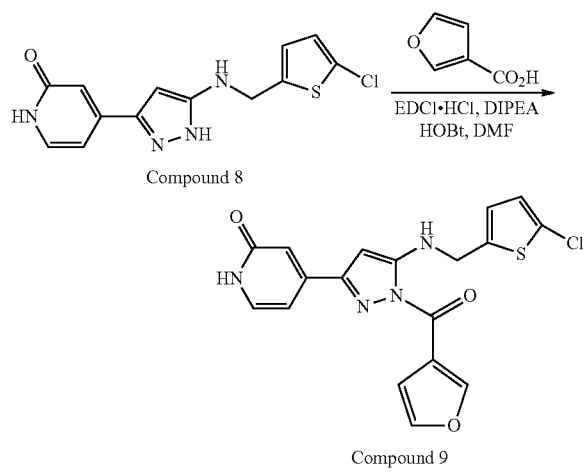

Furan-3-carboxylic acid (0.549 g, 4.9 mmol, 1.5 eq) was dissolved in dimethylformamide (40 mL). EDCI.HCl (0.94 g, 4.9 mmol, 1.5 eq) and DIPEA (0.67 ml, 1.2 eq) were added to the reaction mixture and stirred at 10° C. for 30 minutes. Compound 8 (1.0 g, 3.27 mmol, 1.0 eq) and HOBt (0.088 g, 0.65 mmol, 0.2 eq) were added to the reaction mixture and stirred for 15 hours at room temperature. The reaction was monitored by LCMS. After completion, the reaction mixture was poured into ice cold water (150 mL) under stirring and extracted with ethyl acetate (150 mL×3). The organic layer was dried over sodium sulfate and concentrated under reduced pressure. The residue was purified by column chromatography using neutral silica gel, eluting with 60% ethyl acetate in n-nexane as mobile phase to give pure desired product (0.600 g, yield-45.8%). m/z[M+H]+ 401.30. $^1$H NMR (DMSO-$d_6$, 400 MHz) δ 11.661 (1H, s), 8.905 (1H, s), 7.976-7.944 (1H, t), 7.910-7.901 (1H, s), 7.431-7.415 (1H, s), 7.106-7.089 (2H, t), 6.981-6.971 (1H, d), 6.818 (1H, s), 6.761-6.742 (1H, d), 6.240 (2H, s) ppm.

Example 14—Preparation of Compound 10

The synthesis of Compound 10 followed the procedure of General Procedure 8 following.

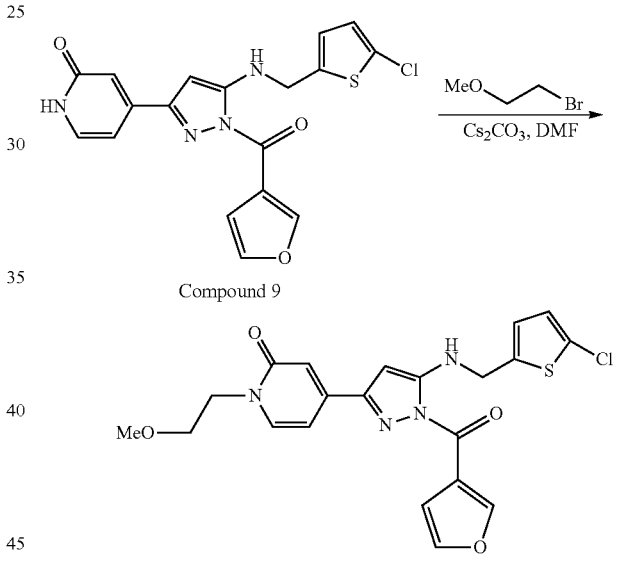

Compound 9 (0.3 g, 0.75 mmol, 1.0 eq) was dissolved in DMF (40.0 mL) and anhydrous cesium carbonate (0.61 g, 1.87 mmol, 2.5 eq) was added. The reaction was stirred for 30 minutes at room temperature. 2-(Bromoethyl) methyl ether (0.15 g, 1.12 mmol, 1.2 eq) was added to the reaction mixture and stirred overnight at room temperature. The reaction was monitored by TLC and LCMS. After completion the reaction mixture was poured into ice cold water (80 mL) under stirring and the product was extracted with ethyl acetate (80 mL×3). The organic layer was dried over sodium sulphate and concentrated under reduced pressure. The crude product was purified by column chromatography using silica gel (60-120 mesh sized), eluting with 30-40% Ethyl acetate as gradient in n-Hexane as mobile phase to give pure desired product. (0.100 g, yield-29.06%). m/z[M+H]+ 459.37. $^1$H NMR (DMSO-$d_6$, 400 MHz) δ 8.933 (1H, s), 7.972-7.939 (1H, t), 7.902 (1H, s), 7.676-7.658 (1H, d), 7.104-7.092 (1H, dd), 6.978-6.968 (2H, m), 6.885 (1H, s), 6.810-6.793 (1H, d), 6.244 (1H, s), 4.555-4.539 (2H, t), 4.100-4.074 (2H, t), 3.602-3.576 (2H, t), 3.293 (3H, s) ppm.

Example 15—Preparation of Compound 11

The synthesis of Compound 11 followed the procedure of General Procedure 8 following.

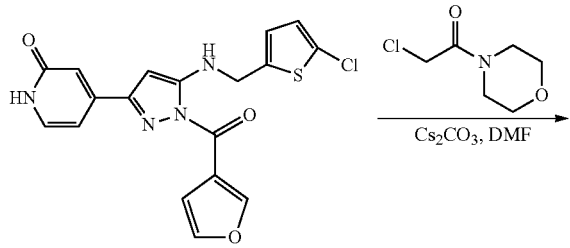

Compound 9

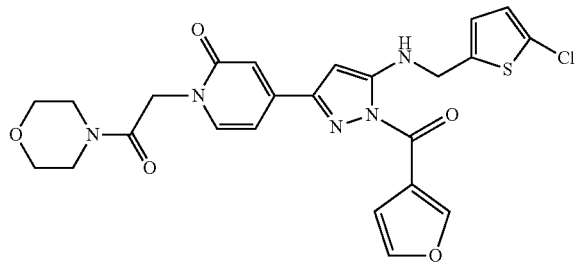

Compound 11

Compound 9 (0.3 g, 0.75 mmol, 1.0 eq) was dissolved in DMF (25.0 mL), anhydrous cesium carbonate (0.61 g, 1.87 mmol, 2.5 eq) was added and the reaction was stirred for 30 minutes at room temperature. To this was added 2-chloro-1-morpholinoethan-1-one (0.184 g, 1.12 mmoles, 1.2 eq.) and the reaction mixture was stirred overnight at room temperature. The reaction was monitored by TLC and LCMS. After completion, the reaction mass was poured into ice cold water (80 mL) under stirring and the product was extracted with ethyl acetate (100 mL×3). The organic layer was dried over sodium sulphate and concentrated under reduced pressure to obtain a crude product, which was purified by column chromatography using silica gel (60-120 mesh sized) and eluting with 70-80% ethyl acetate as gradient in n-hexane as mobile phase. (0.115 g, yield-29.04%). m/z[M+H]+ 528.06. $^1$H NMR (DMSO-d$_6$, 400 MHz) δ 8.950 (1H, s), 7.951-7.983 (1H, t), 7.607-7.625 (1H, d), 7.103-7.113 (2H, t), 6.969-6.978 (1H, d), 6.900 (1H, s), 6.831-6.848 (1H, d), 6.273 (1H, s), 4.864 (2H, s), 4.541-4.556 (2H, d), 3.662 (2H, s), 3.555-3.593 (4H, d), 3.458 (2H, s) ppm.

Example 16—Preparation of Compound 12

The synthesis of Compound 12 followed the procedure of General Procedure 8 following.

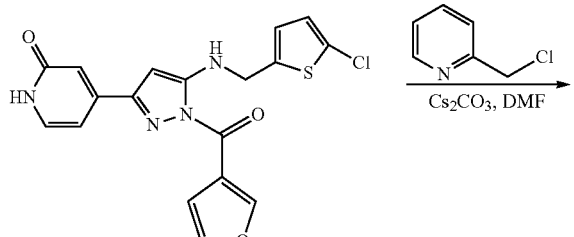

Compound 9

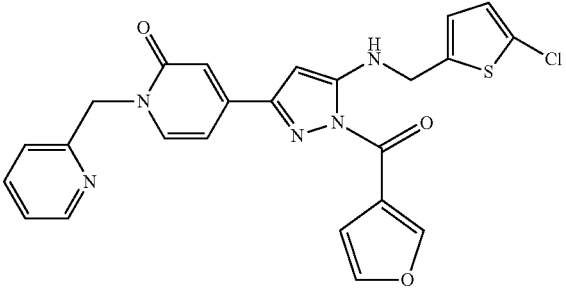

Compound 12

Compound 9 (0.3 g, 0.75 mmol, 1.0 eq) was dissolved in DMF (25.0 mL) and anhydrous cesium carbonate 0.610 g (1.87 mmoles, 2.5 eq.) was added. The reaction was stirred for 30 minutes at room temperature. 2-Chloromethylpyridine hydrochloride (0.185 g, 1.13 mmol, 1.2 eq) was added to the reaction mixture and the reaction mixture was stirred overnight at room temperature. The reaction was monitored by TLC and LCMS. After completion the reaction mixture was poured into ice cold water (80 mL) under stirring and extracted with ethyl acetate (100 mL×3). The organic phase was dried over sodium sulfate, concentrated under reduced pressure and purified by column chromatography using silica gel (100-200 mesh sized). The product was eluted with 60-70% Ethyl acetate as gradient in n-Hexane as mobile phase to give pure desired product. (0.100 g, yield-27.10%) m/z[M+H]+ 492.43. $^1$H NMR (DMSO-d$_6$, 400 MHz) δ 8.949 (1H, s), 8.505-8.514 (1H, dd), 7.971 (1H, d), 7.857-7.905 (2H, m), 7.783 (1H, t), 7.096-7.318 (2H, m), 7.096 (2H, s), 6.967-6.976 (1H, d), 6.881-6.918 (2H, m), 6.270 (1H, s), 5.233 (2H, s), 4.541-4.556 (2H, d) ppm.

Example 17—Preparation of Compound 13

The synthesis of Compound 13 followed the procedure of General Procedure 6 following.

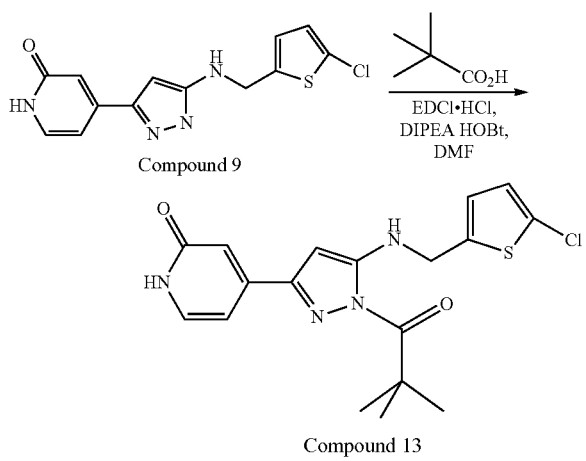

To a solution of pivalic acid (0.544 g, 5.44 mmol, 1.2 eq) in DMF (100 mL) was added EDCI.HCl (1.045 g, 5.44 mmol, 1.2 eq) and DIPEA (0.93 ml, 1.2 eq), and the mixture was stirred at 10° C. for 30 minutes. After completion, Compound 9 (2.0 g, 6.53 mmol, 1.0 eq.) and HOBt (0.199 g, 1.307 mmol, 0.2 eq) were added, and the reaction mixture stirred for 15 hours at room temperature. The reaction was monitored by LCMS. After completion, the reaction mixture was poured into ice cold water (300 mL) under stirring and the product was extracted with ethyl acetate (300 mL×3). The organic phase was dried over sodium sulfate, concentrated under reduced pressure, and chromatographed using neutral silica gel. The product was eluted with 60% ethyl acetate in n-hexane as mobile phase, to give pure desired product (1.56 g, yield-61.41%. m/z[M+H]+ 391.44. $^1$H NMR (DMSO-d$_6$, 400 MHz) δ 9.593 (1H, bs), 7.616-7.586 (1H, t), 7.324-7.305 (1H, dd), 6.955-6.946 (1H, d), 6.879-6.870 (1H, d), 6.731-6.689 (2H, m), 5.862 (1H, s), 4.527-4.509 (2H, t), 1.512 (9H, s) ppm.

Example 18—Preparation of Compound 14

The synthesis of Compound 14 followed the procedure of General Procedure 8 following.

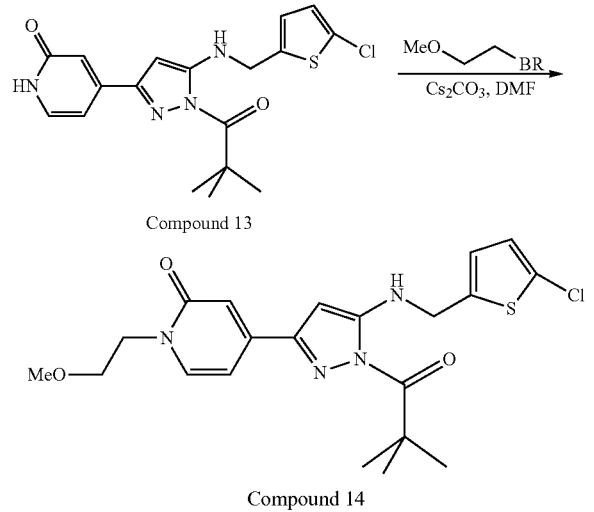

To a solution of Compound 13 (0.3 g, 0.769 mmol, 1.0 eq) in DMF (15.0 mL) was added anhydrous cesium carbonate 0.624 g (1.92 mmol, 2.5 eq). The reaction was stirred for 30 minutes at room temperature. 2-(Bromoethyl) methyl ether (0.16 g, 1.15 mmol, 1.5 eq) was added and the reaction mixture stirred overnight at room temperature. The reaction was monitored by TLC and LCMS. After completion the reaction mixture was poured into ice cold water (80 mL) under stirring, and extracted with ethyl acetate (80 mL×3). The organic phase was dried over sodium sulfate and concentrated under reduced pressure. The crude product was purified by column chromatography using silica gel (60-120 mesh sized), eluting with 30-40% ethyl acetate in n-hexane as mobile phase to give pure desired product. (0.090 g, yield-27.95%. m/z[M+H]+ 449.27. $^1$H NMR (DMSO-d$_6$, 400 MHz) δ 7.874-7.843 (1H, t), 7.681-7.664 (1H, dd), 7.082-7.074 (1H, d), 6.973-6.964 (1H, d), 6.816 (1H, s), 6.645-6.627 (1H, d), 6.120 (1H, s), 4.488-4.473 (2H, t), 4.078-4.052 (2H, t), 3.592-3.567 (2H, s), 3.244 (3H, s), 1.464 (9H, s) ppm.

Example 19—Preparation of Compound 15

The synthesis of Compound 15 followed the procedure of General Procedure 8 following.

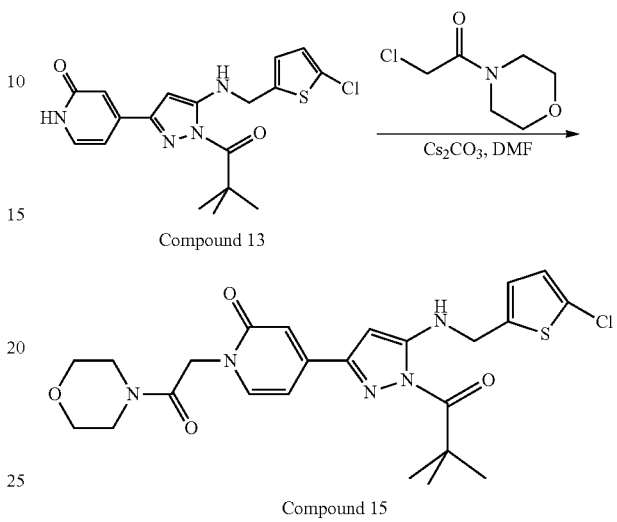

To a solution of Compound 13 (0.3 g, 0.512 mmol, 1.0 eq) in DMF (15.0 mL) was added anhydrous cesium carbonate (0.333 g, 1.02 mmol, 2.5 eq). The reaction was stirred for 30 minutes at room temperature. 2-Chloro-1-morpholinoethan-1-one (0.189 g, 0.615 mmol, 1.5 eq) was added and the reaction mixture was stirred overnight at room temperature. The reaction was monitored by TLC and LCMS. After completion the reaction mixture was poured into ice cold water (80 mL) under stirring and product was extracted with ethyl acetate (100 mL×3). The organic phase was dried over sodium sulfate and concentrated under reduced pressure. The residue was purified by column chromatography using silica gel (60-120 mesh sized), eluting with 70-80% ethyl acetate in n-Hexane as mobile phase to give pure desired product. (0.075 g, yield-18.89%) m/z[M+H]+ 517.83. $^1$H NMR (DMSO-d$_6$, 400 MHz) δ 7.849-7.881 (1H, t), 7.601-7.619 (1H, d), 7.080-7.089 (1H, d), 6.963-6.972 (1H, d), 6.826 (1H, s), 6.654-6.676 (1H, t), 6.143 (1H, s), 4.846 (2H, s), 4.475-4.490 (2H, d), 3.646-3.657 (2H, s), 3.452-3.590 (4H, d), 3.344 (2H, s), 1.470 (9H, s) ppm.

Example 20—Preparation of Compound 16

The synthesis of Compound 16 followed the procedure of General Procedure 8 following.

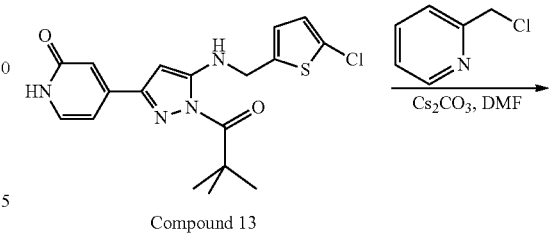

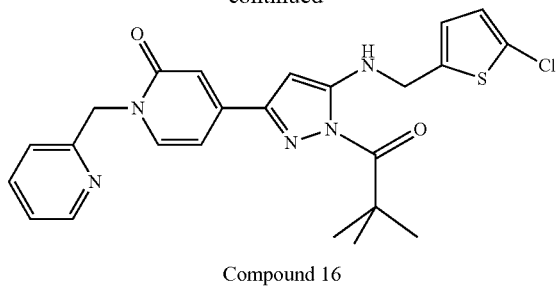

Compound 16

To a solution of Compound 13 (0.350 g, 0.769 mmol, 1.0 eq) in DMF (15.0 mL) was added anhydrous cesium carbonate (0.499 g, 1.15 mmol, 2.5 eq). The reaction was stirred for 30 minutes at room temperature. 2-(Chloromethyl)pyridine hydrochloride (0.189 g, 1.54 mmol, 1.5 eq) was added and the reaction stirred overnight at room temperature. The reaction was monitored by TLC and LCMS. After completion the reaction mixture was poured into ice cold water (100 mL) under stirring and product was extracted with ethyl acetate (100 mL×3). The organic layer was dried over sodium sulfate and concentrated under reduced pressure. The residue was purified by column chromatography using silica gel (100-200 mesh sized), eluting with 50% ethyl acetate in n-hexane to give pure desired product (0.075 g, yield-17.36%) m/z[M+H]+ 482.38. $^1$H NMR (DMSO-d$_6$, 400 MHz) δ 8.497-8.509 (1H, d), 7.856-7.888 (2H, m), 7.752-7.795 (1H, t), 7.282-7.314 (1H, dd), 7.226-7.245 (1H, d), 7.075-7.084 (1H, d), 6.961-6.971 (1H, d), 6.846-6.6.851 (1H, d), 6.707-6.729 (1H, dd), 6.146 (1H, s), 5.212 (1H, s), 4.474-4.490 (2H, d), 1.469 (9H, s) ppm.

Example 21—Preparation of Compound 17

The synthesis of Compound 17 followed the procedure of General Procedure 6 following.

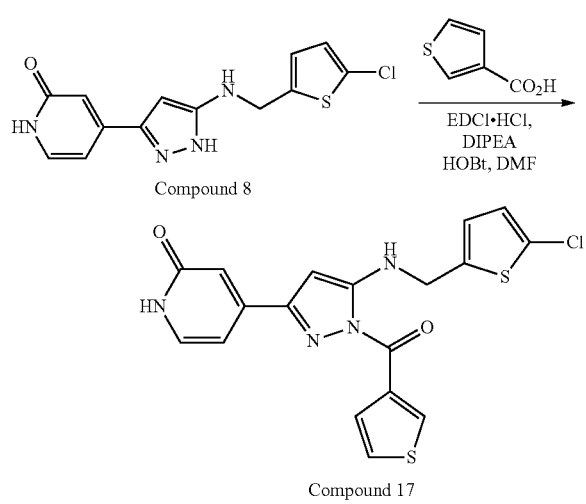

To a cold (10° C.) solution of thiophene-3-carboxylic acid (1 g, 7.84 mmol, 1.2 eq) in DMF (40.0 mL) was added EDCI.HCl (1.5 g, 7.84 mmol, 1.2 eq) and DIPEA (1.47 mL, 1.2 eq). The mixture was stirred at 10° C. for 30 min. After completion, Compound 8 (2.0 g, 6.53 mmol, 1.0 eq) was added, followed by HOBt (0.239 g, 1.56 mmol, 0.2 eq), and the reaction mixture was then stirred for 15 hours at room temperature. The reaction was monitored by LCMS. After completion, the reaction mixture was poured into ice cold water (300 mL) under stirring and extracted with ethyl acetate (300 mL×3). The organic phase was dried over sodium sulfate and concentrated under reduced pressure. The residue was purified by column chromatography using neutral silica gel, eluting with 80% ethyl acetate in n-hexane as mobile phase to give pure desired product (1.023 gm, yield-37.74%). m/z[M+H]+ 417.30. $^1$H NMR (DMSO-d$_6$, 400 MHz) δ 11.651 (1H, bs), 9.002-8.992 (1H, s), 7.993-7.962 (1H, t), 7.834-7.818 (1H, m), 7.706-7.686 (1H, d), 7.439-7.422 (1H, dd), 7.111-7.102 (1H, d), 6.983-6.974 (1H, d), 6.814 (1H, s), 6.711-6.694 (1H, d), 6.244 (1H, s), 4.561-4.546 (2H, t) ppm.

Example 22—Preparation of Compound 18

The synthesis of Compound 18 followed the procedure of General Procedure 8 following.

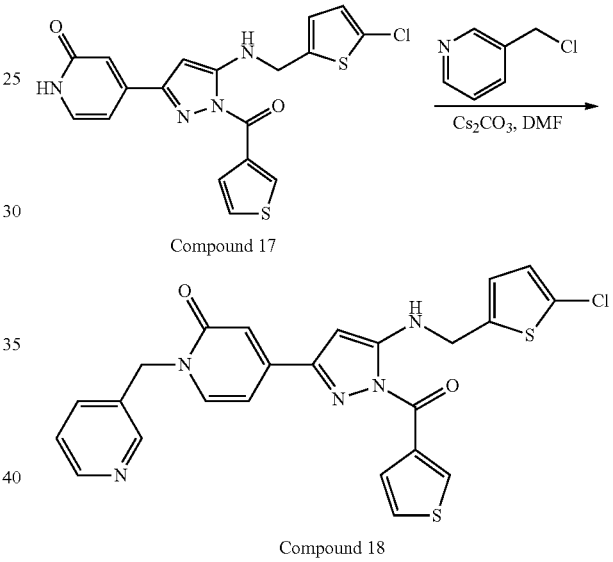

Compound 18

To a solution of Compound 17 (0.3 g, 0.721 mmol, 1.0 eq) in DMF (25.0 mL) was added anhydrous cesium carbonate (0.585 g, 1.80 mmol, 2.5 eq). The reaction was stirred for 30 minutes at room temperature. 3-(Chloromethyl)pyridine hydrochloride (0.236 g, 1.44 mmol, 1.5 eq) was added and the reaction mixture was stirred overnight at room temperature. The reaction was monitored by TLC and LCMS. After completion the reaction mass was poured into ice cold water (100 mL) under stirring and extracted with ethyl acetate (100 mL×3). The organic phase was dried over sodium sulfate and concentrated under reduced pressure. The residue was purified by preparative HPLC chromatography to yield Compound 18 (0.038 g, yield-10.4%). m/z[M+H]+ 508.83. $^1$H NMR (DMSO-d$_6$, 400 MHz) δ 9.030-9.020 (1H, d), 8.614 (1H, s), 8.523-8.510 (1H, d), 7.999-7.828 (2H, m), 7.824-7.812 (1H, m), 7.752-7.732 (1H, d), 7.700-7.679 (1H, dd), 7.423-7.390 (1H, m), 7.104-7.094 (1H, m), 6.974-6.938 (1H, dd), 6.934-6.836 (1H, d), 6.832-6.814 (1H, dd), 6.268 (1H, s), 5.181 (2H, s), 4.555-4.539 (2H, t) ppm.

Example 23—Preparation of Compound 19

The synthesis of Compound 19 followed the procedure of General Procedure 8 following.

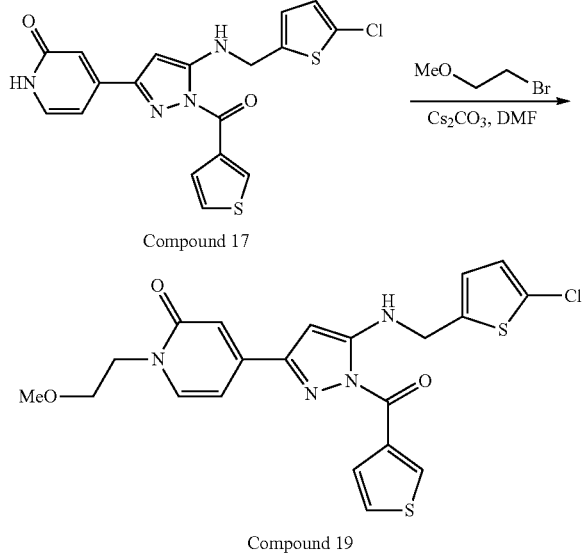

Compound 17

Compound 19

To a solution of Compound 17 (0.3 g, 0.721 mmol, 1.0 eq) in DMF (25.0 mL) was added anhydrous cesium carbonate (0.587 g, 1.80 mmol, 2.5 eq). The reaction was stirred for 30 minutes at room temperature. 2-(Bromoethyl) methyl ether (0.150 g, 1.08 mmol, 1.2 eq) was added and the reaction mixture stirred overnight at room temperature. The reaction was monitored by TLC and LCMS. After completion the reaction mixture was poured into ice cold water (80 mL) under stirring and extracted with ethyl acetate (80 mL×3). The organic phase was dried over sodium sulfate and concentrated under reduced pressure. The resultant residue was purified by column chromatography using silica gel (60-120 mesh sized), eluting with 30-40% ethyl acetate in n-hexane as mobile phase to give pure desired product. (0.090 g, yield-25.28%). m/z[M+H]+ 475.32. $^1$H NMR (DMSO-d$_6$, 400 MHz) δ 9.035-9.025 (1H, d), 7.995-7.964 (1H, t), 7.834-7.819 (1H, dd), 7.704-7.684 (2H, m), 7.111-7.102 (1H, d), 6.982-6.972 (1H, dd), 6.885-6.881 (1H, d), 6.753-6.731 (1H, dd), 6.251 (1H, s), 4.561-4.546 (2H, t), 4.097-4.071 (2H, t), 3.602-3.576 (2H, t), 3.250 (3H, s) ppm.

Example 24—Preparation of Compound 20

The synthesis of Compound 20 followed the procedure of General Procedure 8 following.

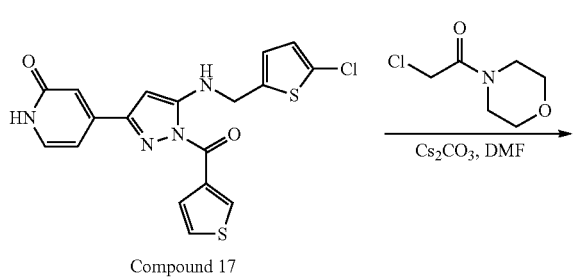

Compound 17

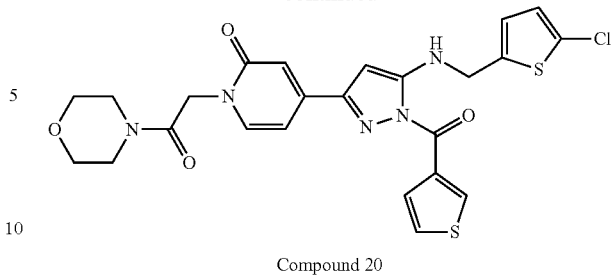

Compound 20

To a solution of Compound 17 (0.3 g, 0.721 mmol, 1.0 eq) in DMF (16.0 mL) was added anhydrous cesium carbonate (0.587 g, 1.80 mmol, 2.5 eq). The reaction mixture was stirred for 30 minutes at room temperature. 2-Chloro-1-morpholinoethan-1-one (0.176 g, 1.08 mmol, 1.2 eq) was added and the reaction mixture was stirred overnight at room temperature. The reaction was monitored by TLC and LCMS. After completion the reaction mixture was poured into ice cold water (100 mL) under stirring and extracted with ethyl acetate (100 mL×3). The organic phase was dried over sodium sulfate and concentrated under reduced pressure. The residue was purified by column chromatography using silica gel (60-120 mesh sized), eluting with 70-80% ethyl acetate in n-hexane as mobile phase to give pure desired product (0.085 g, yield-21.62%). m/z[M+H]+ 545.03. $^1$H NMR (DMSO-d$_6$, 400 MHz) δ 9.036-9.044 (1H, t), 7.968-8.00 (1H, t), 7.825-7.838 (1H, t), 7.686-7.707 (1H, m), 7.613-7.630 (1H, d), 7.109-7.118 (1H, d), 6.972-6.981 (1H, d), 6.892-6.896 (1H, d), 6.760-6.782 (1H, m), 6.276 (1H, s), 5.769 (1H, s), 4.861 (2H, s), 4.549-4.565 (2H, d), 3.653-3.663 (2H, s), 3.555-3.596 (4, m), 3.458-3.469 (2H, s) ppm.

Example 25—Preparation of Compound 21

The synthesis of Compound 21 followed the procedure of General Procedure 8 following:

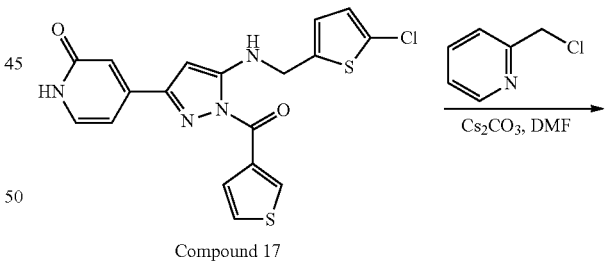

Compound 17

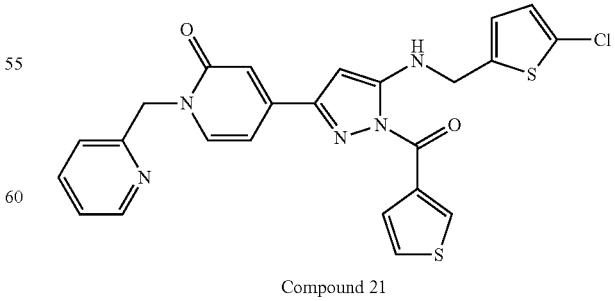

Compound 21

To a solution of Compound 17 (0.300 g, 0.721 mmol, 1.0 eq) in DMF (16.0 mL) was added anhydrous cesium carbonate (0.587 g, 1.80 mmol, 2.5 eq). The reaction mixture was stirred for 30 minutes at room temperature. 2-(Chloromethyl)pyridine hydrochloride (0.177 g, 1.08 mmole, 1.2 eq) was added and the reaction mixture was stirred overnight at room temperature. The reaction was monitored by TLC and LCMS. After completion the reaction mixture was poured into ice cold water (100 mL) under stirring and extracted with ethyl acetate (100 mL×3). The organic phase was dried over sodium sulfate and concentrated under reduced pressure. The residue was purified by column chromatography using silica gel (100-200 mesh sized), eluting with 70% ethyl acetate in n-hexane to give pure desired product (0.065 g, yield-17.75%) m/z[M+H]+ 508.62. $^1$H NMR (DMSO-d$_6$, 400 MHz) δ 9.044 (1H, s), 9.037-9.040 (1H, s), 8.502-8.514 (1H, d), 7.979-7.994 (1H, d), 7.801-7.880 (2H, m), 7.762-7.796 (1H, d), 7.685-7.705 (1H, m), 7.285-7.314 (1H, t), 7.229-7.248 (1H, d), 7.107-7.113, (1H, d), 6.955-6.979 (1H, t) 6.902-6.914 (1H, d), 6.815-6.837 (1H, m), 6.261-6.275 (1H, d), 5.216-5.230 (2H, s), 4.547-4.560 (2H, s) ppm.

Example 26—Preparation of Intermediate 5

The synthesis of Intermediate 5 followed General Procedure 1 following:

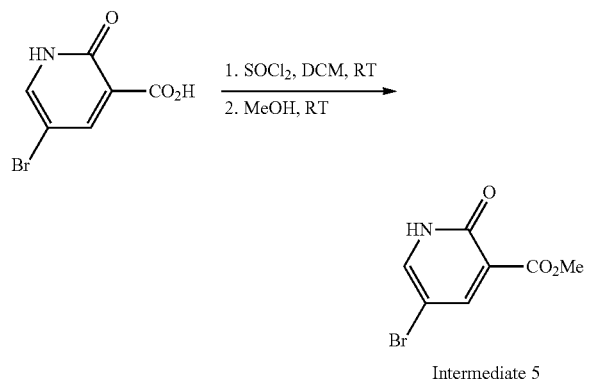

Intermediate 5

To a cold (0° C.) solution of 5-bromo-2-oxo-1,2-dihydropyridine-3-carboxylic acid (100.0 g, 0.459 mol, 1.0 eq) in dichloromethane (1 L) was added thionyl chloride (167.5 g, 4.6 mol, 10.0 eq) dropwise. After 30 min tetrahydrofuran (1 L) was added and the reaction allowed to stir for 14-15 hours at ambient temperature. The mixture was cooled back to 0° C. and to it was added methanol (500 mL) dropwise. The mixture was stirred without cooling for a further 30 minutes. After completion, the reaction mixture was concentrated under reduced pressure to obtain a solid residue, which was washed with hexane and ethyl acetate and dried under reduced pressure to give desire product (98 g, yield-81.9%) m/z 232.02 [M+H]+ $^1$H NMR (DMSO-d$_6$, 400 MHz) δ 12.43 (s, 1H), 8.08 (d, J=2.9 Hz, 1H), 7.99 (d, J=2.9 Hz, 1H), 3.75 (s, 3H) ppm.

Example 27—Preparation of Intermediate 6

The synthesis of Intermediate 6 followed General Procedure 2 following:

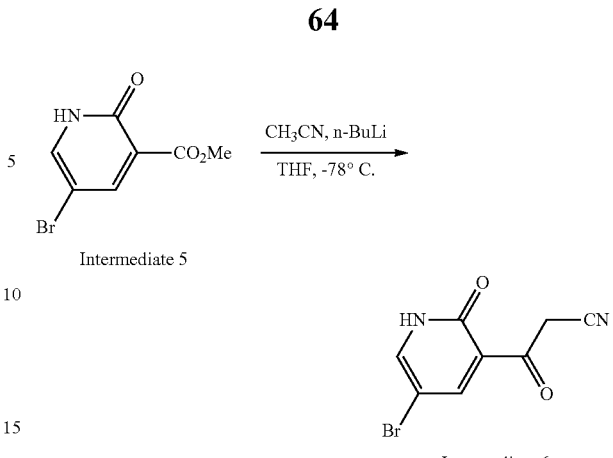

Intermediate 6

Under an atmosphere of nitrogen, acetonitrile (12.01 g, 0.293 mol, 1.7 eq) was added in tetrahydrofuran (600 mL) and the solution cooled to −78° C. A solution of $^n$BuLi (2.5M in hexane, 117 mL, 0.293 mol, 1.7 eq) was added dropwise over a period of 60 minutes and reaction was stirred for another 60 minutes. Methyl 5-bromo-2-oxo-1,2-dihydropyridine-3-carboxylate (Intermediate 5, 40 g, 0.172 mol, 1.0 eq) was added in portions to the reaction mixture at −78° C. and maintained for 3 hours, after which it was allowed to reach room temperature. The reaction mixture was direct evaporated and the residue washed with hexane (200 mL×2), followed by 20% ethyl acetate in hexane (200 mL×2). The resultant solid was dried under reduced pressure to give desired product (35 g; yield-84.33%) m/z 241.02 [M−H].

Example 28—Preparation of Compound 22

The synthesis of Compound 22 followed General Procedure 3 following:

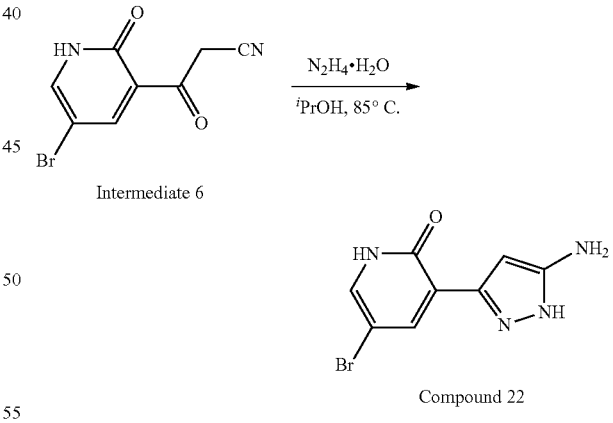

Compound 22

3-(5-Bromo-2-oxo-1,2-dihydropyridin-3-yl)-3-oxopropanenitrile (Intermediate 6, 10.0 g (0.041 mol, 1.0 eq) and acetic acid (2.49 g, 0.041 mol, 1.0 eq) were added to isopropanol (150 mL). To this was added hydrazine monohydrate (3.11 mL, 0.062 mol, 1.5 eq) dropwise. The reaction was stirred at 50-60° C. for 4-5 hours. The reaction was monitored by LC-MS, and after completion the reaction mixture was concentrated. The crude product was purified by column chromatography using neutral silica gel (60-120 mesh), eluting with 6-7% methanol in dichloromethane to give desired product (6 g, yield-57.19%) m/z 255.07

[M+H]+ ¹H NMR (DMSO-d₆, 400 MHz) δ 11.70 (s, 2H), 7.99 (d, J=2.7 Hz, 1H), 7.67 (d, J=2.6 Hz, 1H), 6.14 (s, 1H), 4.77 (s, 2H) ppm.

Example 29—Preparation of Compound 23

The synthesis of Compound 23 followed General Procedure 4 following:

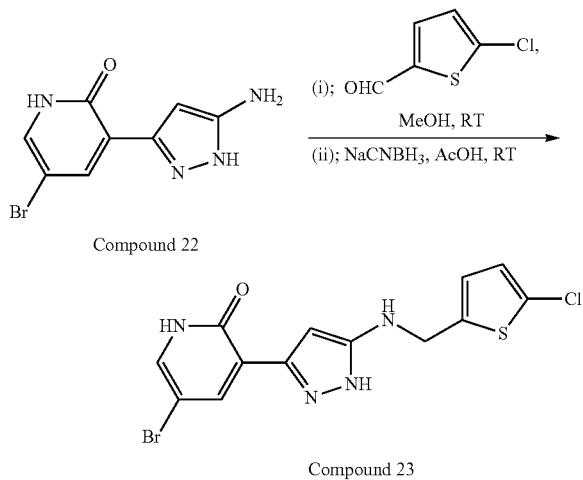

To a solution of 3-(5-amino-1H-pyrazol-3-yl)-5-bromopyridin-2(1H)-one (Compound 22, 5 g, 0.0196 mol, 1 eq) in methanol (50 mL) at 10-15° C. was added acetic acid (1.17 g, 0.0196 mol, 1 eq) dropwise, followed by the portionwise addition of 5-chlorothiophene-2-carbaldehyde (2.86 g, 0.0196 mol, 1 eq). The reaction was stirred for 4-5 hr at room temperature. Sodium cyanoborohydride (2.47 g, 0.0392 mol, 2 eq) was added portionwise at 0° C. over a period of 45 minutes, and the reaction was stirred for 2 hours. The reaction mixture was monitored by LC-MS. After completion the volatiles were distilled off and the residue was poured into ice cold water under stirring. The product was extracted with 10% methanol in dichloromethane. The organic layer was dried over sodium sulfate, then concentrated under reduced pressure. The residue was purified by column chromatography using neutral silica gel, eluting with 9% methanol in dichloromethane to give pure desired product (3.7 g, yield-62.7%) m/z[M+H]+ 387.11 ¹H NMR (DMSO-d₆, 400 MHz) δ 12.02 (m, 2H), 8.01 (d, J=2.6 Hz, 1H), 7.68 (s, 1H), 6.93 (d, J=3.7 Hz, 1H), 6.87 (d, J=3.7 Hz, 1H), 6.24 (s, 1H), 5.96 (s, 1H), 4.35 (d, J=6.3 Hz, 2H) ppm.

Example 30—Preparation of Intermediate 7

The synthesis of Intermediate 7 followed General Procedure 8 following.

General Procedure 8

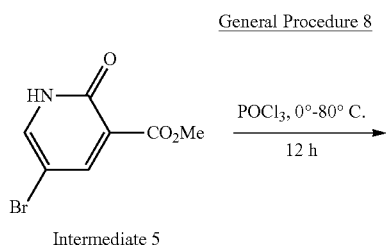

Intermediate 5

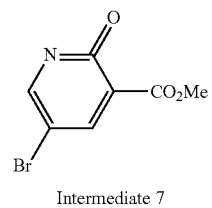

Intermediate 7

To a round-bottomed flask charged with methyl 5-bromo-2-oxo-1,2-dihydropyridine-3-carboxylate (Intermediate 5, 50.0 g, 0.2154 mol, 1.0 eq) at 0° C. under N₂ atmosphere was added POCl₃ (100 mL) dropwise. After 30 minutes the reaction mixture was warmed to 80° C. and stirred for 12-15 hours. After completion of the reaction, the reaction mixture was cooled to room temperature and poured slowly into ice cold water. It was stirred for 30 min, at which point the product precipitated out as a white solid. The solid product was filtered and vacuum dried to give desired Intermediate 7 (40.0 g, yield-94.15%). m/z 252.12 [M+2]+ ¹H NMR (DMSO-d₆, 400 MHz) δ 8.78 (d, J=2.5 Hz, 1H), 8.50 (d, J=2.5 Hz, 1H), 3.89 (s, 3H) ppm.

Example 31—Preparation of Intermediate 8

The synthesis of Intermediate 8 followed General Procedure 9 following.

General Procedure 9

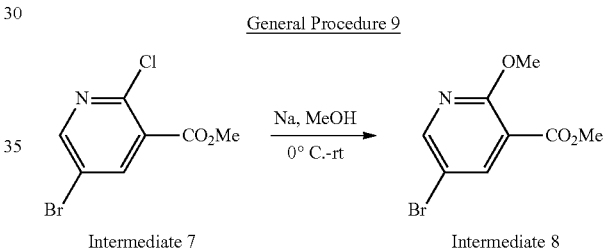

Intermediate 7                Intermediate 8

To cooled (0° C. under N₂ atmosphere) methanol (90 mL) was added sodium metal (10.3 g, 0.449 mol, 3.75 eq) in small pieces. After 30 minutes a clear solution was observed. To this solution was added methyl 5-bromo-2-chloronicotinate (Intermediate 7, 30.0 g, 0.119 mol, 1.0 eq) portionwise. After completion of addition, the reaction mixture was allowed to attain room temperature and stirred for a further 2 hours. After completion of reaction, as monitored by LC-MS, the mixture was cooled to 0° C. To the mixture was added acetic acid, until the mixture reached pH 7, and then stirred at room temperature for a further 30 minutes. The reaction mixture was poured into ice cold water under stirring, and product was extracted with ethyl acetate. The organic layer was dried over sodium sulfate and concentrated under reduced pressure. The resultant residue was purified by column chromatography using neutral silica gel, eluting with 0-6% ethyl acetate in n-hexane as mobile phase to give pure desired product (methyl 5-bromo-2-methoxynicotinate, Intermediate 8, 20.0 g, yield-67.86.7%) m/z[M+2]+ 246.17.10 ¹H NMR (DMSO-d₆, 400 MHz) δ 8.53 (d, J=2.6 Hz, 1H), 8.27 (d, J=2.6 Hz, 1H), 3.92 (s, 3H), 3.82 (s, 3H) ppm.

Example 32—Preparation of Intermediate 9

The synthesis of Intermediate 9 followed General Procedure 2 following:

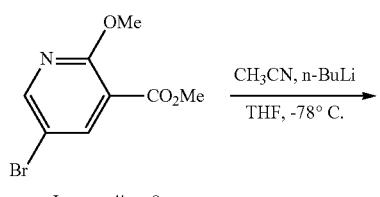

Intermediate 8

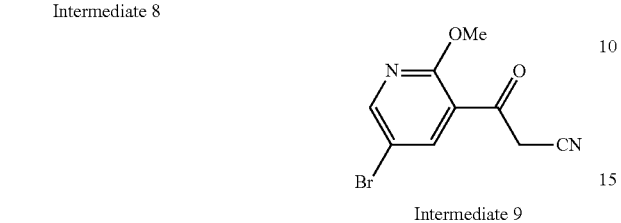

Intermediate 9

Under a nitrogen atmosphere, acetonitrile (5.7 g, 0.138 mol, 1.7 eq) was added to tetrahydrofuran (200 mL), and the solution cooled to −78° C. To this cold solution was added 2.5M $^n$BuLi (in hexane) (55.2 mL, 0.138 mol, 1.7 eq) dropwise over a period of 60 minutes and the reaction was stirred for another 60 minutes. Methyl 5-bromo-2-methoxynicotinate (Intermediate 8, 20.0 g, 0.081 mol, 1.0 eq) was added portionwise to the reaction mixture at −78° C. and stirred for a further 3 hours. The reaction was quenched with saturated ammonium chloride solution, and product was extracted with ethyl acetate. The organic layer was dried over sodium sulfate and concentrated under reduced pressure. The residue was purified by column chromatography using neutral silica gel, eluting with 0-20% ethyl acetate in n-hexane to give pure desired product (3-(5-bromo-2-methoxypyridin-3-yl)-3-oxopropanenitrile, Intermediate 9, 15.0 g (yield-86.83%) m/z[M+2]+ 257.12.).

Example 33—Preparation of Compound 24

The synthesis of compound 24 followed General Procedure 3 following:

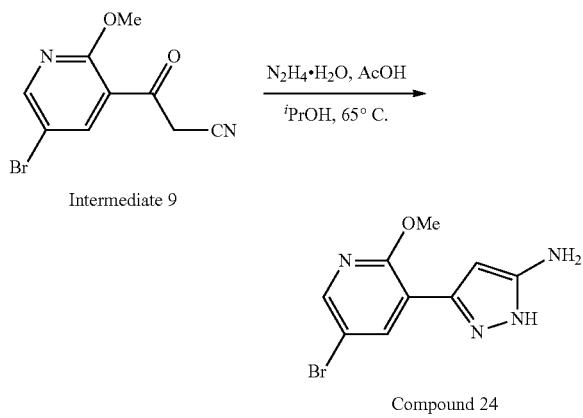

Compound 24

To a room temperature solution of 3-(5-bromo-2-methoxypyridin-3-yl)-3-oxopropanenitrile (Intermediate 9, 20.0 g, 0.0784 mol, 1.0 eq) in isopropanol (200 mL) and acetic acid (5.0 mL) was added hydrazine monohydrate (5.0 mL, 0.078 mol, 1.0 eq) dropwise. The reaction was then stirred at 65° C. for 12 hours. The reaction was monitored by LC-MS, and on completion it was concentrated under reduced pressure, and then purified by column chromatography using neutral silica gel (60-120 mesh). The crude product was eluted by using 0-80% ethyl acetate in n-hexane to give desired product (3-(5-bromo-2-methoxypyridin-3-yl)-1H-pyrazol-5-amine, Compound 24, 15.0 g, yield-71%) m/z [M+2]+ 269.18 $^1$H NMR (DMSO-d$_6$, 400 MHz) δ 11.71 (s, 1H), 8.25 (d, J=2.5 Hz, 1H), 8.21 (d, J=2.4 Hz, 1H), 5.97 (s, 1H), 4.86 (s, 2H), 3.94 (d, J=7.5 Hz, 3H) ppm.

Example 34—Preparation of Compound 25

The synthesis of compound 25 followed General Procedure 4 following:

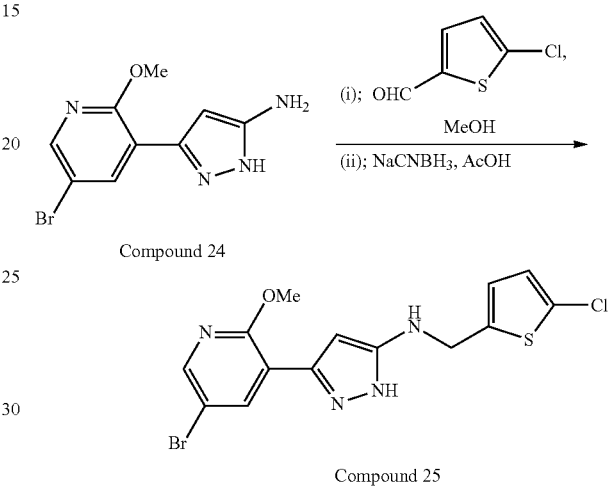

Compound 25

To a solution of 3-(5-bromo-2-methoxypyridin-3-yl)-1H-pyrazol-5-amine, (Compound 24, 10.0 g, 0.037 mol, 1.0 eq) in methanol (150 mL) at 10-15° C. was added acetic acid (5.0 mL) dropwise. To this was added 5-chlorothiophene-2-carbaldehyde (6.53 g, 0.044 mol, 1.2 eq) portionwise, and the reaction was stirred for a further 3-4 hours at room temperature. Sodium cyanoborohydride (3.5 g, 0.055 mol, 1.5 eq) was added portionwise over a period of 45 minutes, and the reaction was stirred for a further 12 hours. After completion, the reaction mixture was poured into ice cold water under stirring, and extracted with ethyl acetate. The organic layer was dried over sodium sulfate and concentrated. The residue was purified by column chromatography using neutral silica gel, eluting with 10-15% ethyl acetate in n-hexane to yield pure desired product (7.3 g, yield-47.2%) m/z[M+2]+ 401.26 $^1$H NMR (DMSO-d$_6$, 400 MHz) δ 12.04 (s, 1H), 8.25 (t, J=5.1 Hz, 2H), 6.93 (s, 1H), 6.88 (s, 1H), 6.16 (s, 1H), 5.96 (s, 1H), 4.37 (d, J=6.3 Hz, 2H), 3.96 (s, 3H) ppm.

Example 35—Preparation of Intermediate 10

The synthesis of Intermediate 10 followed General Procedure 10 following:

General Procedure 10

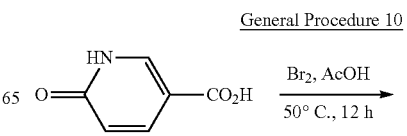

-continued

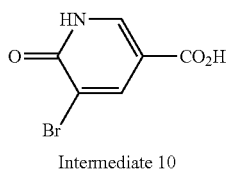

Intermediate 10

To a room temperature solution of 6-hydroxynicotinic acid (13.9 g, 0.1 mol, 1.0 eq) in acetic acid (25 mL, 0.3 mol, 3.0 eq) was added bromine (7.6 mL, 0.05 mol, 0.5 eq) dropwise. The mixture was then stirred at 60° C. for 12 hours. After completion of reaction (starting material consumed as detected by LC-MS), the reaction mixture was poured into cold water. The white precipitate was filtered off and washed with saturated sodium thiosulfate solution, and then dried under reduced pressure to give the desired product (20.0 g, yield-91%) m/z 220.11 [M+H]+ $^1$H NMR (DMSO-d$_6$, 400 MHz) δ 13.01 (s, 1H), 12.62 (s, 1H), 8.16 (d, J=2.3 Hz, 1H), 8.04 (d, J=2.2 Hz, 1H) ppm.

Example 36—Preparation of Intermediate 11

The synthesis of Intermediate 11 followed General Procedure 1 following:

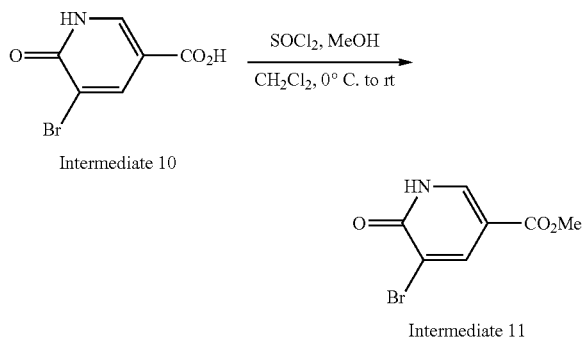

To a cold (0° C.) solution of 5-bromo-6-oxo-1,6-dihydropyridine-3-carboxylic acid (Intermediate 10, 20.0 g, 0.091 mol, 1.0 eq) in dichloromethane (200 mL) was added thionyl chloride (32 g, 3.0 eq) dropwise. After 30 minutes, tetrahydrofuran (200 mL) was added and the reaction allowed to stir for 14-15 hours at ambient temperature. The reaction mixture was cooled back to 0° C. and to it was added methanol (100 mL) dropwise. At the completion of addition, the reaction was stirred for 30 min at room temperature. After completion of reaction (monitored by means of LC-MS), the reaction mixture was concentrated under reduced pressure to obtain a solid. This was washed with hexane and ethyl acetate and then dried under reduced pressure to give the desired product (20.0 g, yield-82.3%) m/z 234.15 [M+H]+ $^1$H NMR (DMSO-d$_6$, 400 MHz) δ 12.74 (s, 1H), 8.18 (d, J=2.4 Hz, 1H), 8.10 (d, J=2.4 Hz, 1H), 3.78 (s, 3H) ppm.

Example 37—Preparation of Intermediate 12

The synthesis of Intermediate 12 followed General Procedure 8 following.

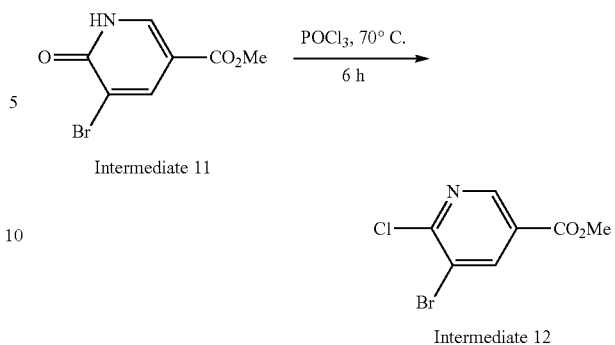

To a round-bottomed flask containing phosphorus oxychloride (57 g, 0.37 mol, 5.0 eq) was added methyl 5-bromo-6-oxo-1,6-dihydropyridine-3-carboxylate (Intermediate 11, 20.0 g, 0.074 mol, 1.0 eq). The reaction was stirred at 70° C. for 4-5 hours. After the completion of reaction, the mixture was poured on to crushed ice, and the precipitate was filtered off and neutralized using saturated sodium bicarbonate. The product was dried under reduced pressure to give desired product (Intermediate 12, 16 g, yield-85.5%) m/z 252.07 [M+H]+ $^1$H NMR (DMSO-d$_6$, 400 MHz) δ 8.94 (d, J=2.0 Hz, 1H), 8.53 (dd, J=7.5, 2.0 Hz, 1H), 3.99 (s, 3H) ppm.

Example 38—Preparation of Intermediate 13

The synthesis of Intermediate 13 followed General Procedure 11 following:

General Procedure 11

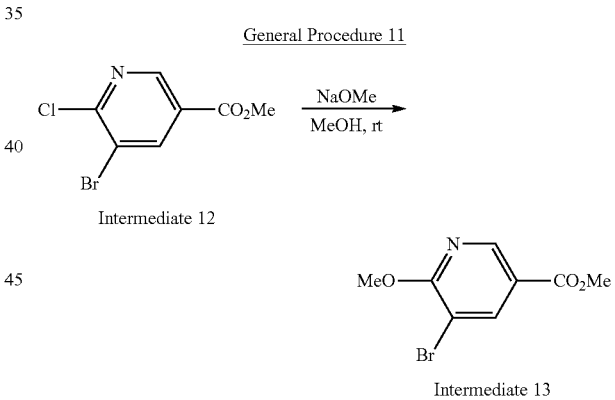

To a cold (0° C.) solution of 3-(5-amino-1H-pyrazol-3-yl)pyridine-2(1H)-one (Intermediate 11, 9.0 g, 0.036 mol, 1 eq) in methanol (25 mL) was added sodium methoxide (25% in methanol, 15.5 mL, 0.072 mol, 2 eq). The reaction was stirred for 2 hours at room temperature. After completion of reaction, the reaction mixture was evaporated under reduced pressure, and the residue was poured into ice cold water under stirring. This mixture was extracted with ethyl acetate. The organic layer was dried over sodium sulphate and concentrated under reduced pressure. The residue was purified by column chromatography using neutral silica gel, eluting with 25-30% ethyl acetate in hexane to give pure desired product (7.5 g, yield-84.74%) m/z[M+H]+ 246.17 $^1$H NMR (DMSO-d$_6$, 400 MHz) δ 8.73 (d, J=1.5 Hz, 1H), 8.41 (d, J=1.5 Hz, 1H), 4.02 (d, J=1.1 Hz, 3H), 3.86 (d, J=1.1 Hz, 3H) ppm.

Example 39—Preparation of Intermediate 14

The synthesis of Intermediate 14 followed General Procedure 2 following:

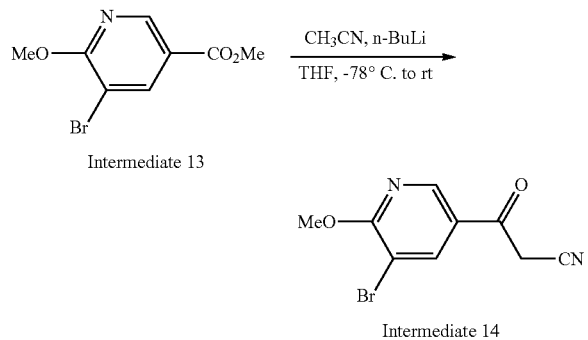

Intermediate 13

Intermediate 14

To a cooled solution (−78° C.) of acetonitrile (1.98 g, 0.048 mol, 1.7 eq) in tetrahydrofuran (70 mL) was added "BuLi (2.5M in hexane, 19 mL, 0.048 mol, 1.7 eq) dropwise over a period of 60 minutes. The reaction was stirred thereafter for another 60 minutes. To this was added methyl 5-bromo-6-methoxynicotinate (Intermediate 13, 7 g, 0.027 mol, 1.0 eq) portionwise, and the reaction mixture maintained at −78° C. for 3 hours. The reaction mixture was quenched with ammonium chloride solution and extracted with ethyl acetate. The organic phase was dried over sodium sulfate and concentrated under reduced pressure. The residue was purified by column chromatography using neutral silica gel, eluting with 45-50% ethyl acetate in hexanes to give pure desired product (6 g, yield-82.75%) m/z[M+H]+ 255.21 $^1$H NMR (DMSO-$d_6$, 400 MHz) δ 8.40 (d, J=1.9 Hz, 1H), 8.20 (d, J=1.9 Hz, 1H), 3.91 (s, 3H), 3.17 (s, 2H) ppm.

Example 40—Preparation of Compound 26

The synthesis of compound 26 followed General Procedure 3 following:

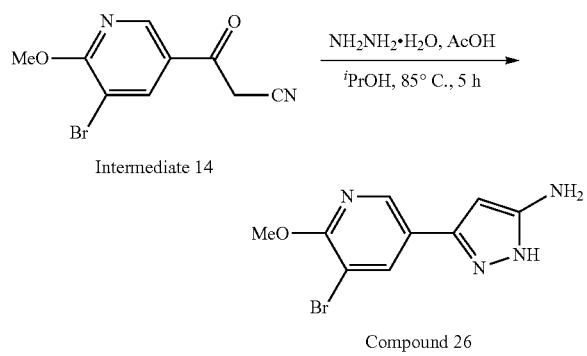

Intermediate 14

Compound 26

To a room temperature solution of 3-(5-bromo-6-methoxypyridin-3-yl)-3-oxopropanenitrile (Intermediate 14, 6.0 g, 0.023 mol, 1.0 eq) in isopropanol (60 mL) and acetic acid (1.41 g, 0.023 mol, 1.0 eq) was added hydrazine monohydrate (1.76 g, 0.035 mol, 1.5 eq) dropwise. The reaction was stirred at 85° C. for 4-5 hours. After reaction completion, the mixture was concentrated. The residue was purified by column chromatography using neutral silica gel (60-120 mesh), eluting with 70-75% ethyl acetate in hexane to give desired product (6 g, yield-95%) m/z 271.18 [M+H]+ $^1$H NMR (DMSO-$d_6$, 400 MHz) δ 8.45 (d, J=2.1 Hz, 1H), 8.26 (d, J=2.0 Hz, 1H), 5.74 (s, 1H), 5.17 (s, 2H), 3.94 (s, 3H) ppm.

Example 41—Preparation of Compound 27

The synthesis of compound 27 followed General Procedure 4 following:

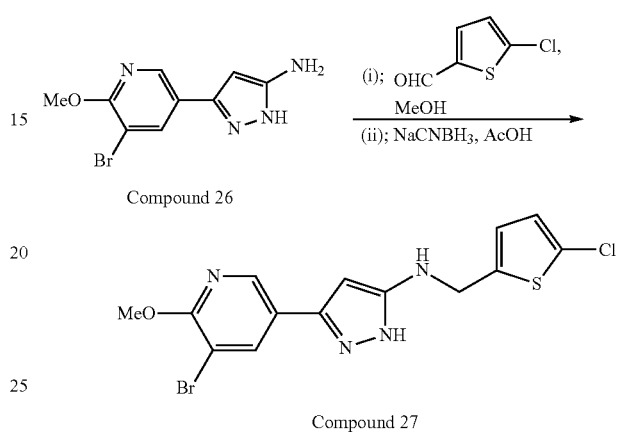

Compound 26

Compound 27

To a cold solution (10-15° C.) of 3-(5-bromo-6-methoxypyridin-3-yl)-1H-pyrazol-5-amine (Compound 26, 6 g, 0.023 mol, 1 eq) in methanol (60 mL) was added acetic acid (1.41 g, 0.023 mol, 1 eq) dropwise. To this was then added 5-chlorothiophene-2-carbaldehyde (3.43 g, 0.023 mol, 1 eq) portionwise, and the reaction then stirred for 2-3 hours at room temperature. The mixture was then cooled back to 0° C., sodium cyanoborohydride (2.96 g, 0.047 mol, 2 eq) was then added portionwise over 45 minutes, and the reaction was stirred at room temperature for 2 hours. The reaction was monitored by LCMS. After completion the reaction mixture was evaporated and the residue was poured into ice cold water under stirring. The product was extracted with ethyl acetate. The organic layer was dried over sodium sulfate and concentrated under reduced pressure. The residue was purified by column chromatography using neutral silica gel eluting with 50-55% ethyl acetate in hexanes to give pure desired product (6.2 g, yield-65.95%) m/z[M+H]+ 401.26 $^1$H NMR (DMSO-$d_6$, 400 MHz) δ 12.05 (s, 1H), 8.48 (d, J=2.1 Hz, 1H), 8.30 (d, J=2.0 Hz, 1H), 6.93 (d, J=3.7 Hz, 1H), 6.90 (d, J=3.7 Hz, 1H), 6.07 (s, 1H), 5.97 (s, 1H), 4.36 (d, J=6.2 Hz, 2H), 3.94 (s, 3H) ppm.

Example 42—Preparation of Intermediate 15

The synthesis of intermediate 15 followed General Procedure 12 following:

General Procedure 12

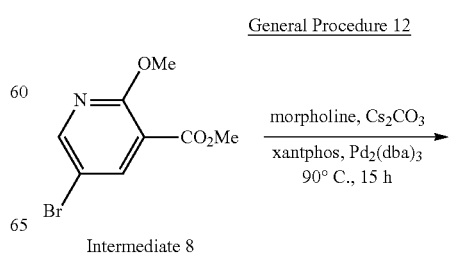

Intermediate 8

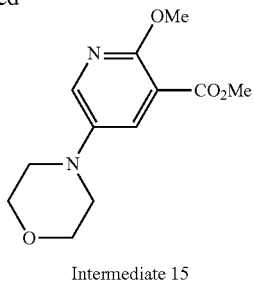

Intermediate 15

Methyl 5-bromo-2-methoxynicotinate (Intermediate 8, 10 g, 0.040 mol, 1.0 eq), morpholine (7.07 g, 0.081 mol, 2.0 eq) and Cs$_2$CO$_3$ (26.4 g, 0.081 mol, 2.0 eq) were dissolved in dioxane (100 mL) at room temperature. The reaction mixture was degassed using N$_2$ for 15 min. To the mixture was then added 4,5-bis(diphenylphosphino)-9,9-dimethylxanthene (xantphos, 1.1 g, 0.002 mol, 0.05 eq) and tris(dibenzylideneacetone)dipalladium(0) (Pd$_2$(dba)$_3$, 1.8 g, 0.002 mol, 0.05 eq) at room temperature. The reaction mixture was stirred at 90° C. for 15 h. After cooling, the reaction mixture was partitioned between EtOAc and water. The organic layer was combined and dried over sodium sulfate (Na$_2$SO$_4$). Solvent was removed under vacuum. Crude product was purified by column chromatography (normal phase silica, using gradient of 0 to 25% EtOAc in Hexane) to give 3.0 g of methyl 2-methoxy-5-morpholinonicotinate (dark green gum). Yield: 29.26%. m/z[M+2]+ 253.41 $^1$H NMR (DMSO-d$_6$, 400 MHz) δ 8.53 (d, J=2.6 Hz, 1H), 8.27 (d, J=2.6 Hz, 1H), 3.92 (s, 3H), 3.82 (s, 3H), 3.741 (m, 4H), 3.072 (m, 4H) ppm.

Example 43—Preparation of Intermediate 16

The synthesis of intermediate 16 followed General Procedure 2 following:

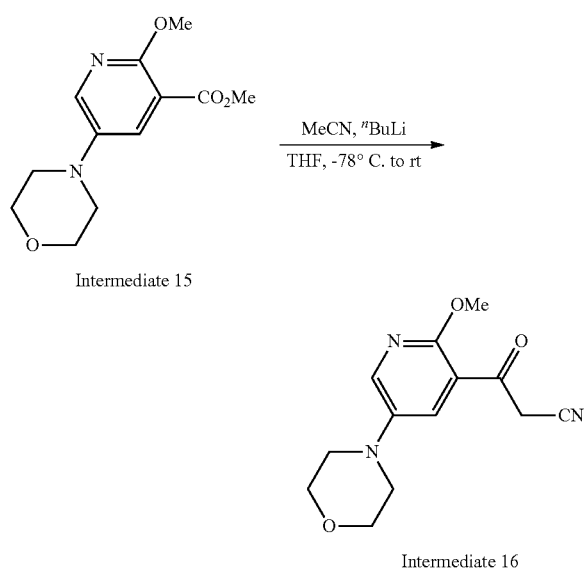

In dry atmosphere with N$_2$ gas flow, acetonitrile (0.828 g, 0.020 mol, 1.7 eq) was added to tetrahydrofuran (30 mL) and the mixture cooled to −78° C. To this was added $^n$BuLi (2.5 M in hexane, 8.3 mL, 0.020 mol, 1.7 eq) dropwise over a period of 60 minutes, and reaction was then stirred for another 60 minutes. Methyl 2-methoxy-5-morpholinonicotinate (Intermediate 15, 3.0 g, 0.011 mol, 1.0 eq) was added in portions to the reaction mixture and the reaction mixture was stirred at −78° C. for 3 hrs. The reaction was quenched with saturated ammonium chloride solution and product was extracted with ethyl acetate. The organic phase was dried over sodium sulfate and concentrated under reduced pressure. The residue was purified by column chromatography using (60-120 mesh size) silica gel, eluting with 0-40% ethyl acetate in n-hexane as mobile phase to yield pure desired product 3-(2-methoxy-5-morpholinopyridin-3-yl)-3-oxopropanenitrile (Intermediate 16, 2.5 g, yield-80.64%) m/z [M+2]+ 262.20 $^1$H NMR (DMSO-d$_6$, 400 MHz) δ 8.19 (d, J=3.1 Hz, 1H), 7.72 (d, J=3.1 Hz, 1H), 4.56 (s, 2H), 3.94 (s, 3H), 3.76-3.73 (m, 4H), 3.18-2.95 (m, 4H) ppm.

Example 44—Preparation of Compound 28

The synthesis of compound 28 followed General Procedure 3 following:

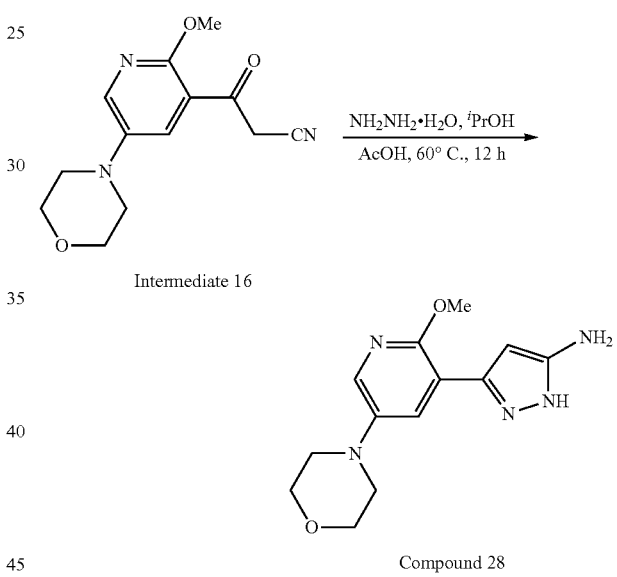

To a solution of 3-(2-methoxy-5-morpholinopyridin-3-yl)-3-oxopropanenitrile (Intermediate 16, 2.5 g, 0.0095 mol, 1.0 eq) in isopropanol (25 mL) and acetic acid (0.5 mL) was added hydrazine monohydrate (380 mg, (0.009 mol, 1.0 eq) dropwise. The reaction was stirred at 65° C. for 12 hours. After reaction completion (monitored by LC-MS), the mixture was concentrated. The residue was purified by column chromatography using silica gel (60-120 mesh), eluting with 0-100% ethyl acetate in n-hexane as gradient to give desired product 3-(2-methoxy-5-morpholinopyridin-3-yl)-1H-pyrazol-5-amine (Compound 28, 1.6 g, yield-60.83%) m/z 276.48 [M+2]+ $^1$H NMR (DMSO-d$_6$, 400 MHz) δ 11.70 (s, 1H), 7.76 (d, J=2.8 Hz, 2H), 5.99 (s, 1H), 4.69 (s, 2H), 3.91 (d, J=11.5 Hz, 3H), 3.79-3.74 (m, 4H), 3.11-3.04 (m, 4H) ppm.

Example 45—Preparation of Compound 29

The synthesis of compound 29 followed General Procedure 13 following:

General Procedure 13

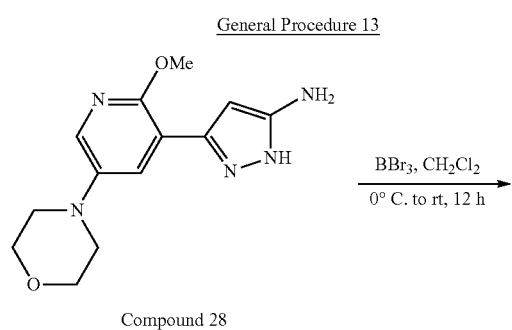

Compound 28

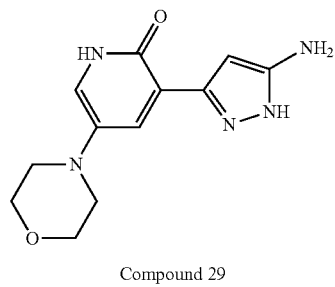

Compound 29

To a solution of 3-(2-methoxy-5-morpholinopyridin-3-yl)-1H-pyrazol-5-amine (compound 28, 1.4 g, 0.005 mol, 1.0 eq) in dry dichloromethane (140 mL) was added BBr$_3$ (6.6 mL, 0.006 mol, 1.3 eq) dropwise at 0° C. The mixture was allowed to reach room temperature over 30 minutes, and was stirred for a further 12 hours at room temperature. After reaction completion, methanol (10 mL) was added and solvents evaporated under reduced pressure. The residue was purified by column chromatography using neutral silica gel, eluting with 10-15% methanol in dichloromethane as mobile phase, yielding desired product 3-(5-amino-1H-pyrazol-3-yl)-5-morpholinopyridin-2(1H)-one (Compound 29, 800 mg, yield-60.60%) m/z[M+2]+ 262.23 $^1$H NMR (DMSO-d$_6$, 400 MHz) δ 11.72 (s, 2H), 7.87 (d, J=3.0 Hz, 1H), 6.81 (s, 1H), 6.16 (s, 1H), 4.65 (s, 2H), 3.75-3.67 (m, 4H), 2.93-2.85 (m, 4H) ppm.

Example 46—Preparation of Compound 30

The synthesis of Compound 30 followed General Procedure 4 following:

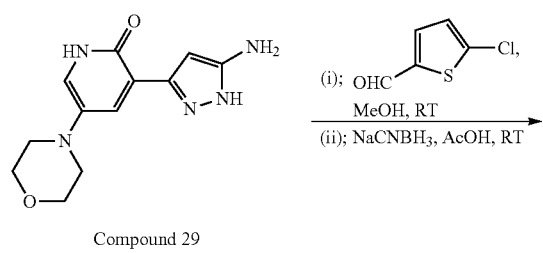

Compound 29

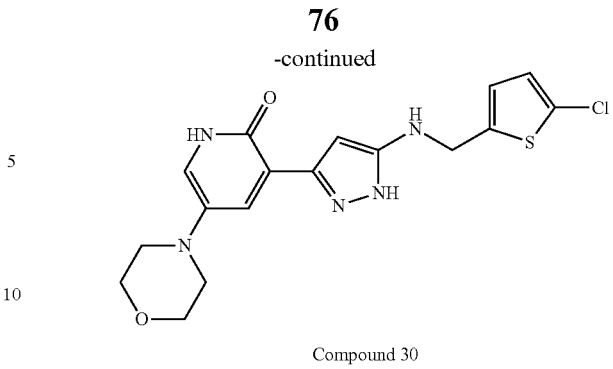

Compound 30

To a cooled solution (10-15° C.) of 3-(5-amino-1H-pyrazol-3-yl)-5-morpholinopyridin-2(1H)-one (compound 29, 0.8 g, 0.0030 mol, 1.0 eq) in methanol (20 mL) was added acetic acid (0.5 mL) dropwise. To this was added 5-chlorothiophene-2-carbaldehyde (0.537 g, 0.0036 mol, 1.2 eq) portionwise. The reaction was stirred for 30-45 minutes at room temperature. Sodium cyanoborohydride (0.460 g, 0.0073 mol, 2.0 eq) was added portionwise over a period of 15 minutes. The reaction mixture was stirred for 12 hours. After reaction completion, the mixture was poured into ice cold water under stirring and extracted with ethyl acetate. The organic phase was dried over sodium sulfate and concentrated under reduced pressure. The residue was purified by column chromatography using silica gel, eluting with 2%-7% methanol in dichloromethane to yield product 3-(5-(((5-chlorothiophen-2-yl)methyl)amino)-1H-pyrazol-3-yl)-5-morpholinopyridin-2(1H)-one (Compound 30, 1.1 g, yield-91.7%) m/z[M+2]+ 392.56 $^1$H NMR (DMSO-d$_6$, 400 MHz) δ 12.17-11.71 (m, 2H), 7.93 (d, J=2.9 Hz, 1H), 6.94 (d, J=3.7 Hz, 1H), 6.88 (d, J=3.8 Hz, 1H), 6.85 (s, 1H), 6.31 (s, 1H), 4.38 (s, 2H), 3.82-3.65 (m, 4H), 2.98-2.82 (m, 4H) ppm.

Example 47—Preparation of Compound 31

The synthesis of compound 31 followed General Procedure 6 following:

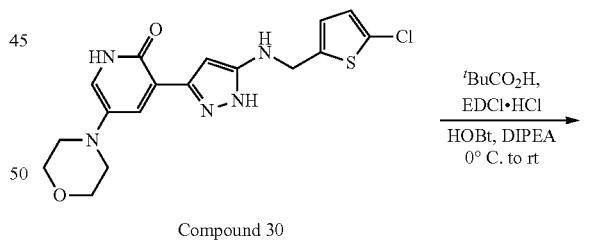

Compound 30

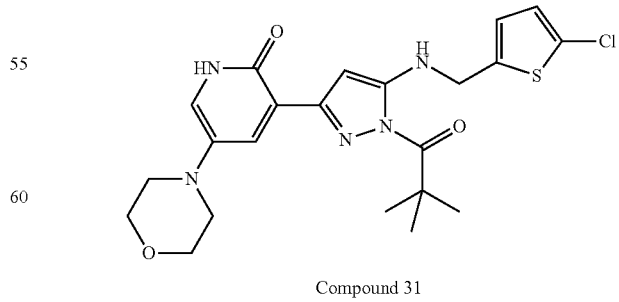

Compound 31

To a cold solution (0° C.) of pivalic acid (0.031 g, 0.0003 mol, 1.2 eq) in THF (3 mL) under nitrogen was added EDCI.HCl (0.031 g, 0.0003 mol, 1.2 eq) and DIPEA (0.077 g, 0.0008 mol, 3.0 eq). The reaction mixture was stirred for 30 minutes, followed by the addition of HOBt (0.006 g, 0.00005 mol, 0.2 eq) and 3-(5-(((5-chlorothiophen-2-yl)methyl) amino)-1H-pyrazol-3-yl)-5-morpholinopyridin-2 (1H)-one (Compound 30, 0.1 g, 0.00026 mol, 1.0 eq). The reaction mixture was stirred for 12 hours at room temperature. After reaction completion (monitored by LC-MS), the mixture was poured into water (10 mL) and extracted with ethyl acetate (3×25 mL). The combined organic layers were washed with water, brine, dried over sodium sulfate and evaporated under reduced pressure. The residue was purified by preparative HPLC using water-ACN as mobile phase to give the desired product 3-(5-(((5-chlorothiophen-2-yl)methyl)amino)-1-pivaloyl-1H-pyrazol-3-yl)-5-morpholinopyridin-2(1H)-one (Compound 31, 0.040 g, yield-32.93%) m/z 476.5 [M+1]+ $^1$H NMR (400 MHz, DMSO) δ 11.66 (s, 1H), 7.94 (d, J=3.2 Hz, 1H), 7.76 (t, J=6.3 Hz, 1H), 6.97-6.93 (m, 3H), 6.22 (s, 1H), 4.48 (d, J=6.1 Hz, 2H), 3.79-3.66 (m, 4H), 2.98-2.74 (m, 4H), 1.47 (s, 9H) ppm.

Example 48—Preparation of Compound 32

The synthesis of Compound 32 followed General Procedure 14 following:

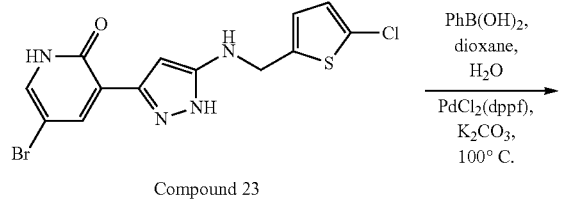

To a solution of 5-bromo-3-(5-(((5-chlorothiophen-2-yl)methyl)amino)-1H-pyrazol-3-yl)pyridin-2(1H)-one (Compound 23, 0.5 g, 1.29 mmol, 1.0 eq) and phenylboronic acid (0.19 g, 1.55 mmol, 1.0 eq) in dioxane: water (5:1, 10 mL) was added potassium carbonate (0.358 g, 2.59 mmol, 2.0 eq). The reaction was then degassed under nitrogen for 30 minutes. To this was then added 1,1'-bis(diphenylphosphino)ferrocene palladium(II) dichloride (0.094 g, 0.129 mmol, 0.1 eq), and the mixture was stirred at 100° C. for 5-6 hours. After reaction completion, the mixture was diluted with water and extract with dichloromethane (25 mL×3). The organic phases were dried over sodium sulfate and concentrated under reduced pressure. The residue was purified by column chromatography using neutral silica gel (100-200 mesh), eluting with 4-5% methanol in dichloromethane as gradient to give pure desired product (Compound 32, 300 mg, yield-62%) m/z 383.31 [M+H]+ $^1$H NMR (400 MHz, DMSO-d$_6$) δ 12.23 (s, 1H), 12.00 (s, 1H), 8.27 (d, J=2.5 Hz, 1H), 7.74 (s, 1H), 7.66 (d, J=7.4 Hz, 2H), 7.43 (dd, J=16.8, 8.9 Hz, 2H), 7.32 (t, J=7.3 Hz, 1H), 6.92 (dd, J=9.8, 7.2 Hz, 1H), 6.91-6.81 (m, 1H), 6.32 (d, J=6.3 Hz, 1H), 5.90 (s, 1H), 4.36 (t, J=7.3 Hz, 2H) ppm.

Example 49—Preparation of Compound 33

The synthesis of Compound 33 followed General Procedure 5 following:

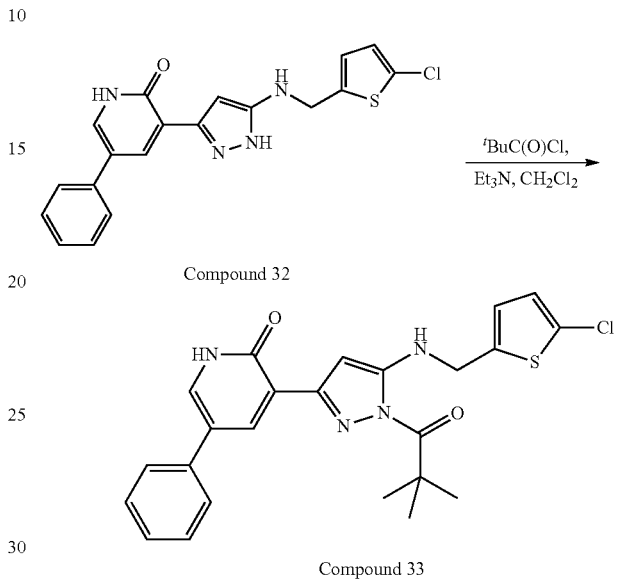

To a cold solution (0° C.) of 3-(5-(((5-chlorothiophen-2-yl)methyl)amino)-1H-pyrazol-3-yl)-5-phenylpyridin-2 (1H)-one (Compound 32, 0.2 g, 0.52 mmol, 1 eq) in dichloromethane (5 mL) was added triethylamine (TEA, 0.157 g, 1.56 mmol, 3 eq), followed by pivaloyl chloride (0.062 g, 0.52 mmol, 1 eq). The reaction mixture was stirred at room temperature for 12 hours. After completion, the reaction mixture was diluted with water and extracted with ethyl acetate (25 mL×3). The organic phase were dried over sodium sulfate and concentrated under reduced pressure. The residue was purified by Combi-flash chromatography, eluting with 0 to 60% ethyl acetate in hexane, to yield desired product (Compound 33, 40 mg, yield-19.20%) m/z 467.52 [M+H]+ $^1$H NMR (DMSO-d$_6$, 400 MHz) δ 12.21 (s, 1H), 8.35 (d, J=2.8 Hz, 1H), 7.78 (dd, J=11.7, 5.4 Hz, 2H), 7.56 (d, J=8.0 Hz, 2H), 7.46 (t, J=7.7 Hz, 2H), 7.33 (t, J=7.3 Hz, 1H), 6.97 (dd, J=11.3, 3.7 Hz, 2H), 6.25 (s, 1H), 4.50 (d, J=6.2 Hz, 2H), 1.48 (s, 9H) ppm.

Example 50—Preparation of Compound 34

The synthesis of Compound 34 followed General Procedure 15 following:

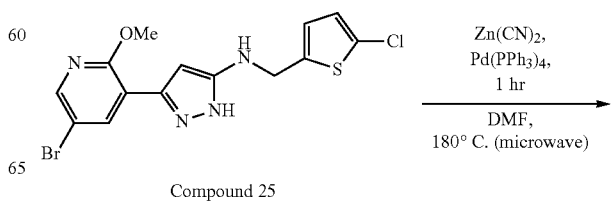

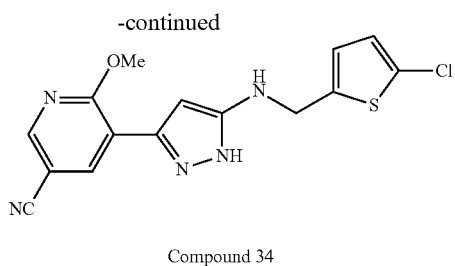

Compound 34

To a solution of 3-(5-bromo-2-methoxypyridin-3-yl)-N-((5-chlorothiophen-2-yl)methyl)-1H-pyrazol-5-amine (Compound 25, 1.0 g, 0.0025 mol, 1.0 eq) in DMF (500 mL) was added zinc cyanide (0.308 g, 0.0026 mol, 1.05 eq). The reaction mixture was degassed for 10 minutes, followed by the addition of tetrakis(triphenylphosphine)palladium(0) (Pd(PPh$_3$)$_4$, 0.436 g (0.00037 mol, 0.15 eq). The reaction mixture was again degassed for 10 minutes, and then heated under microwave irradiation for 1 hour. After completion, (monitored by LC-MS), the reaction mixture was poured into water (10 mL) and extracted with ethyl acetate (2×30 mL). The combined organic phases were washed with water, followed by brine, which was then dried over sodium sulfate and evaporated under reduced pressure. The residue was purified by column chromatography using 60-120 mesh size silica gel, eluting with 0-40% ethyl acetate in n-hexane, to give desired product 5-(5-(((5-chlorothiophen-2-yl)methyl)amino)-1H-pyrazol-3-yl)-6-methoxynicotinonitrile (Compound 34, 0.410 g, yield-47.1%) m/z 346.4 [M+1]+ $^1$H NMR (400 MHz, DMSO-d$_6$) δ 12.08 (s, 1H), 8.63 (s, 1H), 8.48 (s, 1H), 6.93 (s, 1H), 6.89 (s, 1H), 6.18 (s, 1H), 6.01 (s, 1H), 4.38 (d, J=6.2 Hz, 2H), 4.05 (s, 3H) ppm.

Example 51—Preparation of Compound 35

The synthesis of Compound 35 followed General Procedure 16 following:

General Procedure 16

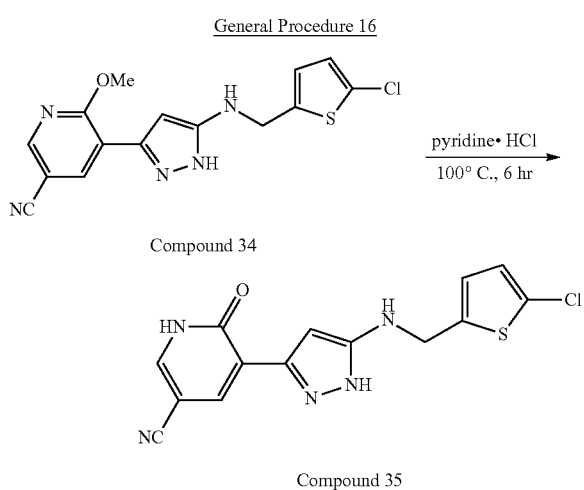

To a sealed tube was added 5-(5-(((5-chlorothiophen-2-yl)methyl)amino)-1H-pyrazol-3-yl)-6-methoxynicotinonitrile (Compound 34, 0.3 g, 0.0009 mol, 1.0 eq) and then pyridine hydrochloride (1.0 g, 0.0026 mol, 3.0 eq). The tube was sealed and heated to 100° C. for 6 hrs. After completion (monitored by LC-MS), the reaction mixture was poured into saturated NaHCO$_3$ (8 mL) and extracted with ethyl acetate. The combined organic phases were washed with water, followed by brine, dried over sodium sulfate and evaporated under reduced pressure. The residue was purified by column chromatography using (60-120 mesh size) silica gel, eluting with 0-5% MeOH in dichloromethane to give desired product 5-(5-(((5-chlorothiophen-2-yl)methyl)amino)-1H-pyrazol-3-yl)-6-oxo-1,6-dihydropyridine-3-carbonitrile (Compound 35, 0.14 g, yield-55.58%) m/z 332.4 [M+1]+ $^1$H NMR (400 MHz, DMSO) δ 12.93 (s, 2H), 8.37 (s, 1H), 8.26 (s, 1H), 6.96 (d, J=3.8 Hz, 1H), 6.92 (d, J=3.8 Hz, 1H), 6.37 (s, 1H), 4.43 (s, 2H) ppm.

Example 52—Preparation of Compound 36

The synthesis of Compound 36 followed General Procedure 6 following:

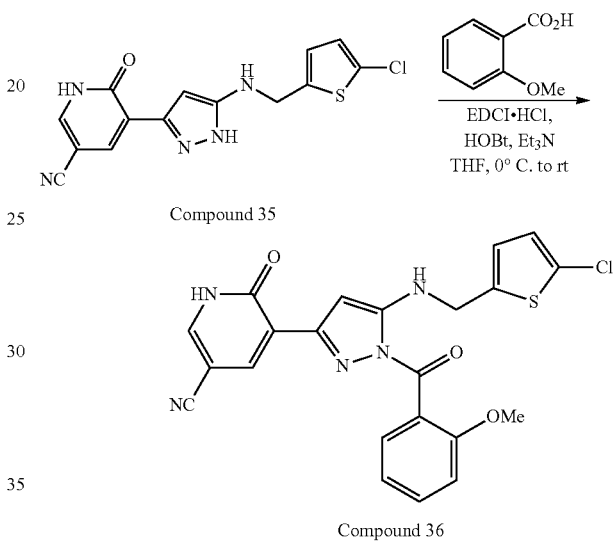

Compound 36

To a cold solution (0° C.) of o-anisic acid (0.077 g, 0.0005 mol, 1.2 eq) in THF (10 mL) was added EDCI.HCl (0.097 g, 0.0005 mol, 1.2 eq), followed by triethylamine (TEA, 0.129 g, 0.0013 mol, 3.0 eq) under nitrogen. The reaction mixture was stirred for 30 minutes, and to it was added HOBt (0.011 g, 0.00008 mol, 0.2 eq), followed by 5-(5-(((5-chlorothiophen-2-yl)methyl)amino)-1H-pyrazol-3-yl)-6-oxo-1,6-dihydropyridine-3-carbonitrile (Compound 35). The reaction mixture was stirred at room temperature for 14 hours. After completion (monitored by LC-MS), reaction mixture was poured into water (5 mL) and extracted with ethyl acetate (3×30 mL). The combined organic phases were washed with water, followed by brine, and then dried over sodium sulfate. Evaporation under reduced pressure gave a residue, which was purified by preparative HPLC using Water-ACN as mobile phase to give the desired product 5-(5-(((5-chlorothiophen-2-yl)methyl)amino)-1-(2-methoxybenzoyl)-1H-pyrazol-3-yl)-6-oxo-1,6-dihydropyridine-3-carbonitrile (Compound 36, 0.035 g, yield-17.8%) m/z 466.66 [M+1]+ $^1$H NMR (400 MHz, DMSO) δ 12.74 (s, 1H), 8.31 (d, J=2.5 Hz, 1H), 7.80 (t, J=6.2 Hz, 1H), 7.70 (s, 1H), 7.59-7.49 (m, 1H), 7.44 (dd, J=7.5, 1.6 Hz, 1H), 7.19 (d, J=8.4 Hz, 1H), 7.05 (dd, J=15.8, 8.5 Hz, 1H), 7.00 (d, J=3.8 Hz, 2H), 6.20 (s, 1H), 4.55 (d, J=6.0 Hz, 2H), 3.76 (s, 3H) ppm.

Example 53—Preparation of Intermediate 17

The synthesis of Intermediate 17 followed General Procedure 14 following:

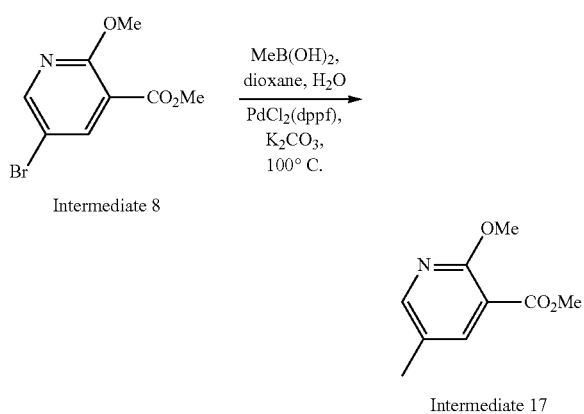

Intermediate 8

Intermediate 17

To a solution of methyl 5-bromo-2-methoxynicotinate (Intermediate 8, 5.0 g, 0.02 mol, 1.0 eq) in dioxane:water (3:1; 80 mL) was added methylboronic acid (1.82 g, 0.03 mol, 1.5 eq), followed by potassium carbonate (8.42 g, 0.06 mol, 3 eq). The reaction mixture was degassed for 10 minutes, followed by the addition of 1,1'-bis(diphenylphosphino)ferrocene palladium(II) dichloride (PdCl$_2$(dppf); 1.48 g, 0.002 mol, 0.1 eq). The reaction mixture was again degassed for 10 minutes, and then stirred at 100° C. for 3 hours. After completion, monitored by LC-MS, the reaction mixture was cooled and diluted with water (100 mL). The mixture was extracted with ethyl acetate (2×60 mL), and the combined organic phases were washed with brine, dried over sodium sulfate and evaporated under reduced pressure. The residue was purified by column chromatography using silica gel (60-120 mesh size), eluting with 5-20% ethyl acetate in n-hexane as mobile phase to give pure desired product methyl 2-methoxy-5-methylnicotinate (1.92 g; Intermediate 17; yield-52.1%) m/z 182.19 [M+1]+ 1H NMR (400 MHz, DMSO) δ 8.20 (dd, J=2.4, 0.7 Hz, 1H), 7.96 (dd, J=2.4, 0.7 Hz, 1H), 3.88 (s, 3H), 3.81 (s, 3H), 2.24 (s, 3H) ppm.

Example 54—Preparation of Intermediate 18

The synthesis of Intermediate 18 followed General Procedure 2 following:

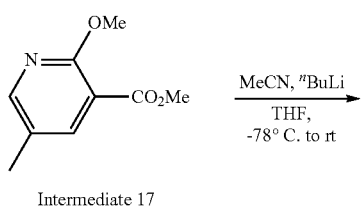

Intermediate 17

Intermediate 18

To a dry (N$_2$ gas flow) and cooled solution (−78° C.) of acetonitrile (0.883 g, 0.022 mol, 1.5 eq) in tetrahydrofuran (30 mL) was added $^n$BuLi (2.5M in hexane, 8.6 mL, 0.022 mol, 1.5 eq) dropwise over a period of 20 minutes. The reaction was stirred for a further 60 minutes. Methyl 2-methoxy-5-methylnicotinate (Intermediate 17, 2.6 g, 0.014 mol, 1.0 eq) was added portionwise and the reaction mixture maintained at −78° C. for 3 hrs. The reaction mixture was quenched with saturated ammonium chloride solution, and extracted with ethyl acetate. The organic layer was dried over sodium sulfate and concentrated under reduced pressure. The residue was purified by column chromatography using silica gel (60-120 mesh size), eluting with 10-40% ethyl acetate in n-hexane as mobile phase, to give pure desired product 3-(2-methoxy-5-methylpyridin-3-yl)-3-oxopropanenitrile (Intermediate 18, 2.05 g, yield-75.1%) m/z 191.19 [M+1]+ $^1$H NMR (400 MHz, CDCl3) δ 8.23 (t, J=4.4 Hz, 1H), 8.05 (dd, J=2.5, 0.5 Hz, 1H), 4.16 (s, 2H), 4.09 (s, 3H), 2.32 (s, 3H) ppm.

Example 55—Preparation of Compound 37

The synthesis of compound 37 followed General Procedure 3 following:

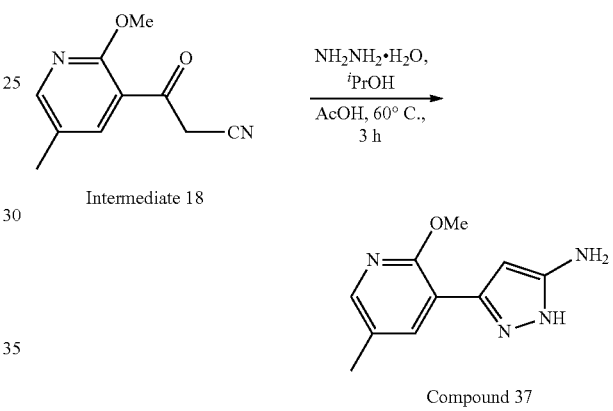

Intermediate 18

Compound 37

To a solution of 3-(2-methoxy-5-morpholinopyridin-3-yl)-3-oxopropanenitrile (Intermediate 18, 2.0 g, 0.011 mol, 1.0 eq) in isopropanol (10 mL) and acetic acid (0.2 mL) was added hydrazine monohydrate (0.789 g, 0.016 mol, 1.5 eq) dropwise. The reaction was stirred at 60° C. for 3 hours. The reaction mixture was monitored by LC-MS, and after completion was concentrated under reduced pressure. The residue was purified by column chromatography using silica gel (60-120 mesh), eluting with 0-5% methanol in dichloromethane, to give desired product 3-(2-methoxy-5-methylpyridin-3-yl)-1H-pyrazol-5-amine (Compound 37, 2.01 g, yield-93.6%) m/z 205.54 [M+1]+ $^1$H NMR (400 MHz, DMSO) δ 11.28 (s, 1H), 7.92-7.90 (m, 2H), 5.93 (s, 1H), 4.72 (s, 2H), 3.91 (s, 3H), 2.24 (s, 3H) ppm.

Example 56—Preparation of Compound 38

The synthesis of compound 38 followed General Procedure 16 following:

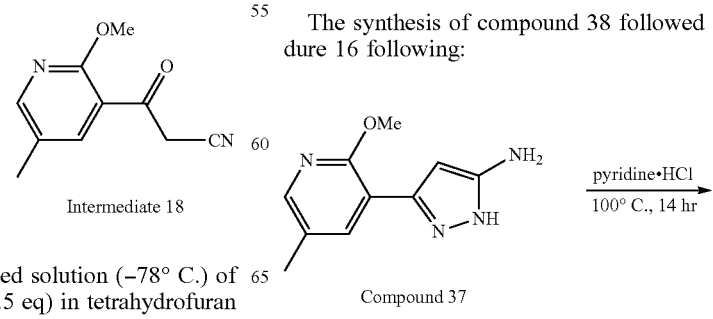

Compound 37

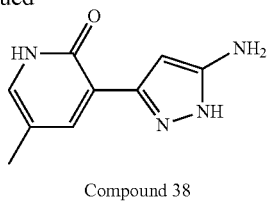

Compound 38

A mixture of 3-(2-methoxy-5-methylpyridin-3-yl)-1H-pyrazol-5-amine (Compound 37, 0.5 g, 0.0024 mol, 1.0 eq) and pyridine hydrochloride (1.697 g, 0.0147 mol, 6.0 eq) in a sealed tube was heated at 100° C. for 14 hours. The reaction was monitored by LC-MS. After completion, the mixture was mixed with saturated sodium bicarbonate (50 mL) and extracted with ethyl acetate (2×20 mL). The combined organic phases were washed with water, then brine, dried over sodium sulfate and evaporated under reduced pressure. The residue was purified by column chromatography using silica gel (60-120 mesh size), eluting with 0-6% methanol in dichloromethane as mobile phase to give pure desired product 3-(5-amino-1H-pyrazol-3-yl)-5-methylpyridin-2(1H)-one (Compound 38, 0.330 g, yield-70.9%) m/z 191.05 [M+1]+ $^1$H NMR (400 MHz, DMSO) δ 11.83 (s, 2H), 7.78 (d, J=2.3 Hz, 1H), 7.20 (s, 1H), 6.03 (s, 1H), 4.72 (m, 2H), 2.08 (s, 3H) ppm.

Example 57—Preparation of Compound 39

The synthesis of Compound 39 followed General Procedure 4 following:

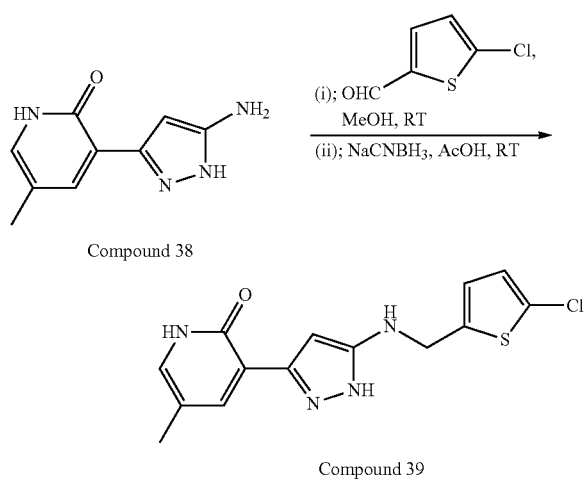

To a cooled solution (0-10° C.) of methanol (10 mL) and acetic acid (0.103 g, 0.002 mol, 1.0 eq) was added 3-(5-amino-1H-pyrazol-3-yl)-5-methylpyridin-2(1H)-one (Compound 38, 0.330 g, 0.0017 mol, 1.0 eq) portionwise. To this was then added 5-chlorothiophene-2-carbaldehyde (0.278 g, 0.0019 mol, 1.1 eq), also portionwise. Cooling was removed and the reaction then stirred for a further 30-45 minutes at room temperature. To the mixture was then added sodium cyanoborohydride (0.325 g, 0.0052 mol, 3.0 eq) portionwise over a period of 15 minutes. The reaction was stirred for a further 3 hours. After reaction completion, the reaction mixture was poured into ice cold water under stirring and extracted with ethyl acetate (2×15 mL). The combined organic layers were dried over sodium sulfate, filtered and concentrated under reduced pressure. The residue was purified by column chromatography using silica gel, eluting with 0-1% methanol in dichloromethane as mobile phase, to give desired product 3-(5-(((5-chlorothiophen-2-yl)methyl)amino)-1H-pyrazol-3-yl)-5-methylpyridin-2(1H)-one (Compound 39, 0.310 g, yield-55.7%) m/z 321.49[M+1]+ $^1$H NMR (400 MHz, DMSO) δ 11.83 (s, 2H), 7.78 (d, J=2.4 Hz, 1H), 7.21 (s, 1H), 6.92 (t, J=7.3 Hz, 1H), 6.87 (d, J=3.7 Hz, 1H), 6.09 (d, J=14.3 Hz, 1H), 5.88 (t, J=6.0 Hz, 1H), 4.35 (d, J=6.3 Hz, 2H), 2.08 (s, 3H) ppm.

Example 58—Preparation of Compound 40

The synthesis of Compound 40 followed General Procedure 6 following:

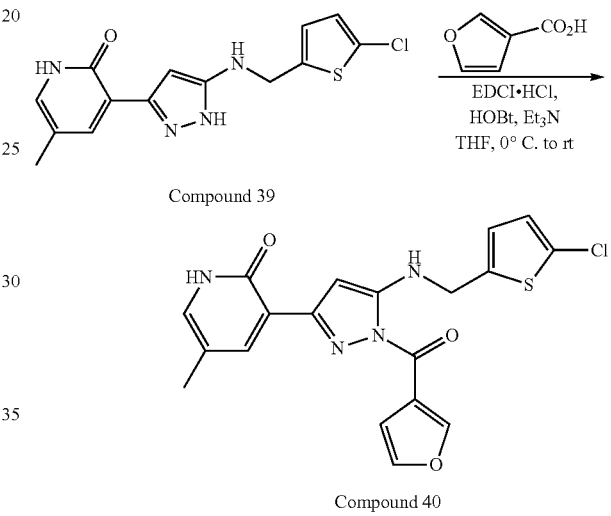

To a cooled (0° C.) and dry (nitrogen) solution of furan-3-carboxylic acid (0.104 g, 0.935 mmol, 1.2 eq) in THF (5 mL) was added EDCI.HCl (0.179 g, 0.935 mmol, 1.2 eq), followed by trimethylamine (0.238 g, 2.33 mmol, 3.0 eq). The reaction mixture was stirred for 30 minutes, and to it was added HOBt (0.021 g, 0.155 mmol, 0.2 eq.), followed by 3-(5-(((5-chlorothiophen-2-yl)methyl)amino)-1H-pyrazol-3-yl)-5-methylpyridin-2(1H)-one (Compound 39). The reaction was monitored by LC-MS, and after reaction completion the mixture was poured into water (5 mL) and extracted with ethyl acetate (3×25 mL). The organic phases were washed with water, then brine, and dried over sodium sulfate and evaporated under reduced pressure. The residue was purified by preparative HPLC, eluting with ammonia-water to give the desired product Compound 40 (0.055 g, yield-17.0%) m/z 415.51 [M+1]+ $^1$H NMR (400 MHz, DMSO) δ 11.72 (s, 1H), 9.06 (d, J=0.8 Hz, 1H), 8.11 (d, J=2.6 Hz, 1H), 7.89 (t, J=1.7 Hz, 1H), 7.82 (t, J=6.2 Hz, 1H), 7.29 (s, 1H), 7.08 (dd, J=7.3, 5.9 Hz, 1H), 7.01-6.93 (m, 2H), 6.33 (d, J=6.5 Hz, 1H), 4.54 (d, J=6.1 Hz, 2H), 2.12 (s, 3H) ppm.

Example 59—Preparation of Intermediate 19

The synthesis of Intermediate 19 followed General Procedure 12 following:

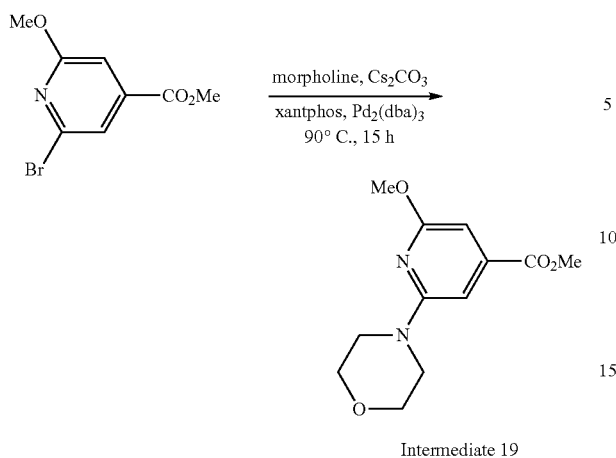

Intermediate 19

To a solution of commercially available methyl 2-bromo-6-methoxyisonicotinate (0.45 g, 1.83 mmol, 1.0 eq) in 1,4-dioxane (5 mL) was added morpholine (0.319 g, 3.67 mmol, 2.0 eq), followed by cesium carbonate (1.19 g, 3.67 mmol, 2.0 eq. The reaction mixture was degassed, bubbling with argon for 30 minutes. To the mixture was added 4,5-bis(diphenylphosphino)-9,9-dimethylxanthene (xantphos, 0.052 g, 0.091 mmol, 0.05 eq) all at once, followed by tris(dibenzylideneacetone)dipalladium(0) (Pd$_2$(dba)$_3$, 0.083 g, 0.091 mmol, 0.05 eq). The reaction mixture was stirred at 90° C. for 5 hours. After completion of reaction, the mixture was cooled to room temperature, filtered through a bed of Celite and washed with ethyl acetate (50 mL×3). The organic phases were combined and concentrated under reduced pressure. The residue was purified by Combi-flash column chromatography (230-400 silica gel), eluting with 3-4% ethyl acetate in hexane to give methyl 2-methoxy-6-morpholinoisonicotinate (Intermediate 19, 0.341 g) as a pale yellow solid. Yield: 73.59% [m/z=253.4 (m+1)] $^1$H NMR (CDCl$_3$, 400 MHz) δ 6.79 (s, 1H), 6.69 (d, J=0.8 Hz, 1H), 3.92 (d, J=2.6 Hz, 6H), 3.88-3.83 (m, 4H), 3.60-3.52 (m, 4H) ppm.

Example 60—Preparation of Intermediate 20

The synthesis of Intermediate 20 followed General Procedure 2 following:

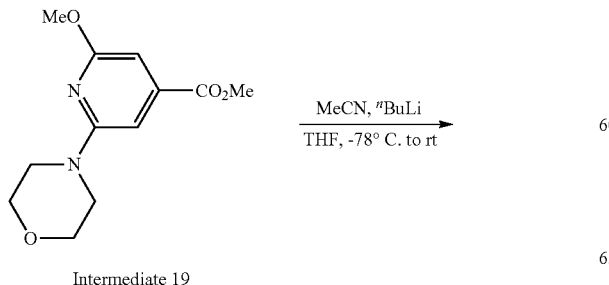

Intermediate 19

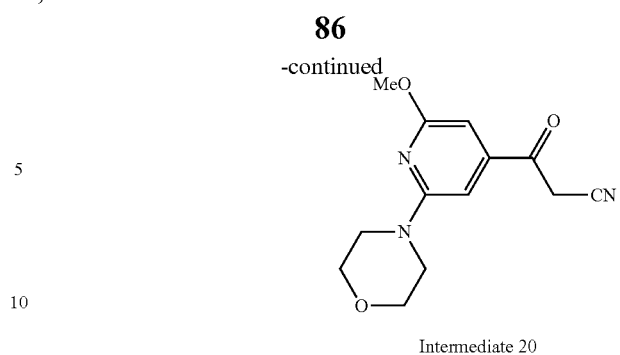

Intermediate 20

To a cooled solution (−78° C.) of acetonitrile (0.072 g, 1.78 mmol, 1.5 eq) in dry tetrahydrofuran (4 mL) was added "BuLi (2.5M in hexane, 0.71 mL, 1.78 mmol, 1.5 eq) dropwise over a period of 30 minutes. The reaction was stirred for another 30 minutes, and then methyl 2-methoxy-6-morpholinoisonicotinate (Intermediate 19, 0.34 g, 1.19 mmol, 1.0 eq) was added portionwise. The reaction mixture was stirred at −78° C. for a further 3 hours. After completion, the mixture was quenched with saturated ammonium chloride solution. The product was then extracted with ethyl acetate, and the organic layer was dried over sodium sulfate and evaporated under reduced pressure. The resultant yellow sticky solid was triturated in diethyl ether to obtain the required product 3-(2-methoxy-6-morpholinopyridin-4-yl)-3-oxopropanenitrile (0.31 g, dark yellow solid). The crude product was carried to the next step without further purification (Yield: 96.5%), m/z=262.20 (m+1)$^+$.

Example 61—Preparation of Compound 41

The synthesis of Compound 41 followed General Procedure 3 following:

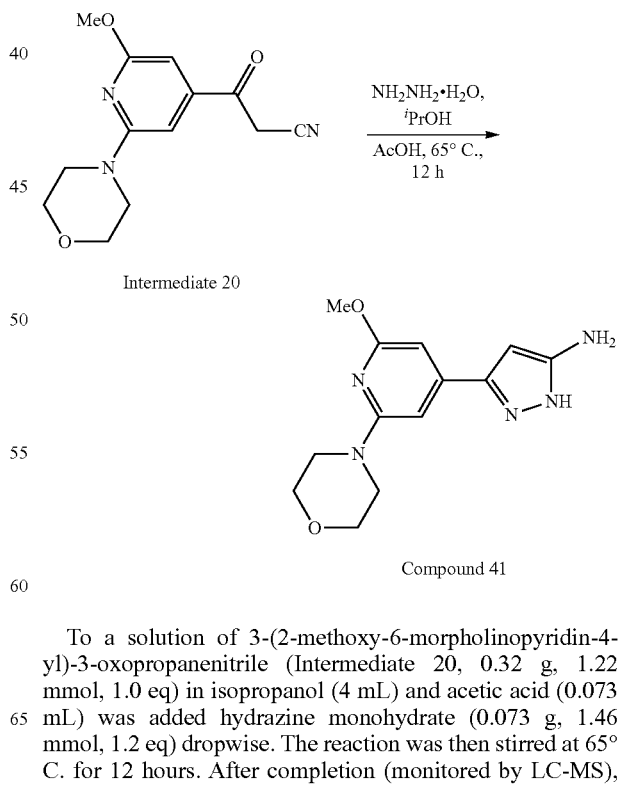

To a solution of 3-(2-methoxy-6-morpholinopyridin-4-yl)-3-oxopropanenitrile (Intermediate 20, 0.32 g, 1.22 mmol, 1.0 eq) in isopropanol (4 mL) and acetic acid (0.073 mL) was added hydrazine monohydrate (0.073 g, 1.46 mmol, 1.2 eq) dropwise. The reaction was then stirred at 65° C. for 12 hours. After completion (monitored by LC-MS), the reaction mixture was concentrated under reduced pressure. The residue was purified by column chromatography using silica gel (60-120 mesh), eluting with 50-60% ethyl acetate in n-hexane as gradient to give desired product 3-(2-methoxy-6-morpholinopyridin-4-yl)-1H-pyrazol-5-amine (Compound 41, 0.21 g, yield-62.3%) m/z=276.48 [M+1]+ $^1$H NMR (DMSO-d$_6$, 400 MHz) δ 6.60 (s, 1H), 6.36 (s, 1H), 5.85 (s, 1H), 4.85 (s, 2H), 3.79 (s, 3H), 3.76-3.64 (m, 4H), 3.54-3.42 (m, 4H) ppm.

Example 62—Preparation of Compound 42

The synthesis of Compound 42 followed General Procedure 17 following:

General Procedure 17

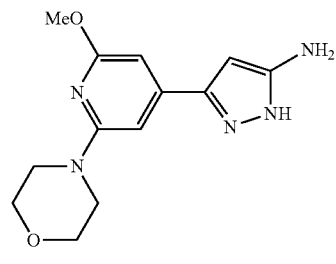

Compound 41

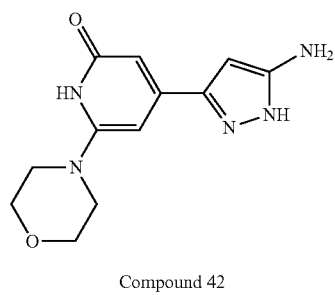

Compound 42

3-(2-methoxy-6-morpholinopyridin-4-yl)-1H-pyrazol-5-amine (Compound 41, 0.15 g, 0.544 mmol, 1.0 eq) was dissolved in conc. HCl (1 mL) and heated to reflux at 100° C. for 5 h. After completion, reaction mass was concentrated under vacuum. The residue was dissolved in methanol and basified with solid bicarbonate to basic pH. Methanol was filtered and concentrated under vacuum to obtain a dark brown solid as desired product 4-(5-amino-1H-pyrazol-3-yl)-6-morpholinopyridin-2(1H)-one (Compound 42, 0.120 g, yield: 84.5%); m/z=262.23 (m+1)+ $^1$H NMR (400 MHz, DMSO) δ 6.37 (s, 1H), 6.17 (s, 1H), 5.78 (s, 1H), 4.85 (s, 2H), 3.74-3.63 (m, 4H), 3.30-3.40 (m, 4H) ppm.

Example 63—Preparation of Compound 43

The synthesis of Compound 43 followed General Procedure 4 following:

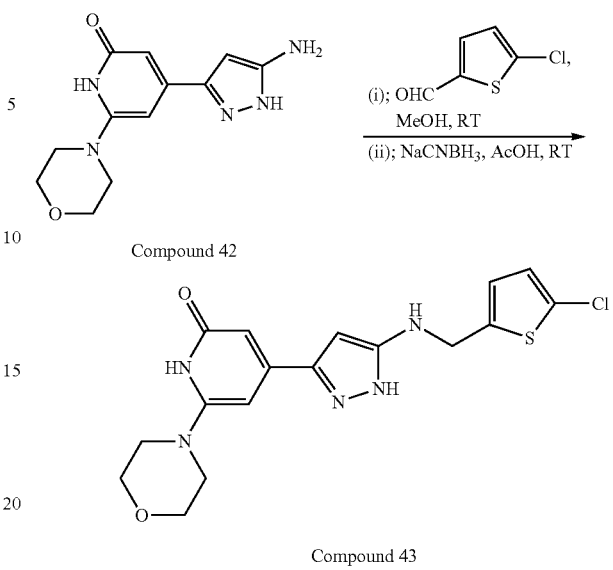

To a cooled solution (10-15° C.) of 4-(5-amino-1H-pyrazol-3-yl)-6-morpholinopyridin-2(1H)-one (Compound 42, 0.12 g, 0.46 mmol, 1.0 eq) in methanol (2 mL) was added acetic acid (0.03 mL, 0.69 mmol, 1.1 eq), followed by 5-chlorothiophene-2-carbaldehyde (0.1 g, 0.69 mmol, 1.5 eq) portionwise. The reaction was then stirred for 45 minutes at room temperature. Sodium cyanoborohydride (0.042 g, 0.69 mmol, 1.5 eq) was added portionwise over a period of 15 minutes. The reaction was then stirred for a further 12 hours. After completion, the reaction mixture was poured into ice cold water under stirring and extracted with 10% methanol in dichloromethane. The organic phase was dried over sodium sulfate and concentrated under reduced pressure. The residue was triturated with ethyl acetate, and the resultant solid was desired product 4-(5-(((5-chlorothiophen-2-yl)methyl)amino)-1H-pyrazol-3-yl)-6-morpholinopyridin-2(1H)-one (Compound 43, 0.051 g, brown solid, yield-27.8%); m/z=392.56 (m+1) $^1$H NMR (DMSO-d$_6$, 400 MHz) δ 7.00-6.83 (m, 2H), 6.38 (s, 1H), 6.17 (s, 1H), 5.98 (s, 1H), 4.36 (d, J=6.1 Hz, 2H), 3.69 (s, 4H), 3.38 (s, 4H) ppm.

Example 64—Preparation of Compound 44

The synthesis of Compound 44 followed General Procedure 6 following:

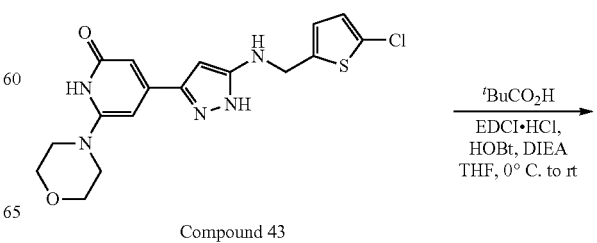

Compound 43

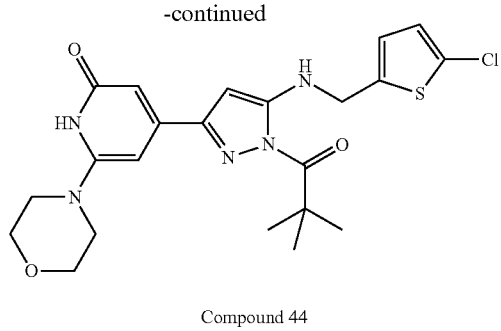

Compound 44

To a cooled solution (0° C.) of pivalic acid (0.022 g, 0.22 mmol, 1.4 eq) in THF (1 mL) was added EDCI.HCl (0.044 g, 0.15 mmol, 1.5 eq), HOBt (0.01 g, 0.08 mmol, 0.5 eq) and DIPEA (0.07 mL, 0.39 mmol, 2.5 eq) under nitrogen. The reaction mixture was stirred for 30 minutes and to this mixture was added 4-(5-(((5-chlorothiophen-2-yl) methyl) amino)-1H-pyrazol-3-yl)-6-morpholinopyridin-2(1H)-one (Compound 43, 0.05 g, 0.16 mmol, 1.0 eq). The reaction mixture was stirred for 12 hours at room temperature. After completion (monitored by LC-MS), the reaction mixture was poured into water (10 mL) and extracted with ethyl acetate (3×25 mL). The combined organic phases were washed with water, brine, dried over sodium sulfate and evaporated under reduced pressure. The residue was purified by preparative HPLC using water-acetonitrile as the mobile phase, to yield the desired product 4-(5-(((5-chlorothiophen-2-yl)methyl)amino)-1-pivaloyl-1H-pyrazol-3-yl)-6-morpholinopyridin-2(1H)-one (Compound 44, 0.008 g) m/z=476.5 [M+1]+ $^1$H NMR (400 MHz, DMSO-d$_6$) δ 12.33 (s, 1H), 7.08-6.84 (m, 3H), 6.64 (s, 1H), 6.19 (s, 1H), 5.99 (s, 1H), 4.37 (d, J=6.3 Hz, 2H), 3.70 (s, 4H), 3.43 (d, J=21.8 Hz, 4H), 1.29 (s, 9H) ppm.

Example 65—Preparation of Intermediate 21

The synthesis of Intermediate 21 followed General Procedure 14 following:

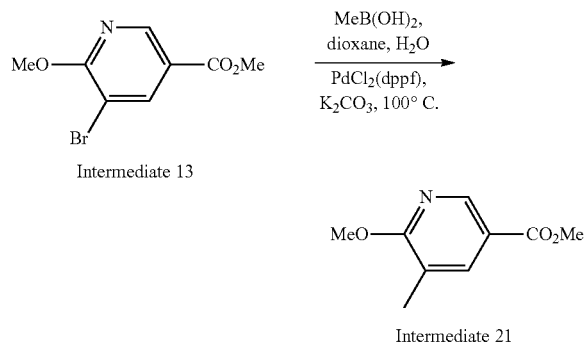

To a solution of methyl 5-bromo-6-methoxynicotinate (Intermediate 13, 8.0 g, 0.034 mol, 1.0 eq) in dioxane: water (4:1, 64:16 mL) was added potassium carbonate (8.2 g, 0.083 mol, 2.5 eq), followed by methylboronic acid (3.0 g, 0.049 mol, 1.5 eq). The mixture was degassed for 20 minutes by bubbling through a stream of argon, followed by the addition of [1,1'-bis(diphenylphosphino)ferrocene]dichloropalladium(II) (Pd(dppf)Cl$_2$, 2.39 g, 3.3 mmol, 0.1 eq). The reaction mixture was stirred at 100° C. for 4 hours. The reaction progress was monitored by LCMS. After reaction completion, the mixture was diluted with cold water and extracted with ethyl acetate (3×100 mL). The combined organic phases were dried over anhydrous sodium sulfate and evaporated under reduced pressure. The residue was purified by column chromatography using silica (100-200 mesh size), eluting with 3% ethyl acetate in hexane. Pure fractions were concentrated under reduced pressure and dried under vacuum to give desired product (Intermediate 21, 1.5 g, yield-91%) m/z 182.1 [M+H]+ $^1$H NMR (DMSO-d$_6$, 400 MHz) δ 8.58 (d, J=2.0 Hz, 1H), 8.05-7.97 (m, 1H), 3.96 (s, 3H), 3.84 (s, 3H), 2.18 (s, 3H) ppm.

Example 66—Preparation of Intermediate 22

The synthesis of Intermediate 22 followed General Procedure 2 following:

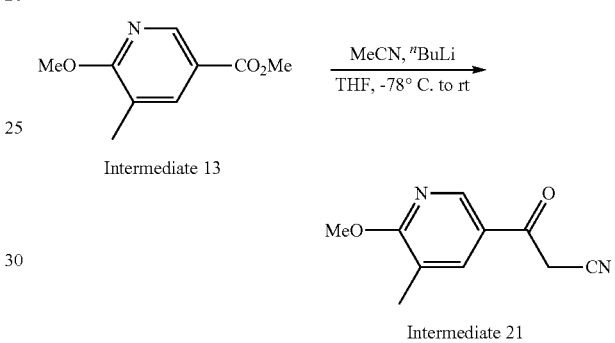

Under an inert and dry N$_2$ atmosphere, acetonitrile (0.564 g, 0.014 mol, 1.7 eq) was added to tetrahydrofuran (20 mL) and the solution then cooled to −78° C. To this was added $^n$BuLi (2.5M in hexane, 5.6 mL, 0.014 mol, 1.7 eq) dropwise over a period of 60 minutes, and the reaction was stirred for another 60 minutes. Methyl 6-methoxy-5-methylnicotinate (Intermediate 13, 1.5 g, 8.3 mmol, 1.0 eq.) was added portionwise to the reaction mixture, and the temperature maintained at −78° C. for a further 3 hours. The reaction progress was monitored by LCMS. After completion, the reaction was quenched with ethyl acetate and the total reaction mixture was concentrated under reduced pressure. The crude residue was triturated with diethyl ether and dried under reduced pressure to obtain product desired product 3-(2-methoxy-5-methyl-1,6-dihydropyridin-3-yl)-3-oxopropanenitrile (Intermediate 21), which was used directly in the next step. 1.5 g (yield-95.5%) m/z[M+1]+ 191.15.

Example 67—Preparation of Compound 45

The synthesis of Compound 45 followed General Procedure 3 following:

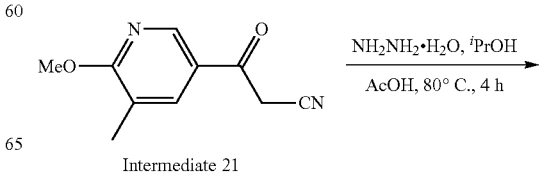

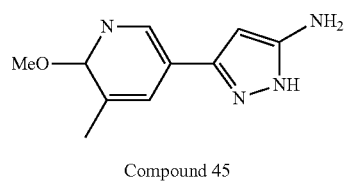

Compound 45

To a solution of 3-(2-methoxy-5-methyl-1,6-dihydropyridin-3-yl)-3-oxopropanenitrile (Intermediate 21, 1.5 g, 7.9 mmol, 1.0 eq) in isopropanol (20 mL) was added acetic acid (0.5 mL). To this was added hydrazine monohydrate (0.592 g, 12 mmoles, 1.5 eq) dropwise, and the reaction was then stirred at 80° C. for 4 hours. The reaction progress was monitored by LCMS. After completion, the reaction mixture was concentrated under reduced pressure. The residue was purified by column chromatography using silica gel (100-200 mesh), eluting with 5% methanol in dichloromethane as gradient, to give desired product 3-(6-methoxy-5-methylpyridin-3-yl)-1H-pyrazol-5-amine (Compound 45, 1.0 g, yield-62.11%) m/z [M+1]+ 205.20.

Example 68—Preparation of Compound 46

The synthesis of Compound 46 followed General Procedure 17 following:

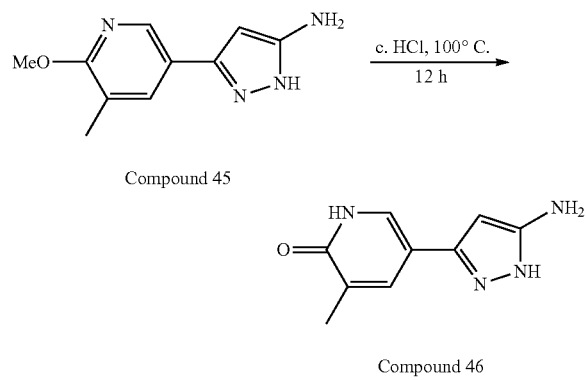

Compound 45

Compound 46

A mixture of 3-(6-methoxy-5-methylpyridin-3-yl)-1H-pyrazol-5-amine (Compound 45, 1.0 g, 4.9 mmol, 1.0 eq) in concentrated HCl (20 mL) was allowed to stir at 100° C. for 12 hours. The reaction progress was monitored by LCMS. After completion of reaction, the reaction mixture was concentrated under vacuum and diluted with methanol. The basicity was adjusted to above pH 7 using solid potassium carbonate, then filtered. The filtrate was concentrated on reduced pressure, and then purified by washing with ethyl acetate (3×10 mL) and dried on vacuum to give desired product 5-(5-amino-1H-pyrazol-3-yl)-3-methylpyridin-2 (1H)-one (Compound 46, 0.8 g, yield-85.92%) m/z [M+1]+ 191.2.

Example 69—Preparation of Compound 47

The synthesis of Compound 47 followed General Procedure 4 following:

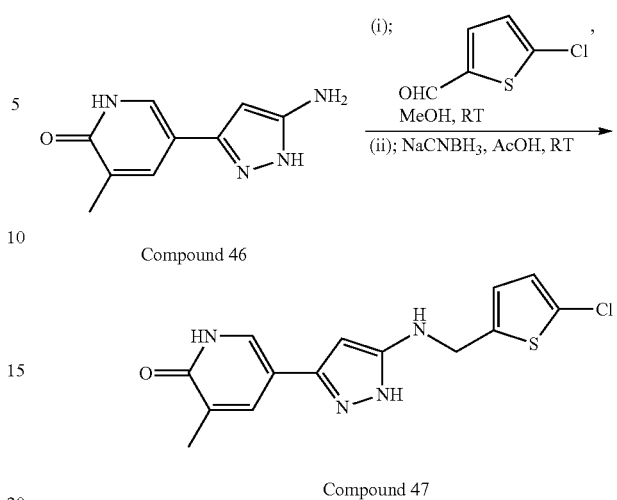

Compound 46

Compound 47

To a cooled solution (10-15° C.) of 5-(5-amino-1H-pyrazol-3-yl)-3-methylpyridin-2(1H)-one (Compound 46, 0.7 g, 3.6 mmol, 1.0 eq) in methanol (20 mL) was added acetic acid (0.5 mL) dropwise. To this was then added 5-chlorothiophene-2-carbaldehyde (0.805 g, 5.8 mmol, 1.5 eq) portionwise, and the reaction mixture was stirred for 30-45 minutes at room temperature. Sodium cyanoborohydride (0.462 g, 7.4 mmol, 2.0 eq) was added portionwise over a period of 15 minutes. The reaction was stirred for 12 hours. After completion of reaction, methanol was evaporated off and the residue was dissolved in ice cold water and extracted with ethyl acetate (3×30 mL). The combined organic layers were dried over anhydrous sodium sulfate and concentrated under reduced pressure. The residue was purified by column chromatography using silica gel (100-200 mesh), eluting with 7% methanol in dichloromethane as mobile phase to give pure desired product 5-(5-(((5-chlorothiophen-2-yl)methyl)amino)-1H-pyrazol-3-yl)-3-methyl-pyridin-2(1H)-one (Compound 47, 0.2 g, yield-16.97%) m/z[M+1]+ 321.25 $^1$H NMR (DMSO-d$_6$, 400 MHz) δ 11.73 (s, 2H), 7.59 (d, J=35.9 Hz, 2H), 7.04-6.82 (m, 2H), 5.92 (s, 1H), 5.74 (s, 1H), 4.33 (d, J=6.3 Hz, 2H), 2.01 (s, 3H) ppm.

Example 70—Preparation of Compound 48

The synthesis of Compound 48 followed General Procedure 6 following:

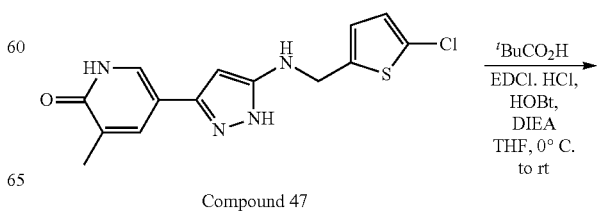

Compound 47

-continued

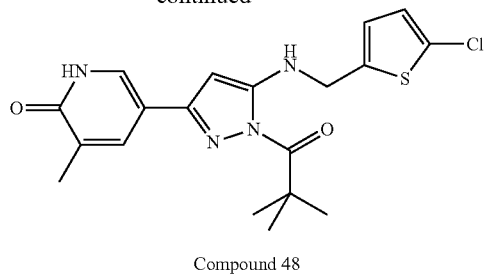

Compound 48

To a cooled solution (0° C.) of pivalic acid (0.15 g, 0.52 mmol, 1.1 eq) in THF was added EDC.HCl (0.134 g, 0.7 mmol, 1.5 eq), HOBT (0.031 g, 0.23 mmol, 0.5 eq) and DIEA (0.152 g, 1.17 mmol, 2.5 eq). The reaction mixture was allowed to stir at 0° C. for 20 minutes, followed by the portionwise addition of 5-(5-(((5-chlorothiophen-2-yl)methyl)amino)-1H-pyrazol-3-yl)-3-methylpyridin-2 (1H)-one (Compound 47, 0.15 g, 0.47 mmol, 1.0 eq). The reaction mixture was allowed to stir at room temperature for 12 hours. After completion of reaction, the reaction mixture was diluted with water and extracted with ethyl acetate (3×50 mL). The combined organic layers were dried over anhydrous sodium sulfate, filtered and concentrated under reduced pressure. The residue was purified by preparative HPLC using acetonitrile/water as the mobile phase to obtain desired product after lyophilization: 5-(5-(((5-chlorothiophen-2-yl)methyl)amino)-1-pivaloyl-1H-pyrazol-3-yl)-3-methyl pyridin-2(1H)-one (Compound 48, 0.044 g, yield-17.46%) m/z[M+1]+ 405.23. $^1$H NMR (400 MHz, DMSO-$d_6$) δ 11.83 (s, 1H), 7.83 (t, J=6.3 Hz, 1H), 7.79-7.66 (m, 2H), 7.04 (d, J=3.8 Hz, 1H), 6.97 (d, J=3.7 Hz, 1H), 5.94 (s, 1H), 4.45 (d, J=6.3 Hz, 2H), 2.04 (s, 3H), 1.45 (s, 9H) ppm.

Example 71—Preparation of Intermediate 22

The synthesis of Intermediate 22 followed General Procedure 2 following:

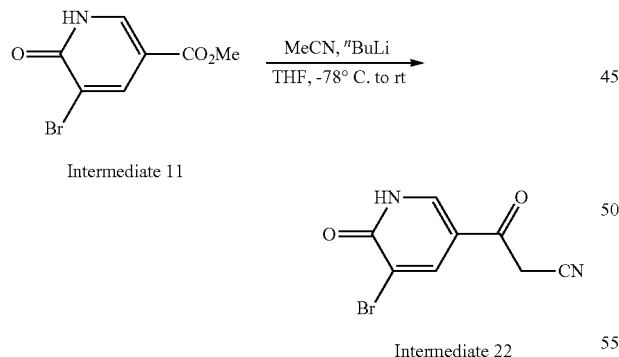

In dry $N_2$ condition, acetonitrile (3 g, 73 mmol, 1.7 eq) was added to tetrahydrofuran (150 mL), and the solution cooled to −78° C. To this was then added "BuLi (2.5M in hexane, 30 mL, 48 mmol, 1.7 eq) dropwise over a period of 60 minutes, and the reaction was then stirred for another 60 minutes. Methyl 5-bromo-6-oxo-1,6-dihydropyridine-3-carboxylate (Intermediate 11, 10 g, 43 mmol, 1.0 eq) was added in portions to the reaction mixture at −78° C. and the mixture stirred for 3 hours, and then warmed to room temperature for 3-4 hours. Ethyl acetate (5 mL) was added slowly. The reaction mixture was evaporated off, then the residue washed with hexane (100 mL×2) and ethyl acetate (100 mL×2). The solid compound was dried under reduced pressure to give desired product (10 g, yield-37.80%) which was directly used in next step without purification. m/z 239.12 [M−H]−.

Example 72—Preparation of Intermediate 23

The synthesis of Intermediate 23 followed General Procedure 3 following:

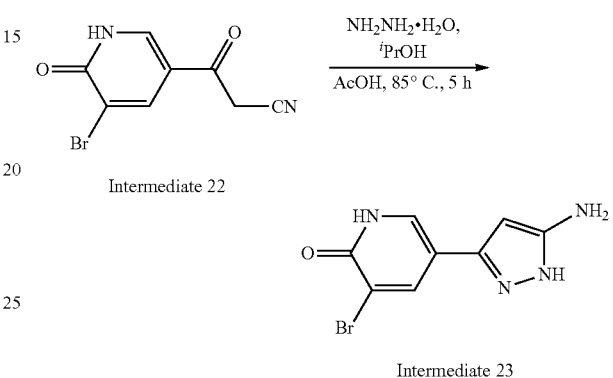

To solution of 3-(5-bromo-6-oxo-1,6-dihydropyridin-3-yl)-3-oxopropanenitrile (Intermediate 22, 10.0 g, 41 mmol, 1.0 eq) in isopropanol (150 mL) and acetic acid (2.49 g, 41 mmol, 1.0 eq) was added hydrazine monohydrate (3.11 mL, 62 mmol, 1.5 eq) dropwise. The reaction was stirred at 85° C. for 5 hours. The reaction mixture was monitored by LC-MS. After completion, the reaction mixture was concentrated to give a residue, which was purified by column chromatography by using silica gel (60-120 mesh). The product was eluted using 8-9% methanol in dichloromethane as gradient to give desired product (7 g, yield-66.2%) m/z 256.85 [M+H]+ $^1$H NMR (DMSO-$d_6$, 400 MHz) δ 9.93 (s, 2H), 8.23 (d, J=2.3 Hz, 1H), 7.73 (d, J=2.3 Hz, 1H), 5.63 (s, 1H), 4.92 (s, 2H) ppm.

Example 73—Preparation of Compound 49

The synthesis of Compound 49 followed General Procedure 4 following:

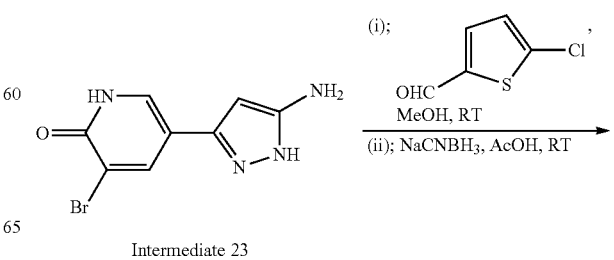

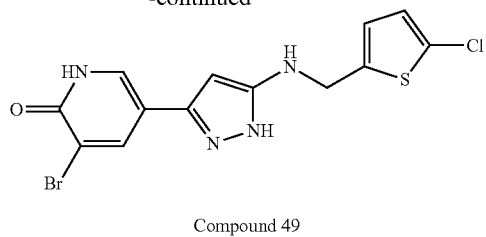

Compound 49

To a cooled solution (10-15° C.) of 5-(5-amino-1H-pyrazol-3-yl)-3-bromopyridin-2(1H)-one (Intermediate 23, 6 g, 23 mmol, 1 eq) in methanol (60 mL) was added acetic acid (1.41 g, 23 mmol, 1 eq) dropwise. To this was then added 5-chlorothiophene-2-carbaldehyde (3.41 g, 23 mol, 1 eq) dropwise, and the reaction was stirred for a further 2-3 hours at room temperature. The mixture was cooled to 0° C., and to it was added sodium cyanoborohydride (2.96 g, 47 mmol, 2 eq) portionwise over a period of 45 minutes and stirred for a further 2 hours. The reaction was monitored by LC-MS. After completion of reaction, the mixture was concentrated and residue was poured into ice cold water under stirring. The product was extracted with 10% methanol in dichloromethane. The organic layer was dried over sodium sulfate and concentrated under reduced pressure. The residue was purified by column chromatography using neutral silica gel, eluting with 8-9% methanol in dichloromethane to give pure desired product (5.5 g, yield-60.90%) m/z[M+H]− 385.34 $^1$H NMR (DMSO-d$_6$, 400 MHz) δ 12.07 (s, 2H), 8.25 (d, J=2.3 Hz, 1H), 7.76 (s, 1H), 6.92 (t, J=5.9 Hz, 1H), 6.88 (d, J=3.7 Hz, 1H), 6.00 (s, 1H), 5.83 (s, 1H), 4.33 (d, J=6.3 Hz, 2H) ppm.

Example 74—Preparation of Compound 50

The synthesis of Compound 50 followed General Procedure 14 following:

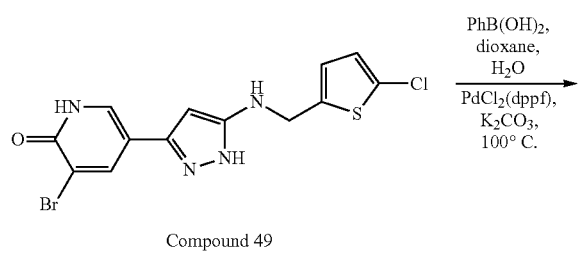

To a solution of 3-bromo-5-(5-(((5-chlorothiophen-2-yl)methyl)amino)-1H-pyrazol-3-yl)pyridin-2(1H)-one (Compound 49, 0.5 g, 1.29 mmol, 1.0 eq) and phenylboronic acid (0.19 g, 1.55 mmol, 1.0 eq) in dioxane: water (5:1, 10 mL) was added potassium carbonate (0.358 g, 2.59 mmol, 2.0 eq). The mixture was degassed by a continuous flow of nitrogen for 30 minutes, and to it was added 1,1′-bis(diphenylphosphino) ferrocene palladium(II) dichloride (0.094 g, 0.13 mmol, 0.1 eq). The reaction mixture was stirred at 100° C. for 6 hours. After completion (monitored by LC-MS), the reaction mixture was cooled to room temperature, diluted with water and extracted with dichloromethane (25 mL×3). The combined organic layers were dried over sodium sulfate and concentrated under reduced pressure. The residue was purified by column chromatography using neutral silica gel (100-200 mesh), eluting with 3-4% methanol in dichloromethane to give pure desired product (250 mg, yield-51%) m/z 383.31 [M+H]+ $^1$H NMR (DMSO-d$_6$, 400 MHz) δ $^1$H NMR (400 MHz, DMSO) δ 12.09-12.00 (m, 1H), 11.94-11.83 (m, 1H), 7.95 (s, 1H), 7.77 (d, J=7.5 Hz, 2H), 7.49-7.31 (m, 4H), 6.93 (d, J=3.7 Hz, 1H), 6.89 (s, 1H), 5.87 (s, 1H), 4.34 (d, J=6.5 Hz, 2H) ppm.

Example 75—Preparation of Compound 51

The synthesis of Compound 51 followed General Procedure 5 following:

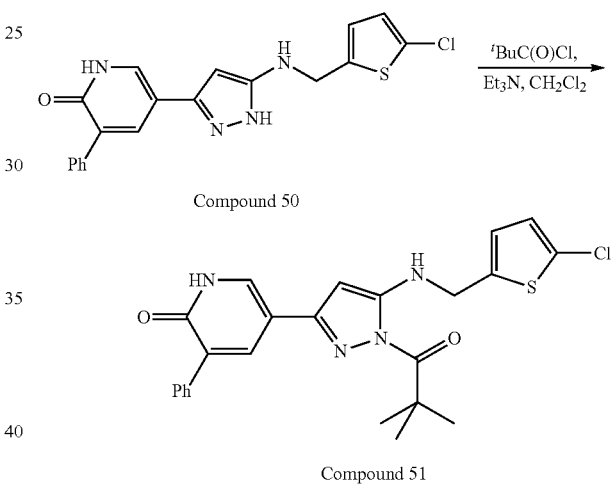

To a cooled solution (0° C.) of 5-(5-(((5-chlorothiophen-2-yl)methyl)amino)-1H-pyrazol-3-yl)-3-phenylpyridin-2(1H)-one (Compound 50, 0.2 g, 0.52 mmol, 1 eq) in dichloromethane (5 ml) was added triethylamine (0.157 g, 1.56 mmol, 3 eq), followed by pivaloyl chloride (0.062 g, 0.52 mmol, 1 eq). The reaction mixture was stirred at room temperature for 12 hours. After completion, the reaction mixture was diluted with water and extracted with ethyl acetate (25 mL×3). The organic layer was dried over sodium sulfate and concentrated under reduced pressure. The residue was purified by preparative HPLC to give pure desired product (60 mg, yield-28.30%) m/z 467.31 [M+H]+ $^1$H NMR (DMSO-d$_6$, 400 MHz) δ 12.12 (s, 1H), 7.99 (d, J=2.5 Hz, 1H), 7.86 (dd, J=12.2, 4.5 Hz, 2H), 7.70 (d, J=7.1 Hz, 2H), 7.43 (t, J=7.5 Hz, 2H), 7.36 (t, J=7.3 Hz, 1H), 7.05 (d, J=3.8 Hz, 1H), 6.97 (d, J=3.7 Hz, 1H), 6.06 (s, 1H), 4.47 (d, J=6.3 Hz, 2H), 1.34 (d, J=87.2 Hz, 9H) ppm.

Example 76—Preparation of Compound 52

The synthesis of Compound 52 followed General Procedure 6 following:

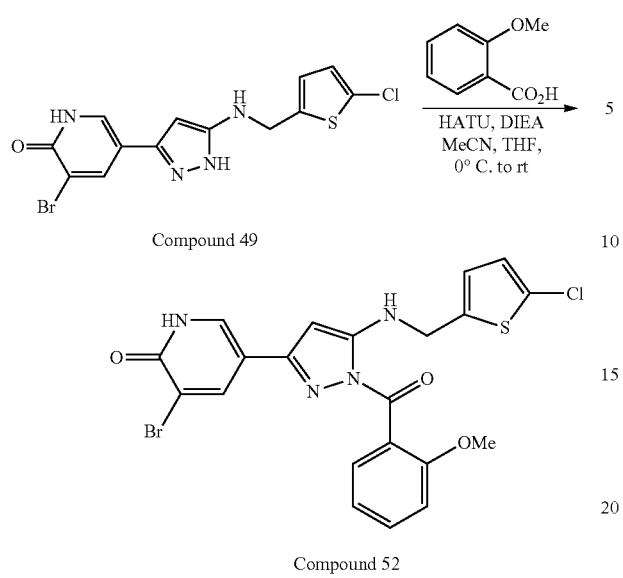

Compound 49

Compound 52

To a solution of 2-methoxybenzoic acid (0.078 g, 0.51 mmol, 1 eq) in acetonitrile:THF (1:1, 5 ml) was added DIPEA (0.2 mL, 1.55 mmol, 3 eq), followed by N-[(dimethylamino)-1H-1,2,3-triazolo-[4,5-b]pyridin-1-ylmethylene]-N-methylmethanaminium hexafluorophosphate N-oxide (HATU, 0.296 g, 0.77 mmol, 1.5 eq). The mixture was stirred at room temperature for 1 hour. To this was then added 3-bromo-5-(5-(((5-chlorothiophen-2-yl)methyl)amino)-1H-pyrazol-3-yl)pyridin-2(1H)-one (Compound 49, 0.2 g, 0.51 mmol, 1.0 eq), and the mixture allowed to stir at room temperature for 12 hours. After completion, the reaction mixture was diluted with water and extract with ethyl acetate (25 mL×3). The organic layer was dried over sodium sulfate and concentrated under reduced pressure. The residue was purified by preparative HPLC to give pure desired product (75 mg, yield-27.8%) m/z 521.57 [M+H]+ $^1$H NMR (DMSO-d$_6$, 400 MHz) δ 12.42 (s, 1H), 7.99 (d, J=2.2 Hz, 1H), 7.87 (t, J=6.3 Hz, 1H), 7.81 (s, 1H), 7.56-7.48 (m, 1H), 7.42 (dd, J=7.5, 1.5 Hz, 1H), 7.18 (d, J=8.4 Hz, 1H), 7.14-7.03 (m, 2H), 6.99 (t, J=6.2 Hz, 1H), 6.10 (s, 1H), 4.51 (d, J=6.2 Hz, 2H), 3.75 (s, 3H) ppm.

Example 77—Preparation of Compound 53

The synthesis of Compound 53 followed General Procedure 14 following:

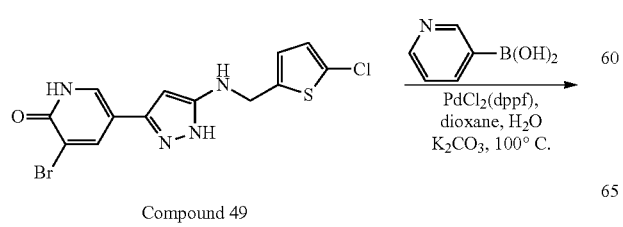

Compound 49

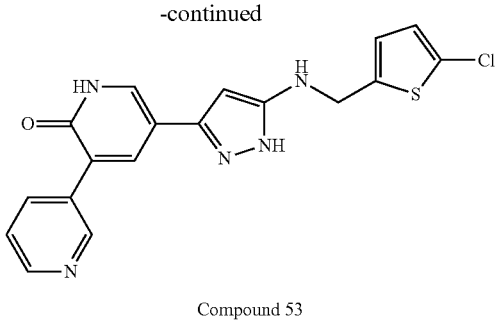

Compound 53

To a solution of 3-bromo-5-(5-(((5-chlorothiophen-2-yl)methyl)amino)-1H-pyrazol-3-yl)pyridin-2(1H)-one (Compound 49, 0.5 g, 1.29 mmol, 1.0 eq) and pyridine-3-boronic acid (0.19 g, 1.55 mmol, 1.0 eq) in dioxane:water (5:1; 10 mL) was added potassium carbonate (0.358 g, 2.59 mmol, 2.0 eq) was added. The reaction mixture was degassed under nitrogen for 30 minutes, and to it was added 1,1'-bis(diphenylphosphino)ferrocene palladium(II) dichloride (0.094 g, 0.13 mmol, 0.1 eq). The mixture was stirred at 100° C. for 5-6 hours. After completion (monitored by LC-MS), the reaction mixture was diluted with water and extracted with dichloromethane (25 mL×3). The combined organic layers were dried over sodium sulfate and concentrated under reduced pressure. The residue was purified by column chromatography using neutral silica gel (100-200 mesh), eluting with 8-9% methanol in dichloromethane as gradient to give pure desired product (200 mg, yield-40%) m/z 384.7 [M+H]+ $^1$H NMR (DMSO-d$_6$, 400 MHz) δ 11.89 (s, 2H), 8.95 (s, 1H), 8.53 (dd, J=4.7, 1.5 Hz, 1H), 8.20 (d, J=8.0 Hz, 1H), 8.07 (d, J=2.5 Hz, 1H), 7.78 (s, 1H), 7.43 (dt, J=33.8, 16.9 Hz, 1H), 6.99-6.90 (m, 1H), 6.89 (d, J=3.5 Hz, 1H), 5.91 (s, 2H), 4.34 (t, J=6.2 Hz, 2H) ppm.

Example 78—Preparation of Compound 54

The synthesis of Compound 54 followed General Procedure 6 following:

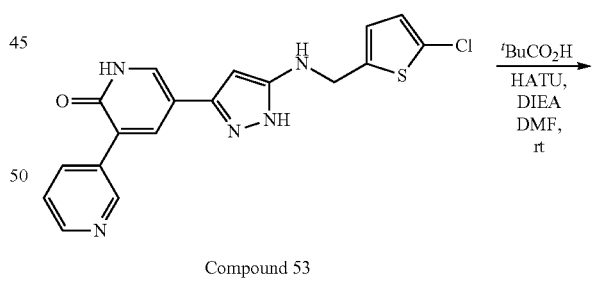

Compound 53

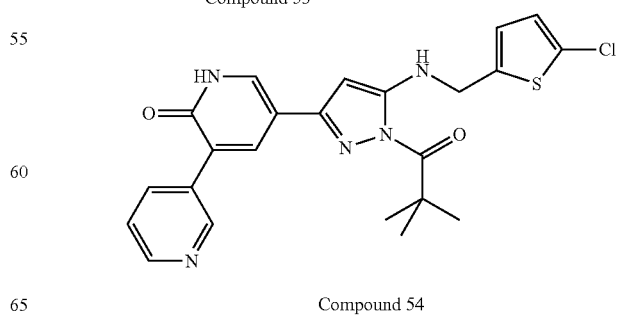

Compound 54

To a solution of pivalic acid (0.053 g, 0.52 mmol, 1 eq) in DMF (5 ml) was added DIPEA (0.2 mL, 1.56 mmol, 3 eq), followed by N-[(dimethylamino)-1H-1,2,3-triazolo-[4,5-b]pyridin-1-ylmethylene]-N-methylmethanaminium hexafluorophosphate N-oxide (HATU, 0.296 g, 0.78 mmol, 1.5 eq). The reaction mixture was stirred at room temperature for 1 hour. To this mixture was then added 5-(5-(((5-chlorothiophen-2-yl)methyl)amino)-1H-pyrazol-3-yl)-[3,3'-bipyridin]-2(1H)-one (Compound 54, 0.2 g, 0.52 mmol, 1.0 eq), and the mixture was allowed to stir at ambient temperature for 12 hours. After completion, the reaction mixture was diluted with water and extracted with ethyl acetate (25 mL×3). The combined organic layers were dried over sodium sulfate and concentrated under reduced pressure. The residue was purified by preparative HPLC to give pure desired product (50 mg, yield-23.2%) m/z 468.57 [M+H]+ $^1$H NMR (DMSO-$d_6$, 400 MHz) δ 12.25 (s, 1H), 8.88 (d, J=1.6 Hz, 1H), 8.55 (dd, J=4.8, 1.6 Hz, 1H), 8.20-8.12 (m, 1H), 8.08 (d, J=2.5 Hz, 1H), 7.94 (d, J=2.4 Hz, 1H), 7.86 (t, J=6.5 Hz, 1H), 7.46 (dd, J=8.0, 4.8 Hz, 1H), 7.05 (d, J=3.8 Hz, 1H), 6.97 (d, J=3.7 Hz, 1H), 6.08 (s, 1H), 4.47 (d, J=6.3 Hz, 2H), 1.45 (s, 9H) ppm.

Example 79—Preparation of Intermediate 24

The synthesis of Intermediate 24 followed General Procedure 2 following:

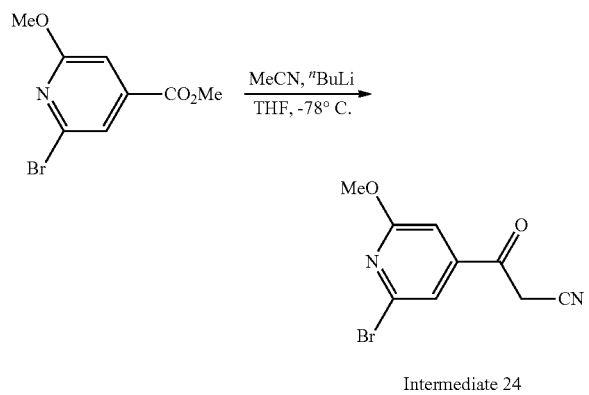

Intermediate 24

To a cooled solution (−78° C.) of acetonitrile (2.4 g, 83 mmol, 1.7 eq) in dry tetrahydrofuran (200 mL) was added $^n$BuLi (2.5M in hexane, 33.2 mL, 83 mmol, 1.7 eq) in a dropwise fashion over a period of 60 minutes. The reaction was stirred for a further 60 minutes. To this was then added commercially available methyl 2-bromo-6-methoxyisonicotinate (12.0 g, 49 mmol, 1.0 eq) portionwise, and the reaction mixture maintained at −78° C. for 3 hrs. The reaction mixture was quenched with saturated ammonium chloride, and extracted with ethyl acetate. The organic layers were dried over sodium sulfate and evaporated to give desired product which was used in next step without further purification (11.5 g, yield-92.3%) m/z 355.12 [M+H]+.

Example 80—Preparation of Compound 55

The synthesis of Compound 55 followed General Procedure 3 following:

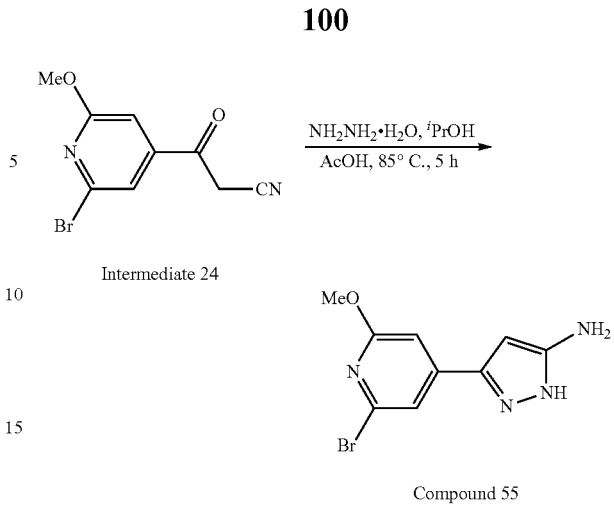

Intermediate 24

Compound 55

To a solution of 3-(2-bromo-6-methoxypyridin-4-yl)-3-oxopropanenitrile (Intermediate 24, 11.5 g, 45 mmol, 1.0 eq) in isopropanol (120 mL) and acetic acid (2.7 g) was added hydrazine monohydrate (7.4 mL, 148 mmol, 1.2 eq) dropwise. The reaction was stirred at 85° C. for 4-5 hours. The reaction was monitored by LC-MS, and was then concentrated under reduced pressure. The residue was purified by column chromatography using neutral silica gel (60-120 mesh), eluting with 3-6% methanol in dichloromethane as gradient to give desired product (11 g, yield-90.3%) m/z 271.13 [M+H]+ $^1$H NMR (DMSO-$d_6$, 400 MHz) δ 13.06-10.70 (m, 1H), 7.49 (d, J=1.0 Hz, 1H), 7.07 (d, J=1.0 Hz, 1H), 5.90 (s, 1H), 5.03 (d, J=98.1 Hz, 2H), 3.86 (s, 3H) ppm.

Example 81—Preparation of Compound 56

The synthesis of Compound 56 followed General Procedure 4 following:

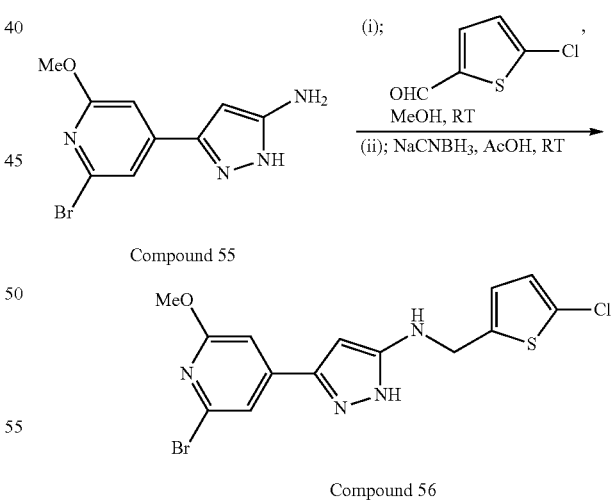

Compound 55

Compound 56

To a cooled solution (10-15° C.) of 3-(2-bromo-6-methoxypyridin-4-yl)-1H-pyrazol-5-amine (Compound 55, 11.0 g, 43 mmol, 1 eq) in methanol (220 mL) was added acetic acid (5 mL) dropwise. To this was then added 5-chlorothiophene-2-carbaldehyde (7.44 g, 50.9 mmol, 1.2 eq) dropwise, and the reaction was stirred for a further 5-6 hours at room temperature. Sodium cyanoborohydride (6.42 g, 86 mmol, 2 eq) was added portionwise over a period of 45 minutes, and the reaction was stirred for a further 12 hours. After completion of reaction, the reaction mixture was concentrated and residue was diluted with water. The product was extracted with ethyl acetate. The organic layers were dried over sodium sulfate and concentrated under reduced pressure. The residue was purified by column chromatography using neutral silica gel and product, eluting with 10-30% ethyl acetate in hexanes as mobile phase to give pure desired product (7.5 g, yield-44.1%) m/z[M+H]+ 401.31 $^1$H NMR (DMSO-d$_6$, 400 MHz) δ 12.33 (d, J=106.6 Hz, 1H), 7.52 (s, 1H), 7.10 (s, 1H), 6.94 (s, 2H), 6.04 (s, 1H), 4.36 (d, J=6.2 Hz, 2H), 3.86 (s, 3H) ppm.

Example 82—Preparation of Compound 57

The synthesis of Compound 57 followed General Procedure 17 following:

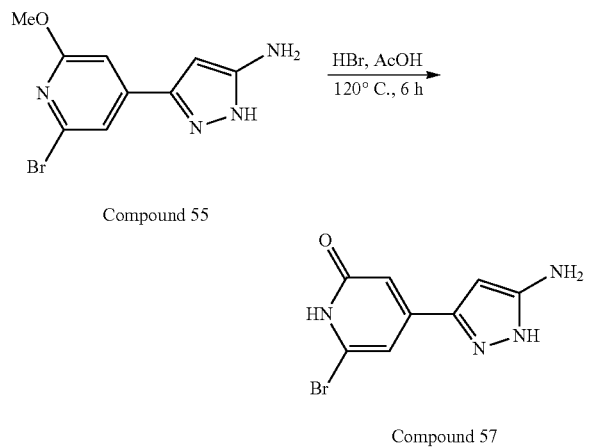

Compound 55

Compound 57

In a round-bottomed flask, 3-(2-bromo-6-methoxypyridin-4-yl)-1H-pyrazol-5-amine (Compound 55, 2.0 g, 7.4 mmol, 1.0 eq) was dissolved in HBr in acetic acid (30%, 20.0 mL). The mixture was stirred at 120° C. for 5-6 hours. After completion of reaction, volatiles were distilled off to give a crude gum, which was dissolved in dichloromethane: methanol (50:50) and neutralized by aq. K$_2$CO$_3$. The precipitates were filtered and the filtrate was evaporated to dryness to give desired product (1.8 g, yield-57%) m/z 255.32 [M+H]+ $^1$H NMR (400 MHz, DMSO-d$_6$) δ 11.75 (s, 2H), 7.32 (d, J=0.7 Hz, 1H), 6.86 (d, J=0.9 Hz, 1H), 5.81 (d, J=34.2 Hz, 1H), 5.06 (s, 2H) ppm.

Example 83—Preparation of Compound 58

The synthesis of Compound 58 followed General Procedure 4 following:

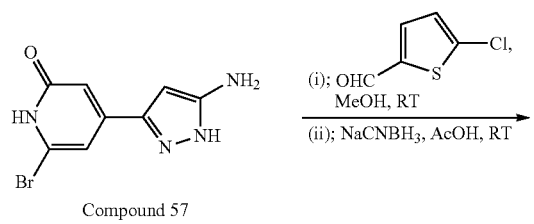

Compound 57

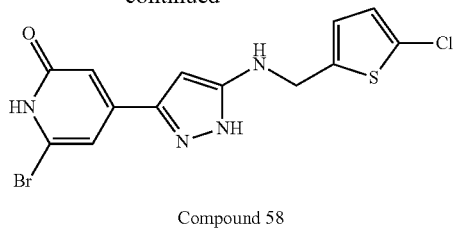

Compound 58

To a cooled solution (10-15° C.) of 4-(5-amino-1H-pyrazol-3-yl)-6-bromopyridin-2(1H)-one (Compound 57, 2.0 g, 7.8 mmol, 1 eq) in methanol (20 mL) was added acetic acid (1 mL) dropwise. To this was then added 5-chlorothiophene-2-carbaldehyde (1.15 g, 9.4 mmol, 1.2 eq) dropwise. The reaction mixture was stirred for 5-6 hours at room temperature. Sodium cyanoborohydride (1.0 g, 15.6 mmol, 2 eq) was added portionwise over a period of 45 minutes. and the reaction was stirred for a further 12 hours. After completion, volatiles were distilled off and the residue was diluted with water. The mixture was extracted with ethyl acetate (40 mL×3). The organic layers were dried over sodium sulfate and concentrated under reduced pressure. The residue was purified by column chromatography using neutral silica gel and product eluted with 80-90% ethyl acetate in hexanes as mobile phase to give pure desired product (1.5 g, yield-51%) m/z[M+H]+ 387.23 $^1$H NMR (DMSO-d$_6$, 400 MHz) δ 12.25 (s, 1H), 11.61 (s, 1H), 7.35 (s, 1H), 7.05-6.75 (m, 3H), 6.09 (s, 2H), 4.36 (d, J=5.9 Hz, 2H) ppm.

Example 84—Preparation of Compound 59

The synthesis of Compound 59 followed General Procedure 6 following:

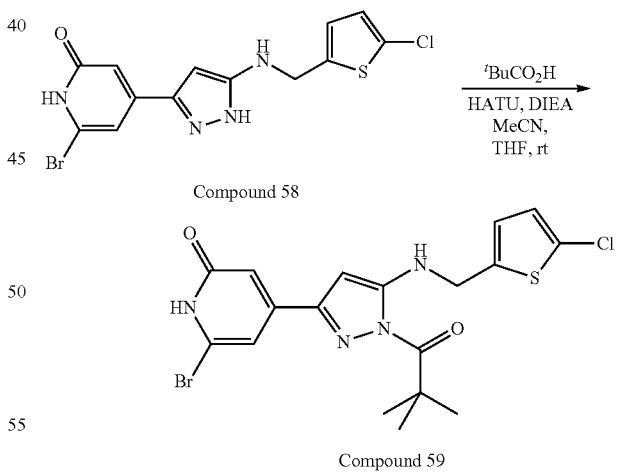

To a solution of pivalic acid (0.16 g, 1.3 mmol, 1 eq) in THF: MeCN (1:1; 10 mL) was added DIPEA (0.5 g, 3.89 mmol, 3 eq), followed by N-[(dimethylamino)-1H-1,2,3-triazolo-[4,5-b]pyridin-1-ylmethylene]-N-methylmethanaminium hexafluorophosphate N-oxide (HATU, 0.74 g, 1.94 mmol, 1.5 eq). The reaction mixture was stirred at room temperature for 1 hour. Then 6-bromo-4-(5-(((5-chlorothiophen-2-yl)methyl)amino)-1H-pyrazol-3-yl)pyridin-2(1H)-one (Compound 58, 0.5 g, 1.29 mmol, 1.0 eq) was added, and the mixture stirred at ambient temperature for 12 hours. After completion, the reaction mixture was diluted with water and extract with dichloromethane (25 mL×3). The organic layers were dried over sodium sulfate and concentrated under reduced pressure. The residue was purified by preparative HPLC to give pure desired product (10 mg, yield-2%) m/z 471.52 [M+H]+ $^1$H NMR (400 MHz, DMSO-$d_6$) δ 10.81 (s, 1H), 7.90 (t, J=6.3 Hz, 1H), 7.41 (s, 1H), 7.07 (d, J=3.7 Hz, 1H), 7.03 (s, 1H), 6.97 (d, J=3.7 Hz, 1H), 6.20 (s, 1H), 4.48 (d, J=6.3 Hz, 2H), 1.47 (s, 9H) ppm.

Example 85—Preparation of Compound 60

The synthesis of Compound 60 followed General Procedure 14 following:

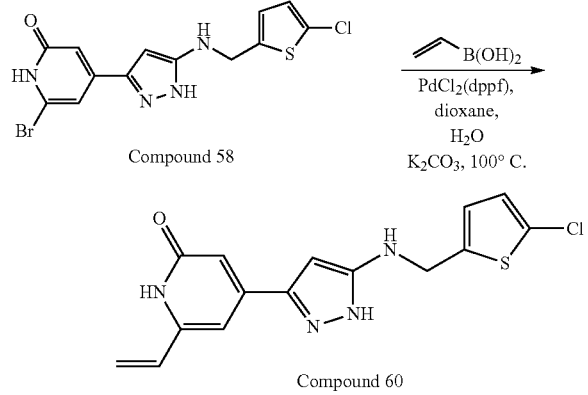

To a solution of 6-bromo-4-(5-4(5-chlorothiophen-2-yl) methyl) amino)-1H-pyrazol-3-yl) pyridin-2-ol (Compound 58, 300 mg, 0.77 mmol, 1.0 eq) in a mixture of dioxane (2 mL) and water (1.0 mL) was added potassium carbonate ($K_2CO_3$, 215 mg, 1.5 mmol, 2.0 eq), vinyl boronic acid (0.203 g, 1.3 mmol, 1.7 eq). The mixture was then degassed under nitrogen flow for 15 minutes. To this mixture was added 1,1'-bis(diphenylphosphino)ferrocene palladium(II) dichloride (PdCl$_2$(dppf), 56 mg, 0.07 mmol, 0.1 eq), and the reaction was stirred at 80° C. for 12 hours. Product formation was monitored by LC-MS. After the mixture was cooled to room temperature, it was diluted with water (5 mL) and extracted with ethyl acetate (25 mL×3). The combined organic layers were dried over sodium sulfate and concentrated under vacuum. The residue was purified by Combiflash chromatography using hexane:ethyl acetate as mobile phase to obtain desire product (130 mg, yield-43.3%) m/z 333.40 [M–H]+ $^1$H NMR (DMSO-$d_6$, 400 MHz) δ 12.45-12.21 (m, 1H), 11.52 (s, 1H), 6.92 (dd, J=20.0, 9.6 Hz, 2H), 6.68 (d, J=5.1 Hz, 1H), 6.50 (dd, J=20.7, 14.4 Hz, 2H), 6.21 (d, J=17.8 Hz, 1H), 6.03 (s, 1H), 5.51 (d, J=11.0 Hz, 1H), 4.36 (s, 2H) ppm.

Example 86—Preparation of Compound 61

The synthesis of Compound 61 followed General Procedure 6 following:

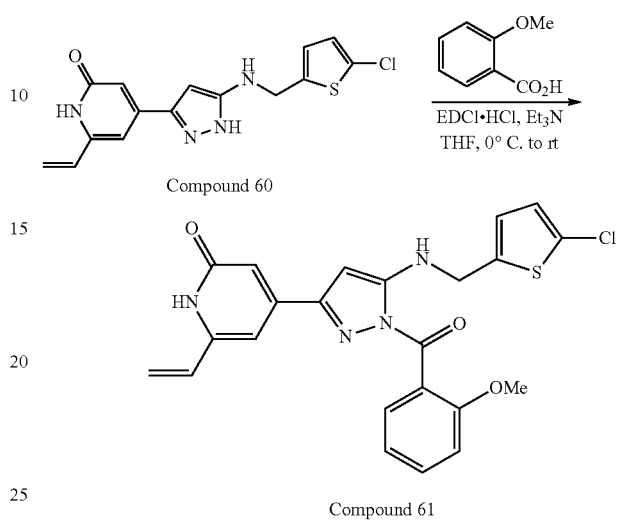

To a cold (0° C.) solution of 2-methoxybenzoic acid (93 mg, 0.61 mmol, 1.7 eq) in THF (4.0 mL) was added 1-(3-dimethylaminopropyl)-3-ethylcarbodiimide hydrochloride (EDCI.HCl, 103 mg, 0.54 mmol, 1.5 eq) and DIPEA (93 mg, 0.72 mmol, 2 eq) and then stirred at 0° C. for 30 minutes. Compound 60 (120 mg, 0.31 mmol, 1 eq) and HOBT (63 mg, 0.036 mmol, 0.1 eq) were and the reaction mixture stirred for 10-12 hours at room temperature. The completion of reaction was confirmed by LC-MS. The reaction mixture was diluted with cold water (5.0 mL) and product was extract by using ethyl acetate (3×5 mL). The organic phases were dried over sodium sulfate and evaporated under vacuum. The residue was purified by preparative HPLC using water:MeCN as mobile phase to obtained desired product (15 mg, yield-16.7%) m/z 467.57 [M–H]+ $^1$H NMR (DMSO-$d_6$) δ 11.67 (s, 1H), 7.58-7.47 (m, 1H), 7.46 (dd, J=7.6, 1.7 Hz, 1H), 7.18 (d, J=8.2 Hz, 1H), 7.06 (t, J=7.4 Hz, 1H), 6.93 (d, J=3.7 Hz, 1H), 6.85 (s, 1H), 6.65 (d, J=3.7 Hz, 1H), 6.47-6.34 (m, 1H), 6.27 (s, 1H), 6.06 (d, J=17.8 Hz, 1H), 5.46 (d, J=11.3 Hz, 1H), 4.00 (s, 2H), 3.77 (s, 3H) ppm.

Example 87—Preparation of Compound 62

The synthesis of Compound 62 followed General Procedure 14 following:

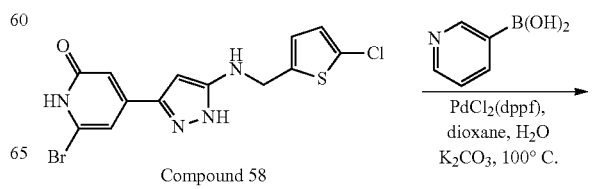

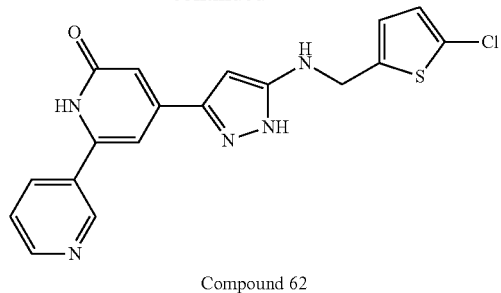

Compound 62

To a solution of 6-bromo-4-(5-(((5-chlorothiophen-2-yl)methyl)amino)-1H-pyrazol-3-yl)pyridin-2(1H)-one (Compound 58, 300 mg, 0.77 mmol, 1.0 eq) in a mixture of dioxane and water (2.0 mL:1.0 mL) was added potassium carbonate ($K_2CO_3$, 215 mg, 1.5 mmol, 2.0 eq), followed by 3-pyridineboronic acid (0.161 g, 1.3 mmol, 1.7 eq). The reaction mixture was degassed with a nitrogen stream for 15 minutes. The mixture was then degassed under nitrogen flow for 15 minutes. To this mixture was the added 1,1'-bis(diphenylphosphino)ferrocene palladium(II) dichloride ($PdCl_2(dppf)$, 56 mg, 0.07 mmol, 0.1 eq), and the reaction was stirred at 80° C. for 12 hours. The reaction was monitored by LC-MS. After completion the reaction mixture was cooled to room temperature. The reaction mixture was diluted with water (5.0 mL) and extracted with ethyl acetate (25 mL×3). The combined organic layers were dried over sodium sulfate and concentrated under vacuum. The residue was purified by Combi-flash chromatography using hexane:ethyl acetate as mobile phase to obtain desire product (60 mg, yield-20%) m/z 384.41 [M−H]+ $^1$H NMR (DMSO-$d_6$, 400 MHz) δ 12.47-12.28 (m, 1H), 8.66 (s, 1H), 8.23 (s, 1H), 7.53 (s, 1H), 6.95 (s, 1H), 6.74 (s, 1H), 6.30-6.15 (m, 1H), 6.10-5.98 (m, 1H), 4.37 (d, J=6.7 Hz, 2H) ppm.

Example 88—Preparation of Compound 63

The synthesis of Compound 63 followed General Procedure 6 following:

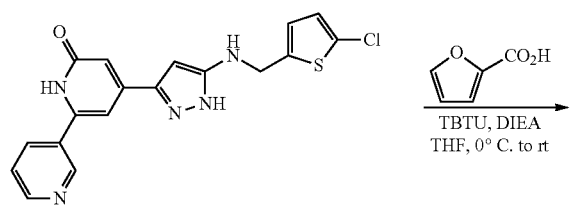

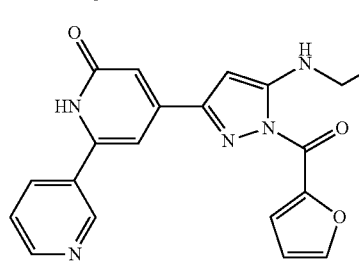

Compound 63

To a cooled solution (0° C.) of 2-furoic acid (40 mg, 0.14 mmol, 1.5 eq) in THF (4.0 mL) was added DIPEA (26 mg, 0.2 mmol, 2 eq) and O-(benzotriazol-1-yl)-N,N,N',N'-tetramethyluronium tetrafluoroborate (TBTU, 50 mg, 0.15 mmol, 1.5 eq). The reaction mixture was stirred for 30 minutes. To this was then added Compound 62 (40 mg, 0.15 mmol, 1 eq) and the reaction stirred for 10-12 hours at room temperature. The reaction was monitored by LC-MS. After completion, the reaction mixture was diluted with cold water (5.0 mL) and product extracted with ethyl acetate (3×5 mL). The combined organic phases were dried over sodium sulfate and evaporated under vacuum. The residue was purified by preparative HPLC using water:MeCN as mobile phase to obtained desired product (5 mg, yield-12.5%) m/z 478.57 [M−H]+ $^1$H NMR (DMSO-$d_6$) δ 12.51-12.20 (m, 1H), 9.10 (s, 1H), 8.75 (s, 1H), 8.40 (s, 1H), 8.19 (s, 1H), 8.10 (d, J=3.5 Hz, 1H), 7.70 (s, 1H), 7.26 (s, 2H), 7.05-6.94 (m, 1H), 6.91 (d, J=3.7 Hz, 1H), 6.83 (dd, J=3.5, 1.7 Hz, 1H), 6.78 (s, 1H), 6.69 (d, J=3.7 Hz, 1H), 4.10 (s, 2H) ppm.

Example 89—Preparation of Intermediate 25

The synthesis of Intermediate 25 followed General Procedure 1 following.

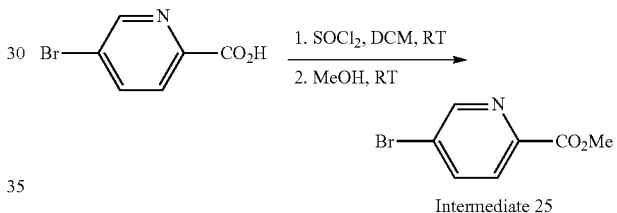

Intermediate 25

To a cooled solution (0° C.) of 5-bromopyridine-2-carboxylic acid (50.0 g, 0.247 mol, 1.0 eq) in anhydrous methanol (400 mL) was added thionyl chloride (107.0 mL, 2.47 mol, 10.0 eq) dropwise. The reaction mixture was slowly brought to ambient temperature and then heated at 50° C. for 12 hours. The reaction was monitored by TLC and LC-MS. After completion, the reaction mixture was concentrated under reduced pressure to obtain a white solid residue, which was slowly quenched with saturated sodium bicarbonate. The white solid was filtered to give desired product methyl-5-bromopyridine-2-carboxylate (43.0 g, yield-80%) m/z 216.14; $^1$H NMR (400 MHz, DMSO) δ 8.86 (d, J=1.9 Hz, 1H), 8.28 (dd, J=8.4, 2.4 Hz, 1H), 8.00 (d, J=8.4 Hz, 1H), 3.89 (s, 3H) ppm.

Example 90—Preparation of Intermediate 26

The synthesis of Intermediate 26 followed General Procedure 18 following.

General Procedure 18

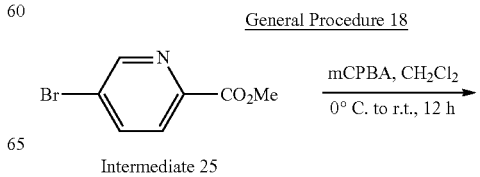

Intermediate 25

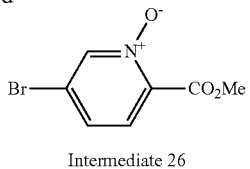

Intermediate 26

To a cooled solution (0° C.) of methyl-5-bromopyridine-2-carboxylate (Intermediate 25, 20.0 g, 92.6 mmol, 1.0 eq) in dichloromethane (200 mL), was added m-CPBA (24.0 g, 139 mmol, 1.5 eq) portionwise. The reaction mixture was slowly brought to ambient temperature and stirred for 12 hours. After completion (monitored by TLC and LC-MS), the reaction mixture was concentrated under reduced pressure to obtain a white solid residue, which was slowly quenched with saturated sodium bicarbonate and extracted with ethyl acetate. The crude compound was purified by column chromatography using silica gel (silica 60-120 mesh size), eluting with dichloromethane:methanol (5%-8% gradient) to give the desire product 5-bromo-2-(methoxycarbonyl)pyridine-1-oxide (12.52 g, yield-58.4%) m/z 234.11 [M+2]+; 1H NMR (400 MHz, CDCl3) δ 8.42 (d, J=1.6 Hz, 1H), 7.61-7.51 (m, 1H), 7.47-7.39 (m, 1H), 3.98 (s, 3H) ppm.

Example 91—Preparation of Intermediate 27

The synthesis of Intermediate 27 followed General Procedure 19 following.

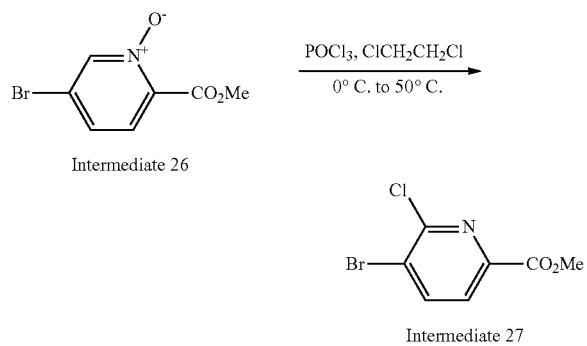

To a cooled solution (0° C.) of 5-bromo-2-(methoxycarbonyl)pyridine-1-oxide (Intermediate 26, 2.0 g, 8.62 mmol, 1.0 eq) in anhydrous 1,2-dichloroethane (10 mL) was added phosphorous oxychloride (3.15 mL, 34.5 mmol, 4.0 eq) dropwise. The reaction mixture was slowly brought to ambient temperature and then stirred at 50° C. for 12 hours. After completion (monitored by TLC and LC-MS), the reaction mixture was concentrated under reduced pressure. The residue was slowly quenched with aqueous saturated sodium bicarbonate, and the solid was filtered to give desire product methyl-5-bromo-6-chloropyridine-2-carboxylate (1.55 g, yield-71.8%) m/z 252.17; 1H NMR (400 MHz, DMSO) δ 8.78 (d, J=2.5 Hz, 1H), 8.50 (d, J=2.5 Hz, 1H), 3.89 (s, 3H) ppm.

Example 92—Preparation of Intermediate 28

The synthesis of Intermediate 28 followed General Procedure 20 following.

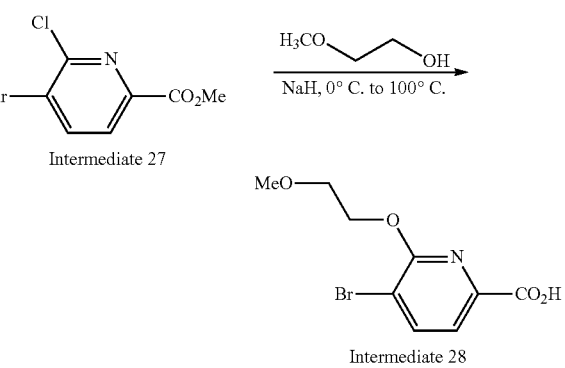

To a dry round-bottomed flask pre-cooled to 0° C. and under N2 gas flow, NaH (0.56 g, 14.0 mmol, 3.5 eq) was added. To this was slowly added methoxyethanol (10.0 mL) dropwise, and the mixture was stirred for 30 minutes. To this was added methyl-5-bromo-6-chloropyridine-2-carboxylate (Intermediate 27, 1.0 g, 4.0 mmol, 1.0 eq) portionwise. The reaction mixture was then stirred at ambient temperature and then heated at 100° C. for 10 minutes. After completion (monitored by TLC and LC-MS), the reaction mixture was concentrated under reduced pressure to obtain a brown solid residue, which was slowly quenched with acetic acid. The mixture was extracted with 10% MeOH:dichloromethane, dried over sodium sulfate and concentrated to give the desired product 5-bromo-6-(2-methoxyethoxy) pyridine-2-carboxylic acid (Intermediate 28, 0.70 g, yield-63%) m/z 278.28 [M+2]+; 1H NMR (400 MHz, DMSO) δ 13.41 (s, 1H), 8.19 (d, J=7.8 Hz, 1H), 7.56 (d, J=7.8 Hz, 1H), 4.52 (dd, J=5.4, 3.8 Hz, 2H), 3.71 (dd, J=5.4, 3.8 Hz, 2H), 3.33 (s, 3H) ppm.

Example 93—Preparation of Intermediate 29

The synthesis of Intermediate 29 followed General Procedure 1 following.

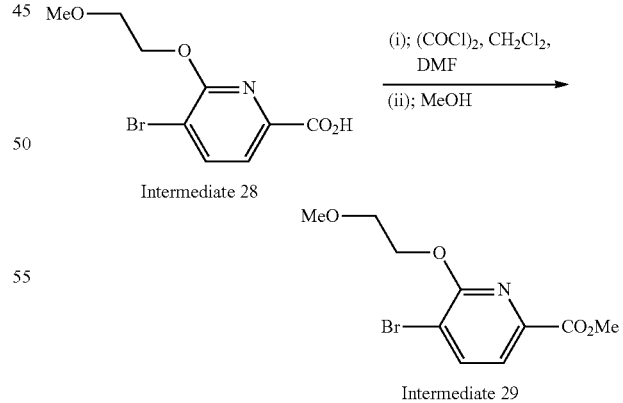

To a cooled solution (0° C.) of 5-bromo-6-(2-methoxyethoxy)pyridine-2-carboxylic acid (Intermediate 28, 3.2 g, 11.6 mmol, 1.0 eq) in anhydrous dichloromethane (40 mL) was added oxalyl chloride (1.50 mL, 17.4 mmol, 1.5 eq) dropwise. To this was added anhydrous DMF (0.2 mL), and the reaction mixture was slowly brought to ambient temperature and then stirred for 12 hours. After completion, as monitored by TLC and LC-MS, the mixture was cooled back to 0° C., and anhydrous MeOH (10.0 mL) was added dropwise and stirred for 10-15 minutes. The reaction mixture was concentrated under reduced pressure to obtain a white solid residue, which was slowly quenched with saturated sodium bicarbonate and filtered to give the desired product methyl-5-bromo-6-(2-methoxyethoxy)pyridine-2-carboxylate (Intermediate 29, 3.0 g, yield-89.2%) m/z 292.28 [M+2]'; $^1$H NMR (400 MHz, CDCl3) δ 8.01-7.88 (m, 1H), 7.60 (d, J=7.8 Hz, 1H), 4.72-4.59 (m, 2H), 3.96 (s, 3H), 3.87-3.78 (m, 2H), 3.48 (s, 3H) ppm.

Example 94—Preparation of Intermediate 30

The synthesis of Intermediate 30 followed General Procedure 2 following.

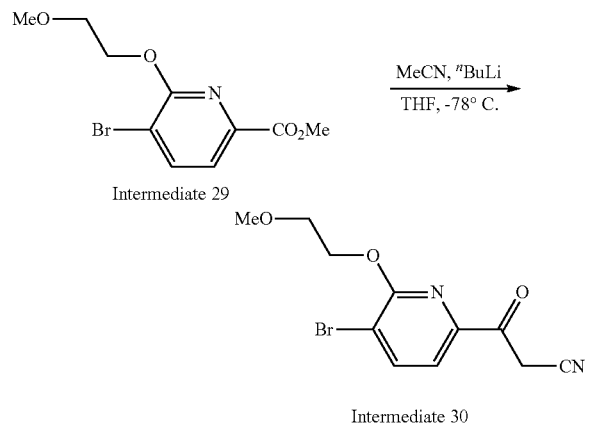

Intermediate 29

Intermediate 30

To a cooled solution (−78° C.) of acetonitrile (1.3 mL, 23.45 mmol, 1.7 eq) in anhydrous THF (75 mL) was added n-BuLi (2.5M in hexane, 9.4 mL, 23.45 mmol, 1.7 eq) dropwise over a period of 60 minutes. The reaction was stirred for a further 60 minutes thereafter. To this was then added a solution of methyl-5-bromo-6-(2-methoxyethoxy) pyridine-2-carboxylate (Intermediate 29, 4.0 g, 13.8 mmol, 1.0 eq) in THF (20 mL), and the solution stirred for a further 3 hours. The reaction mixture was quenched with saturated ammonium chloride solution and product was extracted with ethyl acetate. The organic layer was dried over sodium sulfate and concentrated under reduced pressure. The residue was purified by column chromatography using (60-120 mesh size) silica gel, eluting with 0-40% ethyl acetate in n-hexane as mobile phase to give pure desired product 5-bromo-6-(2-methoxyethoxy)pyridine-2-oxopropanenitrile (Intermediate 30, 3.8 g, yield-92%) m/z 299.19; $^1$H NMR (400 MHz, CDCl3) δ 8.14-7.98 (m, 1H), 7.61 (d, J=7.8 Hz, 1H), 4.71-4.40 (m, 2H), 4.22 (s, 2H), 3.97-3.73 (m, 2H), 3.50 (s, 3H) ppm.

Example 95—Preparation of Compound 64

The synthesis of Compound 64 followed General Procedure 3 following.

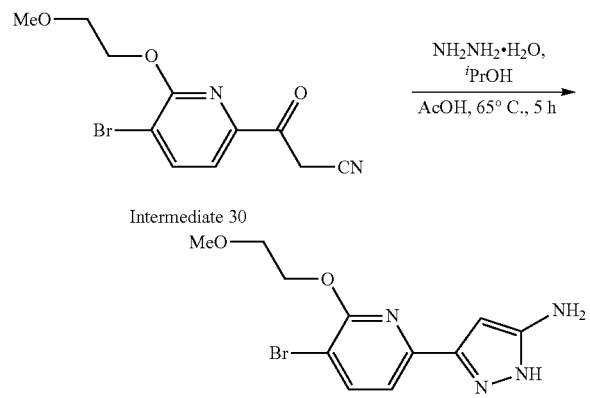

Intermediate 30

Compound 64

To a solution of 5-bromo-6-(2-methoxyethoxy)pyridine-2-oxopropane nitrile (Intermediate 30, 8.0 g, 27 mmol, 1.0 eq) in isopropanol (125 mL) and acetic acid (0.8 mL, 13.4 mmol, 0.5 eq) was added hydrazine monohydrate (0.8 g, 40.5 mmol, 1.5 eq) dropwise. The reaction was stirred at 65° C. for 5 hours. After completion (monitored by TLC and LC-MS), the reaction mixture was concentrated under reduced pressure. The residue was purified by column chromatography using silica gel (60-120 mesh), eluting with 5% MeOH:dichloromethane to give desired product 3-(5-bromo-6-(2-methoxyethoxy)pyridin-2-yl)-1H-pyrazol-5-amine (Compound 64, 8.0 g, yield-94.7%) m/z 314.92; $^1$H NMR (400 MHz, C6D6) δ 7.22 (d, J=7.8 Hz, 1H), 6.95 (s, 3H), 6.45 (t, J=11.9 Hz, 1H), 5.59 (s, 1H), 4.39 (dd, J=15.4, 10.6 Hz, 2H), 3.48-3.50 (m, 2H), 3.14 (s, 3H) ppm.

Example 96—Preparation of Compound 65

The synthesis of Compound 65 followed General Procedure 17 following:

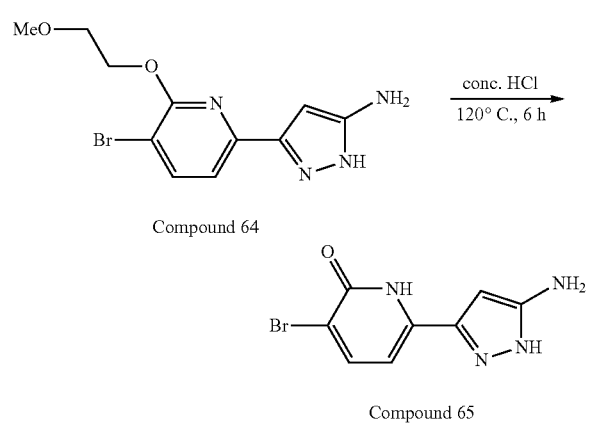

Compound 64

Compound 65

To a round-bottomed flask charged with 3-(5-bromo-6-(2-methoxyethoxy)pyridin-2-yl)-1H-pyrazol-5-amine (1.6 mmol) was added concentrated hydrochloric acid (5 mL). The mixture was heated at 120° C. for 6 hrs. The excess of HCl-water was evaporated under vacuum and the crude mass was quenched with sodium bicarbonate solution. The reaction mixture was extracted with ethyl acetate (3 times). The combined organic mass was dried over sodium sulfate and evaporated under reduced pressure. The residue was purified by column chromatography using (60-120 mesh size) silica gel, eluting with neat methanol as mobile phase to give pure desired product 6-(5-amino-1H-pyrazol-3-yl)-3-bromopyridin-2(1H)-one (Compound 65, 0.220 g, yield-48.9%) m/z 255.34[M+1]+; ¹H NMR (400 MHz, DMSO) δ 11.94 (s, 2H), 7.90 (d, J=7.6 Hz, 1H), 6.54 (d, J=7.4 Hz, 1H), 5.98 (s, 1H), 5.20 (s, 2H) ppm.

Example 97—Preparation of Compound 66

The synthesis of Compound 66 followed General Procedure 4 following:

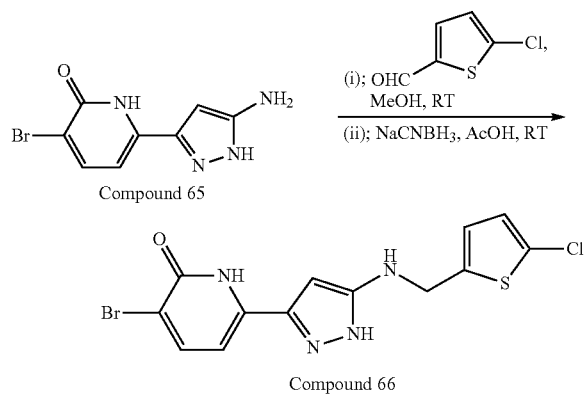

To a cooled solution (0-10° C.) of 3-(5-amino-1H-pyrazol-3-yl)-5-methylpyridin-2(1H)-one (Compound 65, 0.200 g, 0.78 mmol, 1.0 eq) in methanol (5 mL) was added acetic acid (0.046 g, 0.78 mmol, 1.0 eq) dropwise. To this was added 5-chlorothiophene-2-carbaldehyde (0.137 g, 0.93 mmol, 1.2 eq) dropwise, and the mixture was stirred for another 30-45 minutes at room temperature. Sodium cyanoborohydride (0.073 g, 1.17 mmol, 1.5 eq) was added portionwise over a period of 15 minutes. The reaction was stirred for 3 hours. After completion of reaction, the mixture was poured into ice cold water under stirring, and extracted with ethyl acetate. The organic phases were dried over sodium sulfate and concentrated under reduced pressure. The residue was purified by column chromatography using silica gel, eluting with 10-100% methanol in dichloromethane to give pure desired product 3-bromo-6-(5-(((5-chlorothiophen-2-yl)methyl)amino)-1H-pyrazol-3-yl)pyridin-2(1H)-one (Compound 66, 0.250 g, yield-82.7%) m/z 387.08 [M+1]+; ¹H NMR (400 MHz, DMSO) δ11.84 (s, 1H), 7.47 (s, 1H), 6.92 (d, J=3.7 Hz, 1H), 6.87 (d, J=3.7 Hz, 1H), 6.25 (s, 1H), 5.85 (s, 1H), 4.33 (d, J=6.1 Hz, 2H) ppm.

Example 98—Preparation of Compound 67

The synthesis of Compound 67 followed General Procedure 6 following:

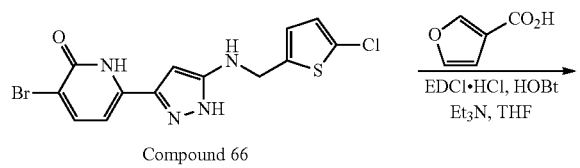

Compound 66

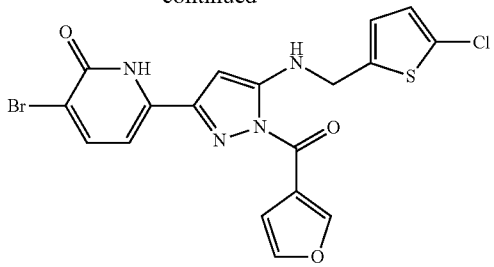

Compound 67

To a dry, cooled solution (0° C.). of furan-3-carboxylic acid (0.0014 g, 0.121 mmol, 1 eq) in THF (2 mL) was added EDCI.HCl (0.027 g, 0.14 mmol, 1.2 eq), followed by triethylamine (0.036 g, 0.36 mmol, 3.0 eq). The reaction mixture was stirred for 30 minutes, and then to it was added hydroxybenzotriazole (HOBt, 3.2 mg, 0.024 mmol, 0.2 eq), followed by 3-bromo-6-(5-(((5-chlorothiophen-2-yl)methyl)amino)-1H-pyrazol-3-yl)pyridin-2(1H)-one (Compound 66, 0.05 g, 0.121 mmol, 1.0 eq). After completion (monitored by LC-MS), the reaction mixture was poured into water (10 mL) and extracted with ethyl acetate. The combined organic phases were washed with water, then brine, and dried over sodium sulfate. After evaporation under reduced pressure, the residue was purified by preparative HPLC using water-acetonitrile as mobile phase to give desired product 3-bromo-6-(5-(((5-chlorothiophen-2-yl)methyl)amino)-1-(furan-3-carbonyl)-1H-pyrazol-3-yl)pyridin-2(1H)-one (Compound 67, 6.4 mg, yield-12.9%) m/z 481.42 [M+1]+ 1H NMR (400 MHz, DMSO) δ 12.35-12.25 (m, 1H), 9.39 (s, 1H), 8.07 (s, 1H), 8.02 (d, J=7.6 Hz, 1H), 7.93-7.87 (m, 1H), 7.13-7.02 (m, 2H), 6.98 (d, J=3.8 Hz, 1H), 6.82-6.74 (m, 1H), 6.26 (s, 1H), 4.53 (d, J=6.5 Hz, 2H) ppm.

Example 99—Preparation of Intermediate 31

The synthesis of Intermediate 31 followed General Procedure 1 following:

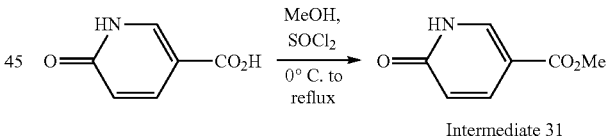

To a cooled solution (0° C.) of 6-hydroxynicotinic acid (25.0 g, 179 mmol, 1.0 eq) in methanol (375 mL) was added thionyl chloride (107 g. 899 mmol, 5.0 eq) dropwise. The reaction mixture was heated at reflux for 12 hours. After completion, the reaction mixture was cooled back to room temperature and then concentrated under reduced pressure. The residue was diluted with methanol and concentrated under vacuum. The residue was washed with hexane and ethyl acetate and dried under vacuum to obtain white a solid compound (Intermediate 31, 27.51 g yield-91.9%) m/z [M+H]+ 154.2. ¹H NMR (DMSO-d₆) δ 12.15 (s, 1H), 8.05 (d, J=2.5 Hz, 1H), 7.80 (dd, J=9.6, 2.7 Hz, 1H), 6.37 (d, J=9.6 Hz, 1H), 3.77 (s, 3H) ppm.

Example 100—Preparation of Intermediate 32

The synthesis of Intermediate 32 followed General Procedure 2 following.

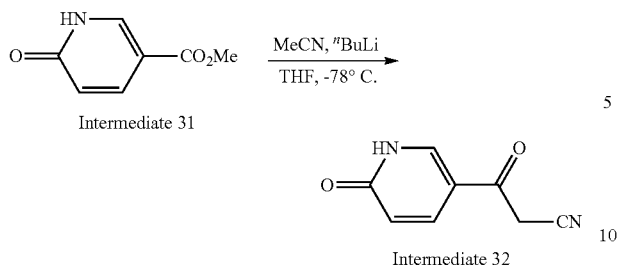

Intermediate 31

Intermediate 32

To a cooled solution (−78° C.) of acetonitrile (8.2 mL, 156 mmol, 1.2 eq) in tetrahydrofuran (300 mL) was added ⁿBuLi (2.5M in hexane, 62.7 mL, 156 mmol, 1.2 eq) dropwise over a period of 60 minutes, and reaction was stirred for another 60 minutes thereafter. To this was added methyl 6-oxo-1,6-dihydropyridine-3-carboxylate (Intermediate 31, 20.0 g, 130 mmol, 1.0 eq) portionwise, and the reaction mixture was maintained at −78° C. for a further 3 hours. After completion, the reaction mixture was quenched with ammonium chloride solution and extracted with ethyl acetate. The organic layer was evaporated to obtain crude product, which was suspended in methanol and stirred for 30 minutes at room temperature. The solid was filtered through suction and dried under high vacuum to yield the desired Intermediate 32 (11.5 g, yield-58%) m/z 162.74 [M+H]+.

Example 101—Preparation of Compound 68

The synthesis of Compound 68 followed General Procedure 3 following.

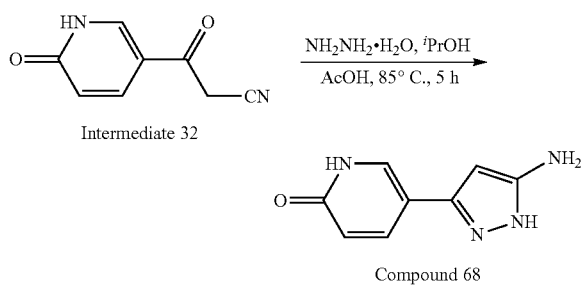

Intermediate 32

Compound 68

To a solution of 3-oxo-3-(6-oxo-1,6-dihydropyridin-3-yl)propanenitrile (Intermediate 32, 20.0 g, 123 mmol, 1.0 eq) in isopropanol (600 mL) was added acetic acid (22.2 mL). To this was added hydrazine monohydrate (7.40 mL, 148 mmol, 1.2 eq) dropwise. The reaction mixture was then stirred at 85° C. for 5 hours. After completion, the reaction mixture was concentrated under reduced pressure. The residue was purified by column chromatography using neutral silica gel (60-120 mesh), eluting with 10-25% methanol in dichloromethane as gradient to give the desired product (Compound 68, 13.25 g, yield-61%) m/z[M+H]+ 176.9 ¹H NMR (400 MHz, DMSO-d₆) δ 11.31 (s, 2H), 7.75 (dd, J=9.5, 2.6 Hz, 1H), 7.63 (d, J=2.1 Hz, 1H), 6.37 (d, J=9.5 Hz, 1H), 5.58 (s, 1H), 4.82 (s, 2H) ppm.

Example 102—Preparation of Compound 69

The synthesis of Compound 69 followed General Procedure 4 following:

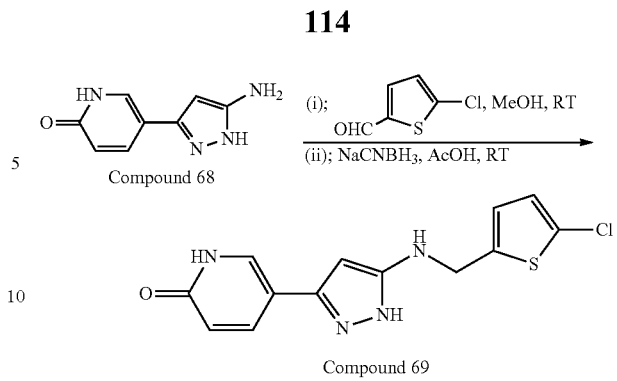

Compound 68

Compound 69

To a cooled solution (10-15° C.) of 5-(5-amino-1H-pyrazol-3-yl)pyridin-2(1H)-one (Compound 68, 56.7 mmol) in methanol (100 mL) was added acetic acid (11.2 mL) dropwise. To this was added 5-chlorothiophene-2-carbaldehyde (9.15 g, 62.4 mmol, 1.1 eq) portionwise, and the reaction mixture was stirred for a further 45 minutes at room temperature. Sodium cyanoborohydride (5.35 g, 85.1 mmol, 1.5 eq) was then added portionwise over a period of 45 minutes and the mixture was stirred for 2 hours. After reaction completion, the mixture was poured into ice cold water under stirring and extracted with ethyl acetate. The organic layer was dried over sodium sulfate and concentrated under reduced pressure. The residue was purified by column chromatography using neutral silica gel, eluting with 10-12% methanol in dichloromethane to give pure desired product (Compound 69, 7.3 g, yield-42.7%) m/z[M+H]+ 307.00 ¹H NMR (DMSO-d₆) δ 11.77 (s, 2H), 7.73 (d, J=9.5 Hz, 1H), 7.68 (s, 1H), 6.96-6.90 (m, 1H), 6.88 (d, J=3.6 Hz, 1H), 6.39 (d, J=9.5 Hz, 1H), 5.95 (s, 1H), 5.75 (s, 1H), 4.33 (d, J=6.3 Hz, 2H) ppm.

Example 103—Preparation of Compound 70

The synthesis of Compound 70 followed General Procedure 6 following:

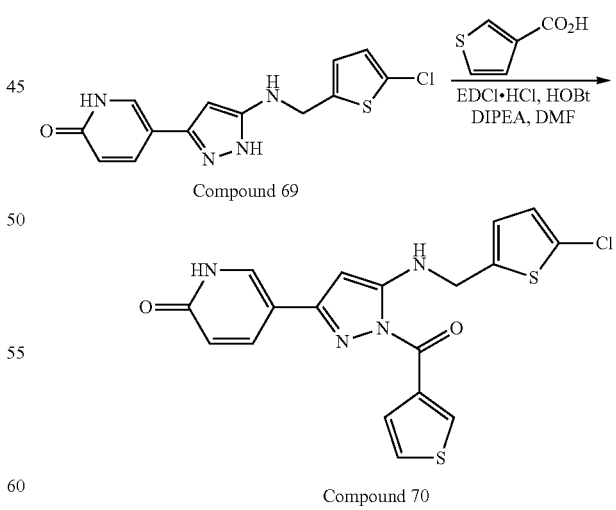

Compound 69

Compound 70

To a cooled solution (0-5° C.) of thiophene-3-carboxylic acid (0.602 g, 1.2 eq, 4.71 mmol) in dimethylformamide (20.0 mL) was added EDCI.HCl (0.903 g, 1.2 eq, 4.71 mmol), and DIPEA (0.606 g, 1.2 eq, 4.71 mmol). After stirring at 0-5° C. for 30 minutes, to the mixture was added Compound 69 (1.2 g, 1.0 eq, 3.9 mmol) and HOBt (0.105 g, 0.2 eq, 0.784 mmol), and the mixture stirred for 14 hours at room temperature. The reaction was monitored by LCMS. After completion, the mixture was poured into ice cold water under stirring and extracted with ethyl acetate (3×25 mL). The organic layer was dried over sodium sulfate and concentrated under reduced pressure. The residue was purified by column chromatography using silica gel (100-200 mesh) in the presence of 0.05% triethylamine, eluting with 20-25% ethyl acetate in n-hexane to give pure desired product (Compound 70, 0.98 g, yield=60.1%) m/z 417.23[M+1]+ $^1$H NMR (400 MHz, DMSO) δ 11.96 (s, 1H), 9.13-9.01 (m, 1H), 7.98 (ddd, J=19.9, 11.5, 4.8 Hz, 3H), 7.82 (dd, J=5.1, 1.1 Hz, 1H), 7.67 (dd, J=5.1, 3.0 Hz, 1H), 7.07 (d, J=3.7 Hz, 1H), 6.98 (d, J=3.7 Hz, 1H), 6.44 (d, J=9.6 Hz, 1H), 6.09 (s, 1H), 4.53 (d, J=6.3 Hz, 2H) ppm.

Example 104—Preparation of Compound 71

The synthesis of Compound 71 followed General Procedure 6 following:

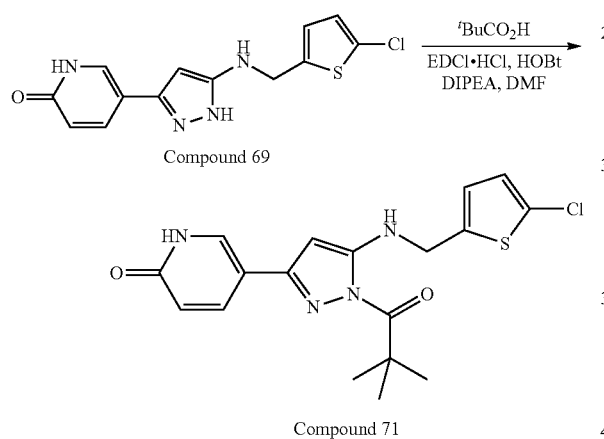

Compound 69

Compound 71

To a cooled solution (0-5° C.) of pivalic acid (0.395 g, 1.2 eq, 3.9 mmol) in dimethylformamide (20.0 mL) was added EDCI.HCl (0.749 g, 1.2 eq, 3.9 mmol) and DIPEA (0.842 g, 2.0 eq, 6.5 mmol). After stirring for 30 minutes, to the reaction mixture was added Compound 69 (1.0 g, 1.0 eq, 3.3 mmol), followed by HOBt (0.119 g, 0.2 eq, 0.784 mmol). The reaction was stirred for 14 hours at room temperature. The reaction was monitored by LCMS. After completion, the mixture was poured into ice cold water under stirring and extracted with ethyl acetate (3×20 mL). The organic phase was dried over sodium sulfate and concentrated under reduced pressure. The residue was purified by column chromatography using silica gel (100-200 mesh) in the presence of 0.05% triethylamine, eluting with 25-30% ethyl acetate in n-hexane as mobile phase to give pure desired product (Compound 71, 0.8 g, yield=62.8%) m/z 391.28 [M+1]+ $^1$H NMR (400 MHz, DMSO) δ 11.90 (s, 1H), 7.94-7.71 (m, 3H), 7.04 (d, J=3.7 Hz, 1H), 6.97 (d, J=3.8 Hz, 1H), 6.45 (d, J=9.7 Hz, 1H), 5.95 (s, 1H), 4.46 (d, J=5.7 Hz, 2H), 1.45 (s, 9H) ppm.

Example 105—Preparation of Compound 72

The synthesis of Compound 72 followed the procedure of General Procedure 8 following.

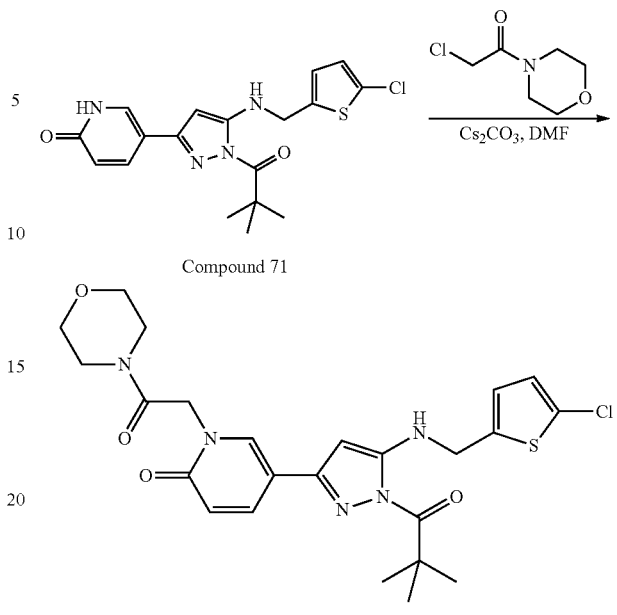

Compound 71

Compound 72

To a solution of Compound 71 (0.4 g, 1.0 eq, 1.03 mmol) in DMF (15 mL) was added anhydrous cesium carbonate (0.839 g, 2.5 eq, 2.6 mmol), followed by the addition of 4-chloroacetyl morpholine (0.252 g, 1.2 eq, 1.54 moles). The reaction mixture was stirred for 12 hours at room temperature. After completion (monitored by TLC and LCMS), the reaction mixture was poured into ice cold water under stirring and extracted with ethyl acetate (3×25 mL). The organic layer was dried over sodium sulfate and concentrated under reduced pressure. The residue was purified by column chromatography using neutral silica gel, eluting with 60-65% ethyl acetate in n-hexane as mobile phase to give pure desired product (Compound 72, 0.065 g, yield=12.7%). m/z 518.31[M+1]+ $^1$H NMR (400 MHz, DMSO) δ 8.08 (d, J=2.3 Hz, 1H), 7.98-7.81 (m, 2H), 6.99 (dd, J=7.5, 3.8 Hz, 2H), 6.52 (d, J=9.4 Hz, 1H), 5.79 (s, 1H), 4.89 (s, 2H), 4.47 (d, J=6.2 Hz, 2H), 3.67 (s, 2H), 3.59 (d, J=5.2 Hz, 4H), 3.46 (s, 2H), 1.47 (s, 9H) ppm.

Example 106—Preparation of Intermediate 33

The synthesis of Intermediate 33 followed General Procedure 1 following.

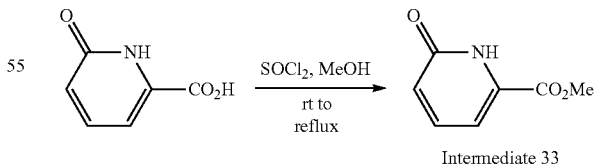

Intermediate 33

To a room temperature solution of commercially available 6-hydroxypicolinic acid (20.0 g, 143 mmol, 1.0 eq) in methanol (200 mL) was slowly added thionyl chloride (84.89 g, 710 mmol, 5.0 eq). The reaction mixture was heated to reflux overnight. After completion, the reaction mixture was concentrated under reduced pressure. The residue was washed with ethyl acetate and dried under vacuum to give the desired compound 6-hydroxypicolinic acid, methyl ester (Intermediate 33, 20.0 g, yield-90%) m/z[M+1]+ 154.15.

Example 107—Preparation of Intermediate 34

The synthesis of Intermediate 34 followed General Procedure 2 following.

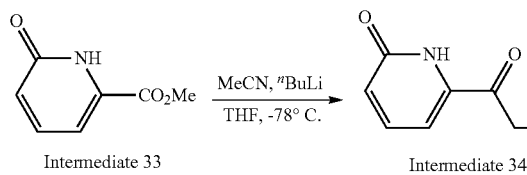

Intermediate 33 → Intermediate 34

To a dry (N₂ gas flow) and cooled solution (−78° C.) of acetonitrile (4.01 g, 98 mmol, 1.5 eq) in tetrahydrofuran (150 mL) was added ⁿBuLi (2.5 M in hexane, 39.2 mL, 98 mmol, 1.5 eq) dropwise over a period of 60 minutes. The reaction was stirred for another 60 minutes thereafter. 6-Hydroxypicolinic acid, methyl ester (Intermediate 33, 10.0 g, 65.4 mmol, 1.0 eq.) was added portionwise to the reaction mixture and the temperature maintained at −78° C. for 3 hours. The reaction progress was monitored by LCMS. After completion, the reaction mass was quenched with ethyl acetate and the mixture concentrated under reduced pressure. The residue was triturated with diethyl ether and dried under reduced pressure to obtain desired product 3-oxo-3-(6-oxo-1,6-dihydropyridin-2-yl)propanenitrile (Intermediate 34) which was used as such for the next step (6.0 g, yield-56.3%) m/z[M+1]+ 163.07.

Example 108—Preparation of Compound 73

The synthesis of Compound 73 followed General Procedure 3 following.

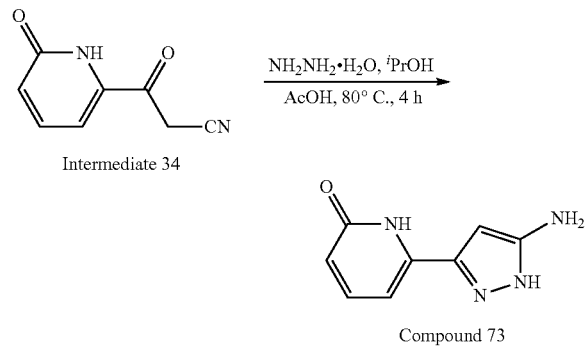

Intermediate 34 → Compound 73

To a solution of 3-oxo-3-(6-oxo-1,6-dihydropyridin-2-yl)propanenitrile (Intermediate 34, 10.0 g, 61 mmol, 1.0 eq) in isopropanol (300 mL) was added acetic acid (3.7 mL, 61 mmol, 1.0 eq), followed by dropwise addition of hydrazine monohydrate (3.37 g, 67 mmol, 1.1 eq). The reaction was then stirred at 80° C. for 4 hours. The reaction progress was monitored by LCMS. After completion, the reaction mixture was concentrated under vacuum. The residue was purified by column chromatography using silica gel (100-200 mesh), eluting with 5% methanol in dichloromethane as gradient to give desired product 6-(5-amino-1H-pyrazol-3-yl)pyridin-2 (1H)-one (Compound 73, 1.0 g, yield-62.1%) m/z [M+1]+ 177.12. ¹H NMR (400 MHz, DMSO-d₆) δ 11.91 (s, 1H), 11.06 (s, 1H), 7.44 (s, 1H), 6.57 (s, 1H), 6.25 (s, 1H), 5.91 (s, 1H), 5.19 (s, 2H) ppm.

Example 109—Preparation of Compound 74

The synthesis of Compound 74 followed General Procedure 4 following:

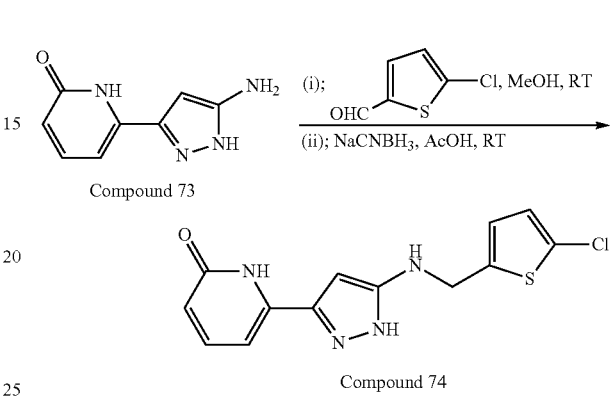

Compound 73 → Compound 74

To a cooled solution (10-15° C.) of 6-(5-amino-1H-pyrazol-3-yl)pyridin-2(1H)-one (Compound 73, 1.0 g, 5.7 mmol, 1.0 eq) in methanol (20 mL) was added acetic acid (0.34 g, 5.7 mmol, 1.0 eq), followed by portionwise addition of 5-chlorothiophene-2-carbaldehyde (0.915 g, 6.3 mmol, 1.1 eq). The reaction was allowed to stir for 2-3 hours at room temperature. To the reaction mixture was then added sodium cyanoborohydride (0.078 g, 12.5 mmol, 2.0 eq) portionwise over a period of 15 minutes. The reaction was then stirred for 12 hours at room temperature. After completion, the reaction mixture was diluted in ice cold water and extracted with ethyl acetate (3×30 mL). The organic layers were combined and dried over anhydrous sodium sulfate and concentrated under reduced pressure. The residue was purified by column chromatography using silica gel (60-120 mesh), eluting with 60% ethyl acetate in hexane as mobile phase to give pure desired product (Compound 74, 0.2 g, yield-9.1%) m/Z 307.1[M+1]H+ ¹H NMR (400 MHz, DMSO-d₆) δ 12.24 (s, 1H), 11.58 (s, 1H), 7.47 (s, 1H), 6.94 (t, J=9.7 Hz, 2H), 6.59 (s, 1H), 6.28 (s, 3H), 4.34 (d, J=6.1 Hz, 2H) ppm.

Example 110—Preparation of Compound 75

The synthesis of Compound 75 followed General Procedure 6 following:

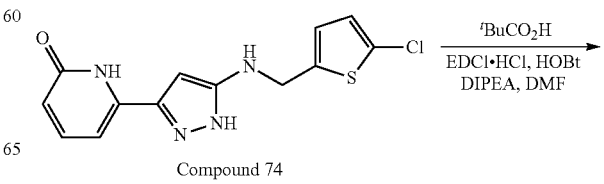

Compound 74

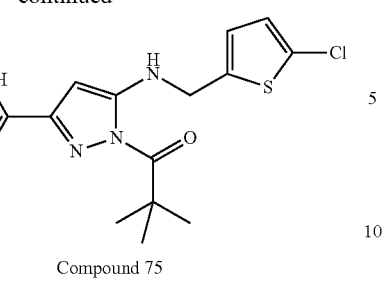

Compound 75

To a cooled solution (0° C.) of pivalic acid (0.25 g, 2.4 mmol, 1.5 eq) in DMF (5 mL) was added 1-(3-dimethylaminopropyl)-3-ethylcarbodiimide hydrochloride (EDCI·HCl, 0.47 g, 2.5 mmol, 1.5 eq), hydroxybenzotriazole (HOBt, 0.043 g, 0.33 mmol, 0.2 eq) and N,N-diisopropylethylamine (DIPEA, 0.231 g, 1.8 mmol, 1.1 eq). The reaction mixture was allowed to stir at 0° C. for 20 minutes and to it was then added 6-(5-(((5-chlorothiophen-2-yl)methyl)amino)-1H-pyrazol-3-yl)pyridin-2(1H)-one (Compound 74, 0.5 g, 1.6 mmol, 1.0 eq). The reaction mixture was stirred at room temperature for 12 hours. After completion of reaction, the mixture was diluted with water and extracted with ethyl acetate (3×20 mL). The combined organic phases were dried over anhydrous sodium sulfate and concentrated under vacuum. The residue was purified by column chromatography using silica (100-200 silica), eluting with 60% ethyl acetate in hexane, yielding desired product 6-(5-(((5-chlorothiophen-2-yl)methyl)amino)-1-pivaloyl-1H-pyrazol-3-yl)pyridin-2(1H)-one (Compound 75, 0.124 g, yield: 19.9%); m/z[M+1]+ 391.24 $^1$H NMR (400 MHz, DMSO) δ 11.37 (s, 1H), 7.93 (s, 1H), 7.56 (s, 1H), 7.01 (dd, J=14.3, 3.6 Hz, 2H), 6.46 (s, 1H), 6.12 (s, 1H), 4.47 (d, J=6.0 Hz, 2H), 1.47 (s, 9H) ppm.

Example 111—Preparation of Compound 76

The synthesis of Compound 76 followed the procedure of General Procedure 8 following.

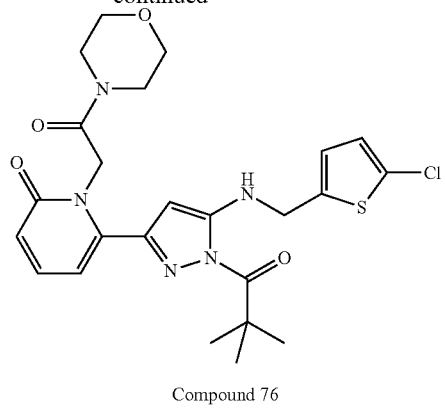

Compound 76

To a solution of 6-(5-(((5-chlorothiophen-2-yl)methyl)amino)-1-pivaloyl-1H-pyrazol-3-yl)pyridin-2(1H)-one (Compound 75, 0.07 g, 1.0 eq, 0.18 mmol) in DMF (1.5 mL) was added anhydrous cesium carbonate (0.146 g, 2.5 eq, 4.5 mmol). The reaction was stirred for 10 minutes, followed by the addition of 4-chloroacetyl morpholine (0.44 g, 1.5 eq, 0.27 mmol). The reaction mixture was stirred for 30 minutes at room temperature. The reaction was monitored by TLC. After completion, the reaction mass was poured onto ice cold water under stirring and extracted with ethyl acetate (3×20 mL). The combined organic layers were dried over sodium sulfate and concentrated under reduced pressure. The residue was purified by column chromatography using (60-120) mesh silica gel in presence of 0.05% trimethylamine, eluting with 60% ethyl acetate in n-hexane as mobile phase, yielding desired product 6-(5-(((5-chlorothiophen-2-yl)methyl)amino)-1-pivaloyl-1H-pyrazol-3-yl)-1-(2-morpholino-2-oxoethyl)pyridin-2(1H)-one (Compound 76, 0.054 g, yield: 58.7%); m/z 518.39[M+1]+ $^1$H NMR (400 MHz, DMSO) δ 7.90 (s, 1H), 7.81 (t, J=7.7 Hz, 1H), 7.57 (d, J=7.4 Hz, 1H), 6.98 (s, 2H), 6.91 (d, J=8.4 Hz, 1H), 5.87 (s, 1H), 5.11 (s, 2H), 4.52 (d, J=5.5 Hz, 2H), 3.62 (s, 2H), 3.53 (s, 4H), 3.39 (s, 2H), 1.49 (s, 9H) ppm.

Example 112—Preparation of Compound 77

The synthesis of Compound 77 followed the procedure of General Procedure 8 following:

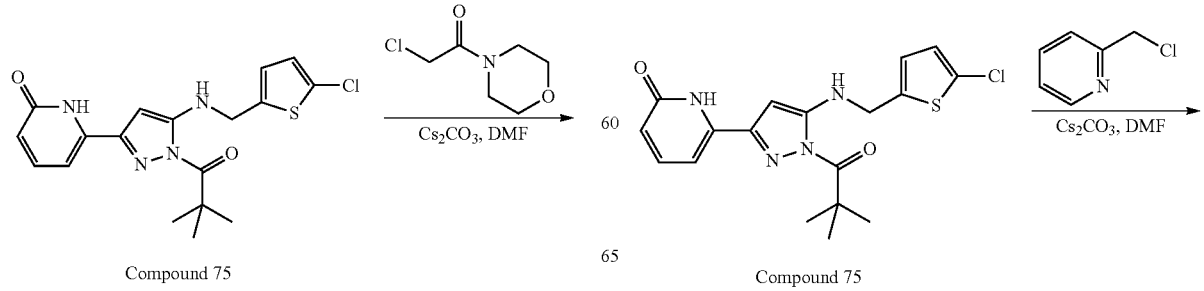

Compound 75

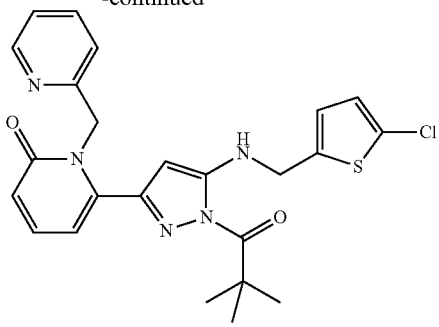

Compound 77

To a dry solution of 6-(5-(((5-chlorothiophen-2-yl)methyl)amino)-1-pivaloyl-1H-pyrazol-3-yl)pyridin-2(1H)-one (Compound 75, 0.309 g, 2.5 eq, 9.5 mmol) in dimethylformamide (5.0 mL) was added 2-(chloromethyl)pyridine hydrochloride (0.93 g, 1.5 eq, 0.6 mmol), followed by cesium carbonate and stirred for 16 hours at room temperature. The reaction was monitored by TLC and LCMS. After completion the reaction mass was poured into ice cold water under stirring and product was extracted with ethyl acetate (3×20 mL). The organic layer was dried over sodium sulfate and concentrated under reduced pressure. The residue was purified by column chromatography using (60-120) mesh silica gel in presence of 0.05% trimethylamine, eluting with 10-20% ethyl acetate in n-hexane as mobile phase to give pure desired product 6-(5-(((5-chlorothiophen-2-yl)methyl)amino)-1-pivaloyl-1H-pyrazol-3-yl)-1-(pyridin-2-ylmethyl)pyridin-2(1H)-one (Compound 77, 0.0272 g, yield: 14.6%) m/z=482.51[M+1]+ $^1$H NMR (400 MHz, DMSO-$d_6$) δ 8.57 (d, J=4.8 Hz, 1H), 7.90-7.73 (m, 3H), 7.58 (d, J=7.4 Hz, 1H), 7.48 (d, J=7.8 Hz, 1H), 7.38-7.24 (m, 1H), 7.07-6.83 (m, 3H), 5.91 (s, 1H), 5.51 (s, 2H), 4.52 (d, J=6.2 Hz, 2H), 1.48 (s, 9H) ppm.

Example 113—Preparation of Compound 78

The synthesis of Compound 78 followed General Procedure 14 following:

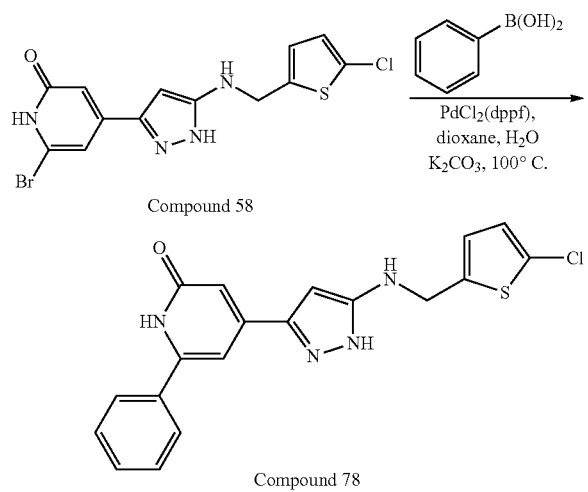

To a solution of 6-bromo-4-(5-(((5-chlorothiophen-2-yl)methyl)amino)-1H-pyrazol-3-yl)pyridin-2(1H)-one (Compound 58, 0.2 g, 0.51 mmol, 1.0 eq) and phenylboronic acid (0.063 g, 0.51 mmol, 1.0 eq) in dioxane: water (5:1, 10 mL) was added potassium carbonate (0.215 g, 1.5 mmol, 3.0 eq). The reaction mixture was degassed under nitrogen for 30 minutes, and to it was added 1,1'-bis(diphenylphosphino)ferrocene palladium(II) dichloride (PdCl$_2$(dppf), 0.037 g, 0.05 mmol, 0.1 eq). The reaction mixture was stirred at 100° C. for 5-6 hours. After completion the reaction mixture was diluted with water and extracted with dichloromethane (25 mL×3). The combined organic layers were dried over sodium sulfate and concentrated under reduced pressure. The residue was purified by column chromatography using neutral silica gel (100-200 mesh), eluting with 4-5% methanol in dichloromethane as gradient to give pure desired product (Compound 78, 0.12 g, yield-60%) m/z 383.15.05 [M+H]+ $^1$H NMR (DMSO-$d_6$, 400 MHz) δ 12.41 (s, 1H), 11.82 (s, 1H), 7.82 (s, 2H), 7.50 (d, J=6.5 Hz, 3H), 6.95 (dd, J=16.0, 12.4 Hz, 3H), 6.65 (s, 1H), 6.16 (s, 2H), 4.37 (d, J=6.4 Hz, 2H) ppm.

Example 114—Preparation of Compound 79

The synthesis of Compound 79 followed General Procedure 6 following:

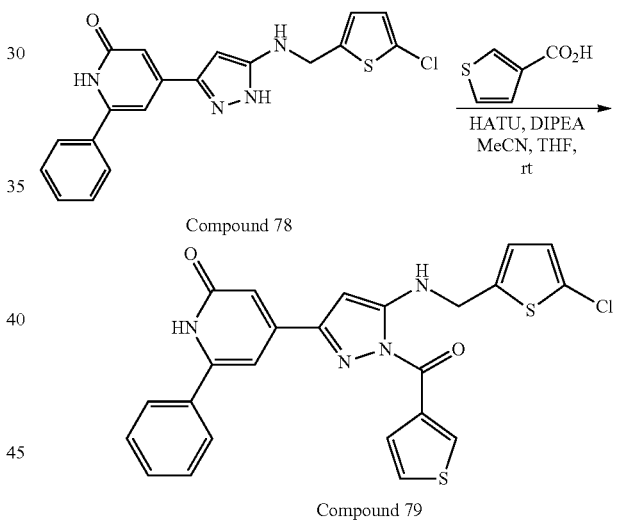

To a solution of thiophene-3-carboxylic acid (0.040 g, 0.31 mmol, 1.2 eq) in THF:acetonitrile (1:1; 5 mL) was added N,N-diisopropylethylamine (DIPEA, 0.1 mL, 0.78 mmol, 3 eq), then N-[(Dimethylamino)-1H-1,2,3-triazolo-[4,5-b]pyridin-1-ylmethylene]-N-methylmethanaminium hexafluorophosphate N-oxide (HATU, 0.148 g, 0.39 mmol, 1.5 eq). The mixture was stirred at room temperature for 1 hour. To this was then added 4-(5-(((5-chlorothiophen-2-yl)methyl) amino)-1H-pyrazol-3-yl)-6-phenylpyridin-2(1H)-one (Compound 78, 0.2 g, 0.51 mmol, 1.0 eq) and stirring continued for 12 hours. After completion, the reaction mixture was diluted with water and extracted with dichloromethane (25 mL×3). The organic phase were dried over sodium sulfate and concentrated under reduced pressure. The residue was purified by preparative HPLC to give pure desired product (Compound 79, 30 mg, yield: 33%) m/z 493.2 [M+H]+ $^1$H NMR (DMSO-$d_6$, 400 MHz) δ 12.43 (d, J=132.0 Hz, 1H), 8.72 (s, 1H), 8.36-8.03 (m, 3H), 7.78 (d, J=24.4 Hz, 1H), 7.75-7.62 (m, 1H), 7.55 (d, J=8.9 Hz, 3H), 7.30-6.67 (m, 3H), 6.40 (s, 1H), 6.16 (d, J=37.6 Hz, 1H), 4.40 (d, J=6.2 Hz, 2H) ppm.

Example 115—Preparation of Compound 80

The synthesis of Compound 80 followed General Procedure 14 following:

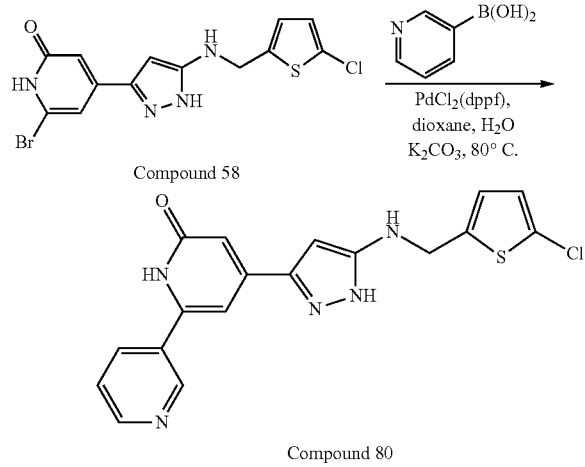

Compound 80

To a solution of 6-bromo-4-(5-(((5-chlorothiophen-2-yl)methyl)amino)-1H-pyrazol-3-yl)pyridin-2(1H)-one (Compound 58, 300 mg, 0.77 mmol, 1.0 eq) in dioxane and water (2.0 mL: 1.0 mL) was added potassium carbonate ($K_2CO_3$, 215 mg, 1.5 mmoles, 2.0 eq), followed by 3-pyridineboronic acid (0.161 g, 1.3 mmol, 1.7 eq). The reaction mixture was degassed with a stream of nitrogen for 15 minutes. To the reaction was then added 1,1'-bis(diphenylphosphino)ferrocene palladium(II) dichloride ($PdCl_2(dppf)$, 56 mg, 0.07 mmol, 0.1 eq), and the reaction was stirred at 80° C. for 12 hours. The reaction was monitored by LC-MS and after completion the reaction mixture was cooled to room temperature. The reaction mixture was diluted with water (5 mL) and extracted with ethyl acetate (25 mL×3). The combined organic layers were dried over sodium sulfate and concentrated under vacuum. The residue was purified by Combi-flash chromatography using hexane:ethyl acetate as mobile phase to obtain desired product (Compound 80, 60 mg, yield-20%) m/z 384.41 [M−H]+ $^1$H NMR (DMSO-$d_6$, 400 MHz) δ 12.47-12.28 (m, 1H), 8.66 (s, 1H), 8.23 (s, 1H), 7.53 (s, 1H), 6.95 (s, 1H), 6.74 (s, 1H), 6.30-6.15 (m, 1H), 6.10-5.98 (m, 1H), 4.37 (d, J=6.7 Hz, 2H) ppm.

Example 116—Preparation of Compound 81

The synthesis of Compound 81 followed General Procedure 6 following:

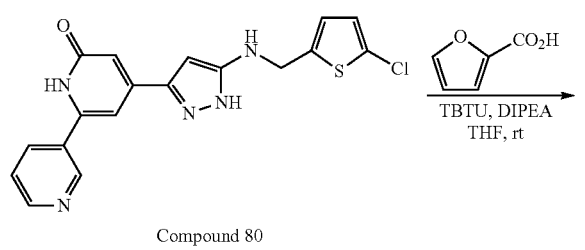

Compound 80

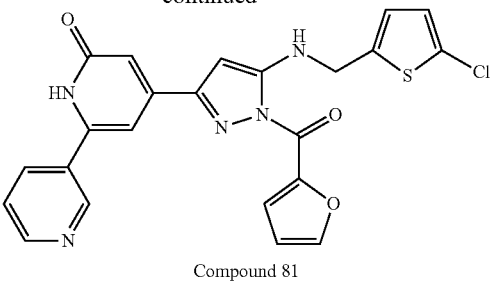

Compound 81

To a cooled solution (0° C.) of 2-furoic acid (40 mg, 0.14 mmol, 1.5 eq) in THF (4 mL) was added N,N-diisopropylethylamine (DIPEA, 26 mg, 0.2 mmol, 2 eq) and O-(benzotriazol-1-yl)-N,N,N',N'-tetramethyluronium tetrafluoroborate (TBTU, 50 mg, 0.15 mmol, 1.5 eq). The reaction was stirred for 30 minutes. Compound 80 (40 mg, 0.15 mmol, 1 eq) was added, and the reaction mixture stirred for 12 hours at room temperature. The reaction was monitored by LC-MS. After completion, the reaction mixture was diluted with cold water (5 mL) and extracted with ethyl acetate (3×5 mL). The combined organic phases were dried over sodium sulfate and evaporated under vacuum. The residue was purified by preparative HPLC using water: acetonitrile as mobile phase to obtained desired product (Compound 81, 5 mg, yield: 12.5%) m/z 478.57 [M−H]+ $^1$H NMR (DMSO-$d_6$) δ 12.51-12.20 (m, 1H), 9.10 (s, 1H), 8.75 (s, 1H), 8.40 (s, 1H), 8.19 (s, 1H), 8.10 (d, J=3.5 Hz, 1H), 7.70 (s, 1H), 7.26 (s, 2H), 7.05-6.94 (m, 1H), 6.91 (d, J=3.7 Hz, 1H), 6.83 (dd, J=3.5, 1.7 Hz, 1H), 6.78 (s, 1H), 6.69 (d, J=3.7 Hz, 1H), 4.10 (s, 2H) ppm.

Example 117—Preparation of Compound 82

The synthesis of Compound 82 followed General Procedure 14 following:

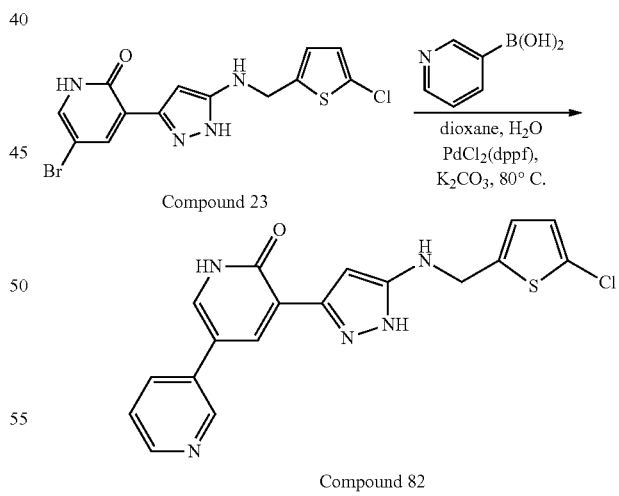

Compound 82

To a solution of 5-bromo-3-(5-(((5-chlorothiophen-2-yl)methyl)amino)-1H-pyrazol-3-yl)pyridin-2(1H)-one (Compound 23, 600 mg, 1.03 mmol, 1.0 eq) in a mixture of dioxane (2 mL) and water (1 mL) was added potassium carbonate ($K_2CO_3$, 286 mg, 2.0 mmol, 2.0 eq). Pyridine-3-boronic acid (190 mg, 1.5 mmol, 1.5 eq) was added to reaction mixture and degassed by nitrogen bubbling for 15 minutes. To the mixture was then added 1,1'-bis(diphenylphosphino)ferrocene palladium(II) dichloride (PdCl₂(dppf), 0.1 mmol, 0.1 eq). and the reaction was stirred at 80° C. for 12 hours. Product formation was monitored by LC-MS, and on completion the reaction mixture was cooled back down to room temperature. The reaction mixture was diluted with water (5 mL) and extracted with ethyl acetate (25 mL×3). The combined organic layers were dried over sodium sulfate and concentrated under vacuum. The residue was purified by Combi-flash chromatography using hexane:ethyl acetate as mobile phase to obtain desire product (Compound 82, 130 mg, yield: 21.7%) m/z 384.56 [M–H]+ ¹H NMR (DMSO-d₆, 400 MHz) δ 12.39 (s, 1H), 11.91 (s, 1H), 8.91 (s, 1H), 8.52 (d, J=4.6 Hz, 1H), 8.32 (d, J=2.6 Hz, 1H), 8.08 (d, J=7.8 Hz, 1H), 7.87 (s, 1H), 7.49-7.46 (m, 1H), 6.93 (d, J=3.7 Hz, 1H), 6.88 (d, J=3.7 Hz, 1H), 6.34 (s, 1H), 5.90 (s, 1H), 4.37 (d, J=6.3 Hz, 2H) ppm.

Example 118—Preparation of Compound 83

The synthesis of Compound 83 followed General Procedure 6 following:

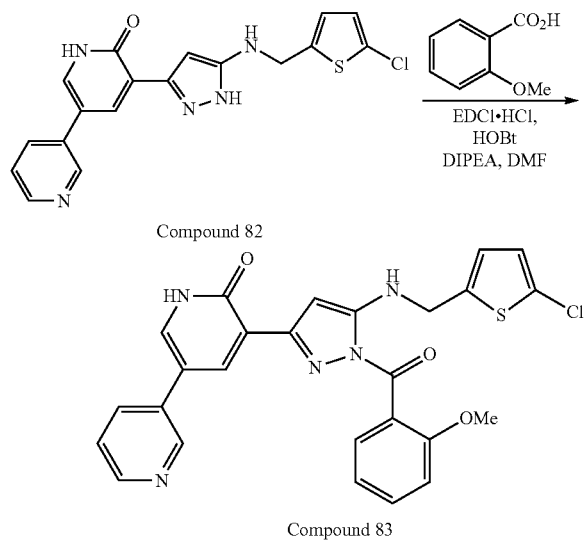

To a cooled solution (0° C.) of 2-methoxybenzoic acid (120 mg, 0.46 mmol, 1.5 eq) in THF (4.0 mL) was added 1-(3-dimethylaminopropyl)-3-ethylcarbodiimide hydrochloride (EDCI.HCl, 89 mg, 0.46 mmol, 1.5 eq), followed by N,N-diisopropylethylamine (DIPEA, 80 mg, 0.62 mmol, 2 eq). After stirring at 0° C. for a further 30 minutes, 5-(5-(((5-chlorothiophen-2-yl)methyl)amino)-1H-pyrazol-3-yl)-[3,3'-bipyridin]-6(1H)-one (Compound 82, 120 mg, 0.31 mmol, 1 eq) and hydroxybenzotriazole (HOBt, 63 mg, 0.46 mmol, 1.5 eq) were added. The reaction mixture was stirred for 12 hours at room temperature. After completion of reaction, as confirmed by LC-MS, the reaction mixture was diluted with cold water (5 mL), extracted with ethyl acetate (3×5 mL), dried over sodium sulphate and evaporated under vacuum. The residue was purified by preparative HPLC using Water:acetonitrile as mobile phase (Compound 83, 0.038 g, yield: 25%) m/z 518.68 [M–H]+1H NMR (DMSO-d6, 400 MHz) δ 12.32-12.20 (m, 1H), 8.65 (s, 1H), 8.49 (s, 1H), 7.98 (s, 1H), 7.87 (s, 2H), 7.77 (s, 1H), 7.59-7.31 (m, 3H), 7.17 (d, J=8.3 Hz, 1H), 7.03 (d, J=15.4 Hz, 3H), 6.27 (s, 1H), 4.57 (d, J=6.2 Hz, 2H), 3.77 (s, 3H) ppm.

Example 119—Preparation of Compound 84

The synthesis of Compound 84 followed the procedure of General Procedure 21 following:

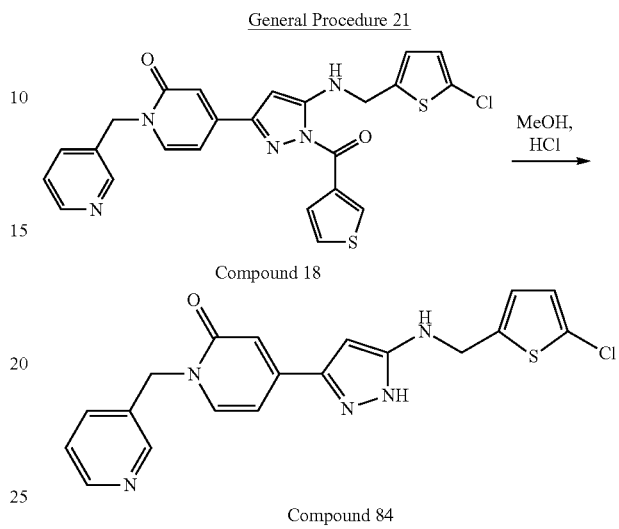

A solution of Compound 18 (0.070 g, 1.0 eq) in MeOH/HCl (1%, 20 mL) was stirred for 16 hours at room temperature. The reaction was monitored by TLC and LCMS. After completion volatiles were evaporated under reduced pressure, which was purified by prep HPLC to yield Compound 84 (0.0182 g, yield: 33%) m/z 398.1 [M]+ ¹H NMR (400 MHz, DMSO) δ 12.35 (s, 1H), 8.58 (d, J=1.7 Hz, 1H), 8.49 (dd, J=4.8, 1.5 Hz, 1H), 7.88 (s, 1H), 7.70 (d, J=7.9 Hz, 1H), 7.37 (dd, J=7.8, 4.8 Hz, 1H), 6.93 (t, J=6.3 Hz, 2H), 6.69 (s, 1H), 6.62 (s, 1H), 6.05 (s, 2H), 5.12 (s, 2H), 4.35 (d, J=6.2 Hz, 2H) ppm.

Example 120—Preparation of Compound 85

The synthesis of Compound 85 followed the procedure of General Procedure 8 following.

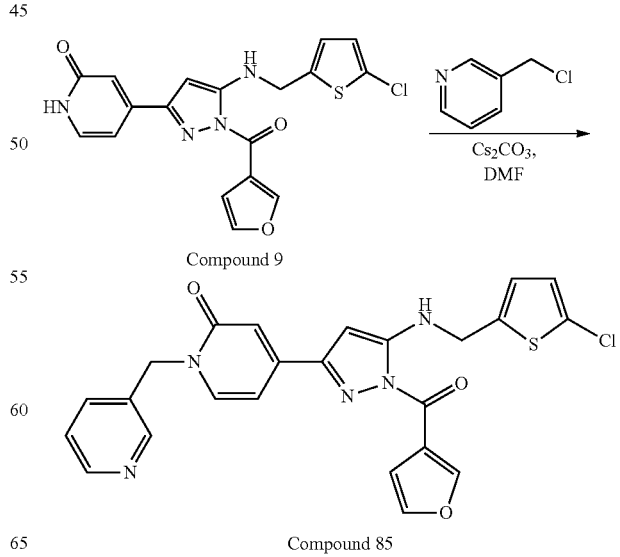

To a solution of Compound 9 (0.11 g, 1.0 eq, 0.28 mmol) in DMF (10 mL) was added anhydrous cesium carbonate (0.178 g, 2.5 eq, 0.55 mmol). After stirring for 15 minutes at room temperature, 3-(chloromethyl)pyridine hydrochloride (0.09 g, 2.0 eq, 0.55 mmol) was added and the reaction was stirred for a further 14 hours at room temperature. The reaction was monitored by TLC and LCMS. After completion, the reaction mixture was diluted with ice cold water under stirring and extracted with ethyl acetate (10 mL×3). The organic phases were dried over sodium sulfate and concentrated under reduced pressure. The residue was purified by preparative HPLC to furnish the desired product, Compound 85 (0.018 g, yield: 13.3%) m/z 492.1 [M]+ $^1$H NMR (400 MHz, DMSO-d$_6$) δ 8.93 (s, 1H), 8.60 (s, 1H), 8.50 (d, J=3.4 Hz, 1H), 7.94 (d, J=7.0 Hz, 2H), 7.89 (s, 1H), 7.72 (d, J=7.4 Hz, 1H), 7.41-7.36 (m, 1H), 7.09 (s, 2H), 7.00-6.92 (m, 2H), 6.88 (d, J=6.6 Hz, 1H), 6.26 (s, 1H), 5.18 (s, 2H), 4.55 (d, J=5.9 Hz, 2H) ppm.

Example 121—Preparation of Compound 86

The synthesis of Compound 86 followed the procedure of General Procedure 8 following.

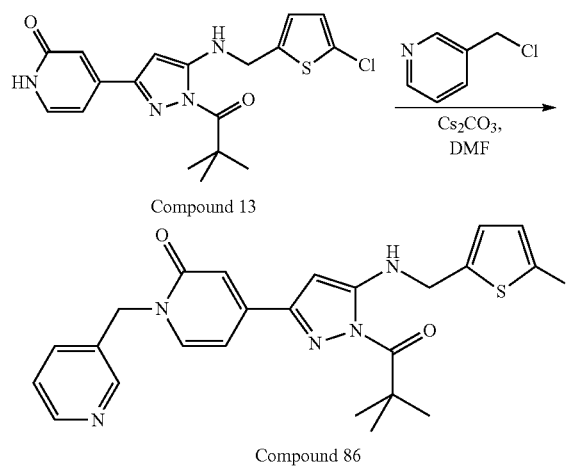

To a solution of Compound 13 (0.2 g, 1.0 eq, 513 mmoles) in DMF (10 mL) was added anhydrous cesium carbonate (0.416 g, 2.5 eq, 1.28 mmoles). After stirring for 30 minutes, the at room temperature, (3-chloromethyl)pyridine hydrochloride (0.126 g, 1.2 eq, 0.76 mmol) was added, and the reaction mixture stirred for 3 hours at 80° C. The reaction was monitored by TLC and LCMS. After completion, the reaction mixture was poured into ice cold water under stirring and extracted with ethyl acetate. The organic layer was dried over sodium sulfate and concentrated under reduced pressure. The residue was purified by column chromatography using 60-120 mesh silica gel in the presence of 0.05% trimethylamine, eluting with 30-35% ethyl acetate in n-hexane, to give pure desired product Compound 86 (0.105 g, yield: 39%) m/z 482.41 [M]+ $^1$H NMR (400 MHz, DMSO) δ 8.59 (s, 1H), 8.51 (s, 1H), 7.95 (d, J=6.8 Hz, 1H), 7.87 (s, 1H), 7.70 (d, J=7.8 Hz, 1H), 7.38 (d, J=5.2 Hz, 1H), 7.07 (d, J=3.7 Hz, 1H), 6.96 (d, J=3.6 Hz, 1H), 6.87 (s, 1H), 6.72 (d, J=6.5 Hz, 1H), 6.14 (s, 1H), 5.14 (d, J=16.4 Hz, 2H), 4.47 (d, J=6.4 Hz, 2H), 1.46 (s, 9H) ppm.

Example 122—Preparation of Compound 87

The synthesis of Compound 87 followed the procedure of General Procedure 8 following.

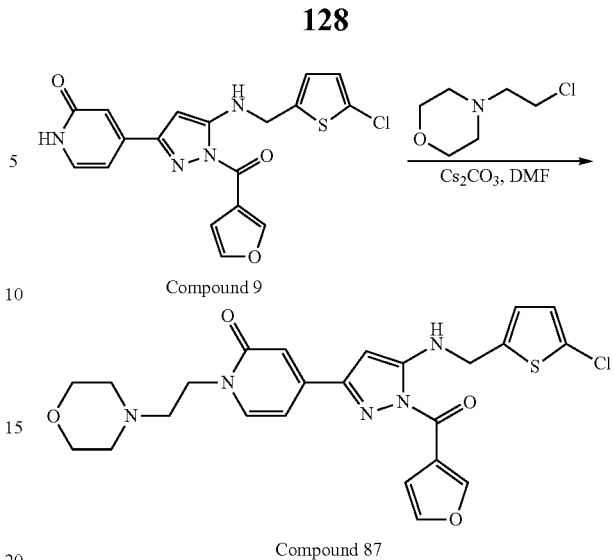

To a solution of Compound 9 (0.5 g, 1.0 eq, 1.25 mmol) in DMF (10 mL) was added anhydrous cesium carbonate (1.0 g, 2.5 eq, 3.1 mmol). After stirring for 15 minutes at room temperature, 4-(2-chloroethyl)morpholine (0.349 g, 1.5 eq, 1.88 mmol) was added and the reaction was stirred for 12 hours at room temperature. The reaction was monitored by TLC and LCMS. The reaction mixture was poured into ice cold water under stirring and extracted with ethyl acetate. The organic layer was dried over sodium sulfate and concentrated under reduced pressure. The residue was purified by preparative HPLC to yield Compound 87 (0.08 g, yield: 12%) m/z[M+H]+ 514.33 $^1$H NMR (400 MHz, DMSO) δ 8.94 (d, J=0.7 Hz, 1H), 7.96 (t, J=6.3 Hz, 1H), 7.90 (t, J=1.7 Hz, 1H), 7.71 (d, J=7.1 Hz, 1H), 7.10 (t, J=3.1 Hz, 2H), 6.97 (d, J=3.7 Hz, 1H), 6.88 (s, 1H), 6.81 (d, J=6.9 Hz, 1H), 6.25 (s, 1H), 4.55 (d, J=6.3 Hz, 2H), 4.04 (d, J=5.6 Hz, 2H), 3.55 (s, 4H), 2.56 (d, J=5.5 Hz, 2H), 2.43 (s, 4H) ppm.

Example 123—Preparation of Compound 88

The synthesis of Compound 88 followed the procedure of General Procedure 8 following.

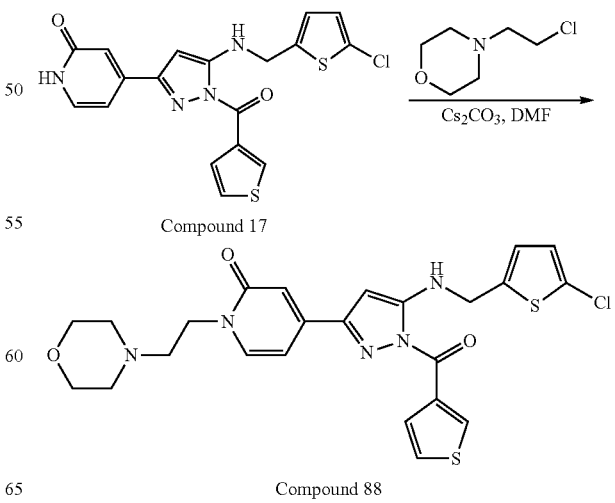

To a solution of Compound 17 (0.8 g, 1.0 eq, 1.92 mmol) in DMF (15 mL) was added anhydrous cesium carbonate (1.246 g, 2.0 eq, 3.8 mmole). After stirring the reaction for 15 minutes at room temperature, 4-(2-chloroethyl)morpholine (0.428 g, 1.5 eq, 2.9 mmol) was added and the reaction stirred for a further 48 hours at room temperature. The reaction was monitored by TLC and LCMS. After completion the reaction mass was poured into ice cold water under stirring and extracted with ethyl acetate. The organic layer was dried over sodium sulfate and concentrated under reduced pressure. The residue was purified by preparative HPLC to yield Compound 88 (0.035 g, yield: 4.2%) m/z [M+H]+ 530.58 $^1$H NMR (400 MHz, DMSO) δ 9.03 (s, 1H), 7.98 (s, 1H), 7.83 (d, J=4.9 Hz, 1H), 7.72 (d, J=7.5 Hz, 2H), 7.10 (s, 1H), 6.98 (s, 1H), 6.87 (s, 1H), 6.74 (d, J=6.2 Hz, 1H), 6.25 (s, 1H), 4.55 (d, J=5.7 Hz, 2H), 4.02 (s, 2H), 3.54 (s, 4H), 2.57 (s, 2H), 2.43 (s, 4H) ppm.

Example 124—Preparation of Compound 89

The synthesis of Compound 89 followed General Procedure 6 following:

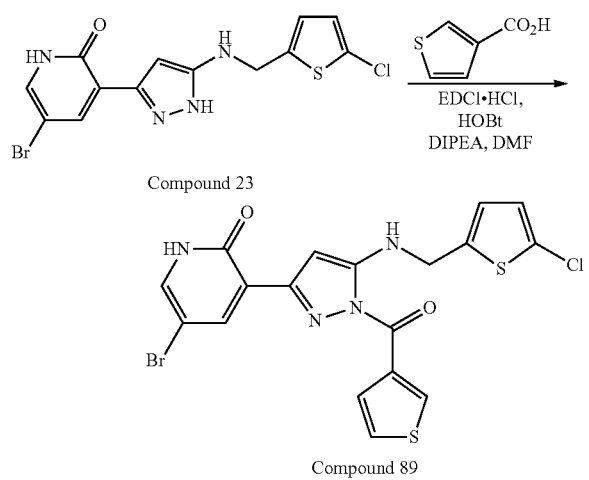

To a cold solution (0° C.) of thiophene-3-carboxylic acid (0.15 g, 1.2 mmol, 1.5 eq) in THF (25 mL) was added 1-(3-dimethylaminopropyl)-3-ethylcarbodiimide hydrochloride (EDCI.HCl, 0.224 g, 1.2 mmol, 1.5 eq) and N,N-diisopropylethylamine (DIPEA, 0.2 mL, 1.29 mmol, 1.1 eq) under nitrogen. After stirring for 30 minutes, hydroxybenzotriazole (HOBt, 0.021 g, 0.156 mmol, 0.2 eq) and 5-bromo-3-(5-(((5-chlorothiophen-2-yl)methyl)amino)-1H-pyrazol-3-yl) pyridin-2(1H)-one (Compound 23, 0.3 g, 0.78 mmol, 1.0 eq) were added. After completion, (monitored by LC-MS), the reaction mixture was poured into water (20 mL) and extracted with ethyl acetate. The combined organic phases were washed with water, brine, and dried over sodium sulfate, and then evaporated under reduced pressure. The residue was purified by preparative HPLC using water-acetonitrile as mobile phase to give desired product 5-bromo-3-(5-(((5-chlorothiophen-2-yl)methyl)amino)-1-(thiophene-3-carbonyl)-1H-pyrazol-3-yl)pyridin-2(1H)-one (Compound 89, 0.1 g, yield: 25.8%) m/z 497.13 [M+1]+ $^1$H NMR (400 MHz, DMSO-$d_6$) δ 12.26 (s, 1H), 9.06 (dd, J=2.9, 1.1 Hz, 1H), 8.17 (d, J=2.7 Hz, 1H), 7.89 (t, J=6.1 Hz, 1H), 7.83 (dd, J=5.1, 1.1 Hz, 1H), 7.80 (s, 1H), 7.69 (dd, J=5.1, 3.0 Hz, 1H), 6.98 (s, 2H), 6.33 (s, 1H), 4.55 (d, J=6.1 Hz, 2H) ppm.

Example 125—Preparation of Compound 90

The synthesis of Compound 90 followed General Procedure 6 following:

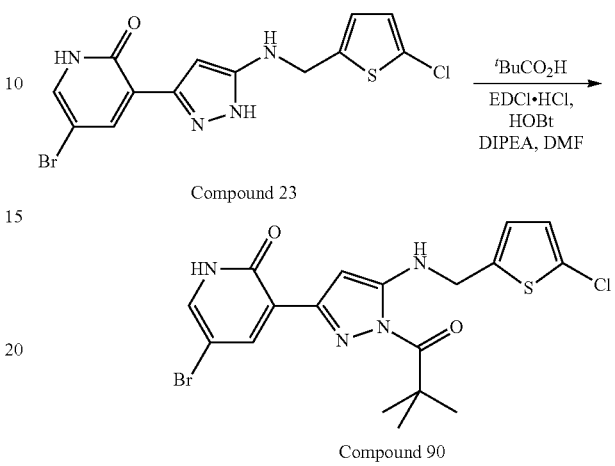

To a cooled solution (0° C.) of pivalic acid (0.278 g, 2.5 mmol, 1.2 eq) in THF (30 mL) was added 1-(3-dimethylaminopropyl)-3-ethylcarbodiimide hydrochloride (EDCI.HCl, 0.477 g, 2.5 mmol, 1.2 eq) and N,N-diisopropylethylamine (DIPEA, 0.32 g, 2.5 mmol, 1.2 eq) under nitrogen. After stirring for 30 minutes, hydroxybenzotriazole (HOBt, 0.063 g, 0.41 mmol, 0.2 eq) and 5-bromo-3-(5-(((5-chlorothiophen-2-yl)methyl)amino)-1H-pyrazol-3-yl)pyridin-2 (1H)-one (Compound 23, 0.8 g, 2.1 mmol, 1.0 eq) were added. After completion, (monitored by LC-MS), the reaction mixture was poured into water (20 mL) and extracted with ethyl acetate. The combined organic phases were washed with water, brine, dried over sodium sulfate and evaporated under reduced pressure. The residue was purified by preparative HPLC using water-acetonitrile as mobile phase to give desired product 5-bromo-3-(5-(((5-chlorothiophen-2-yl)methyl)amino)-1-pivaloyl-1H-pyrazol-3-yl) pyridin-2(1H)-one (Compound 90, 0.45 g, yield: 48.3%) m/z 471.46 [M+1]+ $^1$H NMR (400 MHz, DMSO-$d_6$) δ 12.27 (s, 1H), 8.04 (d, J=2.7 Hz, 1H), 7.79 (s, 2H), 6.96 (dd, J=13.5, 3.7 Hz, 2H), 6.20 (s, 1H), 4.48 (d, J=6.0 Hz, 2H), 1.47 (s, 9H) ppm.

Example 126—Preparation of Compound 91

The synthesis of Compound 91 followed the procedure of General Procedure 8 following.

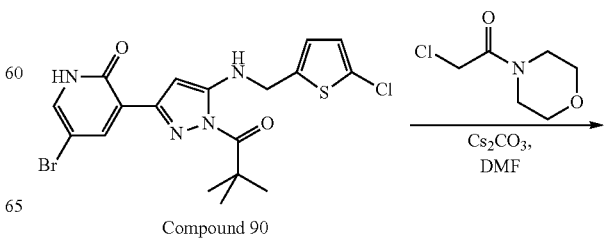

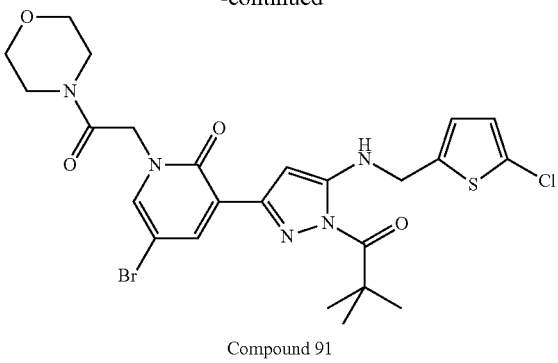

Compound 91

To a solution of Compound 90 at room temperature (0.2 g, 0.41 mmol, 1.0 eq) in DMF (12 mL) was added cesium carbonate (0.334 g, 1.02 mmol, 2.5 eq) and 4-(chloroacetyl)morpholine (0.101 g, 0.62 mmol, 1.5 eq). The reaction mixture was stirred for 12 hours. After completion (monitored by TLC), the reaction mixture was poured into water (30 mL) and extracted with ethyl acetate. The combined organic phases were washed with water, then brine, dried over sodium sulfate and then evaporated under reduced pressure. The residue was purified by column chromatography using ethyl acetate-hexane as mobile phase to afford the desired product 5-bromo-3-(5-(((5-chlorothiophen-2-yl)methyl)amino)-1-pivaloyl-1H-pyrazol-3-yl)-1-(2-morpholino-2-oxoethyl)pyridin-2(1H)-one (Compound 91, 0.075 g, yield: 30.6%) m/z 598.40 [M+1]+ $^1$H NMR (400 MHz, DMSO-$d_6$) δ 8.08-8.04 (m, 2H), 7.81 (s, 1H), 6.97 (d, J=3.7 Hz, 1H), 6.93 (d, J=3.7 Hz, 1H), 6.17 (s, 1H), 4.91 (s, 2H), 4.47 (d, J=6.0 Hz, 2H), 3.66 (s, 2H), 3.59 (s, 2H), 3.54 (s, 2H), 3.45 (s, 2H), 1.48 (s, 9H) ppm.

Example 127—Preparation of Compound 92

The synthesis of Compound 92 followed General Procedure 14 following:

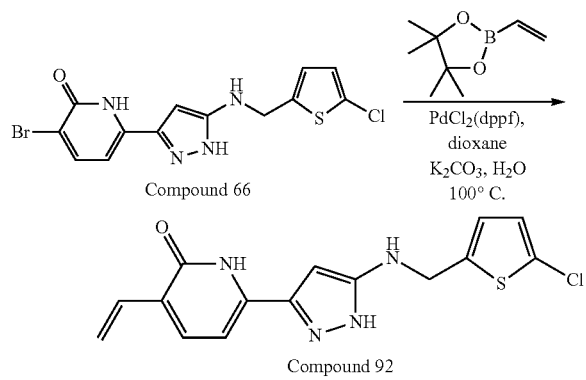

To a stirred solution of 3-bromo-6-(5-(((5-chlorothiophene-2-yl)methyl)amino)-1H-pyrazol-3-yl)pyridine-2(1H)-one (Compound 66, 0.120 g, 0.31 mmol, 1.0 eq) in dioxane:water (4:1; 15 mL) was added vinylboronic acid pinacol ester (0.071 g, 0.47 mmol, 1.5 eq), followed by potassium carbonate ($K_2CO_3$, 0.127 g, 0.93 mmol, 3 eq). The reaction mixture was degassed for 10 minutes, followed by the addition of 1,1'-bis(diphenylphosphino)ferrocene palladium(II) dichloride (PdCl$_2$(dppf), 0.0226 g, 0.03 mmol, 0.1 eq). The reaction mixture was again degassed for 10 minutes and then heated at 100° C. for 2 hours. After completion (as monitored by LC-MS), the reaction mixture was poured into water (5 mL) and extracted with ethyl acetate (2×15 mL). The combined organic phases were washed with water, brine, dried over sodium sulfate and evaporated under reduced pressure. The residue was purified by column chromatography using 60-120 mesh size silica gel, eluting with 0-20% ethyl acetate in n-hexane as mobile phase to give pure desired product 6-(5-(((5-chlorothiophen-2-yl)methyl)amino)-1H-pyrazol-3-yl)-3-vinylpyridin-2(1H)-one (Compound 92, 0.090 g, yield: 86.9%) m/z 333.4 [M+1]+ $^1$H NMR (400 MHz, DMSO) δ 12.29 (s, 1H), 11.12 (s, 1H), 7.63 (s, 1H), 6.95 (s, 2H), 6.81-6.59 (m, 2H), 6.37 (d, J=41.2 Hz, 2H), 6.12 (d, J=17.9 Hz, 2H), 5.24 (d, J=10.8 Hz, 1H), 4.34 (d, J=6.0 Hz, 2H) ppm.

Example 128—Preparation of Compound 93

The synthesis of Compound 93 followed the procedure of General Procedure 6 following:

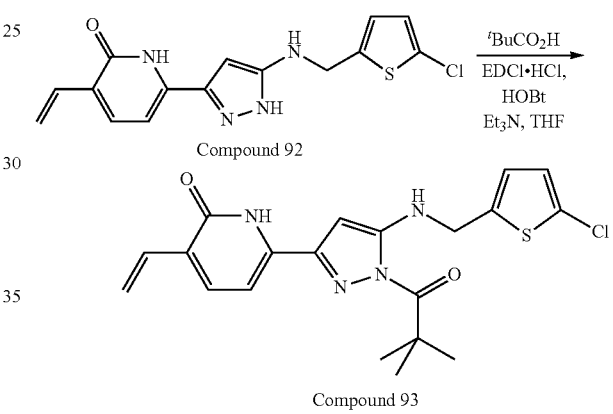

To a cooled solution (0° C.) of pivalic acid (0.011 g, 0.11 mmol, 1.2 eq) in THF (5 mL) was added 1-(3-dimethylaminopropyl)-3-ethylcarbodiimide hydrochloride (EDCI.HCl, 0.021 g, 0.11 mmol, 1.2 eq), followed by triethylamine (0.028 g, 0.27 mmol, 3.0 eq) under nitrogen. After stirring for 30 minutes, hydroxybenzotriazole (HOBt, 0.0024 g, 0.018 mmol, 0.2 eq) and 6-(5-(((5-chlorothiophen-2-yl)methyl)amino)-1H-pyrazol-3-yl)-3-vinylpyridin-2(1H)-one (Compound 92) were added. The reaction was monitored by LC-MS. After completion, the reaction mixture was poured into water (10 mL) and extracted with ethyl acetate. The combined organic phases were washed with water, brine, dried over sodium sulphate and evaporated under reduced pressure. The residue was purified by preparative HPLC using water-acetonitrile as mobile phase to give the desired product 6-(5-(((5-chlorothiophen-2-yl)methyl)amino)-1-pivaloyl-1H-pyrazol-3-yl)-3-vinylpyridin-2(1H)-one (Compound 93, 0.005 g, yield-13.3%) m/z 416.51 [M]+ $^1$H NMR (400 MHz, DMSO) δ 12.56 (s, 1H), 8.19 (d, J=7.4 Hz, 1H), 8.01 (d, J=6.1 Hz, 1H), 7.52 (d, J=7.7 Hz, 1H), 7.16-6.82 (m, 4H), 6.53 (s, 1H), 6.27 (s, 1H), 4.46 (d, J=6.1 Hz, 2H), 1.46 (s, 9H) ppm.

Exemplary thrombin- and kallikrein-inhibiting compounds in accordance with the present disclosure are prepared according to any of Examples 1-128 and are listed in Table B (Appendix A).

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

APPENDIX A

Table B 1-(2-aminobenzoyl)-3-[1-benzyl-5-(morpholin-4-yl)-6-oxo-1,6-dihydropyridin-2-yl]-5-{[(5-chlorothiophen-2-yl)methyl]amino}-1H-pyrazole-4-carbonitrile
1-(2-carboxy-2-oxoethyl)-4-(5-{[(5-chlorothiophen-2-yl)methyl]amino}-1-(2,2-dimethylpropanoyl)-1H-pyrazol-3-yl)-2-oxo-1,2-dihydropyridine-3-carboxylic acid
1-benzoyl-3-(1-benzyl-2-oxo-6-phenyl-1,2-dihydropyridin-3-yl)-5-{[(5-chlorothiophen-2-yl)methyl]amino}-1H-pyrazole-4-carbonitrile
1-benzoyl-5-{[(5-chlorothiophen-2-yl)methyl]amino}-3-[1-(morpholin-4-ylmethyl)-2-oxo-6-(2-phenylethynyl)-1,2-dihydropyridin-4-yl]-1H-pyrazole-4-carbonitrile APPENDIX A-continued Table B 1-benzyl-4-(5-{[(5-chlorothiophen-2-yl)methyl]amino}-1-[3-(hydroxymethyl)benzoyl]-1H-pyrazol-3-yl)-5-(morpholin-4-yl)-1,2-dihydropyridin-2-one
1-benzyl-4-(5-{[(5-chlorothiophen-2-yl)methyl]amino}-4-fluoro-1-(1,3-thiazole-5-carbonyl)-1H-pyrazol-3-yl)-3-ethenyl-1,2-dihydropyridin-2-one
1-benzyl-5-(5-{[(5-chlorothiophen-2-yl)methyl]amino}-4-methoxy-1-(1,2-oxazole-4-carbonyl)-1H-pyrazol-3-yl)-4-hydroxy-1,2-dihydropyridin-2-one
2-(5-{[(5-chlorothiophen-2-yl)methyl](methyl)amino}-1-(2,2-dimethylpropanoyl)-1H-pyrazol-3-yl)-1-[2-(4-methylpiperazin-1-yl)-2-oxoethyl]-6-oxo-1,6-dihydropyridine-3-carbonitrile
2-(5-{[(5-chlorothiophen-2-yl)methyl]amino}-1-(1,3-thiazole-4-carbonyl)-1H-pyrazol-3-yl)-6-oxo-1-[2-oxo-2-(pyrimidin-4-yl)ethyl]-1,6-dihydropyridine-3-carbonitrile
2-(5-{[(5-chlorothiophen-2-yl)methyl]amino}-1-(2,2-dimethylpropanoyl)-1H-pyrazol-3-yl)-1-[2-(1,2-oxazol-5-yl)-2-oxoethyl]-6-oxo-1,6-dihydropyridine-3-carboxylic acid
2-(5-{[(5-chlorothiophen-2-yl)methyl]amino}-1-(2,2-dimethylpropanoyl)-1H-pyrazol-3-yl)-1-[2-(furan-3-yl)-2-oxoethyl]-N,N-dimethyl-6-oxo-1,6-dihydropyridine-3-carboxamide
2-(5-{[(5-chlorothiophen-2-yl)methyl]amino}-1-(2,2-dimethylpropanoyl)-1H-pyrazol-3-yl)-6-oxo-1-[2-oxo-2-(1,2-thiazol-3-yl)ethyl]-1,6-dihydropyridine-3-carbonitrile
2-(5-{[(5-chlorothiophen-2-yl)methyl]amino}-1-[2-(trifluoromethyl)benzoyl]-1H-pyrazol-3-yl)-1-[2-(4-methylpiperazin-1-yl)ethyl]-6-oxo-1,6-dihydropyridine-3-carbonitrile
2-(5-{[(5-chlorothiophen-2-yl)methyl]amino}-4-fluoro-1-(2-methoxybenzoyl)-1H-pyrazol-3-yl)-1-(1,3-oxazol-5-ylmethyl)-6-oxo-1,6-dihydropyridine-3-carbonitrile
2-[1-(2-aminobenzoyl)-5-{[(5-chlorothiophen-2-yl)methyl]amino}-1H-pyrazol-3-yl]-6-oxo-1-[2-oxo-2-(thiophen-2-yl)ethyl]-1,6-dihydropyridine-3-carbonitrile
2-[3-(1-benzoyl-5-{[(5-chlorothiophen-2-yl)methyl]amino}-1H-pyrazol-3-yl)-4-(morpholin-4-yl)-2-oxo-1,2-dihydropyridin-1-yl]acetic acid
2-[3-(5-{[(5-chlorothiophen-2-yl)methyl](methyl)amino}-1-(2,2-dimethylpropanoyl)-1H-pyrazol-3-yl)-4-fluoro-2-oxo-1,2-dihydropyridin-1-yl]acetaldehyde
2-[3-(5-{[(5-chlorothiophen-2-yl)methyl]amino}-1-(2,2-dimethylpropanoyl)-1H-pyrazol-3-yl)-5-ethenyl-2-oxo-1,2-dihydropyridin-1-yl]acetaldehyde
2-[3-(5-{[(5-chlorothiophen-2-yl)methyl]amino}-1-(2,2-dimethylpropanoyl)-1H-pyrazol-3-yl)-6-hydroxy-2-oxo-1,2-dihydropyridin-1-yl]acetaldehyde
2-[3-(5-{[(5-chlorothiophen-2-yl)methyl]amino}-1-(3-methoxy-2,2-dimethylpropanoyl)-1H-pyrazol-3-yl)-6-methoxy-2-oxo-1,2-dihydropyridin-1-yl]acetaldehyde
2-[3-(5-{[(5-chlorothiophen-2-yl)methyl]amino}-1-[4-(hydroxymethyl)benzoyl]-1H-pyrazol-3-yl)-2-oxo-4-(pyridin-2-yl)-1,2-dihydropyridin-1-yl]acetaldehyde
2-[3-(5-{[(5-chlorothiophen-2-yl)methyl]sulfanyl}-1-(2,2-dimethylpropanoyl)-1H-pyrazol-3-yl)-2-oxo-5-phenyl-1,2-dihydropyridin-1-yl]acetaldehyde
2-[3-(5-{[(5-chlorothiophen-2-yl)methyl]sulfanyl}-1-(2,2-dimethylpropanoyl)-1H-pyrazol-3-yl)-6-(dimethylamino)-2-oxo-1,2-dihydropyridin-1-yl]acetaldehyde
2-[4-(5-{[(5-chlorothiophen-2-yl)methyl]amino}-1-(1,2-oxazole-3-carbonyl)-1H-pyrazol-3-yl)-2-oxo-3-(pyridin-2-yl)-1,2-dihydropyridin-1-yl]acetaldehyde
2-[4-(5-{[(5-chlorothiophen-2-yl)methyl]amino}-1-(1,3-oxazole-5-carbonyl)-1H-pyrazol-3-yl)-6-fluoro-2-oxo-1,2-dihydropyridin-1-yl]acetaldehyde
2-[4-(5-{[(5-chlorothiophen-2-yl)methyl]amino}-1-(1,3-thiazole-2-carbonyl)-1H-pyrazol-3-yl)-5-methoxy-2-oxo-1,2-dihydropyridin-1-yl]acetaldehyde
2-[4-(5-{[(5-chlorothiophen-2-yl)methyl]amino}-1-(2,2-dimethylpropanoyl)-1H-pyrazol-3-yl)-2-oxo-5-(pyridine-2-carbonyl)-1,2-dihydropyridin-1-yl]acetaldehyde
2-[4-(5-{[(5-chlorothiophen-2-yl)methyl]amino}-1-(2,2-dimethylpropanoyl)-1H-pyrazol-3-yl)-2-oxo-6-(prop-2-enoyl)-1,2-dihydropyridin-1-yl]acetaldehyde
2-[4-(5-{[(5-chlorothiophen-2-yl)methyl]amino}-4-fluoro-1-(1,2-oxazole-4-carbonyl)-1H-pyrazol-3-yl)-6-hydroxy-2-oxo-1,2-dihydropyridin-1-yl]acetic acid
2-[4-(5-{[(5-chlorothiophen-2-yl)methyl]amino}-4-methoxy-1-(3-methoxy-2,2-dimethylpropanoyl)-1H-pyrazol-3-yl)-5-(methoxycarbonyl)-2-oxo-1,2-dihydropyridin-1-yl]acetic acid
2-[4-chloro-5-(5-{[(5-chlorothiophen-2-yl)methyl]amino}-4-cyano-1-(3-hydroxy-2,2-dimethylpropanoyl)-1H-pyrazol-3-yl)-2-oxo-1,2-dihydropyridin-1-yl]acetic acid
2-[5-(1-benzoyl-5-{[(5-chlorothiophen-2-yl)methyl]amino}-1H-pyrazol-3-yl)-2-oxo-3-(pyridin-3-yl)-1,2-dihydropyridin-1-yl]acetaldehyde
2-[5-(1-benzoyl-5-{[(5-chlorothiophen-2-yl)methyl]amino}-4-cyano-1H-pyrazol-3-yl)-6-ethenyl-2-oxo-1,2-dihydropyridin-1-yl]acetic acid
2-[5-(5-{[(5-chlorothiophen-2-yl)methyl](methyl)amino}-1-(2,2-dimethylpropanoyl)-1H-pyrazol-3-yl)-2-oxo-6-(pyridin-3-yl)-1,2-dihydropyridin-1-yl]acetaldehyde APPENDIX A-continued Table B 2-[5-(5-{[(5-chlorothiophen-2-yl)methyl]amino}-1-(1,2-thiazole-4-carbonyl)-1H-pyrazol-3-yl)-2-oxo-6-(2-phenylethynyl)-1,2-dihydropyridin-1-yl]acetaldehyde
2-[5-(5-{[(5-chlorothiophen-2-yl)methyl]amino}-1-(2,2-dimethylpropanoyl)-1H-pyrazol-3-yl)-3-hydroxy-2-oxo-1,2-dihydropyridin-1-yl]acetaldehyde
2-[5-(5-{[(5-chlorothiophen-2-yl)methyl]amino}-1-(2,2-dimethylpropanoyl)-1H-pyrazol-3-yl)-4-fluoro-2-oxo-1,2-dihydropyridin-1-yl]acetaldehyde
2-[5-(5-{[(5-chlorothiophen-2-yl)methyl]sulfanyl}-1-(2,2-dimethylpropanoyl)-1H-pyrazol-3-yl)-4-fluoro-2-oxo-1,2-dihydropyridin-1-yl]acetaldehyde
2-[5-bromo-3-(5-{[(5-chlorothiophen-2-yl)methyl]amino}-1-[2-(trifluoromethyl)benzoyl]-1H-pyrazol-3-yl)-2-oxo-1,2-dihydropyridin-1-yl]acetaldehyde
2-[6-(5-{[(5-chlorothiophen-2-yl)methyl]amino}-1-(1,2-oxazole-4-carbonyl)-1H-pyrazol-3-yl)-2-oxo-4-(pyridin-2-yl)-1,2-dihydropyridin-1-yl]acetic acid
2-[6-(5-{[(5-chlorothiophen-2-yl)methyl]amino}-1-(2,2-dimethylpropanoyl)-1H-pyrazol-3-yl)-2-oxo-5-(pyridin-2-yl)-1,2-dihydropyridin-1-yl]acetaldehyde
2-[6-(5-{[(5-chlorothiophen-2-yl)methyl]amino}-1-(2,2-dimethylpropanoyl)-1H-pyrazol-3-yl)-3-(morpholin-4-yl)-2-oxo-1,2-dihydropyridin-1-yl]acetaldehyde
2-[6-(5-{[(5-chlorothiophen-2-yl)methyl]amino}-1-(2,2-dimethylpropanoyl)-1H-pyrazol-3-yl)-4-ethenyl-2-oxo-1,2-dihydropyridin-1-yl]acetaldehyde
2-[6-(5-{[(5-chlorothiophen-2-yl)methyl]sulfanyl}-1-(2,2-dimethylpropanoyl)-1H-pyrazol-3-yl)-2-oxo-5-(pyridin-2-yl)-1,2-dihydropyridin-1-yl]acetaldehyde
2-[6-(5-{[(5-chlorothiophen-2-yl)methyl]sulfanyl}-1-(2,2-dimethylpropanoyl)-1H-pyrazol-3-yl)-3-(morpholin-4-yl)-2-oxo-1,2-dihydropyridin-1-yl]acetaldehyde
2-{3-[1-(3-carbamoylbenzoyl)-5-{[(5-chlorothiophen-2-yl)methyl]amino}-1H-pyrazol-3-yl]-5-chloro-2-oxo-1,2-dihydropyridin-1-yl}acetic acid
2-{4-[1-(2-aminobenzoyl)-5-{[(5-chlorothiophen-2-yl)methyl]amino}-4-methoxy-1H-pyrazol-3-yl]-3-(morpholin-4-yl)-2-oxo-1,2-dihydropyridin-1-yl}acetic acid
2-{6-[1-(2-aminobenzoyl)-5-{[(5-chlorothiophen-2-yl)methyl]amino}-1H-pyrazol-3-yl]-2-oxo-3-phenyl-1,2-dihydropyridin-1-yl}acetaldehyde
2-{6-[1-(4-carbamoylbenzoyl)-5-{[(5-chlorothiophen-2-yl)methyl]amino}-1H-pyrazol-3-yl]-2-oxo-5-(2-phenylethynyl)-1,2-dihydropyridin-1-yl}acetic acid
3-(1-benzoyl-5-{[(5-chlorothiophen-2-yl)methyl]amino}-1H-pyrazol-3-yl)-1-[2-oxo-2-(1,2-thiazol-3-yl)ethyl]-5-(pyridin-4-yl)-1,2-dihydropyridin-2-one
3-(1-benzoyl-5-{[(5-chlorothiophen-2-yl)methyl]amino}-1H-pyrazol-3-yl)-5-methoxy-1-[2-(piperidin-1-yl)ethyl]-1,2-dihydropyridin-2-one
3-(1-benzoyl-5-{[(5-chlorothiophen-2-yl)methyl]amino}-1H-pyrazol-3-yl)-6-(2-phenylethynyl)-1-[2-(piperidin-1-yl)ethyl]-1,2-dihydropyridin-2-one
3-(1-benzoyl-5-{[(5-chlorothiophen-2-yl)methyl]amino}-1H-pyrazol-3-yl)-6-(dimethylamino)-1-[2-oxo-2-(pyrimidin-5-yl)ethyl]-1,2-dihydropyridin-2-one
3-(1-benzoyl-5-{[(5-chlorothiophen-2-yl)methyl]amino}-1H-pyrazol-3-yl)-6-oxo-1-[2-(thiophen-2-yl)ethyl]-1,6-dihydropyridine-2-carbonitrile
3-(3-{2-chloro-6-oxo-1-[2-oxo-2-(1,2-thiazol-5-yl)ethyl]-1,6-dihydropyridin-3-yl}-5-{[(5-chlorothiophen-2-yl)methyl]amino}-1H-pyrazole-1-carbonyl)benzamide
3-(3-{3-chloro-6-oxo-1-[2-oxo-2-(pyrazin-2-yl)ethyl]-1,6-dihydropyridin-2-yl}-5-{[(5-chlorothiophen-2-yl)methyl]amino}-1H-pyrazole-1-carbonyl)benzamide
3-(3-{5-bromo-6-oxo-1-[2-(1,2-thiazol-4-yl)ethyl]-1,6-dihydropyridin-2-yl}-5-{[(5-chlorothiophen-2-yl)methyl]amino}-1H-pyrazole-1-carbonyl)benzamide
3-(3-{6-chloro-2-oxo-1-[2-(thiophen-3-yl)ethyl]-1,2-dihydropyridin-4-yl}-5-{[(5-chlorothiophen-2-yl)methyl]amino}-1H-pyrazole-1-carbonyl)benzamide
3-(5-{[(5-chlorothiophen-2-yl)methyl](methyl)amino}-1-(2,2-dimethylpropanoyl)-1H-pyrazol-3-yl)-1-[2-(1,2-oxazol-3-yl)-2-oxoethyl]-6-(pyridin-2-yl)-1,2-dihydropyridin-2-one
3-(5-{[(5-chlorothiophen-2-yl)methyl](methyl)amino}-1-(2,2-dimethylpropanoyl)-1H-pyrazol-3-yl)-1-[2-(furan-2-yl)-2-oxoethyl]-5-(pyridin-2-yl)-1,2-dihydropyridin-2-one
3-(5-{[(5-chlorothiophen-2-yl)methyl](methyl)amino}-1-(2,2-dimethylpropanoyl)-1H-pyrazol-3-yl)-1-[2-(furan-2-yl)-2-oxoethyl]-6-(morpholin-4-yl)-1,2-dihydropyridin-2-one
3-(5-{[(5-chlorothiophen-2-yl)methyl](methyl)amino}-1-(2,2-dimethylpropanoyl)-1H-pyrazol-3-yl)-1-[2-oxo-2-(1,3-thiazol-2-yl)ethyl]-4-(pyridin-2-yl)-1,2-dihydropyridin-2-one
3-(5-{[(5-chlorothiophen-2-yl)methyl](methyl)amino}-1-(2,2-dimethylpropanoyl)-1H-pyrazol-3-yl)-1-[2-oxo-2-(piperidin-1-yl)ethyl]-5-(pyridin-4-yl)-1,2-dihydropyridin-2-one
3-(5-{[(5-chlorothiophen-2-yl)methyl](methyl)amino}-1-(2,2-dimethylpropanoyl)-1H-pyrazol-3-yl)-1-[2-oxo-2-(piperidin-1-yl)ethyl]-6-(2-phenylethynyl)-1,2-dihydropyridin-2-one
3-(5-{[(5-chlorothiophen-2-yl)methyl](methyl)amino}-1-(2,2-dimethylpropanoyl)-1H-pyrazol-3-yl)-1-[2-oxo-2-(pyridazin-4-yl)ethyl]-4-(2-phenylethynyl)-1,2-dihydropyridin-2-one
3-(5-{[(5-chlorothiophen-2-yl)methyl](methyl)amino}-1-(2,2-dimethylpropanoyl)-1H-pyrazol-3-yl)-1-[2-oxo-2-(pyridin-3-yl)ethyl]-4-(pyridin-4-yl)-1,2-dihydropyridin-2-one APPENDIX A-continued Table B 3-(5-{[(5-chlorothiophen-2-yl)methyl](methyl)amino}-1-(2,2-dimethylpropanoyl)-1H-pyrazol-3-yl)-1-[2-oxo-2-(pyridin-3-yl)ethyl]-5-(2-phenylethynyl)-1,2-dihydropyridin-2-one
3-(5-{[(5-chlorothiophen-2-yl)methyl](methyl)amino}-1-(2,2-dimethylpropanoyl)-1H-pyrazol-3-yl)-1-[2-oxo-2-(thiophen-2-yl)ethyl]-6-(pyridin-4-yl)-1,2-dihydropyridin-2-one
3-(5-{[(5-chlorothiophen-2-yl)methyl](methyl)amino}-1-(2,2-dimethylpropanoyl)-1H-pyrazol-3-yl)-4-(morpholin-4-yl)-1-[2-(1,2-oxazol-4-yl)-2-oxoethyl]-1,2-dihydropyridin-2-one
3-(5-{[(5-chlorothiophen-2-yl)methyl](methyl)amino}-1-(2,2-dimethylpropanoyl)-1H-pyrazol-3-yl)-4-methoxy-1-[2-oxo-2-(pyridin-2-yl)ethyl]-1,2-dihydropyridin-2-one
3-(5-{[(5-chlorothiophen-2-yl)methyl](methyl)amino}-1-(2,2-dimethylpropanoyl)-1H-pyrazol-3-yl)-5-(morpholin-4-yl)-1-[2-oxo-2-(1,3-thiazol-2-yl)ethyl]-1,2-dihydropyridin-2-one
3-(5-{[(5-chlorothiophen-2-yl)methyl](methyl)amino}-1-(2,2-dimethylpropanoyl)-1H-pyrazol-3-yl)-5-fluoro-1-[2-(1,2-oxazol-4-yl)-2-oxoethyl]-1,2-dihydropyridin-2-one
3-(5-{[(5-chlorothiophen-2-yl)methyl](methyl)amino}-1-(2,2-dimethylpropanoyl)-1H-pyrazol-3-yl)-5-methoxy-1-[2-oxo-2-(thiophen-3-yl)ethyl]-1,2-dihydropyridin-2-one
3-(5-{[(5-chlorothiophen-2-yl)methyl](methyl)amino}-1-(2,2-dimethylpropanoyl)-1H-pyrazol-3-yl)-6-fluoro-1-[2-oxo-2-(1,3-thiazol-2-yl)ethyl]-1,2-dihydropyridin-2-one
3-(5-{[(5-chlorothiophen-2-yl)methyl](methyl)amino}-1-(2,2-dimethylpropanoyl)-1H-pyrazol-3-yl)-6-methoxy-1-[2-oxo-2-(1,2-thiazol-4-yl)ethyl]-1,2-dihydropyridin-2-one
3-(5-{[(5-chlorothiophen-2-yl)methyl](methyl)amino}-1-(2,2-dimethylpropanoyl)-1H-pyrazol-3-yl)-6-oxo-1-[2-oxo-2-(thiophen-2-yl)ethyl]-1,6-dihydropyridine-2-carbonitrile
3-(5-{[(5-chlorothiophen-2-yl)methyl]amino}-1-(1,2-oxazole-3-carbonyl)-1H-pyrazol-3-yl)-1-[2-(1,2-oxazol-3-yl)-2-oxoethyl]-6-(pyridin-2-yl)-1,2-dihydropyridin-2-one
3-(5-{[(5-chlorothiophen-2-yl)methyl]amino}-1-(1,2-oxazole-3-carbonyl)-1H-pyrazol-3-yl)-1-[2-(furan-2-yl)-2-oxoethyl]-5-methoxy-1,2-dihydropyridin-2-one
3-(5-{[(5-chlorothiophen-2-yl)methyl]amino}-1-(1,2-oxazole-3-carbonyl)-1H-pyrazol-3-yl)-4-fluoro-1-[2-oxo-2-(1,3-thiazol-2-yl)ethyl]-1,2-dihydropyridin-2-one
3-(5-{[(5-chlorothiophen-2-yl)methyl]amino}-1-(1,2-oxazole-3-carbonyl)-1H-pyrazol-3-yl)-5-(morpholin-4-yl)-1-[2-(1,2-thiazol-4-yl)ethyl]-1,2-dihydropyridin-2-one
3-(5-{[(5-chlorothiophen-2-yl)methyl]amino}-1-(1,2-oxazole-4-carbonyl)-1H-pyrazol-3-yl)-1-[2-(1,3-oxazol-4-yl)-2-oxoethyl]-5-(pyridin-3-yl)-1,2-dihydropyridin-2-one
3-(5-{[(5-chlorothiophen-2-yl)methyl]amino}-1-(1,2-oxazole-4-carbonyl)-1H-pyrazol-3-yl)-1-[2-(1,3-oxazol-5-yl)-2-oxoethyl]-6-phenyl-1,2-dihydropyridin-2-one
3-(5-{[(5-chlorothiophen-2-yl)methyl]amino}-1-(1,2-oxazole-4-carbonyl)-1H-pyrazol-3-yl)-2-oxo-1-[2-oxo-2-(1,2-thiazol-4-yl)ethyl]-1,2-dihydropyridine-4-carbonitrile
3-(5-{[(5-chlorothiophen-2-yl)methyl]amino}-1-(1,2-oxazole-4-carbonyl)-1H-pyrazol-3-yl)-4-fluoro-1-[2-(pyridin-3-yl)ethyl]-1,2-dihydropyridin-2-one
3-(5-{[(5-chlorothiophen-2-yl)methyl]amino}-1-(1,2-oxazole-4-carbonyl)-1H-pyrazol-3-yl)-5-(pyridin-3-yl)-1-(thiophen-2-ylmethyl)-1,2-dihydropyridin-2-one
3-(5-{[(5-chlorothiophen-2-yl)methyl]amino}-1-(1,2-oxazole-5-carbonyl)-1H-pyrazol-3-yl)-1-[2-(1,2-oxazol-3-yl)ethyl]-6-(pyridin-4-yl)-1,2-dihydropyridin-2-one
3-(5-{[(5-chlorothiophen-2-yl)methyl]amino}-1-(1,2-oxazole-5-carbonyl)-1H-pyrazol-3-yl)-4-hydroxy-1-[2-oxo-2-(pyridin-3-yl)ethyl]-1,2-dihydropyridin-2-one
3-(5-{[(5-chlorothiophen-2-yl)methyl]amino}-1-(1,2-oxazole-5-carbonyl)-1H-pyrazol-3-yl)-5-(pyridin-4-yl)-1-(pyrimidin-2-ylmethyl)-1,2-dihydropyridin-2-one
3-(5-{[(5-chlorothiophen-2-yl)methyl]amino}-1-(1,2-oxazole-5-carbonyl)-1H-pyrazol-3-yl)-5-ethenyl-1-(1,2-thiazol-3-ylmethyl)-1,2-dihydropyridin-2-one
3-(5-{[(5-chlorothiophen-2-yl)methyl]amino}-1-(1,2-oxazole-5-carbonyl)-1H-pyrazol-3-yl)-6-(morpholin-4-yl)-1-[2-oxo-2-(thiophen-2-yl)ethyl]-1,2-dihydropyridin-2-one
3-(5-{[(5-chlorothiophen-2-yl)methyl]amino}-1-(1,2-thiazole-3-carbonyl)-1H-pyrazol-3-yl)-4-ethenyl-1-[2-(4-methylpiperazin-1-yl)-2-oxoethyl]-1,2-dihydropyridin-2-one
3-(5-{[(5-chlorothiophen-2-yl)methyl]amino}-1-(1,2-thiazole-3-carbonyl)-1H-pyrazol-3-yl)-6-hydroxy-1-[2-oxo-2-(1,3-thiazol-4-yl)ethyl]-1,2-dihydropyridin-2-one
3-(5-{[(5-chlorothiophen-2-yl)methyl]amino}-1-(1,2-thiazole-4-carbonyl)-1H-pyrazol-3-yl)-1-(2-oxo-2-phenylethyl)-4-(pyridin-2-yl)-1,2-dihydropyridin-2-one

APPENDIX A-continued

Table B 3-(5-{[(5-chlorothiophen-2-yl)methyl]amino}-1-(1,2-thiazole-5-carbonyl)-1H-pyrazol-3-yl)-1-[2-oxo-2-(1,2-thiazol-5-yl)ethyl]-4-(pyridin-4-yl)-1,2-dihydropyridin-2-one 3-(5-{[(5-chlorothiophen-2-yl)methyl]amino}-1-(1,2-thiazole-5-carbonyl)-1H-pyrazol-3-yl)-4-phenyl-1-(1,3-thiazol-4-ylmethyl)-1,2-dihydropyridin-2-one 3-(5-{[(5-chlorothiophen-2-yl)methyl]amino}-1-(1,2-thiazole-5-carbonyl)-1H-pyrazol-3-yl)-5-(dimethylamino)-1-(1,3-thiazol-4-ylmethyl)-1,2-dihydropyridin-2-one 3-(5-{[(5-chlorothiophen-2-yl)methyl]amino}-1-(1,2-thiazole-5-carbonyl)-1H-pyrazol-3-yl)-5-(dimethylamino)-1-[2-oxo-2-(1,3-thiazol-5-yl)ethyl]-1,2-dihydropyridin-2-one 3-(5-{[(5-chlorothiophen-2-yl)methyl]amino}-1-(1,3-oxazole-2-carbonyl)-1H-pyrazol-3-yl)-1-[2-(1,3-oxazol-4-yl)-2-oxoethyl]-6-(pyridin-4-yl)-1,2-dihydropyridin-2-one 3-(5-{[(5-chlorothiophen-2-yl)methyl]amino}-1-(1,3-oxazole-2-carbonyl)-1H-pyrazol-3-yl)-1-[2-oxo-2-(1,2-thiazol-4-yl)ethyl]-5-phenyl-1,2-dihydropyridin-2-one 3-(5-{[(5-chlorothiophen-2-yl)methyl]amino}-1-(1,3-oxazole-2-carbonyl)-1H-pyrazol-3-yl)-1-[2-oxo-2-(thiophen-3-yl)ethyl]-4-(pyridin-3-yl)-1,2-dihydropyridin-2-one 3-(5-{[(5-chlorothiophen-2-yl)methyl]amino}-1-(1,3-oxazole-2-carbonyl)-1H-pyrazol-3-yl)-4-fluoro-1-(1,2-thiazol-4-ylmethyl)-1,2-dihydropyridin-2-one 3-(5-{[(5-chlorothiophen-2-yl)methyl]amino}-1-(1,3-oxazole-2-carbonyl)-1H-pyrazol-3-yl)-6-(pyridin-2-yl)-1-[2-(thiophen-2-yl)ethyl]-1,2-dihydropyridin-2-one 3-(5-{[(5-chlorothiophen-2-yl)methyl]amino}-1-(1,3-oxazole-4-carbonyl)-1H-pyrazol-3-yl)-5-(morpholin-4-yl)-1-[2-oxo-2-(pyridin-3-yl)ethyl]-1,2-dihydropyridin-2-one 3-(5-{[(5-chlorothiophen-2-yl)methyl]amino}-1-(1,3-oxazole-4-carbonyl)-1H-pyrazol-3-yl)-6-ethenyl-1-[2-oxo-2-(piperidin-1-yl)ethyl]-1,2-dihydropyridin-2-one 3-(5-{[(5-chlorothiophen-2-yl)methyl]amino}-1-(1,3-oxazole-4-carbonyl)-1H-pyrazol-3-yl)-6-fluoro-1-[2-(1,3-thiazol-4-yl)ethyl]-1,2-dihydropyridin-2-one 3-(5-{[(5-chlorothiophen-2-yl)methyl]amino}-1-(1,3-oxazole-5-carbonyl)-1H-pyrazol-3-yl)-1-[2-(4-methylpiperazin-1-yl)ethyl]-4-(2-phenylethynyl)-1,2-dihydropyridin-2-one 3-(5-{[(5-chlorothiophen-2-yl)methyl]amino}-1-(1,3-oxazole-5-carbonyl)-1H-pyrazol-3-yl)-1-[2-(furan-2-yl)-2-oxoethyl]-6-(2-phenylethynyl)-1,2-dihydropyridin-2-one 3-(5-{[(5-chlorothiophen-2-yl)methyl]amino}-1-(1,3-oxazole-5-carbonyl)-1H-pyrazol-3-yl)-1-[2-oxo-2-(1,3-thiazol-2-yl)ethyl]-5-(pyridin-2-yl)-1,2-dihydropyridin-2-one 3-(5-{[(5-chlorothiophen-2-yl)methyl]amino}-1-(1,3-oxazole-5-carbonyl)-1H-pyrazol-3-yl)-4-methoxy-1-[2-(1,2-oxazol-4-yl)-2-oxoethyl]-1,2-dihydropyridin-2-one 3-(5-{[(5-chlorothiophen-2-yl)methyl]amino}-1-(1,3-thiazole-2-carbonyl)-1H-pyrazol-3-yl)-1-[2-oxo-2-(pyrimidin-4-yl)ethyl]-4-(2-phenylethynyl)-1,2-dihydropyridin-2-one 3-(5-{[(5-chlorothiophen-2-yl)methyl]amino}-1-(1,3-thiazole-2-carbonyl)-1H-pyrazol-3-yl)-4-hydroxy-1-[2-(1,2-thiazol-4-yl)ethyl]-1,2-dihydropyridin-2-one 3-(5-{[(5-chlorothiophen-2-yl)methyl]amino}-1-(1,3-thiazole-2-carbonyl)-1H-pyrazol-3-yl)-5-methoxy-1-(1,3-oxazol-4-ylmethyl)-1,2-dihydropyridin-2-one 3-(5-{[(5-chlorothiophen-2-yl)methyl]amino}-1-(1,3-thiazole-4-carbonyl)-1H-pyrazol-3-yl)-1-[2-(1,2-oxazol-3-yl)-2-oxoethyl]-6-oxo-1,6-dihydropyridine-2-carbonitrile 3-(5-{[(5-chlorothiophen-2-yl)methyl]amino}-1-(1,3-thiazole-4-carbonyl)-1H-pyrazol-3-yl)-1-[2-oxo-2-(1,3-thiazol-5-yl)ethyl]-6-(pyridin-3-yl)-1,2-dihydropyridin-2-one 3-(5-{[(5-chlorothiophen-2-yl)methyl]amino}-1-(1,3-thiazole-4-carbonyl)-1H-pyrazol-3-yl)-2-oxo-1-(piperidin-1-ylmethyl)-1,2-dihydropyridine-4-carbonitrile 3-(5-{[(5-chlorothiophen-2-yl)methyl]amino}-1-(1,3-thiazole-4-carbonyl)-1H-pyrazol-3-yl)-4-(dimethylamino)-1-[2-oxo-2-(pyridin-4-yl)ethyl]-1,2-dihydropyridin-2-one 3-(5-{[(5-chlorothiophen-2-yl)methyl]amino}-1-(1,3-thiazole-4-carbonyl)-1H-pyrazol-3-yl)-5-hydroxy-1-(pyrazin-2-ylmethyl)-1,2-dihydropyridin-2-one 3-(5-{[(5-chlorothiophen-2-yl)methyl]amino}-1-(1,3-thiazole-5-carbonyl)-1H-pyrazol-3-yl)-5-fluoro-1-(1,3-oxazol-5-ylmethyl)-1,2-dihydropyridin-2-one 3-(5-{[(5-chlorothiophen-2-yl)methyl]amino}-1-(1,3-thiazole-5-carbonyl)-1H-pyrazol-3-yl)-5-hydroxy-1-[2-(4-methylpiperazin-1-yl)-2-oxoethyl]-1,2-dihydropyridin-2-one 3-(5-{[(5-chlorothiophen-2-yl)methyl]amino}-1-(2,2-dimethylpropanoyl)-1H-pyrazol-3-yl)-1-(1,3-oxazol-5-ylmethyl)-6-(pyridin-2-yl)-1,2-dihydropyridin-2-one 3-(5-{[(5-chlorothiophen-2-yl)methyl]amino}-1-(2,2-dimethylpropanoyl)-1H-pyrazol-3-yl)-1-(2-oxo-2-phenylethyl)-6-(prop-2-enoyl)-1,2-dihydropyridin-2-one APPENDIX A-continued Table B 3-(5-{[(5-chlorothiophen-2-yl)methyl]amino}-1-(2,2-dimethylpropanoyl)-1H-pyrazol-3-yl)-1-[2-(1,2-oxazol-3-yl)-2-oxoethyl]-2-oxo-1,2-dihydropyridine-4-carbonitrile 3-(5-{[(5-chlorothiophen-2-yl)methyl]amino}-1-(2,2-dimethylpropanoyl)-1H-pyrazol-3-yl)-1-[2-(1,2-oxazol-3-yl)-2-oxoethyl]-5-(pyridin-3-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(1,2-oxazol-4-yl)-2-oxoethyl]-4-(pyridine-2-carbonyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(1,2-oxazol-5-yl)-2-oxoethyl]-4-(prop-2-enoyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(1,2-oxazol-5-yl)-2-oxoethyl]-5-(pyridin-2-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-4-(2-phenylethynyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(1,3-oxazol-5-yl)-2-oxoethyl]-4-phenyl-1,2-dihydropyridin-2-one 3-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-6-(pyridin-4-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(furan-2-yl)-2-oxoethyl]-2-oxo-1,2-dihydropyridine-4-carbonitrile 3-(5-{[(5-chlorothiophen-2-yl)methyl]amino}-1-(2,2-dimethylpropanoyl)-1H-pyrazol-3-yl)-1-[2-(furan-2-yl)-2-oxoethyl]-6-(pyridine-2-carbonyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(furan-2-yl)-2-oxoethyl]-6-oxo-1,6-dihydropyridine-2-carboxylic acid 3-(5-{[(5-chlorothiophen-2-yl)methyl]amino}-1-(2,2-dimethylpropanoyl)-1H-pyrazol-3-yl)-1-[2-(furan-3-yl)-2-oxoethyl]-5-(pyridin-4-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(furan-3-yl)-2-oxoethyl]-6-(2-phenylethynyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-4-(pyridin-4-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-5-(2-phenylethynyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(1,2-thiazol-5-yl)ethyl]-5-(pyridine-3-carbonyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(1,3-thiazol-2-yl)ethyl]-5-(pyridine-2-carbonyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(1,3-thiazol-5-yl)ethyl]-6-(pyridine-3-carbonyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(piperidin-1-yl)ethyl]-6-(pyridine-4-carbonyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-4-(pyridin-3-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-6-phenyl-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-4-(pyridine-4-carbonyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-5-(3-phenylprop-2-ynoyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-6-phenyl-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyridin-2-yl)ethyl]-5-(pyridin-3-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyridin-3-yl)ethyl]-5-(pyridine-4-carbonyl)-1,2-dihydropyridin-2-one

APPENDIX A-continued

Table B 3-(5-{[(5-chlorothiophen-2-yl)methyl]amino}-1-(2,2-dimethylpropanoyl)-1H-pyrazol-3-yl)-1-[2-oxo-2-(pyridin-3-yl)ethyl]-6-(3-phenylprop-2-ynoyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyridin-4-yl)ethyl]-4-(pyridine-3-carbonyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyrimidin-2-yl)ethyl]-4-(pyridin-2-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyrimidin-4-yl)ethyl]-5-(prop-2-enoyl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(pyrimidin-4-yl)ethyl]-6-(pyridin-2-yl)-1,2-dihydropyridin-2-one 3-(5-{[(5-chlorothiophen-2-yl)methyl]amino}-1-(2,2-dimethylpropanoyl)-1H-pyrazol-3-yl)-1-[2-oxo-2-(thiophen-3-yl)ethyl]-6-(pyridin-3-yl)-1,2-dihydropyridin-2-one 3-(5-{[(5-chlorothiophen-2-yl)methyl]amino}-1-(2,2-dimethylpropanoyl)-1H-pyrazol-3-yl)-2-oxo-1-[2-oxo-2-(pyrazin-2-yl)ethyl]-1,2-dihydropyridine-4-carboxylic acid 3-(5-{[(5-chlorothiophen-2-yl)methyl]amino}-1-(2,2-dimethylpropanoyl)-1H-pyrazol-3-yl)-4-(dimethylamino)-1-[2-(1,3-oxazol-4-yl)-2-oxoethyl]-1,2-dihydropyridin-2-one 3-(5-{[(5-chlorothiophen-2-yl)methyl]amino}-1-(2,2-dimethylpropanoyl)-1H-pyrazol-3-yl)-4-(morpholin-4-yl)-1-[2-oxo-2-(1,3-thiazol-4-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-4-(morpholine-4-carbonyl)-1-[2-oxo-2-(pyrimidin-5-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-4-ethenyl-1-[2-oxo-2-(thiophen-2-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-4-fluoro-1-[2-oxo-2-(pyrazin-2-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-4-hydroxy-1-[2-oxo-2-(piperidin-1-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-5-(dimethylamino)-1-[2-(1,3-oxazol-5-yl)-2-oxoethyl]-1,2-dihydropyridin-2-one 3-(5-{[(5-chlorothiophen-2-yl)methyl]amino}-1-(2,2-dimethylpropanoyl)-1H-pyrazol-3-yl)-5-(morpholin-4-yl)-1-[2-oxo-2-(pyrimidin-2-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-5-(morpholine-4-carbonyl)-1-[2-oxo-2-(pyridin-4-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-5-fluoro-1-[2-oxo-2-(1,3-thiazol-4-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-5-hydroxy-1-[2-oxo-2-(thiophen-2-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-5-methoxy-1-[2-oxo-2-(1,2-thiazol-3-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-6-(morpholin-4-yl)-1-[2-(1,2-oxazol-5-yl)-2-oxoethyl]-1,2-dihydropyridin-2-one 3-(5-{[(5-chlorothiophen-2-yl)methyl]amino}-1-(2,2-dimethylpropanoyl)-1H-pyrazol-3-yl)-6-(morpholine-4-carbonyl)-1-[2-oxo-2-(1,2-thiazol-5-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-6-ethenyl-1-[2-(1,2-oxazol-4-yl)-2-oxoethyl]-1,2-dihydropyridin-2-one 3-(5-{[(5-chlorothiophen-2-yl)methyl]amino}-1-(2,2-dimethylpropanoyl)-1H-pyrazol-3-yl)-6-fluoro-1-[2-oxo-2-(pyrimidin-2-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-6-methoxy-1-[2-oxo-2-(pyrimidin-5-yl)ethyl]-1,2-dihydropyridin-2-one 3-(5-{[(5-chlorothiophen-2-yl)methyl]amino}-1-(2,2-dimethylpropanoyl)-1H-pyrazol-3-yl)-6-oxo-1-[2-oxo-2-(thiophen-3-yl)ethyl]-1,6-dihydropyridine-2-carbonitrile 3-(5-{[(5-chlorothiophen-2-yl)methyl]amino}-1-(2,2-dimethylpropanoyl)-1H-pyrazol-3-yl)-N,N-dimethyl-2-oxo-1-(2-oxoethyl)-1,2-dihydropyridine-4-carboxamide

APPENDIX A-continued

Table B 3-(5-{[(5-chlorothiophen-2-yl)methyl]amino}-1-(2,2-dimethylpropanoyl)-1H-pyrazol-3-yl)-N,N-dimethyl-6-oxo-1-[2-oxo-2-(piperidin-1-yl)ethyl]-1,6-dihydropyridine-2-carboxamide
3-(5-{[(5-chlorothiophen-2-yl)methyl]amino}-1-(2-fluorobenzoyl)-1H-pyrazol-3-yl)-1-(1,3-oxazol-2-ylmethyl)-5-(2-phenylethynyl)-1,2-dihydropyridin-2-one
3-(5-{[(5-chlorothiophen-2-yl)methyl]amino}-1-(2-fluorobenzoyl)-1H-pyrazol-3-yl)-1-methyl-6-phenyl-1,2-dihydropyridin-2-one
3-(5-{[(5-chlorothiophen-2-yl)methyl]amino}-1-(2-fluorobenzoyl)-1H-pyrazol-3-yl)-5-(morpholin-4-yl)-1-[2-(morpholin-4-yl)-2-oxoethyl]-1,2-dihydropyridin-2-one
3-(5-{[(5-chlorothiophen-2-yl)methyl]amino}-1-(2-fluorobenzoyl)-1H-pyrazol-3-yl)-6-ethenyl-1-[2-(furan-3-yl)-2-oxoethyl]-1,2-dihydropyridin-2-one
3-(5-{[(5-chlorothiophen-2-yl)methyl]amino}-1-(2-methoxybenzoyl)-1H-pyrazol-3-yl)-1-[2-(1,2-oxazol-5-yl)-2-oxoethyl]-6-(2-phenylethynyl)-1,2-dihydropyridin-2-one
3-(5-{[(5-chlorothiophen-2-yl)methyl]amino}-1-(2-methoxybenzoyl)-1H-pyrazol-3-yl)-1-[2-oxo-2-(pyrimidin-2-yl)ethyl]-5-(pyridin-2-yl)-1,2-dihydropyridin-2-one
3-(5-{[(5-chlorothiophen-2-yl)methyl]amino}-1-(2-methoxybenzoyl)-1H-pyrazol-3-yl)-4-methoxy-1-[2-oxo-2-(1,3-thiazol-4-yl)ethyl]-1,2-dihydropyridin-2-one
3-(5-{[(5-chlorothiophen-2-yl)methyl]amino}-1-(3-hydroxy-2,2-dimethylpropanoyl)-1H-pyrazol-3-yl)-1-[2-(pyrazin-2-yl)ethyl]-4-(pyridin-2-yl)-1,2-dihydropyridin-2-one
3-(5-{[(5-chlorothiophen-2-yl)methyl]amino}-1-(3-hydroxy-2,2-dimethylpropanoyl)-1H-pyrazol-3-yl)-4-(morpholin-4-yl)-1-[2-oxo-2-(1,3-thiazol-5-yl)ethyl]-1,2-dihydropyridin-2-one
3-(5-{[(5-chlorothiophen-2-yl)methyl]amino}-1-(3-hydroxy-2,2-dimethylpropanoyl)-1H-pyrazol-3-yl)-5-ethenyl-1-[2-(1,3-oxazol-2-yl)-2-oxoethyl]-1,2-dihydropyridin-2-one
3-(5-{[(5-chlorothiophen-2-yl)methyl]amino}-1-(3-hydroxy-2,2-dimethylpropanoyl)-1H-pyrazol-3-yl)-6-(dimethylamino)-1-(1,2-oxazol-5-ylmethyl)-1,2-dihydropyridin-2-one
3-(5-{[(5-chlorothiophen-2-yl)methyl]amino}-1-(3-hydroxy-2,2-dimethylpropanoyl)-4-methoxy-1H-pyrazol-3-yl)-6-(morpholin-4-yl)-1-(1,2-thiazol-5-ylmethyl)-1,2-dihydropyridin-2-one
3-(5-{[(5-chlorothiophen-2-yl)methyl]amino}-1-(3-methoxy-2,2-dimethylpropanoyl)-1H-pyrazol-3-yl)-5-fluoro-1-[2-oxo-2-(thiophen-2-yl)ethyl]-1,2-dihydropyridin-2-one
3-(5-{[(5-chlorothiophen-2-yl)methyl]amino}-1-(3-methoxy-2,2-dimethylpropanoyl)-1H-pyrazol-3-yl)-6-(morpholin-4-yl)-1-[2-(1,3-oxazol-5-yl)ethyl]-1,2-dihydropyridin-2-one
3-(5-{[(5-chlorothiophen-2-yl)methyl]amino}-1-(furan-2-carbonyl)-1H-pyrazol-3-yl)-4-(pyridin-2-yl)-1-(1,3-thiazol-5-ylmethyl)-1,2-dihydropyridin-2-one
3-(5-{[(5-chlorothiophen-2-yl)methyl]amino}-1-(furan-2-carbonyl)-1H-pyrazol-3-yl)-5-ethenyl-1-[2-oxo-2-(pyridazin-4-yl)ethyl]-1,2-dihydropyridin-2-one
3-(5-{[(5-chlorothiophen-2-yl)methyl]amino}-1-(furan-3-carbonyl)-1H-pyrazol-3-yl)-1-(pyrazin-2-ylmethyl)-4-(pyridin-4-yl)-1,2-dihydropyridin-2-one
3-(5-{[(5-chlorothiophen-2-yl)methyl]amino}-1-(furan-3-carbonyl)-1H-pyrazol-3-yl)-1-[2-(furan-2-yl)ethyl]-5-phenyl-1,2-dihydropyridin-2-one
3-(5-{[(5-chlorothiophen-2-yl)methyl]amino}-1-(furan-3-carbonyl)-1H-pyrazol-3-yl)-1-[2-oxo-2-(pyridin-2-yl)ethyl]-4-phenyl-1,2-dihydropyridin-2-one
3-(5-{[(5-chlorothiophen-2-yl)methyl]amino}-1-(furan-3-carbonyl)-1H-pyrazol-3-yl)-1-[2-oxo-2-(thiophen-3-yl)ethyl]-5-(pyridin-4-yl)-1,2-dihydropyridin-2-one
3-(5-{[(5-chlorothiophen-2-yl)methyl]amino}-1-(furan-3-carbonyl)-1H-pyrazol-3-yl)-4-(pyridin-3-yl)-1-[2-(1,3-thiazol-2-yl)ethyl]-1,2-dihydropyridin-2-one
3-(5-{[(5-chlorothiophen-2-yl)methyl]amino}-1-(furan-3-carbonyl)-1H-pyrazol-3-yl)-6-(dimethylamino)-1-[2-oxo-2-(1,2-thiazol-4-yl)ethyl]-1,2-dihydropyridin-2-one
3-(5-{[(5-chlorothiophen-2-yl)methyl]amino}-1-(thiophene-2-carbonyl)-1H-pyrazol-3-yl)-1-[2-oxo-2-(1,2-thiazol-5-yl)ethyl]-6-phenyl-1,2-dihydropyridin-2-one
3-(5-{[(5-chlorothiophen-2-yl)methyl]amino}-1-(thiophene-2-carbonyl)-1H-pyrazol-3-yl)-1-[2-oxo-2-(pyridin-4-yl)ethyl]-5-(pyridin-3-yl)-1,2-dihydropyridin-2-one
3-(5-{[(5-chlorothiophen-2-yl)methyl]amino}-1-(thiophene-2-carbonyl)-1H-pyrazol-3-yl)-2-oxo-1-[2-oxo-2-(pyrimidin-5-yl)ethyl]-1,2-dihydropyridine-4-carbonitrile
3-(5-{[(5-chlorothiophen-2-yl)methyl]amino}-1-(thiophene-2-carbonyl)-1H-pyrazol-3-yl)-5-(pyridin-2-yl)-1-[2-(pyridin-3-yl)ethyl]-1,2-dihydropyridin-2-one
3-(5-{[(5-chlorothiophen-2-yl)methyl]amino}-1-(thiophene-3-carbonyl)-1H-pyrazol-3-yl)-5-fluoro-1-[2-oxo-2-(pyrimidin-4-yl)ethyl]-1,2-dihydropyridin-2-one
3-(5-{[(5-chlorothiophen-2-yl)methyl]amino}-1-(thiophene-3-carbonyl)-1H-pyrazol-3-yl)-6-(morpholin-4-yl)-1-(pyrazin-2-ylmethyl)-1,2-dihydropyridin-2-one
3-(5-{[(5-chlorothiophen-2-yl)methyl]amino}-1-(thiophene-3-carbonyl)-1H-pyrazol-3-yl)-6-methoxy-1-(2-oxo-2-phenylethyl)-1,2-dihydropyridin-2-one

APPENDIX A-continued

Table B 3-(5-{[(5-chlorothiophen-2-yl)methyl]amino}-1-[2-(trifluoromethyl)benzoyl]-1H-pyrazol-3-yl)-1-(2-phenylethyl)-4-(pyridin-4-yl)-1,2-dihydropyridin-2-one 3-(5-{[(5-chlorothiophen-2-yl)methyl]amino}-1-[2-(trifluoromethyl)benzoyl]-1H-pyrazol-3-yl)-1-[2-oxo-2-(thiophen-2-yl)ethyl]-4-(2-phenylethynyl)-1,2-dihydropyridin-2-one 3-(5-{[(5-chlorothiophen-2-yl)methyl]amino}-1-[2-(trifluoromethyl)benzoyl]-1H-pyrazol-3-yl)-6-fluoro-1-[2-(1,2-oxazol-4-yl)-2-oxoethyl]-1,2-dihydropyridin-2-one 3-(5-{[(5-chlorothiophen-2-yl)methyl]amino}-1-[2-(trifluoromethyl)benzoyl]-1H-pyrazol-3-yl)-6-hydroxy-1-[2-(1,3-oxazol-2-yl)ethyl]-1,2-dihydropyridin-2-one 3-(5-{[(5-chlorothiophen-2-yl)methyl]amino}-1-[3-(hydroxymethyl)benzoyl]-1H-pyrazol-3-yl)-1-[2-oxo-2-(pyrimidin-4-yl)ethyl]-6-(pyridin-2-yl)-1,2-dihydropyridin-2-one 3-(5-{[(5-chlorothiophen-2-yl)methyl]amino}-1-[3-(hydroxymethyl)benzoyl]-1H-pyrazol-3-yl)-4-(dimethylamino)-1-[2-(pyrimidin-4-yl)ethyl]-1,2-dihydropyridin-2-one 3-(5-{[(5-chlorothiophen-2-yl)methyl]amino}-1-[3-(hydroxymethyl)benzoyl]-1H-pyrazol-3-yl)-4-ethenyl-1-[2-(1,2-thiazol-5-yl)ethyl]-1,2-dihydropyridin-2-one 3-(5-{[(5-chlorothiophen-2-yl)methyl]amino}-1-[3-(hydroxymethyl)benzoyl]-1H-pyrazol-3-yl)-4-fluoro-1-[2-oxo-2-(pyrimidin-2-yl)ethyl]-1,2-dihydropyridin-2-one 3-(5-{[(5-chlorothiophen-2-yl)methyl]amino}-1-[3-(hydroxymethyl)benzoyl]-1H-pyrazol-3-yl)-5-methoxy-1-[2-(1,2-oxazol-5-yl)-2-oxoethyl]-1,2-dihydropyridin-2-one 3-(5-{[(5-chlorothiophen-2-yl)methyl]amino}-1-[4-(hydroxymethyl)benzoyl]-1H-pyrazol-3-yl)-1-[2-(1,2-oxazol-4-yl)-2-oxoethyl]-5-(2-phenylethynyl)-1,2-dihydropyridin-2-one 3-(5-{[(5-chlorothiophen-2-yl)methyl]amino}-1-[4-(hydroxymethyl)benzoyl]-4-methoxy-1H-pyrazol-3-yl)-6-hydroxy-1-(thiophen-3-ylmethyl)-1,2-dihydropyridin-2-one 3-(5-{[(5-chlorothiophen-2-yl)methyl]amino}-3-[1-(furan-2-ylmethyl)-4-hydroxy-2-oxo-1,2-dihydropyridin-3-yl]-1H-pyrazole-1-carbonyl)benzoic acid 3-(5-{[(5-chlorothiophen-2-yl)methyl]amino}-3-[1-methyl-5-(morpholin-4-yl)-6-oxo-1,6-dihydropyridin-2-yl]-1H-pyrazole-1-carbonyl)benzoic acid 3-(5-{[(5-chlorothiophen-2-yl)methyl]amino}-3-[2-fluoro-6-oxo-1-(pyridin-4-ylmethyl)-1,6-dihydropyridin-3-yl]-1H-pyrazole-1-carbonyl)benzamide 3-(5-{[(5-chlorothiophen-2-yl)methyl]amino}-3-[2-oxo-1-(2-oxo-2-phenylethyl)-3-(pyridin-4-yl)-1,2-dihydropyridin-4-yl]-1H-pyrazole-1-carbonyl)benzoic acid 3-(5-{[(5-chlorothiophen-2-yl)methyl]amino}-3-[2-oxo-5-(2-phenylethynyl)-1-[2-(1,3-thiazol-4-yl)ethyl]-1,2-dihydropyridin-3-yl]-1H-pyrazole-1-carbonyl)benzamide 3-(5-{[(5-chlorothiophen-2-yl)methyl]amino}-3-[4-(dimethylamino)-1-(1,3-oxazol-5-ylmethyl)-6-oxo-1,6-dihydropyridin-2-yl]-1H-pyrazole-1-carbonyl)benzamide 3-(5-{[(5-chlorothiophen-2-yl)methyl]amino}-3-[4-(methoxycarbonyl)-1-[2-(1,2-oxazol-3-yl)ethyl]-6-oxo-1,6-dihydropyridin-3-yl]-1H-pyrazole-1-carbonyl)benzoic acid 3-(5-{[(5-chlorothiophen-2-yl)methyl]amino}-3-[4-(morpholin-4-yl)-6-oxo-1-(1,3-thiazol-4-ylmethyl)-1,6-dihydropyridin-2-yl]-1H-pyrazole-1-carbonyl)benzamide 3-(5-{[(5-chlorothiophen-2-yl)methyl]amino}-3-[4-hydroxy-2-oxo-1-(pyrimidin-5-ylmethyl)-1,2-dihydropyridin-3-yl]-4-methoxy-1H-pyrazole-1-carbonyl)benzamide 3-(5-{[(5-chlorothiophen-2-yl)methyl]amino}-3-[5-(dimethylamino)-1-[2-(1,2-oxazol-5-yl)-2-oxoethyl]-6-oxo-1,6-dihydropyridin-2-yl]-1H-pyrazole-1-carbonyl)benzoic acid 3-(5-{[(5-chlorothiophen-2-yl)methyl]amino}-3-[5-(dimethylamino)-1-[2-(furan-2-yl)-2-oxoethyl]-2-oxo-1,2-dihydropyridin-4-yl]-1H-pyrazole-1-carbonyl)benzoic acid 3-(5-{[(5-chlorothiophen-2-yl)methyl]amino}-3-[5-(morpholin-4-yl)-1-[2-(1,2-oxazol-3-yl)ethyl]-6-oxo-1,6-dihydropyridin-3-yl]-1H-pyrazole-1-carbonyl)benzamide 3-(5-{[(5-chlorothiophen-2-yl)methyl]amino}-3-[5-(morpholin-4-yl)-6-oxo-1-[2-oxo-2-(pyridin-4-yl)ethyl]-1,6-dihydropyridin-3-yl]-1H-pyrazole-1-carbonyl)benzamide 3-(5-{[(5-chlorothiophen-2-yl)methyl]amino}-3-[5-fluoro-2-oxo-1-(thiophen-3-ylmethyl)-1,2-dihydropyridin-4-yl]-1H-pyrazole-1-carbonyl)benzoic acid 3-(5-{[(5-chlorothiophen-2-yl)methyl]amino}-3-[6-(morpholin-4-yl)-1-[2-(1,3-oxazol-4-yl)-2-oxoethyl]-2-oxo-1,2-dihydropyridin-4-yl]-1H-pyrazole-1-carbonyl)benzamide 3-(5-{[(5-chlorothiophen-2-yl)methyl]amino}-3-[6-(morpholin-4-yl)-2-oxo-1-(pyrimidin-4-ylmethyl)-1,2-dihydropyridin-4-yl]-1H-pyrazole-1-carbonyl)benzamide 3-(5-{[(5-chlorothiophen-2-yl)methyl]amino}-3-[6-oxo-1-(2-oxoethyl)-4-(pyridin-4-yl)-1,6-dihydropyridin-2-yl]-1H-pyrazole-1-carbonyl)benzoic acid

APPENDIX A-continued

Table B 3-(5-{[(5-chlorothiophen-2-yl)methyl]amino}-3-{2-oxo-1-[2-oxo-2-(1,2-thiazol-3-yl)ethyl]-4-(pyridin-3-yl)-1,2-dihydropyridin-3-yl}-1H-pyrazole-1-carbonyl)benzoic acid 3-(5-{[(5-chlorothiophen-2-yl)methyl]amino}-3-{2-oxo-1-[2-oxo-2-(pyridin-4-yl)ethyl]-6-(pyridin-4-yl)-1,2-dihydropyridin-3-yl}-1H-pyrazole-1-carbonyl)benzoic acid 3-(5-{[(5-chlorothiophen-2-yl)methyl]amino}-3-{2-oxo-1-[2-oxo-2-(pyrimidin-5-yl)ethyl]-5-phenyl-1,2-dihydropyridin-3-yl}-1H-pyrazole-1-carbonyl)benzoic acid 3-(5-{[(5-chlorothiophen-2-yl)methyl]amino}-3-{3-hydroxy-2-oxo-1-[2-oxo-2-(1,2-thiazol-4-yl)ethyl]-1,2-dihydropyridin-4-yl}-1H-pyrazole-1-carbonyl)benzamide 3-(5-{[(5-chlorothiophen-2-yl)methyl]amino}-3-{4-cyano-6-oxo-1-[2-(piperidin-1-yl)ethyl]-1,6-dihydropyridin-2-yl}-1H-pyrazole-1-carbonyl)benzamide 3-(5-{[(5-chlorothiophen-2-yl)methyl]amino}-3-{4-ethenyl-1-[2-(1,3-oxazol-5-yl)-2-oxoethyl]-2-oxo-1,2-dihydropyridin-3-yl}-1H-pyrazole-1-carbonyl)benzamide 3-(5-{[(5-chlorothiophen-2-yl)methyl]amino}-3-{4-ethenyl-6-oxo-1-[2-oxo-2-(thiophen-3-yl)ethyl]-1,6-dihydropyridin-3-yl}-1H-pyrazole-1-carbonyl)benzamide 3-(5-{[(5-chlorothiophen-2-yl)methyl]amino}-3-{4-hydroxy-6-oxo-1-[2-oxo-2-(pyrimidin-5-yl)ethyl]-1,6-dihydropyridin-2-yl}-1H-pyrazole-1-carbonyl)benzamide 3-(5-{[(5-chlorothiophen-2-yl)methyl]amino}-3-{5-cyano-1-[2-(1,2-oxazol-4-yl)-2-oxoethyl]-6-oxo-1,6-dihydropyridin-3-yl}-1H-pyrazole-1-carbonyl)benzoic acid 3-(5-{[(5-chlorothiophen-2-yl)methyl]amino}-3-{6-ethenyl-1-[2-(1,3-oxazol-4-yl)ethyl]-2-oxo-1,2-dihydropyridin-3-yl}-1H-pyrazole-1-carbonyl)benzamide 3-(5-{[(5-chlorothiophen-2-yl)methyl]amino}-3-{6-hydroxy-2-oxo-1-[2-oxo-2-(pyridazin-4-yl)ethyl]-1,2-dihydropyridin-3-yl}-1H-pyrazole-1-carbonyl)benzamide 3-(5-{[(5-chlorothiophen-2-yl)methyl]amino}-3-{6-oxo-1-[2-oxo-2-(1,3-thiazol-2-yl)ethyl]-2-phenyl-1,6-dihydropyridin-3-yl}-1H-pyrazole-1-carbonyl)benzoic acid 3-(5-{[(5-chlorothiophen-2-yl)methyl]amino}-3-{6-oxo-1-[2-oxo-2-(pyrimidin-2-yl)ethyl]-3-phenyl-1,6-dihydropyridin-2-yl}-1H-pyrazole-1-carbonyl)benzoic acid 3-(5-{[(5-chlorothiophen-2-yl)methyl]amino}-3-{6-oxo-1-[2-oxo-2-(pyrimidin-4-yl)ethyl]-4-(pyridin-3-yl)-1,6-dihydropyridin-3-yl}-1H-pyrazole-1-carbonyl)benzoic acid 3-(5-{[(5-chlorothiophen-2-yl)methyl]amino}-4-cyano-3-[5-cyano-2-oxo-1-(pyrimidin-2-ylmethyl)-1,2-dihydropyridin-4-yl]-1H-pyrazole-1-carbonyl)benzamide 3-(5-{[(5-chlorothiophen-2-yl)methyl]amino}-4-cyano-3-[6-methoxy-2-oxo-1-(pyrazin-2-ylmethyl)-1,2-dihydropyridin-3-yl]-1H-pyrazole-1-carbonyl)benzamide 3-(5-{[(5-chlorothiophen-2-yl)methyl]amino}-4-cyano-3-{1-[(4-methylpiperazin-1-yl)methyl]-6-oxo-5-(pyridin-4-yl)-1,6-dihydropyridin-2-yl}-1H-pyrazole-1-carbonyl)benzamide 3-(5-{[(5-chlorothiophen-2-yl)methyl]amino}-4-fluoro-1-(1,2-oxazole-3-carbonyl)-1H-pyrazol-3-yl)-1-(furan-3-ylmethyl)-6-(2-phenylethynyl)-1,2-dihydropyridin-2-one 3-(5-{[(5-chlorothiophen-2-yl)methyl]amino}-4-fluoro-1-(1,2-oxazole-3-carbonyl)-1H-pyrazol-3-yl)-4-(dimethylamino)-1-(thiophen-2-ylmethyl)-1,2-dihydropyridin-2-one 3-(5-{[(5-chlorothiophen-2-yl)methyl]amino}-4-fluoro-1-(1,3-oxazole-4-carbonyl)-1H-pyrazol-3-yl)-6-ethenyl-1-(pyridin-4-ylmethyl)-1,2-dihydropyridin-2-one 3-(5-{[(5-chlorothiophen-2-yl)methyl]amino}-4-fluoro-1-(1,3-thiazole-4-carbonyl)-1H-pyrazol-3-yl)-1-(1,2-oxazol-4-ylmethyl)-6-(pyridin-3-yl)-1,2-dihydropyridin-2-one 3-(5-{[(5-chlorothiophen-2-yl)methyl]amino}-4-fluoro-1-(2-fluorobenzoyl)-1H-pyrazol-3-yl)-1-(1,3-oxazol-5-ylmethyl)-4-(2-phenylethynyl)-1,2-dihydropyridin-2-one 3-(5-{[(5-chlorothiophen-2-yl)methyl]amino}-4-fluoro-1-(2-fluorobenzoyl)-1H-pyrazol-3-yl)-1-(morpholin-4-ylmethyl)-5-(pyridin-2-yl)-1,2-dihydropyridin-2-one 3-(5-{[(5-chlorothiophen-2-yl)methyl]amino}-4-fluoro-1-(furan-3-carbonyl)-1H-pyrazol-3-yl)-4-methoxy-1-(1,3-oxazol-2-ylmethyl)-1,2-dihydropyridin-2-one 3-(5-{[(5-chlorothiophen-2-yl)methyl]amino}-4-fluoro-1-(furan-3-carbonyl)-1H-pyrazol-3-yl)-6-fluoro-1-(pyridazin-4-ylmethyl)-1,2-dihydropyridin-2-one 3-(5-{[(5-chlorothiophen-2-yl)methyl]amino}-4-fluoro-1-(thiophene-3-carbonyl)-1H-pyrazol-3-yl)-4-(pyridin-3-yl)-1-(pyrimidin-2-ylmethyl)-1,2-dihydropyridin-2-one 3-(5-{[(5-chlorothiophen-2-yl)methyl]amino}-4-fluoro-1-[2-(trifluoromethyl)benzoyl]-1H-pyrazol-3-yl)-1-(1,2-oxazol-5-ylmethyl)-5-phenyl-1,2-dihydropyridin-2-one APPENDIX A-continued Table B 3-(5-{[(5-chlorothiophen-2-yl)methyl]amino}-4-fluoro-1-[4-(hydroxymethyl)benzoyl]-1H-pyrazol-3-yl)-6-(pyridin-4-yl)-1-(pyrimidin-4-ylmethyl)-1,2-dihydropyridin-2-one
3-(5-{[(5-chlorothiophen-2-yl)methyl]amino}-4-methoxy-1-(1,2-oxazole-3-carbonyl)-1H-pyrazol-3-yl)-4-fluoro-1-(morpholin-4-ylmethyl)-1,2-dihydropyridin-2-one
3-(5-{[(5-chlorothiophen-2-yl)methyl]amino}-4-methoxy-1-(1,3-thiazole-2-carbonyl)-1H-pyrazol-3-yl)-1-methyl-4-(pyridin-4-yl)-1,2-dihydropyridin-2-one
3-(5-{[(5-chlorothiophen-2-yl)methyl]amino}-4-methoxy-1-(1,3-thiazole-5-carbonyl)-1H-pyrazol-3-yl)-1-[(4-methylpiperazin-1-yl)methyl]-6-(pyridin-2-yl)-1,2-dihydropyridin-2-one
3-(5-{[(5-chlorothiophen-2-yl)methyl]amino}-4-methoxy-1-(2-methoxybenzoyl)-1H-pyrazol-3-yl)-4-ethenyl-1-(pyrazin-2-ylmethyl)-1,2-dihydropyridin-2-one
3-(5-{[(5-chlorothiophen-2-yl)methyl]amino}-4-methoxy-1-(3-methoxy-2,2-dimethylpropanoyl)-1H-pyrazol-3-yl)-5-(2-phenylethynyl)-1-(pyridazin-4-ylmethyl)-1,2-dihydropyridin-2-one
3-(5-{[(5-chlorothiophen-2-yl)methyl]amino}-4-methoxy-1-(3-methoxy-2,2-dimethylpropanoyl)-1H-pyrazol-3-yl)-5-(dimethylamino)-1-(1,2-oxazol-4-ylmethyl)-1,2-dihydropyridin-2-one
3-(5-{[(5-chlorothiophen-2-yl)methyl]amino}-4-methoxy-1-(thiophene-3-carbonyl)-1H-pyrazol-3-yl)-1-(furan-3-ylmethyl)-5-methoxy-1,2-dihydropyridin-2-one
3-(5-{[(5-chlorothiophen-2-yl)methyl]amino}-4-methoxy-3-[5-(methoxycarbonyl)-2-oxo-1-(pyridin-4-ylmethyl)-1,2-dihydropyridin-3-yl]-1H-pyrazole-1-carbonyl)benzoic acid
3-(5-{[(5-chlorothiophen-2-yl)methyl]amino}-4-methoxy-3-[6-oxo-5-(2-phenylethynyl)-1-(pyridin-4-ylmethyl)-1,6-dihydropyridin-2-yl]-1H-pyrazole-1-carbonyl)benzamide
3-(5-{[(5-chlorothiophen-2-yl)methyl]sulfanyl}-1-(2,2-dimethylpropanoyl)-1H-pyrazol-3-yl)-1-[2-(1,2-oxazol-4-yl)-2-oxoethyl]-6-phenyl-1,2-dihydropyridin-2-one
3-(5-{[(5-chlorothiophen-2-yl)methyl]sulfanyl}-1-(2,2-dimethylpropanoyl)-1H-pyrazol-3-yl)-1-[2-(1,3-oxazol-4-yl)-2-oxoethyl]-2-oxo-1,2-dihydropyridine-4-carbonitrile
3-(5-{[(5-chlorothiophen-2-yl)methyl]sulfanyl}-1-(2,2-dimethylpropanoyl)-1H-pyrazol-3-yl)-1-[2-(1,3-oxazol-5-yl)-2-oxoethyl]-4-(pyridin-3-yl)-1,2-dihydropyridin-2-one
3-(5-{[(5-chlorothiophen-2-yl)methyl]sulfanyl}-1-(2,2-dimethylpropanoyl)-1H-pyrazol-3-yl)-1-[2-(furan-2-yl)-2-oxoethyl]-4-hydroxy-1,2-dihydropyridin-2-one
3-(5-{[(5-chlorothiophen-2-yl)methyl]sulfanyl}-1-(2,2-dimethylpropanoyl)-1H-pyrazol-3-yl)-1-[2-oxo-2-(pyridazin-4-yl)ethyl]-6-(pyridin-3-yl)-1,2-dihydropyridin-2-one
3-(5-{[(5-chlorothiophen-2-yl)methyl]sulfanyl}-1-(2,2-dimethylpropanoyl)-1H-pyrazol-3-yl)-1-[2-oxo-2-(thiophen-2-yl)ethyl]-4-phenyl-1,2-dihydropyridin-2-one
3-(5-{[(5-chlorothiophen-2-yl)methyl]sulfanyl}-1-(2,2-dimethylpropanoyl)-1H-pyrazol-3-yl)-4-(dimethylamino)-1-[2-oxo-2-(piperidin-1-yl)ethyl]-1,2-dihydropyridin-2-one
3-(5-{[(5-chlorothiophen-2-yl)methyl]sulfanyl}-1-(2,2-dimethylpropanoyl)-1H-pyrazol-3-yl)-4-ethenyl-1-[2-(1,2-oxazol-3-yl)-2-oxoethyl]-1,2-dihydropyridin-2-one
3-(5-{[(5-chlorothiophen-2-yl)methyl]sulfanyl}-1-(2,2-dimethylpropanoyl)-1H-pyrazol-3-yl)-5-(dimethylamino)-1-[2-oxo-2-(thiophen-2-yl)ethyl]-1,2-dihydropyridin-2-one
3-(5-{[(5-chlorothiophen-2-yl)methyl]sulfanyl}-1-(2,2-dimethylpropanoyl)-1H-pyrazol-3-yl)-5-ethenyl-1-[2-oxo-2-(pyrazin-2-yl)ethyl]-1,2-dihydropyridin-2-one
3-(5-{[(5-chlorothiophen-2-yl)methyl]sulfanyl}-1-(2,2-dimethylpropanoyl)-1H-pyrazol-3-yl)-5-hydroxy-1-[2-(1,2-oxazol-3-yl)-2-oxoethyl]-1,2-dihydropyridin-2-one
3-(5-{[(5-chlorothiophen-2-yl)methyl]sulfanyl}-1-(2,2-dimethylpropanoyl)-1H-pyrazol-3-yl)-6-ethenyl-1-[2-oxo-2-(pyridin-2-yl)ethyl]-1,2-dihydropyridin-2-one
3-(5-{[(5-chlorothiophen-2-yl)methyl]sulfanyl}-1-(2,2-dimethylpropanoyl)-1H-pyrazol-3-yl)-6-hydroxy-1-[2-oxo-2-(pyrazin-2-yl)ethyl]-1,2-dihydropyridin-2-one
3-[1-(2-aminobenzoyl)-5-{[(5-chlorothiophen-2-yl)methyl]amino}-1H-pyrazol-3-yl]-1-[2-oxo-2-(pyridin-2-yl)ethyl]-6-(pyridin-3-yl)-1,2-dihydropyridin-2-one
3-[1-(2-aminobenzoyl)-5-{[(5-chlorothiophen-2-yl)methyl]amino}-1H-pyrazol-3-yl]-4-(dimethylamino)-1-[2-(1,2-oxazol-3-yl)-2-oxoethyl]-1,2-dihydropyridin-2-one
3-[1-(2-aminobenzoyl)-5-{[(5-chlorothiophen-2-yl)methyl]amino}-1H-pyrazol-3-yl]-4-bromo-1-(1,3-oxazol-4-ylmethyl)-1,2-dihydropyridin-2-one
3-[1-(2-aminobenzoyl)-5-{[(5-chlorothiophen-2-yl)methyl]amino}-1H-pyrazol-3-yl]-6-oxo-1-[2-oxo-2-(pyrimidin-4-yl)ethyl]-1,6-dihydropyridine-2-carbonitrile APPENDIX A-continued Table B 3-[1-(2-aminobenzoyl)-5-{[(5-chlorothiophen-2-yl)methyl]amino}-4-fluoro-1H-pyrazol-3-yl]-5-(morpholin-4-yl)-1-(pyrimidin-5-ylmethyl)-1,2-dihydropyridin-2-one
3-[1-(2-chlorobenzoyl)-5-{[(5-chlorothiophen-2-yl)methyl]amino}-1H-pyrazol-3-yl]-5-hydroxy-1-[2-(1,3-oxazol-5-yl)-2-oxoethyl]-1,2-dihydropyridin-2-one
3-[1-(2-chlorobenzoyl)-5-{[(5-chlorothiophen-2-yl)methyl]amino}-4-fluoro-1H-pyrazol-3-yl]-1-[(4-methylpiperazin-1-yl)methyl]-6-oxo-1,6-dihydropyridine-2-carbonitrile
3-[3-(1-benzoyl-5-{[(5-chlorothiophen-2-yl)methyl]amino}-1H-pyrazol-3-yl)-2-oxo-4-phenyl-1,2-dihydropyridin-1-yl]-2-oxopropanoic acid
3-[3-(5-{[(5-chlorothiophen-2-yl)methyl]amino}-1-(1,2-thiazole-4-carbonyl)-1H-pyrazol-3-yl)-2-oxo-5-(2-phenylethynyl)-1,2-dihydropyridin-1-yl]-2-oxopropanoic acid
3-[3-(5-{[(5-chlorothiophen-2-yl)methyl]amino}-1-(1,3-oxazole-5-carbonyl)-1H-pyrazol-3-yl)-2-oxo-6-(pyridin-3-yl)-1,2-dihydropyridin-1-yl]propanoic acid
3-[3-(5-{[(5-chlorothiophen-2-yl)methyl]amino}-1-(1,3-thiazole-2-carbonyl)-1H-pyrazol-3-yl)-6-fluoro-2-oxo-1,2-dihydropyridin-1-yl]-2-oxopropanoic acid
3-[3-(5-{[(5-chlorothiophen-2-yl)methyl]amino}-1-(2,2-dimethylpropanoyl)-1H-pyrazol-3-yl)-4-methoxy-2-oxo-1,2-dihydropyridin-1-yl]-2-oxopropanoic acid
3-[3-(5-{[(5-chlorothiophen-2-yl)methyl]amino}-1-[2-(trifluoromethyl)benzoyl]-1H-pyrazol-3-yl)-5-(dimethylamino)-2-oxo-1,2-dihydropyridin-1-yl]propanoic acid
3-[3-chloro-1-(1,2-oxazol-3-ylmethyl)-2-oxo-1,2-dihydropyridin-4-yl]-5-{[(5-chlorothiophen-2-yl)methyl]amino}-1-(thiophene-3-carbonyl)-1H-pyrazole-4-carbonitrile
3-[4-(5-{[(5-chlorothiophen-2-yl)methyl](methyl)amino}-1-(2,2-dimethylpropanoyl)-1H-pyrazol-3-yl)-2-oxo-1,2-dihydropyridin-1-yl]-2-oxopropanoic acid
3-[4-(5-{[(5-chlorothiophen-2-yl)methyl]amino}-1-(2,2-dimethylpropanoyl)-1H-pyrazol-3-yl)-2-oxo-5-(pyridin-2-yl)-1,2-dihydropyridin-1-yl]-2-oxopropanoic acid
3-[4-(5-{[(5-chlorothiophen-2-yl)methyl]amino}-1-(2,2-dimethylpropanoyl)-1H-pyrazol-3-yl)-6-ethenyl-2-oxo-1,2-dihydropyridin-1-yl]-2-oxopropanoic acid
3-[4-(5-{[(5-chlorothiophen-2-yl)methyl]amino}-1-(thiophene-2-carbonyl)-1H-pyrazol-3-yl)-2-oxo-3-phenyl-1,2-dihydropyridin-1-yl]-2-oxopropanoic acid
3-[4-(5-{[(5-chlorothiophen-2-yl)methyl]sulfanyl}-1-(2,2-dimethylpropanoyl)-1H-pyrazol-3-yl)-2-oxo-5-(pyridin-2-yl)-1,2-dihydropyridin-1-yl]-2-oxopropanoic acid
3-[4-bromo-1-(furan-3-ylmethyl)-2-oxo-1,2-dihydropyridin-3-yl]-5-{[(5-chlorothiophen-2-yl)methyl]amino}-1-(1,2-oxazole-5-carbonyl)-1H-pyrazole-4-carbonitrile
3-[4-chloro-2-oxo-1-(pyridin-4-ylmethyl)-1,2-dihydropyridin-3-yl]-5-{[(5-chlorothiophen-2-yl)methyl]amino}-1-(furan-3-carbonyl)-1H-pyrazole-4-carbonitrile
3-[5-(5-{[(5-chlorothiophen-2-yl)methyl](methyl)amino}-1-(2,2-dimethylpropanoyl)-1H-pyrazol-3-yl)-4-(dimethylamino)-2-oxo-1,2-dihydropyridin-1-yl]-2-oxopropanoic acid
3-[5-(5-{[(5-chlorothiophen-2-yl)methyl]amino}-1-(1,3-oxazole-2-carbonyl)-1H-pyrazol-3-yl)-3-cyano-2-oxo-1,2-dihydropyridin-1-yl]-2-oxopropanoic acid
3-[5-(5-{[(5-chlorothiophen-2-yl)methyl]amino}-1-(1,3-thiazole-4-carbonyl)-1H-pyrazol-3-yl)-4-(dimethylamino)-2-oxo-1,2-dihydropyridin-1-yl]-2-oxopropanoic acid
3-[5-(5-{[(5-chlorothiophen-2-yl)methyl]amino}-1-(2,2-dimethylpropanoyl)-1H-pyrazol-3-yl)-2-oxo-3-(pyridine-3-carbonyl)-1,2-dihydropyridin-1-yl]-2-oxopropanoic acid
3-[5-(5-{[(5-chlorothiophen-2-yl)methyl]amino}-1-(2,2-dimethylpropanoyl)-1H-pyrazol-3-yl)-4-(2-methoxy-2-oxoacetyl)-2-oxo-1,2-dihydropyridin-1-yl]-2-oxopropanoic acid
3-[5-(5-{[(5-chlorothiophen-2-yl)methyl]amino}-1-(2,2-dimethylpropanoyl)-1H-pyrazol-3-yl)-6-(morpholine-4-carbonyl)-2-oxo-1,2-dihydropyridin-1-yl]-2-oxopropanoic acid
3-[5-(5-{[(5-chlorothiophen-2-yl)methyl]amino}-1-(furan-3-carbonyl)-1H-pyrazol-3-yl)-2-oxo-6-(pyridin-4-yl)-1,2-dihydropyridin-1-yl]-2-oxopropanoic acid
3-[5-(5-{[(5-chlorothiophen-2-yl)methyl]amino}-1-(thiophene-3-carbonyl)-1H-pyrazol-3-yl)-3-hydroxy-2-oxo-1,2-dihydropyridin-1-yl]propanoic acid
3-[5-chloro-6-(5-{[(5-chlorothiophen-2-yl)methyl]amino}-1-(2,2-dimethylpropanoyl)-1H-pyrazol-3-yl)-2-oxo-1,2-dihydropyridin-1-yl]-2-oxopropanoic acid
3-[6-(5-{[(5-chlorothiophen-2-yl)methyl](methyl)amino}-1-(2,2-dimethylpropanoyl)-1H-pyrazol-3-yl)-2-oxo-3-phenyl-1,2-dihydropyridin-1-yl]-2-oxopropanoic acid
3-[6-(5-{[(5-chlorothiophen-2-yl)methyl]amino}-1-(1,2-oxazole-4-carbonyl)-1H-pyrazol-3-yl)-2-oxo-4-phenyl-1,2-dihydropyridin-1-yl]-2-oxopropanoic acid
3-[6-(5-{[(5-chlorothiophen-2-yl)methyl]amino}-1-(1,2-oxazole-4-carbonyl)-1H-pyrazol-3-yl)-3-(methoxycarbonyl)-2-oxo-1,2-dihydropyridin-1-yl]propanoic acid APPENDIX A-continued Table B 3-[6-(5-{[(5-chlorothiophen-2-yl)methyl]amino}-1-(1,2-thiazole-5-carbonyl)-1H-pyrazol-3-yl)-2-oxo-3-(pyridin-3-yl)-1,2-dihydropyridin-1-yl]-2-oxopropanoic acid
3-[6-(5-{[(5-chlorothiophen-2-yl)methyl]amino}-1-(3-hydroxy-2,2-dimethylpropanoyl)-1H-pyrazol-3-yl)-5-ethenyl-2-oxo-1,2-dihydropyridin-1-yl]-2-oxopropanoic acid
3-[6-(5-{[(5-chlorothiophen-2-yl)methyl]amino}-1-(furan-3-carbonyl)-1H-pyrazol-3-yl)-4-(morpholin-4-yl)-2-oxo-1,2-dihydropyridin-1-yl]propanoic acid
3-[6-chloro-2-oxo-1-(1,2-thiazol-4-ylmethyl)-1,2-dihydropyridin-3-yl]-5-{[(5-chlorothiophen-2-yl)methyl]amino}-1-(1,3-oxazole-5-carbonyl)-1H-pyrazole-4-carbonitrile
3-benzoyl-4-(5-{[(5-chlorothiophen-2-yl)methyl]amino}-1-(2,2-dimethylpropanoyl)-1H-pyrazol-3-yl)-1-[2-(1,3-oxazol-5-yl)-2-oxoethyl]-1,2-dihydropyridin-2-one
3-benzoyl-5-(5-{[(5-chlorothiophen-2-yl)methyl]amino}-1-(2,2-dimethylpropanoyl)-1H-pyrazol-3-yl)-1-[2-oxo-2-(1,3-thiazol-5-yl)ethyl]-1,2-dihydropyridin-2-one
3-benzoyl-6-(5-{[(5-chlorothiophen-2-yl)methyl]amino}-1-(2,2-dimethylpropanoyl)-1H-pyrazol-3-yl)-1-[2-oxo-2-(1,2-thiazol-4-yl)ethyl]-1,2-dihydropyridin-2-one
3-bromo-4-(5-{[(5-chlorothiophen-2-yl)methyl]amino}-1-(1,2-thiazole-4-carbonyl)-1H-pyrazol-3-yl)-1-[2-(1,2-oxazol-5-yl)-2-oxoethyl]-1,2-dihydropyridin-2-one
3-bromo-4-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-1,2-dihydropyridin-2-one
3-bromo-4-(5-{[(5-chlorothiophen-2-yl)methyl]amino}-1-(3-methoxy-2,2-dimethylpropanoyl)-1H-pyrazol-3-yl)-1-[2-(furan-3-yl)ethyl]-1,2-dihydropyridin-2-one
3-bromo-4-(5-{[(5-chlorothiophen-2-yl)methyl]amino}-1-[3-(hydroxymethyl)benzoyl]-1H-pyrazol-3-yl)-1-(pyridin-4-ylmethyl)-1,2-dihydropyridin-2-one
3-bromo-4-(5-{[(5-chlorothiophen-2-yl)methyl]amino}-1-[4-(hydroxymethyl)benzoyl]-1H-pyrazol-3-yl)-1-[2-oxo-2-(piperidin-1-yl)ethyl]-1,2-dihydropyridin-2-one
3-bromo-4-(5-{[(5-chlorothiophen-2-yl)methyl]amino}-4-methoxy-1-(2-methoxybenzoyl)-1H-pyrazol-3-yl)-1-(1,3-oxazol-4-ylmethyl)-1,2-dihydropyridin-2-one
3-bromo-4-(5-{[(5-chlorothiophen-2-yl)methyl]sulfanyl}-1-(2,2-dimethylpropanoyl)-1H-pyrazol-3-yl)-1-[2-oxo-2-(pyridazin-4-yl)ethyl]-1,2-dihydropyridin-2-one
3-bromo-5-(5-{[(5-chlorothiophen-2-yl)methyl]amino}-1-(1,2-oxazole-3-carbonyl)-1H-pyrazol-3-yl)-1-[2-oxo-2-(1,3-thiazol-4-yl)ethyl]-1,2-dihydropyridin-2-one
3-bromo-5-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-1,2-dihydropyridin-2-one
3-bromo-5-(5-{[(5-chlorothiophen-2-yl)methyl]amino}-1-(furan-3-carbonyl)-4-methoxy-1H-pyrazol-3-yl)-1-(thiophen-3-ylmethyl)-1,2-dihydropyridin-2-one
3-bromo-5-(5-{[(5-chlorothiophen-2-yl)methyl]amino}-1-[3-(hydroxymethyl)benzoyl]-1H-pyrazol-3-yl)-1-[2-oxo-2-(pyridazin-4-yl)ethyl]-1,2-dihydropyridin-2-one
3-bromo-5-(5-{[(5-chlorothiophen-2-yl)methyl]sulfanyl}-1-(2,2-dimethylpropanoyl)-1H-pyrazol-3-yl)-1-[2-(morpholin-4-yl)-2-oxoethyl]-1,2-dihydropyridin-2-one
3-bromo-6-(5-{[(5-chlorothiophen-2-yl)methyl]amino}-1-(1,3-oxazole-5-carbonyl)-1H-pyrazol-3-yl)-1-[2-oxo-2-(pyridin-3-yl)ethyl]-1,2-dihydropyridin-2-one
3-bromo-6-(5-{[(5-chlorothiophen-2-yl)methyl]amino}-1-(2,2-dimethylpropanoyl)-1H-pyrazol-3-yl)-1-[2-(1,3-oxazol-5-yl)-2-oxoethyl]-1,2-dihydropyridin-2-one
3-bromo-6-(5-{[(5-chlorothiophen-2-yl)methyl]amino}-1-(2-methoxybenzoyl)-1H-pyrazol-3-yl)-1-[2-(morpholin-4-yl)-2-oxoethyl]-1,2-dihydropyridin-2-one
3-bromo-6-(5-{[(5-chlorothiophen-2-yl)methyl]amino}-4-fluoro-1-(1,3-oxazole-4-carbonyl)-1H-pyrazol-3-yl)-1-(pyrimidin-5-ylmethyl)-1,2-dihydropyridin-2-one
3-bromo-6-(5-{[(5-chlorothiophen-2-yl)methyl]sulfanyl}-1-(2,2-dimethylpropanoyl)-1H-pyrazol-3-yl)-1-[2-(1,3-oxazol-5-yl)-2-oxoethyl]-1,2-dihydropyridin-2-one
3-chloro-4-(5-{[(5-chlorothiophen-2-yl)methyl](methyl)amino}-1-(2,2-dimethylpropanoyl)-1H-pyrazol-3-yl)-1-[2-oxo-2-(1,3-thiazol-4-yl)ethyl]-1,2-dihydropyridin-2-one
3-chloro-4-(5-{[(5-chlorothiophen-2-yl)methyl]amino}-1-(1,2-oxazole-3-carbonyl)-1H-pyrazol-3-yl)-1-(pyrimidin-4-ylmethyl)-1,2-dihydropyridin-2-one
3-chloro-4-(5-{[(5-chlorothiophen-2-yl)methyl]amino}-1-(2,2-dimethylpropanoyl)-1H-pyrazol-3-yl)-1-[2-oxo-2-(pyridin-4-yl)ethyl]-1,2-dihydropyridin-2-one APPENDIX A-continued Table B 3-chloro-4-(5-{[(5-chlorothiophen-2-yl)methyl]amino}-1-(3-hydroxy-2,2-dimethylpropanoyl)-1H-pyrazol-3-yl)-1-[2-oxo-2-(pyridin-4-yl)ethyl]-1,2-dihydropyridin-2-one
3-chloro-4-(5-{[(5-chlorothiophen-2-yl)methyl]amino}-1-(furan-2-carbonyl)-1H-pyrazol-3-yl)-1-[2-(1,3-oxazol-4-yl)-2-oxoethyl]-1,2-dihydropyridin-2-one
3-chloro-5-(5-{[(5-chlorothiophen-2-yl)methyl](methyl)amino}-1-(2,2-dimethylpropanoyl)-1H-pyrazol-3-yl)-1-[2-oxo-2-(pyridin-3-yl)ethyl]-1,2-dihydropyridin-2-one
3-chloro-5-(5-{[(5-chlorothiophen-2-yl)methyl]amino}-1-(1,2-oxazole-5-carbonyl)-1H-pyrazol-3-yl)-1-[2-(1,3-oxazol-2-yl)-2-oxoethyl]-1,2-dihydropyridin-2-one
3-chloro-5-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-1,2-dihydropyridin-2-one
3-chloro-5-(5-{[(5-chlorothiophen-2-yl)methyl]amino}-4-methoxy-1-(thiophene-3-carbonyl)-1H-pyrazol-3-yl)-1-(1,3-thiazol-2-ylmethyl)-1,2-dihydropyridin-2-one
3-chloro-6-(5-{[(5-chlorothiophen-2-yl)methyl](methyl)amino}-1-(2,2-dimethylpropanoyl)-1H-pyrazol-3-yl)-1-[2-(4-methylpiperazin-1-yl)-2-oxoethyl]-1,2-dihydropyridin-2-one
3-chloro-6-(5-{[(5-chlorothiophen-2-yl)methyl]amino}-1-(1,2-oxazole-4-carbonyl)-1H-pyrazol-3-yl)-1-[2-(furan-2-yl)ethyl]-1,2-dihydropyridin-2-one
3-chloro-6-(5-{[(5-chlorothiophen-2-yl)methyl]amino}-1-(1,3-oxazole-4-carbonyl)-1H-pyrazol-3-yl)-1-[2-oxo-2-(1,2-thiazol-4-yl)ethyl]-1,2-dihydropyridin-2-one
3-chloro-6-(5-{[(5-chlorothiophen-2-yl)methyl]amino}-1-(2,2-dimethylpropanoyl)-1H-pyrazol-3-yl)-1-[2-oxo-2-(1,2-thiazol-3-yl)ethyl]-1,2-dihydropyridin-2-one
3-chloro-6-(5-{[(5-chlorothiophen-2-yl)methyl]amino}-1-(2-fluorobenzoyl)-1H-pyrazol-3-yl)-1-[2-oxo-2-(pyrimidin-5-yl)ethyl]-1,2-dihydropyridin-2-one
3-chloro-6-(5-{[(5-chlorothiophen-2-yl)methyl]amino}-4-fluoro-1-(1,2-thiazole-4-carbonyl)-1H-pyrazol-3-yl)-1-(1,2-oxazol-5-ylmethyl)-1,2-dihydropyridin-2-one
3-{3-[1-(2-carboxy-2-oxoethyl)-6-cyano-2-oxo-1,2-dihydropyridin-4-yl]-5-{[(5-chlorothiophen-2-yl)methyl]amino}-1H-pyrazole-1-carbonyl}benzoic acid
3-{3-[4-bromo-6-oxo-1-(1,3-thiazol-5-ylmethyl)-1,6-dihydropyridin-3-yl]-5-{[(5-chlorothiophen-2-yl)methyl]amino}-4-cyano-1H-pyrazole-1-carbonyl}benzoic acid
3-{3-[4-bromo-6-oxo-1-(pyridin-4-ylmethyl)-1,6-dihydropyridin-2-yl]-5-{[(5-chlorothiophen-2-yl)methyl]amino}-4-methoxy-1H-pyrazole-1-carbonyl}benzoic acid
3-{3-[5-bromo-6-oxo-1-(1,2-thiazol-3-ylmethyl)-1,6-dihydropyridin-3-yl]-5-{[(5-chlorothiophen-2-yl)methyl]amino}-1H-pyrazole-1-carbonyl}benzoic acid
4-(1-benzoyl-5-{[(5-chlorothiophen-2-yl)methyl]amino}-1H-pyrazol-3-yl)-1-(2-oxo-2-phenylethyl)-6-(pyridin-3-yl)-1,2-dihydropyridin-2-one
4-(1-benzoyl-5-{[(5-chlorothiophen-2-yl)methyl]amino}-1H-pyrazol-3-yl)-3-(dimethylamino)-1-[2-oxo-2-(pyrimidin-4-yl)ethyl]-1,2-dihydropyridin-2-one
4-(1-benzoyl-5-{[(5-chlorothiophen-2-yl)methyl]amino}-1H-pyrazol-3-yl)-6-hydroxy-1-[2-(pyridin-2-yl)ethyl]-1,2-dihydropyridin-2-one
4-(1-benzoyl-5-{[(5-chlorothiophen-2-yl)methyl]amino}-1H-pyrazol-3-yl)-6-oxo-1-[2-oxo-2-(1,3-thiazol-2-yl)ethyl]-1,6-dihydropyridine-3-carbonitrile
4-(3-{2-bromo-1-[2-(1,3-oxazol-5-yl)ethyl]-6-oxo-1,6-dihydropyridin-3-yl}-5-{[(5-chlorothiophen-2-yl)methyl]amino}-1H-pyrazole-1-carbonyl)benzoic acid
4-(3-{3-bromo-6-oxo-1-[2-(1,2-thiazol-5-yl)ethyl]-1,6-dihydropyridin-2-yl}-5-{[(5-chlorothiophen-2-yl)methyl]amino}-1H-pyrazole-1-carbonyl)benzoic acid
4-(3-{5-chloro-6-oxo-1-[2-(1,2-thiazol-3-yl)ethyl]-1,6-dihydropyridin-3-yl}-5-{[(5-chlorothiophen-2-yl)methyl]amino}-1H-pyrazole-1-carbonyl)benzoic acid
4-(3-{5-chloro-6-oxo-1-[2-oxo-2-(thiophen-3-yl)ethyl]-1,6-dihydropyridin-3-yl}-5-{[(5-chlorothiophen-2-yl)methyl]amino}-1H-pyrazole-1-carbonyl)benzamide
4-(3-{6-chloro-1-[2-(1,3-oxazol-2-yl)-2-oxoethyl]-2-oxo-1,2-dihydropyridin-4-yl}-5-{[(5-chlorothiophen-2-yl)methyl]amino}-1H-pyrazole-1-carbonyl)benzamide
4-(5-{[(5-chlorothiophen-2-yl)methyl](methyl)amino}-1-(2,2-dimethylpropanoyl)-1H-pyrazol-3-yl)-1-[2-(1,2-oxazol-3-yl)-2-oxoethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-1-[2-(1,2-oxazol-4-yl)-2-oxoethyl]-5-(pyridin-3-yl)-1,2-dihydropyridin-2-one
4-(5-{[(5-chlorothiophen-2-yl)methyl](methyl)amino}-1-(2,2-dimethylpropanoyl)-1H-pyrazol-3-yl)-1-[2-(1,2-oxazol-5-yl)-2-oxoethyl]-3-(pyridin-3-yl)-1,2-dihydropyridin-2-one
4-(5-{[(5-chlorothiophen-2-yl)methyl](methyl)amino}-1-(2,2-dimethylpropanoyl)-1H-pyrazol-3-yl)-1-[2-(1,2-oxazol-5-yl)-2-oxoethyl]-6-oxo-1,6-dihydropyridine-2-carbonitrile
4-(5-{[(5-chlorothiophen-2-yl)methyl](methyl)amino}-1-(2,2-dimethylpropanoyl)-1H-pyrazol-3-yl)-1-[2-oxo-2-(1,2-thiazol-3-yl)ethyl]-1,2-dihydropyridin-2-one APPENDIX A-continued Table B 4-(5-{[(5-chlorothiophen-2-yl)methyl](methyl)amino}-1-(2,2-dimethylpropanoyl)-1H-pyrazol-3-yl)-1-[2-oxo-2-(pyridin-2-yl)ethyl]-5-phenyl-1,2-dihydropyridin-2-one
4-(5-{[(5-chlorothiophen-2-yl)methyl](methyl)amino}-1-(2,2-dimethylpropanoyl)-1H-pyrazol-3-yl)-1-[2-oxo-2-(pyridin-4-yl)ethyl]-6-phenyl-1,2-dihydropyridin-2-one
4-(5-{[(5-chlorothiophen-2-yl)methyl](methyl)amino}-1-(2,2-dimethylpropanoyl)-1H-pyrazol-3-yl)-1-[2-oxo-2-(pyrimidin-4-yl)ethyl]-6-(pyridin-3-yl)-1,2-dihydropyridin-2-one
4-(5-{[(5-chlorothiophen-2-yl)methyl](methyl)amino}-1-(2,2-dimethylpropanoyl)-1H-pyrazol-3-yl)-1-[2-oxo-2-(pyrimidin-5-yl)ethyl]-3-phenyl-1,2-dihydropyridin-2-one
4-(5-{[(5-chlorothiophen-2-yl)methyl](methyl)amino}-1-(2,2-dimethylpropanoyl)-1H-pyrazol-3-yl)-2-oxo-1-[2-oxo-2-(pyrimidin-2-yl)ethyl]-1,2-dihydropyridine-3-carbonitrile
4-(5-{[(5-chlorothiophen-2-yl)methyl](methyl)amino}-1-(2,2-dimethylpropanoyl)-1H-pyrazol-3-yl)-3-(dimethylamino)-1-[2-oxo-2-(1,2-thiazol-3-yl)ethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-3-ethenyl-1-[2-(morpholin-4-yl)-2-oxoethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-3-hydroxy-1-[2-(1,3-oxazol-2-yl)-2-oxoethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-5-(dimethylamino)-1-[2-oxo-2-(pyrazin-2-yl)ethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-5-hydroxy-1-[2-(1,3-oxazol-5-yl)-2-oxoethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-6-(dimethylamino)-1-[2-oxo-2-(pyrimidin-5-yl)ethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-6-ethenyl-1-[2-(furan-3-yl)-2-oxoethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-6-hydroxy-1-[2-(morpholin-4-yl)-2-oxoethyl]-1,2-dihydropyridin-2-one
4-(5-{[(5-chlorothiophen-2-yl)methyl](methyl)amino}-1-(2,2-dimethylpropanoyl)-1H-pyrazol-3-yl)-6-oxo-1-(2-oxoethyl)-1,6-dihydropyridine-3-carbonitrile
4-(5-{[(5-chlorothiophen-2-yl)methyl]amino}-1-(1,2-oxazole-3-carbonyl)-1H-pyrazol-3-yl)-1-[2-(1,2-oxazol-5-yl)-2-oxoethyl]-5-(2-phenylethynyl)-1,2-dihydropyridin-2-one
4-(5-{[(5-chlorothiophen-2-yl)methyl]amino}-1-(1,2-oxazole-3-carbonyl)-1H-pyrazol-3-yl)-6-methoxy-1-(1,2-thiazol-5-ylmethyl)-1,2-dihydropyridin-2-one
4-(5-{[(5-chlorothiophen-2-yl)methyl]amino}-1-(1,2-oxazole-4-carbonyl)-1H-pyrazol-3-yl)-1-[2-(furan-3-yl)ethyl]-6-(pyridin-2-yl)-1,2-dihydropyridin-2-one
4-(5-{[(5-chlorothiophen-2-yl)methyl]amino}-1-(1,2-oxazole-4-carbonyl)-1H-pyrazol-3-yl)-1-[2-oxo-2-(pyridin-2-yl)ethyl]-3-phenyl-1,2-dihydropyridin-2-one
4-(5-{[(5-chlorothiophen-2-yl)methyl]amino}-1-(1,2-oxazole-4-carbonyl)-1H-pyrazol-3-yl)-1-[2-oxo-2-(pyridin-4-yl)ethyl]-5-(pyridin-4-yl)-1,2-dihydropyridin-2-one
4-(5-{[(5-chlorothiophen-2-yl)methyl]amino}-1-(1,2-oxazole-4-carbonyl)-1H-pyrazol-3-yl)-5-(pyridin-2-yl)-1-(1,2-thiazol-5-ylmethyl)-1,2-dihydropyridin-2-one
4-(5-{[(5-chlorothiophen-2-yl)methyl]amino}-1-(1,2-oxazole-4-carbonyl)-1H-pyrazol-3-yl)-6-(dimethylamino)-1-[2-oxo-2-(thiophen-3-yl)ethyl]-1,2-dihydropyridin-2-one
4-(5-{[(5-chlorothiophen-2-yl)methyl]amino}-1-(1,2-oxazole-5-carbonyl)-1H-pyrazol-3-yl)-5-ethenyl-1-[2-(furan-3-yl)-2-oxoethyl]-1,2-dihydropyridin-2-one
4-(5-{[(5-chlorothiophen-2-yl)methyl]amino}-1-(1,2-thiazole-3-carbonyl)-1H-pyrazol-3-yl)-1-[2-(1,2-oxazol-5-yl)ethyl]-6-(pyridin-4-yl)-1,2-dihydropyridin-2-one
4-(5-{[(5-chlorothiophen-2-yl)methyl]amino}-1-(1,2-thiazole-3-carbonyl)-1H-pyrazol-3-yl)-1-[2-(furan-3-yl)-2-oxoethyl]-6-(morpholin-4-yl)-1,2-dihydropyridin-2-one
4-(5-{[(5-chlorothiophen-2-yl)methyl]amino}-1-(1,2-thiazole-3-carbonyl)-1H-pyrazol-3-yl)-3-hydroxy-1-[2-(morpholin-4-yl)-2-oxoethyl]-1,2-dihydropyridin-2-one
4-(5-{[(5-chlorothiophen-2-yl)methyl]amino}-1-(1,2-thiazole-4-carbonyl)-1H-pyrazol-3-yl)-3-(morpholin-4-yl)-1-[2-(pyridin-2-yl)ethyl]-1,2-dihydropyridin-2-one
4-(5-{[(5-chlorothiophen-2-yl)methyl]amino}-1-(1,2-thiazole-4-carbonyl)-1H-pyrazol-3-yl)-5-fluoro-1-[2-(1,2-oxazol-4-yl)-2-oxoethyl]-1,2-dihydropyridin-2-one APPENDIX A-continued Table B 4-(5-{[(5-chlorothiophen-2-yl)methyl]amino}-1-(1,2-thiazole-4-carbonyl)-1H-pyrazol-3-yl)-6-methoxy-1-[2-oxo-2-(pyrimidin-4-yl)ethyl]-1,2-dihydropyridin-2-one
4-(5-{[(5-chlorothiophen-2-yl)methyl]amino}-1-(1,2-thiazole-5-carbonyl)-1H-pyrazol-3-yl)-1-[2-(1,2-oxazol-4-yl)ethyl]-6-oxo-1,6-dihydropyridine-2-carbonitrile
4-(5-{[(5-chlorothiophen-2-yl)methyl]amino}-1-(1,2-thiazole-5-carbonyl)-1H-pyrazol-3-yl)-1-[2-oxo-2-(pyridin-2-yl)ethyl]-5-(pyridin-3-yl)-1,2-dihydropyridin-2-one
4-(5-{[(5-chlorothiophen-2-yl)methyl]amino}-1-(1,2-thiazole-5-carbonyl)-1H-pyrazol-3-yl)-1-[2-oxo-2-(pyridin-2-yl)ethyl]-6-phenyl-1,2-dihydropyridin-2-one
4-(5-{[(5-chlorothiophen-2-yl)methyl]amino}-1-(1,2-thiazole-5-carbonyl)-1H-pyrazol-3-yl)-2-oxo-1-[2-oxo-2-(pyrimidin-5-yl)ethyl]-1,2-dihydropyridine-3-carbonitrile
4-(5-{[(5-chlorothiophen-2-yl)methyl]amino}-1-(1,2-thiazole-5-carbonyl)-1H-pyrazol-3-yl)-5-(2-phenylethynyl)-1-(pyridin-4-ylmethyl)-1,2-dihydropyridin-2-one
4-(5-{[(5-chlorothiophen-2-yl)methyl]amino}-1-(1,3-oxazole-2-carbonyl)-1H-pyrazol-3-yl)-1-[2-oxo-2-(pyrazin-2-yl)ethyl]-3-(pyridin-4-yl)-1,2-dihydropyridin-2-one
4-(5-{[(5-chlorothiophen-2-yl)methyl]amino}-1-(1,3-oxazole-2-carbonyl)-1H-pyrazol-3-yl)-5-(dimethylamino)-1-[2-oxo-2-(pyrimidin-5-yl)ethyl]-1,2-dihydropyridin-2-one
4-(5-{[(5-chlorothiophen-2-yl)methyl]amino}-1-(1,3-oxazole-2-carbonyl)-1H-pyrazol-3-yl)-6-oxo-1-[2-oxo-2-(pyridin-2-yl)ethyl]-1,6-dihydropyridine-2-carbonitrile
4-(5-{[(5-chlorothiophen-2-yl)methyl]amino}-1-(1,3-oxazole-4-carbonyl)-1H-pyrazol-3-yl)-3-ethenyl-1-[2-(1,3-oxazol-5-yl)-2-oxoethyl]-1,2-dihydropyridin-2-one
4-(5-{[(5-chlorothiophen-2-yl)methyl]amino}-1-(1,3-oxazole-5-carbonyl)-1H-pyrazol-3-yl)-1-(furan-3-ylmethyl)-2-oxo-1,2-dihydropyridine-3-carbonitrile
4-(5-{[(5-chlorothiophen-2-yl)methyl]amino}-1-(1,3-oxazole-5-carbonyl)-1H-pyrazol-3-yl)-1-[2-oxo-2-(thiophen-2-yl)ethyl]-3-(2-phenylethynyl)-1,2-dihydropyridin-2-one
4-(5-{[(5-chlorothiophen-2-yl)methyl]amino}-1-(1,3-thiazole-2-carbonyl)-1H-pyrazol-3-yl)-1-[2-(1,2-oxazol-5-yl)-2-oxoethyl]-6-(pyridin-2-yl)-1,2-dihydropyridin-2-one
4-(5-{[(5-chlorothiophen-2-yl)methyl]amino}-1-(1,3-thiazole-2-carbonyl)-1H-pyrazol-3-yl)-3-fluoro-1-[2-oxo-2-(pyrimidin-2-yl)ethyl]-1,2-dihydropyridin-2-one
4-(5-{[(5-chlorothiophen-2-yl)methyl]amino}-1-(1,3-thiazole-4-carbonyl)-1H-pyrazol-3-yl)-1-[2-oxo-2-(1,2-thiazol-3-yl)ethyl]-3-(pyridin-3-yl)-1,2-dihydropyridin-2-one
4-(5-{[(5-chlorothiophen-2-yl)methyl]amino}-1-(1,3-thiazole-4-carbonyl)-1H-pyrazol-3-yl)-1-[2-oxo-2-(pyrazin-2-yl)ethyl]-5-phenyl-1,2-dihydropyridin-2-one
4-(5-{[(5-chlorothiophen-2-yl)methyl]amino}-1-(1,3-thiazole-4-carbonyl)-1H-pyrazol-3-yl)-1-[2-oxo-2-(pyrimidin-5-yl)ethyl]-6-(pyridin-4-yl)-1,2-dihydropyridin-2-one
4-(5-{[(5-chlorothiophen-2-yl)methyl]amino}-1-(1,3-thiazole-4-carbonyl)-1H-pyrazol-3-yl)-3-(dimethylamino)-1-[(4-methylpiperazin-1-yl)methyl]-1,2-dihydropyridin-2-one
4-(5-{[(5-chlorothiophen-2-yl)methyl]amino}-1-(1,3-thiazole-4-carbonyl)-1H-pyrazol-3-yl)-3-(pyridin-2-yl)-1-(pyridin-2-ylmethyl)-1,2-dihydropyridin-2-one
4-(5-{[(5-chlorothiophen-2-yl)methyl]amino}-1-(1,3-thiazole-5-carbonyl)-1H-pyrazol-3-yl)-1-(pyridazin-4-ylmethyl)-5-(pyridin-3-yl)-1,2-dihydropyridin-2-one
4-(5-{[(5-chlorothiophen-2-yl)methyl]amino}-1-(1,3-thiazole-5-carbonyl)-1H-pyrazol-3-yl)-5-(morpholin-4-yl)-1-[2-(1,3-oxazol-5-yl)-2-oxoethyl]-1,2-dihydropyridin-2-one
4-(5-{[(5-chlorothiophen-2-yl)methyl]amino}-1-(1,3-thiazole-5-carbonyl)-1H-pyrazol-3-yl)-6-ethenyl-1-(furan-2-ylmethyl)-1,2-dihydropyridin-2-one
4-(5-{[(5-chlorothiophen-2-yl)methyl]amino}-1-(1,3-thiazole-5-carbonyl)-1H-pyrazol-3-yl)-6-ethenyl-1-[2-(morpholin-4-yl)-2-oxoethyl]-1,2-dihydropyridin-2-one
4-(5-{[(5-chlorothiophen-2-yl)methyl]amino}-1-(2,2-dimethylpropanoyl)-1H-pyrazol-3-yl)-1-[2-(1,2-oxazol-3-yl)-2-oxoethyl]-6-(pyridin-2-yl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(1,2-oxazol-3-yl)-2-oxoethyl]-6-oxo-1,6-dihydropyridine-3-carboxylic acid
4-(5-{[(5-chlorothiophen-2-yl)methyl]amino}-1-(2,2-dimethylpropanoyl)-1H-pyrazol-3-yl)-1-[2-(1,2-oxazol-4-yl)-2-oxoethyl]-3-phenyl-1,2-dihydropyridin-2-one
4-(5-{[(5-chlorothiophen-2-yl)methyl]amino}-1-(2,2-dimethylpropanoyl)-1H-pyrazol-3-yl)-1-[2-(1,2-oxazol-4-yl)ethyl]-5-(pyridin-3-yl)-1,2-dihydropyridin-2-one APPENDIX A-continued Table B 4-(5-{[(5-chlorothiophen-2-yl)methyl]amino}-1-(2,2-dimethylpropanoyl)-1H-pyrazol-3-yl)-1-[2-(1,2-oxazol-5-yl)-2-oxoethyl]-6-(pyridine-2-carbonyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-3-(3-phenylprop-2-ynoyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-6-(pyridin-3-yl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(1,3-oxazol-4-yl)-2-oxoethyl]-5-(pyridin-3-yl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(1,3-oxazol-5-yl)-2-oxoethyl]-5-(3-phenylprop-2-ynoyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-1,2-dihydropyridin-2-one
4-(5-{[(5-chlorothiophen-2-yl)methyl]amino}-1-(2,2-dimethylpropanoyl)-1H-pyrazol-3-yl)-1-[2-(furan-2-yl)-2-oxoethyl]-3-(pyridin-2-yl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(furan-2-yl)-2-oxoethyl]-6-(morpholin-4-yl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(furan-3-yl)-2-oxoethyl]-1,2-dihydropyridin-2-one
4-(5-{[(5-chlorothiophen-2-yl)methyl]amino}-1-(2,2-dimethylpropanoyl)-1H-pyrazol-3-yl)-1-[2-(furan-3-yl)-2-oxoethyl]-6-(pyridine-4-carbonyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-3-(pyridine-4-carbonyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-6-(3-phenylprop-2-ynoyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(1,3-thiazol-4-yl)ethyl]-5-(pyridin-4-yl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(1,3-thiazol-4-yl)ethyl]-6-phenyl-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(1,3-thiazol-5-yl)ethyl]-3-(pyridin-3-yl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(piperidin-1-yl)ethyl]-3-(pyridin-4-yl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(piperidin-1-yl)ethyl]-5-phenyl-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(piperidin-1-yl)ethyl]-6-(2-phenylethynyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-3-(pyridine-3-carbonyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-3-phenyl-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-5-(2-phenylethynyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(pyridin-2-yl)ethyl]-6-(pyridine-3-carbonyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(pyridin-3-yl)ethyl]-3-(2-phenylethynyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(pyrimidin-2-yl)ethyl]-3-(pyridine-2-carbonyl)-1,2-dihydropyridin-2-one
4-(5-{[(5-chlorothiophen-2-yl)methyl]amino}-1-(2,2-dimethylpropanoyl)-1H-pyrazol-3-yl)-1-[2-oxo-2-(pyrimidin-2-yl)ethyl]-5-(prop-2-enoyl)-1,2-dihydropyridin-2-one APPENDIX A-continued Table B 4-(5-{[(5-chlorothiophen-2-yl)methyl]amino}-1-(2,2-dimethylpropanoyl)-1H-pyrazol-3-yl)-1-[2-oxo-2-(pyrimidin-4-yl)ethyl]-5-(pyridin-4-yl)-1,2-dihydropyridin-2-one 4-(5-{[(5-chlorothiophen-2-yl)methyl]amino}-1-(2,2-dimethylpropanoyl)-1H-pyrazol-3-yl)-1-[2-oxo-2-(pyrimidin-5-yl)ethyl]-5-(pyridine-3-carbonyl)-1,2-dihydropyridin-2-one 4-(5-{[(5-chlorothiophen-2-yl)methyl]amino}-1-(2,2-dimethylpropanoyl)-1H-pyrazol-3-yl)-1-[2-oxo-2-(thiophen-2-yl)ethyl]-3-(prop-2-enoyl)-1,2-dihydropyridin-2-one 4-(5-{[(5-chlorothiophen-2-yl)methyl]amino}-1-(2,2-dimethylpropanoyl)-1H-pyrazol-3-yl)-1-[2-oxo-2-(thiophen-2-yl)ethyl]-6-(pyridin-4-yl)-1,2-dihydropyridin-2-one 4-(5-{[(5-chlorothiophen-2-yl)methyl]amino}-1-(2,2-dimethylpropanoyl)-1H-pyrazol-3-yl)-2-oxo-1-[2-oxo-2-(1,2-thiazol-5-yl)ethyl]-1,2-dihydropyridine-3-carbonitrile 4-(5-{[(5-chlorothiophen-2-yl)methyl]amino}-1-(2,2-dimethylpropanoyl)-1H-pyrazol-3-yl)-3-(dimethylamino)-1-[2-(4-methylpiperazin-1-yl)-2-oxoethyl]-1,2-dihydropyridin-2-one 4-(5-{[(5-chlorothiophen-2-yl)methyl]amino}-1-(2,2-dimethylpropanoyl)-1H-pyrazol-3-yl)-3-(morpholin-4-yl)-1-[2-oxo-2-(1,3-thiazol-2-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-3-(morpholine-4-carbonyl)-1-[2-(1,2-oxazol-3-yl)-2-oxoethyl]-1,2-dihydropyridin-2-one 4-(5-{[(5-chlorothiophen-2-yl)methyl]amino}-1-(2,2-dimethylpropanoyl)-1H-pyrazol-3-yl)-3-ethenyl-1-(2-oxo-2-phenylethyl)-1,2-dihydropyridin-2-one 4-(5-{[(5-chlorothiophen-2-yl)methyl]amino}-1-(2,2-dimethylpropanoyl)-1H-pyrazol-3-yl)-3-fluoro-1-[2-(1,2-oxazol-4-yl)-2-oxoethyl]-1,2-dihydropyridin-2-one 4-(5-{[(5-chlorothiophen-2-yl)methyl]amino}-1-(2,2-dimethylpropanoyl)-1H-pyrazol-3-yl)-3-hydroxy-1-[2-oxo-2-(pyrimidin-4-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-3-methoxy-1-[2-oxo-2-(thiophen-3-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-5-(dimethylamino)-1-[2-oxo-2-(pyridin-3-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-5-(morpholin-4-yl)-1-(2-oxo-2-phenylethyl)-1,2-dihydropyridin-2-one 4-(5-{[(5-chlorothiophen-2-yl)methyl]amino}-1-(2,2-dimethylpropanoyl)-1H-pyrazol-3-yl)-5-(morpholine-4-carbonyl)-1-[2-oxo-2-(1,2-thiazol-3-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-5-ethenyl-1-[2-(furan-2-yl)-2-oxoethyl]-1,2-dihydropyridin-2-one 4-(5-{[(5-chlorothiophen-2-yl)methyl]amino}-1-(2,2-dimethylpropanoyl)-1H-pyrazol-3-yl)-5-fluoro-1-[2-(pyridazin-4-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-5-fluoro-1-[2-oxo-2-(pyrimidin-4-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-5-hydroxy-1-[2-oxo-2-(1,3-thiazol-2-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-5-methoxy-1-[2-oxo-2-(1,2-thiazol-5-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-6-(dimethylamino)-1-[2-oxo-2-(1,3-thiazol-2-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-6-(dimethylamino)-1-[2-oxo-2-(pyrazin-2-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-6-(morpholine-4-carbonyl)-1-[2-oxo-2-(pyrazin-2-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-6-fluoro-1-[2-oxo-2-(1,3-thiazol-2-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-6-hydroxy-1-(2-oxo-2-phenylethyl)-1,2-dihydropyridin-2-one 4-(5-{[(5-chlorothiophen-2-yl)methyl]amino}-1-(2,2-dimethylpropanoyl)-1H-pyrazol-3-yl)-6-methoxy-1-[2-oxo-2-(1,2-thiazol-4-yl)ethyl]-1,2-dihydropyridin-2-one 4-(5-{[(5-chlorothiophen-2-yl)methyl]amino}-1-(2,2-dimethylpropanoyl)-1H-pyrazol-3-yl)-6-oxo-1-[2-oxo-2-(1,2-thiazol-3-yl)ethyl]-1,6-dihydropyridine-2-carboxylic acid APPENDIX A-continued Table B 4-(5-{[(5-chlorothiophen-2-yl)methyl]amino}-1-(2,2-dimethylpropanoyl)-1H-pyrazol-3-yl)-6-oxo-1-[2-oxo-2-(1,2-thiazol-4-yl)ethyl]-1,6-dihydropyridine-3-carbonitrile
4-(5-{[(5-chlorothiophen-2-yl)methyl]amino}-1-(2,2-dimethylpropanoyl)-1H-pyrazol-3-yl)-6-oxo-1-[2-oxo-2-(1,3-thiazol-5-yl)ethyl]-1,6-dihydropyridine-2-carbonitrile
4-(5-{[(5-chlorothiophen-2-yl)methyl]amino}-1-(2,2-dimethylpropanoyl)-1H-pyrazol-3-yl)-N,N-dimethyl-2-oxo-1-[2-oxo-2-(1,3-thiazol-4-yl)ethyl]-1,2-dihydropyridine-3-carboxamide
4-(5-{[(5-chlorothiophen-2-yl)methyl]amino}-1-(2,2-dimethylpropanoyl)-1H-pyrazol-3-yl)-N,N-dimethyl-6-oxo-1-[2-oxo-2-(pyrimidin-2-yl)ethyl]-1,6-dihydropyridine-2-carboxamide
4-(5-{[(5-chlorothiophen-2-yl)methyl]amino}-1-(2,2-dimethylpropanoyl)-1H-pyrazol-3-yl)-N,N-dimethyl-6-oxo-1-[2-oxo-2-(thiophen-2-yl)ethyl]-1,6-dihydropyridine-3-carboxamide
4-(5-{[(5-chlorothiophen-2-yl)methyl]amino}-1-(2-fluorobenzoyl)-1H-pyrazol-3-yl)-3-ethenyl-1-[2-oxo-2-(1,2-thiazol-5-yl)ethyl]-1,2-dihydropyridin-2-one
4-(5-{[(5-chlorothiophen-2-yl)methyl]amino}-1-(2-fluorobenzoyl)-1H-pyrazol-3-yl)-6-hydroxy-1-[2-oxo-2-(1,3-thiazol-5-yl)ethyl]-1,2-dihydropyridin-2-one
4-(5-{[(5-chlorothiophen-2-yl)methyl]amino}-1-(2-methoxybenzoyl)-1H-pyrazol-3-yl)-1-[2-(4-methylpiperazin-1-yl)-2-oxoethyl]-3-(2-phenylethynyl)-1,2-dihydropyridin-2-one
4-(5-{[(5-chlorothiophen-2-yl)methyl]amino}-1-(2-methoxybenzoyl)-1H-pyrazol-3-yl)-6-fluoro-1-[2-oxo-2-(pyrazin-2-yl)ethyl]-1,2-dihydropyridin-2-one
4-(5-{[(5-chlorothiophen-2-yl)methyl]amino}-1-(3-hydroxy-2,2-dimethylpropanoyl)-1H-pyrazol-3-yl)-1-(pyrazin-2-ylmethyl)-6-(pyridin-3-yl)-1,2-dihydropyridin-2-one
4-(5-{[(5-chlorothiophen-2-yl)methyl]amino}-1-(3-hydroxy-2,2-dimethylpropanoyl)-1H-pyrazol-3-yl)-1-[2-(furan-3-yl)ethyl]-5-(2-phenylethynyl)-1,2-dihydropyridin-2-one
4-(5-{[(5-chlorothiophen-2-yl)methyl]amino}-1-(3-hydroxy-2,2-dimethylpropanoyl)-1H-pyrazol-3-yl)-5-hydroxy-1-[2-oxo-2-(thiophen-3-yl)ethyl]-1,2-dihydropyridin-2-one
4-(5-{[(5-chlorothiophen-2-yl)methyl]amino}-1-(3-hydroxy-2,2-dimethylpropanoyl)-1H-pyrazol-3-yl)-6-(dimethylamino)-1-(pyridin-3-ylmethyl)-1,2-dihydropyridin-2-one
4-(5-{[(5-chlorothiophen-2-yl)methyl]amino}-1-(3-methoxy-2,2-dimethylpropanoyl)-1H-pyrazol-3-yl)-1-[2-(4-methylpiperazin-1-yl)-2-oxoethyl]-5-(pyridin-2-yl)-1,2-dihydropyridin-2-one
4-(5-{[(5-chlorothiophen-2-yl)methyl]amino}-1-(3-methoxy-2,2-dimethylpropanoyl)-1H-pyrazol-3-yl)-1-[2-oxo-2-(pyridin-3-yl)ethyl]-6-(2-phenylethynyl)-1,2-dihydropyridin-2-one
4-(5-{[(5-chlorothiophen-2-yl)methyl]amino}-1-(3-methoxy-2,2-dimethylpropanoyl)-1H-pyrazol-3-yl)-3-methoxy-1-[2-oxo-2-(pyridazin-4-yl)ethyl]-1,2-dihydropyridin-2-one
4-(5-{[(5-chlorothiophen-2-yl)methyl]amino}-1-(furan-2-carbonyl)-1H-pyrazol-3-yl)-1-ethyl-3-(pyridin-4-yl)-1,2-dihydropyridin-2-one
4-(5-{[(5-chlorothiophen-2-yl)methyl]amino}-1-(furan-2-carbonyl)-1H-pyrazol-3-yl)-5-ethenyl-1-[2-(pyridin-4-yl)ethyl]-1,2-dihydropyridin-2-one
4-(5-{[(5-chlorothiophen-2-yl)methyl]amino}-1-(furan-2-carbonyl)-1H-pyrazol-3-yl)-5-hydroxy-1-[2-(1,3-oxazol-2-yl)-2-oxoethyl]-1,2-dihydropyridin-2-one
4-(5-{[(5-chlorothiophen-2-yl)methyl]amino}-1-(furan-3-carbonyl)-1H-pyrazol-3-yl)-1-[2-(1,3-oxazol-5-yl)ethyl]-3-(2-phenylethynyl)-1,2-dihydropyridin-2-one
4-(5-{[(5-chlorothiophen-2-yl)methyl]amino}-1-(furan-3-carbonyl)-1H-pyrazol-3-yl)-1-[2-oxo-2-(pyrazin-2-yl)ethyl]-6-(pyridin-3-yl)-1,2-dihydropyridin-2-one
4-(5-{[(5-chlorothiophen-2-yl)methyl]amino}-1-(furan-3-carbonyl)-1H-pyrazol-3-yl)-3-(dimethylamino)-1-[2-(1,2-oxazol-3-yl)-2-oxoethyl]-1,2-dihydropyridin-2-one
4-(5-{[(5-chlorothiophen-2-yl)methyl]amino}-1-(furan-3-carbonyl)-1H-pyrazol-3-yl)-6-oxo-1-[2-oxo-2-(1,2-thiazol-3-yl)ethyl]-1,6-dihydropyridine-3-carbonitrile
4-(5-{[(5-chlorothiophen-2-yl)methyl]amino}-1-(furan-3-carbonyl)-4-methoxy-1H-pyrazol-3-yl)-5-fluoro-1-(1,3-oxazol-2-ylmethyl)-1,2-dihydropyridin-2-one
4-(5-{[(5-chlorothiophen-2-yl)methyl]amino}-1-(thiophene-2-carbonyl)-1H-pyrazol-3-yl)-1-[(4-methylpiperazin-1-yl)methyl]-6-phenyl-1,2-dihydropyridin-2-one
4-(5-{[(5-chlorothiophen-2-yl)methyl]amino}-1-(thiophene-2-carbonyl)-1H-pyrazol-3-yl)-1-[2-(1,2-oxazol-3-yl)-2-oxoethyl]-5-(pyridin-4-yl)-1,2-dihydropyridin-2-one
4-(5-{[(5-chlorothiophen-2-yl)methyl]amino}-1-(thiophene-2-carbonyl)-1H-pyrazol-3-yl)-1-[2-(1,2-oxazol-5-yl)ethyl]-2-oxo-1,2-dihydropyridine-3-carbonitrile
4-(5-{[(5-chlorothiophen-2-yl)methyl]amino}-1-(thiophene-2-carbonyl)-1H-pyrazol-3-yl)-3-phenyl-1-(pyridazin-4-ylmethyl)-1,2-dihydropyridin-2-one
4-(5-{[(5-chlorothiophen-2-yl)methyl]amino}-1-(thiophene-2-carbonyl)-1H-pyrazol-3-yl)-5-ethenyl-1-(pyrimidin-4-ylmethyl)-1,2-dihydropyridin-2-one
4-(5-{[(5-chlorothiophen-2-yl)methyl]amino}-1-(thiophene-2-carbonyl)-1H-pyrazol-3-yl)-5-hydroxy-1-(1,3-thiazol-2-ylmethyl)-1,2-dihydropyridin-2-one APPENDIX A-continued Table B 4-(5-{[(5-chlorothiophen-2-yl)methyl]amino}-1-(thiophene-2-carbonyl)-1H-pyrazol-3-yl)-6-(dimethylamino)-1-[2-oxo-2-(1,2-thiazol-3-yl)ethyl]-1,2-dihydropyridin-2-one
4-(5-{[(5-chlorothiophen-2-yl)methyl]amino}-1-(thiophene-2-carbonyl)-1H-pyrazol-3-yl)-6-(morpholin-4-yl)-1-[2-(pyridin-4-yl)ethyl]-1,2-dihydropyridin-2-one
4-(5-{[(5-chlorothiophen-2-yl)methyl]amino}-1-(thiophene-2-carbonyl)-1H-pyrazol-3-yl)-6-phenyl-1-[2-(pyrimidin-4-yl)ethyl]-1,2-dihydropyridin-2-one
4-(5-{[(5-chlorothiophen-2-yl)methyl]amino}-1-(thiophene-3-carbonyl)-1H-pyrazol-3-yl)-1-[2-oxo-2-(pyrimidin-2-yl)ethyl]-6-(2-phenylethynyl)-1,2-dihydropyridin-2-one
4-(5-{[(5-chlorothiophen-2-yl)methyl]amino}-1-(thiophene-3-carbonyl)-1H-pyrazol-3-yl)-1-[2-oxo-2-(thiophen-2-yl)ethyl]-5-(pyridin-2-yl)-1,2-dihydropyridin-2-one
4-(5-{[(5-chlorothiophen-2-yl)methyl]amino}-1-(thiophene-3-carbonyl)-1H-pyrazol-3-yl)-3-(pyridin-3-yl)-1-[2-(pyrimidin-2-yl)ethyl]-1,2-dihydropyridin-2-one
4-(5-{[(5-chlorothiophen-2-yl)methyl]amino}-1-(thiophene-3-carbonyl)-1H-pyrazol-3-yl)-3-ethenyl-1-[2-(pyrazin-2-yl)ethyl]-1,2-dihydropyridin-2-one
4-(5-{[(5-chlorothiophen-2-yl)methyl]amino}-1-(thiophene-3-carbonyl)-1H-pyrazol-3-yl)-3-hydroxy-1-(1,2-oxazol-5-ylmethyl)-1,2-dihydropyridin-2-one
4-(5-{[(5-chlorothiophen-2-yl)methyl]amino}-1-(thiophene-3-carbonyl)-1H-pyrazol-3-yl)-3-methoxy-1-[2-oxo-2-(1,3-thiazol-4-yl)ethyl]-1,2-dihydropyridin-2-one
4-(5-{[(5-chlorothiophen-2-yl)methyl]amino}-1-[2-(trifluoromethyl)benzoyl]-1H-pyrazol-3-yl)-1-[2-oxo-2-(piperidin-1-yl)ethyl]-6-(pyridin-2-yl)-1,2-dihydropyridin-2-one
4-(5-{[(5-chlorothiophen-2-yl)methyl]amino}-1-[2-(trifluoromethyl)benzoyl]-1H-pyrazol-3-yl)-3-(morpholin-4-yl)-1-(1,2-oxazol-4-ylmethyl)-1,2-dihydropyridin-2-one
4-(5-{[(5-chlorothiophen-2-yl)methyl]amino}-1-[2-(trifluoromethyl)benzoyl]-1H-pyrazol-3-yl)-3-fluoro-1-[2-oxo-2-(pyridin-3-yl)ethyl]-1,2-dihydropyridin-2-one
4-(5-{[(5-chlorothiophen-2-yl)methyl]amino}-1-[2-(trifluoromethyl)benzoyl]-1H-pyrazol-3-yl)-5-methoxy-1-[2-oxo-2-(pyrazin-2-yl)ethyl]-1,2-dihydropyridin-2-one
4-(5-{[(5-chlorothiophen-2-yl)methyl]amino}-1-[3-(hydroxymethyl)benzoyl]-1H-pyrazol-3-yl)-1-[2-oxo-2-(piperidin-1-yl)ethyl]-5-(2-phenylethynyl)-1,2-dihydropyridin-2-one
4-(5-{[(5-chlorothiophen-2-yl)methyl]amino}-1-[3-(hydroxymethyl)benzoyl]-1H-pyrazol-3-yl)-1-[2-oxo-2-(pyrazin-2-yl)ethyl]-3-(pyridin-2-yl)-1,2-dihydropyridin-2-one
4-(5-{[(5-chlorothiophen-2-yl)methyl]amino}-1-[3-(hydroxymethyl)benzoyl]-1H-pyrazol-3-yl)-3-fluoro-1-[2-(morpholin-4-yl)ethyl]-1,2-dihydropyridin-2-one
4-(5-{[(5-chlorothiophen-2-yl)methyl]amino}-1-[3-(hydroxymethyl)benzoyl]-4-methoxy-1H-pyrazol-3-yl)-5-ethenyl-1-(1,2-oxazol-3-ylmethyl)-1,2-dihydropyridin-2-one
4-(5-{[(5-chlorothiophen-2-yl)methyl]amino}-1-[4-(hydroxymethyl)benzoyl]-1H-pyrazol-3-yl)-5-fluoro-1-[2-oxo-2-(1,3-thiazol-4-yl)ethyl]-1,2-dihydropyridin-2-one
4-(5-{[(5-chlorothiophen-2-yl)methyl]amino}-1-[4-(hydroxymethyl)benzoyl]-1H-pyrazol-3-yl)-6-methoxy-1-[2-oxo-2-(thiophen-2-yl)ethyl]-1,2-dihydropyridin-2-one
4-(5-{[(5-chlorothiophen-2-yl)methyl]amino}-1-[4-(hydroxymethyl)benzoyl]-4-methoxy-1H-pyrazol-3-yl)-5-(pyridin-3-yl)-1-(1,3-thiazol-4-ylmethyl)-1,2-dihydropyridin-2-one
4-(5-{[(5-chlorothiophen-2-yl)methyl]amino}-3-(1-ethyl-2-oxo-5-phenyl-1,2-dihydropyridin-4-yl)-1H-pyrazole-1-carbonyl)benzoic acid
4-(5-{[(5-chlorothiophen-2-yl)methyl]amino}-3-[2-(dimethylamino)-6-oxo-1-(2-oxo-2-phenylethyl)-1,6-dihydropyridin-3-yl]-1H-pyrazole-1-carbonyl)benzoic acid
4-(5-{[(5-chlorothiophen-2-yl)methyl]amino}-3-[2-oxo-6-(2-phenylethynyl)-1-(1,2-thiazol-4-ylmethyl)-1,2-dihydropyridin-4-yl]-1H-pyrazole-1-carbonyl)benzoic acid
4-(5-{[(5-chlorothiophen-2-yl)methyl]amino}-3-[3-(dimethylamino)-6-oxo-1-(2-oxoethyl)-1,6-dihydropyridin-2-yl]-1H-pyrazole-1-carbonyl)benzoic acid
4-(5-{[(5-chlorothiophen-2-yl)methyl]amino}-3-[3-(morpholin-4-yl)-2-oxo-1-[2-oxo-2-(1,3-thiazol-5-yl)ethyl]-1,2-dihydropyridin-4-yl]-1H-pyrazole-1-carbonyl)benzamide
4-(5-{[(5-chlorothiophen-2-yl)methyl]amino}-3-[3-methoxy-2-oxo-1-(thiophen-3-ylmethyl)-1,2-dihydropyridin-4-yl]-1H-pyrazole-1-carbonyl)benzamide
4-(5-{[(5-chlorothiophen-2-yl)methyl]amino}-3-[4-(morpholin-4-yl)-6-oxo-1-[2-oxo-2-(pyridin-2-yl)ethyl]-1,6-dihydropyridin-2-yl]-1H-pyrazole-1-carbonyl)benzamide
4-(5-{[(5-chlorothiophen-2-yl)methyl]amino}-3-[4-hydroxy-6-oxo-1-(piperidin-1-ylmethyl)-1,6-dihydropyridin-2-yl]-1H-pyrazole-1-carbonyl)benzoic acid
4-(5-{[(5-chlorothiophen-2-yl)methyl]amino}-3-[5-(dimethylamino)-1-[2-(1,2-oxazol-5-yl)ethyl]-2-oxo-1,2-dihydropyridin-4-yl]-1H-pyrazole-1-carbonyl)benzoic acid

APPENDIX A-continued

Table B 4-(5-{[(5-chlorothiophen-2-yl)methyl]amino}-3-[5-(dimethylamino)-2-oxo-1-[2-oxo-2-(pyridin-2-yl)ethyl]-1,2-dihydropyridin-3-yl]-1H-pyrazole-1-carbonyl)benzoic acid
4-(5-{[(5-chlorothiophen-2-yl)methyl]amino}-3-[5-(methoxycarbonyl)-1-(1,2-oxazol-3-ylmethyl)-2-oxo-1,2-dihydropyridin-3-yl]-1H-pyrazole-1-carbonyl)benzoic acid
4-(5-{[(5-chlorothiophen-2-yl)methyl]amino}-3-[6-hydroxy-2-oxo-1-(1,2-thiazol-3-ylmethyl)-1,2-dihydropyridin-3-yl]-1H-pyrazole-1-carbonyl)benzoic acid
4-(5-{[(5-chlorothiophen-2-yl)methyl]amino}-3-[6-oxo-4-(pyridin-3-yl)-1-[2-(pyridin-3-yl)ethyl]-1,6-dihydropyridin-2-yl]-1H-pyrazole-1-carbonyl)benzamide
4-(5-{[(5-chlorothiophen-2-yl)methyl]amino}-3-[6-oxo-5-(pyridin-3-yl)-1-[2-(1,3-thiazol-4-yl)ethyl]-1,6-dihydropyridin-2-yl]-1H-pyrazole-1-carbonyl)benzoic acid
4-(5-{[(5-chlorothiophen-2-yl)methyl]amino}-3-{1-[(4-methylpiperazin-1-yl)methyl]-2-oxo-5-(pyridin-4-yl)-1,2-dihydropyridin-4-yl}-1H-pyrazole-1-carbonyl)benzoic acid
4-(5-{[(5-chlorothiophen-2-yl)methyl]amino}-3-{1-[2-(1,2-oxazol-3-yl)-2-oxoethyl]-2-oxo-6-phenyl-1,2-dihydropyridin-4-yl}-1H-pyrazole-1-carbonyl)benzoic acid
4-(5-{[(5-chlorothiophen-2-yl)methyl]amino}-3-{1-[2-(1,2-oxazol-4-yl)-2-oxoethyl]-6-oxo-5-(pyridin-3-yl)-1,6-dihydropyridin-2-yl}-1H-pyrazole-1-carbonyl)benzoic acid
4-(5-{[(5-chlorothiophen-2-yl)methyl]amino}-3-{1-[2-(4-methylpiperazin-1-yl)-2-oxoethyl]-6-(morpholin-4-yl)-2-oxo-1,2-dihydropyridin-3-yl}-1H-pyrazole-1-carbonyl)benzamide
4-(5-{[(5-chlorothiophen-2-yl)methyl]amino}-3-{1-[2-(furan-2-yl)ethyl]-4-hydroxy-6-oxo-1,6-dihydropyridin-2-yl}-1H-pyrazole-1-carbonyl)benzamide
4-(5-{[(5-chlorothiophen-2-yl)methyl]amino}-3-{2-oxo-1-[2-oxo-2-(pyrazin-2-yl)ethyl]-4-(pyridin-4-yl)-1,2-dihydropyridin-3-yl}-1H-pyrazole-1-carbonyl)benzoic acid
4-(5-{[(5-chlorothiophen-2-yl)methyl]amino}-3-{3-cyano-1-[2-(furan-2-yl)-2-oxoethyl]-2-oxo-1,2-dihydropyridin-4-yl}-1H-pyrazole-1-carbonyl)benzoic acid
4-(5-{[(5-chlorothiophen-2-yl)methyl]amino}-3-{3-hydroxy-2-oxo-1-[2-(pyrimidin-5-yl)ethyl]-1,2-dihydropyridin-4-yl}-1H-pyrazole-1-carbonyl)benzoic acid
4-(5-{[(5-chlorothiophen-2-yl)methyl]amino}-3-{4-cyano-1-[2-(1,2-oxazol-5-yl)-2-oxoethyl]-6-oxo-1,6-dihydropyridin-2-yl}-1H-pyrazole-1-carbonyl)benzoic acid
4-(5-{[(5-chlorothiophen-2-yl)methyl]amino}-3-{4-hydroxy-1-[2-(morpholin-4-yl)-2-oxoethyl]-2-oxo-1,2-dihydropyridin-3-yl}-1H-pyrazole-1-carbonyl)benzamide
4-(5-{[(5-chlorothiophen-2-yl)methyl]amino}-3-{4-hydroxy-6-oxo-1-[2-oxo-2-(1,2-thiazol-5-yl)ethyl]-1,6-dihydropyridin-3-yl}-1H-pyrazole-1-carbonyl)benzamide
4-(5-{[(5-chlorothiophen-2-yl)methyl]amino}-3-{4-methoxy-2-oxo-1-[2-(pyridazin-4-yl)ethyl]-1,2-dihydropyridin-3-yl}-1H-pyrazole-1-carbonyl)benzamide
4-(5-{[(5-chlorothiophen-2-yl)methyl]amino}-3-{5-ethenyl-1-[2-(1,3-oxazol-4-yl)-2-oxoethyl]-2-oxo-1,2-dihydropyridin-4-yl}-1H-pyrazole-1-carbonyl)benzamide
4-(5-{[(5-chlorothiophen-2-yl)methyl]amino}-3-{5-ethenyl-6-oxo-1-[2-oxo-2-(pyridin-4-yl)ethyl]-1,6-dihydropyridin-2-yl}-1H-pyrazole-1-carbonyl)benzamide
4-(5-{[(5-chlorothiophen-2-yl)methyl]amino}-3-{5-fluoro-1-[2-(1,3-oxazol-2-yl)ethyl]-6-oxo-1,6-dihydropyridin-2-yl}-1H-pyrazole-1-carbonyl)benzoic acid
4-(5-{[(5-chlorothiophen-2-yl)methyl]amino}-3-{6-cyano-2-oxo-1-[2-oxo-2-(thiophen-3-yl)ethyl]-1,2-dihydropyridin-3-yl}-1H-pyrazole-1-carbonyl)benzoic acid
4-(5-{[(5-chlorothiophen-2-yl)methyl]amino}-3-{6-methoxy-1-[2-(4-methylpiperazin-1-yl)ethyl]-2-oxo-1,2-dihydropyridin-4-yl}-1H-pyrazole-1-carbonyl)benzamide
4-(5-{[(5-chlorothiophen-2-yl)methyl]amino}-3-{6-oxo-1-[2-oxo-2-(1,3-thiazol-2-yl)ethyl]-4-(pyridin-4-yl)-1,6-dihydropyridin-3-yl}-1H-pyrazole-1-carbonyl)benzoic acid
4-(5-{[(5-chlorothiophen-2-yl)methyl]amino}-3-{6-oxo-1-[2-oxo-2-(pyrimidin-4-yl)ethyl]-5-phenyl-1,6-dihydropyridin-3-yl}-1H-pyrazole-1-carbonyl)benzoic acid
4-(5-{[(5-chlorothiophen-2-yl)methyl]amino}-4-cyano-3-[4-cyano-1-(1,2-oxazol-5-ylmethyl)-2-oxo-1,2-dihydropyridin-3-yl]-1H-pyrazole-1-carbonyl)benzamide
4-(5-{[(5-chlorothiophen-2-yl)methyl]amino}-4-cyano-3-[5-(morpholin-4-yl)-2-oxo-1-(pyrazin-2-ylmethyl)-1,2-dihydropyridin-4-yl]-1H-pyrazole-1-carbonyl)benzoic acid
4-(5-{[(5-chlorothiophen-2-yl)methyl]amino}-4-cyano-3-[5-hydroxy-2-oxo-1-(1,2-thiazol-3-ylmethyl)-1,2-dihydropyridin-4-yl]-1H-pyrazole-1-carbonyl)benzoic acid APPENDIX A-continued Table B 4-(5-{[(5-chlorothiophen-2-yl)methyl]amino}-4-cyano-3-[6-oxo-1-(pyridazin-4-ylmethyl)-3-(pyridin-4-yl)-1,6-dihydropyridin-2-yl]-1H-pyrazole-1-carbonyl)benzoic acid
4-(5-{[(5-chlorothiophen-2-yl)methyl]amino}-4-cyano-3-[6-oxo-2-(pyridin-4-yl)-1-(1,3-thiazol-4-ylmethyl)-1,6-dihydropyridin-3-yl]-1H-pyrazole-1-carbonyl)benzoic acid
4-(5-{[(5-chlorothiophen-2-yl)methyl]amino}-4-fluoro-1-(1,2-thiazole-3-carbonyl)-1H-pyrazol-3-yl)-5-phenyl-1-(pyrazin-2-ylmethyl)-1,2-dihydropyridin-2-one
4-(5-{[(5-chlorothiophen-2-yl)methyl]amino}-4-fluoro-1-(1,2-thiazole-3-carbonyl)-1H-pyrazol-3-yl)-6-oxo-1-(1,3-thiazol-4-ylmethyl)-1,6-dihydropyridine-2-carbonitrile
4-(5-{[(5-chlorothiophen-2-yl)methyl]amino}-4-fluoro-1-(1,2-thiazole-4-carbonyl)-1H-pyrazol-3-yl)-3-(2-phenylethynyl)-1-(1,2-thiazol-5-ylmethyl)-1,2-dihydropyridin-2-one
4-(5-{[(5-chlorothiophen-2-yl)methyl]amino}-4-fluoro-1-(1,3-oxazole-2-carbonyl)-1H-pyrazol-3-yl)-5-(dimethylamino)-1-(piperidin-1-ylmethyl)-1,2-dihydropyridin-2-one
4-(5-{[(5-chlorothiophen-2-yl)methyl]amino}-4-fluoro-1-(1,3-thiazole-4-carbonyl)-1H-pyrazol-3-yl)-1-(1,3-oxazol-4-ylmethyl)-6-(pyridin-2-yl)-1,2-dihydropyridin-2-one
4-(5-{[(5-chlorothiophen-2-yl)methyl]amino}-4-fluoro-1-(1,3-thiazole-5-carbonyl)-1H-pyrazol-3-yl)-3-(pyridin-3-yl)-1-(pyridin-3-ylmethyl)-1,2-dihydropyridin-2-one
4-(5-{[(5-chlorothiophen-2-yl)methyl]amino}-4-fluoro-1-(furan-2-carbonyl)-1H-pyrazol-3-yl)-3-fluoro-1-(1,2-thiazol-4-ylmethyl)-1,2-dihydropyridin-2-one
4-(5-{[(5-chlorothiophen-2-yl)methyl]amino}-4-fluoro-1-[3-(hydroxymethyl)benzoyl]-1H-pyrazol-3-yl)-1-(piperidin-1-ylmethyl)-6-(pyridin-4-yl)-1,2-dihydropyridin-2-one
4-(5-{[(5-chlorothiophen-2-yl)methyl]amino}-4-fluoro-3-[4-(methoxycarbonyl)-6-oxo-1-(pyrimidin-4-ylmethyl)-1,6-dihydropyridin-3-yl]-1H-pyrazole-1-carbonyl)benzoic acid
4-(5-{[(5-chlorothiophen-2-yl)methyl]amino}-4-fluoro-3-[6-fluoro-2-oxo-1-(1,3-thiazol-5-ylmethyl)-1,2-dihydropyridin-4-yl]-1H-pyrazole-1-carbonyl)benzamide
4-(5-{[(5-chlorothiophen-2-yl)methyl]amino}-4-methoxy-1-(1,2-thiazole-3-carbonyl)-1H-pyrazol-3-yl)-2-oxo-1-(piperidin-1-ylmethyl)-1,2-dihydropyridine-3-carbonitrile
4-(5-{[(5-chlorothiophen-2-yl)methyl]amino}-4-methoxy-1-(1,2-thiazole-3-carbonyl)-1H-pyrazol-3-yl)-3-(pyridin-2-yl)-1-(1,3-thiazol-5-ylmethyl)-1,2-dihydropyridin-2-one
4-(5-{[(5-chlorothiophen-2-yl)methyl]amino}-4-methoxy-1-(1,3-oxazole-5-carbonyl)-1H-pyrazol-3-yl)-1-(furan-2-ylmethyl)-3-hydroxy-1,2-dihydropyridin-2-one
4-(5-{[(5-chlorothiophen-2-yl)methyl]amino}-4-methoxy-1-(1,3-thiazole-4-carbonyl)-1H-pyrazol-3-yl)-1-(1,3-oxazol-4-ylmethyl)-5-(2-phenylethynyl)-1,2-dihydropyridin-2-one
4-(5-{[(5-chlorothiophen-2-yl)methyl]amino}-4-methoxy-1-(3-methoxy-2,2-dimethylpropanoyl)-1H-pyrazol-3-yl)-6-phenyl-1-(thiophen-2-ylmethyl)-1,2-dihydropyridin-2-one
4-(5-{[(5-chlorothiophen-2-yl)methyl]amino}-4-methoxy-1-[2-(trifluoromethyl)benzoyl]-1H-pyrazol-3-yl)-6-methoxy-1-(1,3-oxazol-5-ylmethyl)-1,2-dihydropyridin-2-one
4-(5-{[(5-chlorothiophen-2-yl)methyl]amino}-4-methoxy-3-[6-(morpholin-4-yl)-1-(1,2-oxazol-3-ylmethyl)-2-oxo-1,2-dihydropyridin-4-yl]-1H-pyrazole-1-carbonyl)benzamide
4-(5-{[(5-chlorothiophen-2-yl)methyl]amino}-4-methoxy-3-[6-oxo-1-(pyridin-3-ylmethyl)-4-(pyridin-4-yl)-1,6-dihydropyridin-3-yl]-1H-pyrazole-1-carbonyl)benzoic acid
4-(5-{[(5-chlorothiophen-2-yl)methyl]sulfanyl}-1-(2,2-dimethylpropanoyl)-1H-pyrazol-3-yl)-1-[2-(1,2-oxazol-3-yl)-2-oxoethyl]-6-(pyridin-2-yl)-1,2-dihydropyridin-2-one
4-(5-{[(5-chlorothiophen-2-yl)methyl]sulfanyl}-1-(2,2-dimethylpropanoyl)-1H-pyrazol-3-yl)-1-[2-(furan-2-yl)-2-oxoethyl]-3-(pyridin-2-yl)-1,2-dihydropyridin-2-one
4-(5-{[(5-chlorothiophen-2-yl)methyl]sulfanyl}-1-(2,2-dimethylpropanoyl)-1H-pyrazol-3-yl)-1-[2-(furan-2-yl)-2-oxoethyl]-6-(morpholin-4-yl)-1,2-dihydropyridin-2-one
4-(5-{[(5-chlorothiophen-2-yl)methyl]sulfanyl}-1-(2,2-dimethylpropanoyl)-1H-pyrazol-3-yl)-1-[2-oxo-2-(1,3-thiazol-4-yl)ethyl]-5-(pyridin-4-yl)-1,2-dihydropyridin-2-one
4-(5-{[(5-chlorothiophen-2-yl)methyl]sulfanyl}-1-(2,2-dimethylpropanoyl)-1H-pyrazol-3-yl)-1-[2-oxo-2-(piperidin-1-yl)ethyl]-3-(pyridin-4-yl)-1,2-dihydropyridin-2-one
4-(5-{[(5-chlorothiophen-2-yl)methyl]sulfanyl}-1-(2,2-dimethylpropanoyl)-1H-pyrazol-3-yl)-1-[2-oxo-2-(piperidin-1-yl)ethyl]-6-(2-phenylethynyl)-1,2-dihydropyridin-2-one APPENDIX A-continued Table B 4-(5-{[(5-chlorothiophen-2-yl)methyl]sulfanyl}-1-(2,2-dimethylpropanoyl)-1H-pyrazol-3-yl)-1-[2-oxo-2-(pyrazin-2-yl)ethyl]-5-(2-phenylethynyl)-1,2-dihydropyridin-2-one
4-(5-{[(5-chlorothiophen-2-yl)methyl]sulfanyl}-1-(2,2-dimethylpropanoyl)-1H-pyrazol-3-yl)-1-[2-oxo-2-(pyridin-3-yl)ethyl]-3-(2-phenylethynyl)-1,2-dihydropyridin-2-one
4-(5-{[(5-chlorothiophen-2-yl)methyl]sulfanyl}-1-(2,2-dimethylpropanoyl)-1H-pyrazol-3-yl)-1-[2-oxo-2-(thiophen-2-yl)ethyl]-6-(pyridin-4-yl)-1,2-dihydropyridin-2-one
4-(5-{[(5-chlorothiophen-2-yl)methyl]sulfanyl}-1-(2,2-dimethylpropanoyl)-1H-pyrazol-3-yl)-3-(morpholin-4-yl)-1-[2-oxo-2-(1,3-thiazol-2-yl)ethyl]-1,2-dihydropyridin-2-one
4-(5-{[(5-chlorothiophen-2-yl)methyl]sulfanyl}-1-(2,2-dimethylpropanoyl)-1H-pyrazol-3-yl)-3-fluoro-1-[2-(1,2-oxazol-4-yl)-2-oxoethyl]-1,2-dihydropyridin-2-one
4-(5-{[(5-chlorothiophen-2-yl)methyl]sulfanyl}-1-(2,2-dimethylpropanoyl)-1H-pyrazol-3-yl)-3-methoxy-1-[2-oxo-2-(thiophen-3-yl)ethyl]-1,2-dihydropyridin-2-one
4-(5-{[(5-chlorothiophen-2-yl)methyl]sulfanyl}-1-(2,2-dimethylpropanoyl)-1H-pyrazol-3-yl)-5-(morpholin-4-yl)-1-(2-oxo-2-phenylethyl)-1,2-dihydropyridin-2-one
4-(5-{[(5-chlorothiophen-2-yl)methyl]sulfanyl}-1-(2,2-dimethylpropanoyl)-1H-pyrazol-3-yl)-5-fluoro-1-[2-oxo-2-(pyrimidin-4-yl)ethyl]-1,2-dihydropyridin-2-one
4-(5-{[(5-chlorothiophen-2-yl)methyl]sulfanyl}-1-(2,2-dimethylpropanoyl)-1H-pyrazol-3-yl)-5-methoxy-1-[2-oxo-2-(1,2-thiazol-5-yl)ethyl]-1,2-dihydropyridin-2-one
4-(5-{[(5-chlorothiophen-2-yl)methyl]sulfanyl}-1-(2,2-dimethylpropanoyl)-1H-pyrazol-3-yl)-6-fluoro-1-[2-oxo-2-(1,3-thiazol-2-yl)ethyl]-1,2-dihydropyridin-2-one
4-(5-{[(5-chlorothiophen-2-yl)methyl]sulfanyl}-1-(2,2-dimethylpropanoyl)-1H-pyrazol-3-yl)-6-methoxy-1-[2-oxo-2-(1,2-thiazol-4-yl)ethyl]-1,2-dihydropyridin-2-one
4-[1-(2-aminobenzoyl)-5-{[(5-chlorothiophen-2-yl)methyl]amino}-1H-pyrazol-3-yl]-1-(2-oxo-2-phenylethyl)-5-phenyl-1,2-dihydropyridin-2-one
4-[1-(2-aminobenzoyl)-5-{[(5-chlorothiophen-2-yl)methyl]amino}-1H-pyrazol-3-yl]-1-[2-(furan-2-yl)-2-oxoethyl]-6-(pyridin-4-yl)-1,2-dihydropyridin-2-one
4-[1-(2-aminobenzoyl)-5-{[(5-chlorothiophen-2-yl)methyl]amino}-1H-pyrazol-3-yl]-1-[2-oxo-2-(1,3-thiazol-2-yl)ethyl]-3-(pyridin-3-yl)-1,2-dihydropyridin-2-one
4-[1-(2-chlorobenzoyl)-5-{[(5-chlorothiophen-2-yl)methyl]amino}-1H-pyrazol-3-yl]-5-(morpholin-4-yl)-1-[2-oxo-2-(1,2-thiazol-5-yl)ethyl]-1,2-dihydropyridin-2-one
4-[1-(2-chlorobenzoyl)-5-{[(5-chlorothiophen-2-yl)methyl]amino}-1H-pyrazol-3-yl]-6-ethenyl-1-[2-oxo-2-(1,2-thiazol-4-yl)ethyl]-1,2-dihydropyridin-2-one
4-[1-(2-chlorobenzoyl)-5-{[(5-chlorothiophen-2-yl)methyl]amino}-1H-pyrazol-3-yl]-6-oxo-1-(pyridin-3-ylmethyl)-1,6-dihydropyridine-3-carbonitrile
4-[1-(2-chlorobenzoyl)-5-{[(5-chlorothiophen-2-yl)methyl]amino}-4-fluoro-1H-pyrazol-3-yl]-1-(pyrazin-2-ylmethyl)-3-(pyridin-4-yl)-1,2-dihydropyridin-2-one
4-[1-(2-chlorobenzoyl)-5-{[(5-chlorothiophen-2-yl)methyl]amino}-4-fluoro-1H-pyrazol-3-yl]-5-methoxy-1-(1,3-thiazol-5-ylmethyl)-1,2-dihydropyridin-2-one
4-[3-(1-benzyl-2-chloro-6-oxo-1,6-dihydropyridin-3-yl)-5-{[(5-chlorothiophen-2-yl)methyl]amino}-4-methoxy-1H-pyrazole-1-carbonyl]benzamide
4-[3-(1-benzyl-4-ethenyl-2-oxo-1,2-dihydropyridin-3-yl)-5-{[(5-chlorothiophen-2-yl)methyl]amino}-1H-pyrazole-1-carbonyl]benzamide
4-benzoyl-3-(5-{[(5-chlorothiophen-2-yl)methyl]amino}-1-(2,2-dimethylpropanoyl)-1H-pyrazol-3-yl)-1-[2-(furan-2-yl)-2-oxoethyl]-1,2-dihydropyridin-2-one
4-benzoyl-5-(5-{[(5-chlorothiophen-2-yl)methyl]amino}-1-(2,2-dimethylpropanoyl)-1H-pyrazol-3-yl)-1-[2-(1,3-oxazol-4-yl)-2-oxoethyl]-1,2-dihydropyridin-2-one
4-benzoyl-6-(5-{[(5-chlorothiophen-2-yl)methyl]amino}-1-(2,2-dimethylpropanoyl)-1H-pyrazol-3-yl)-1-[2-oxo-2-(1,2-thiazol-5-yl)ethyl]-1,2-dihydropyridin-2-one
4-bromo-3-(5-{[(5-chlorothiophen-2-yl)methyl]amino}-1-(2,2-dimethylpropanoyl)-1H-pyrazol-3-yl)-1-[2-oxo-2-(1,3-thiazol-5-yl)ethyl]-1,2-dihydropyridin-2-one
4-bromo-3-(5-{[(5-chlorothiophen-2-yl)methyl]amino}-1-(3-methoxy-2,2-dimethylpropanoyl)-1H-pyrazol-3-yl)-1-[2-oxo-2-(piperidin-1-yl)ethyl]-1,2-dihydropyridin-2-one
4-bromo-3-(5-{[(5-chlorothiophen-2-yl)methyl]amino}-1-(thiophene-3-carbonyl)-1H-pyrazol-3-yl)-1-[2-(1,2-oxazol-5-yl)-2-oxoethyl]-1,2-dihydropyridin-2-one
4-bromo-5-(5-{[(5-chlorothiophen-2-yl)methyl]amino}-1-(1,2-oxazole-3-carbonyl)-1H-pyrazol-3-yl)-1-(pyridin-2-ylmethyl)-1,2-dihydropyridin-2-one
4-bromo-5-(5-{[(5-chlorothiophen-2-yl)methyl]amino}-1-(thiophene-3-carbonyl)-1H-pyrazol-3-yl)-1-[2-oxo-2-(pyrazin-2-yl)ethyl]-1,2-dihydropyridin-2-one APPENDIX A-continued Table B 4-bromo-6-(5-{[(5-chlorothiophen-2-yl)methyl]amino}-1-(1,2-thiazole-4-carbonyl)-1H-pyrazol-3-yl)-1-[2-oxo-2-(piperidin-1-yl)ethyl]-1,2-dihydropyridin-2-one
4-bromo-6-(5-{[(5-chlorothiophen-2-yl)methyl]amino}-1-(1,3-thiazole-2-carbonyl)-1H-pyrazol-3-yl)-1-[2-(1,3-oxazol-4-yl)ethyl]-1,2-dihydropyridin-2-one
4-bromo-6-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-1,2-dihydropyridin-2-one
4-bromo-6-(5-{[(5-chlorothiophen-2-yl)methyl]amino}-1-[4-(hydroxymethyl)benzoyl]-1H-pyrazol-3-yl)-1-[2-(furan-3-yl)-2-oxoethyl]-1,2-dihydropyridin-2-one
4-bromo-6-(5-{[(5-chlorothiophen-2-yl)methyl]sulfanyl}-1-(2,2-dimethylpropanoyl)-1H-pyrazol-3-yl)-1-[2-(1,3-oxazol-2-yl)-2-oxoethyl]-1,2-dihydropyridin-2-one
4-chloro-3-(5-{[(5-chlorothiophen-2-yl)methyl]amino}-1-(1,3-thiazole-5-carbonyl)-1H-pyrazol-3-yl)-1-[2-(furan-3-yl)-2-oxoethyl]-1,2-dihydropyridin-2-one
4-chloro-3-(5-{[(5-chlorothiophen-2-yl)methyl]amino}-1-(2,2-dimethylpropanoyl)-1H-pyrazol-3-yl)-1-[2-(furan-2-yl)-2-oxoethyl]-1,2-dihydropyridin-2-one
4-chloro-3-(5-{[(5-chlorothiophen-2-yl)methyl]sulfanyl}-1-(2,2-dimethylpropanoyl)-1H-pyrazol-3-yl)-1-[2-oxo-2-(1,2-thiazol-4-yl)ethyl]-1,2-dihydropyridin-2-one
4-chloro-3-[1-(2-chlorobenzoyl)-5-{[(5-chlorothiophen-2-yl)methyl]amino}-1H-pyrazol-3-yl]-1-[2-(1,3-oxazol-4-yl)-2-oxoethyl]-1,2-dihydropyridin-2-one
4-chloro-5-(5-{[(5-chlorothiophen-2-yl)methyl](methyl)amino}-1-(2,2-dimethylpropanoyl)-1H-pyrazol-3-yl)-1-[2-oxo-2-(pyrazin-2-yl)ethyl]-1,2-dihydropyridin-2-one
4-chloro-5-(5-{[(5-chlorothiophen-2-yl)methyl]amino}-1-(1,3-thiazole-5-carbonyl)-1H-pyrazol-3-yl)-1-[2-oxo-2-(1,3-thiazol-5-yl)ethyl]-1,2-dihydropyridin-2-one
4-chloro-5-(5-{[(5-chlorothiophen-2-yl)methyl]amino}-1-(2,2-dimethylpropanoyl)-1H-pyrazol-3-yl)-1-[2-oxo-2-(pyrimidin-5-yl)ethyl]-1,2-dihydropyridin-2-one
4-chloro-5-(5-{[(5-chlorothiophen-2-yl)methyl]amino}-1-(2-methoxybenzoyl)-1H-pyrazol-3-yl)-1-(1,2-oxazol-4-ylmethyl)-1,2-dihydropyridin-2-one
4-chloro-5-[1-(2-chlorobenzoyl)-5-{[(5-chlorothiophen-2-yl)methyl]amino}-1H-pyrazol-3-yl]-1-[2-oxo-2-(pyridin-2-yl)ethyl]-1,2-dihydropyridin-2-one
4-chloro-6-(5-{[(5-chlorothiophen-2-yl)methyl](methyl)amino}-1-(2,2-dimethylpropanoyl)-1H-pyrazol-3-yl)-1-[2-oxo-2-(pyridazin-4-yl)ethyl]-1,2-dihydropyridin-2-one
4-chloro-6-(5-{[(5-chlorothiophen-2-yl)methyl]amino}-1-(2,2-dimethylpropanoyl)-1H-pyrazol-3-yl)-1-[2-(1,2-oxazol-3-yl)-2-oxoethyl]-1,2-dihydropyridin-2-one
4-chloro-6-(5-{[(5-chlorothiophen-2-yl)methyl]amino}-1-(3-hydroxy-2,2-dimethylpropanoyl)-1H-pyrazol-3-yl)-1-[2-(1,2-oxazol-3-yl)-2-oxoethyl]-1,2-dihydropyridin-2-one
4-chloro-6-(5-{[(5-chlorothiophen-2-yl)methyl]amino}-1-(furan-2-carbonyl)-1H-pyrazol-3-yl)-1-[2-oxo-2-(pyridin-4-yl)ethyl]-1,2-dihydropyridin-2-one
4-chloro-6-(5-{[(5-chlorothiophen-2-yl)methyl]amino}-1-[3-(hydroxymethyl)benzoyl]-1H-pyrazol-3-yl)-1-(thiophen-2-ylmethyl)-1,2-dihydropyridin-2-one
4-{3-[1-(2-carboxy-2-oxoethyl)-2-oxo-5-(pyridin-3-yl)-1,2-dihydropyridin-4-yl]-5-{[(5-chlorothiophen-2-yl)methyl]amino}-1H-pyrazole-1-carbonyl}benzoic acid
4-{3-[3-chloro-6-oxo-1-(pyrazin-2-ylmethyl)-1,6-dihydropyridin-2-yl]-5-{[(5-chlorothiophen-2-yl)methyl]amino}-1H-pyrazole-1-carbonyl}benzoic acid
4-{3-[4-chloro-1-(1,2-oxazol-3-ylmethyl)-2-oxo-1,2-dihydropyridin-3-yl]-5-{[(5-chlorothiophen-2-yl)methyl]amino}-1H-pyrazole-1-carbonyl}benzamide
4-{3-[4-chloro-6-oxo-1-(pyrimidin-4-ylmethyl)-1,6-dihydropyridin-2-yl]-5-{[(5-chlorothiophen-2-yl)methyl]amino}-4-cyano-1H-pyrazole-1-carbonyl}benzamide
5-(1-benzoyl-5-{[(5-chlorothiophen-2-yl)methyl]amino}-1H-pyrazol-3-yl)-1-[2-(1,2-oxazol-4-yl)-2-oxoethyl]-6-(pyridin-4-yl)-1,2-dihydropyridin-2-one
5-(1-benzoyl-5-{[(5-chlorothiophen-2-yl)methyl]amino}-1H-pyrazol-3-yl)-1-[2-(1,2-oxazol-5-yl)-2-oxoethyl]-4-phenyl-1,2-dihydropyridin-2-one
5-(1-benzoyl-5-{[(5-chlorothiophen-2-yl)methyl]amino}-1H-pyrazol-3-yl)-3-chloro-1-(pyrimidin-2-ylmethyl)-1,2-dihydropyridin-2-one
5-(1-benzoyl-5-{[(5-chlorothiophen-2-yl)methyl]amino}-1H-pyrazol-3-yl)-4-methoxy-1-[2-(1,3-oxazol-4-yl)ethyl]-1,2-dihydropyridin-2-one
5-(1-benzoyl-5-{[(5-chlorothiophen-2-yl)methyl]amino}-4-cyano-1H-pyrazol-3-yl)-2-oxo-1-(pyrazin-2-ylmethyl)-1,2-dihydropyridine-4-carbonitrile
5-(1-benzoyl-5-{[(5-chlorothiophen-2-yl)methyl]amino}-4-fluoro-1H-pyrazol-3-yl)-1-[(4-methylpiperazin-1-yl)methyl]-4-(pyridin-3-yl)-1,2-dihydropyridin-2-one APPENDIX A-continued Table B 5-(1-benzoyl-5-{[(5-chlorothiophen-2-yl)methyl]amino}-4-methoxy-1H-pyrazol-3-yl)-1-[(4-methylpiperazin-1-yl)methyl]-3-phenyl-1,2-dihydropyridin-2-one 5-(5-{[(5-chlorothiophen-2-yl)methyl](methyl)amino}-1-(2,2-dimethylpropanoyl)-1H-pyrazol-3-yl)-1-(2-oxo-2-phenylethyl)-1,2-dihydropyridin-2-one 5-(5-{[(5-chlorothiophen-2-yl)methyl](methyl)amino}-1-(2,2-dimethylpropanoyl)-1H-pyrazol-3-yl)-1-[2-(1,2-oxazol-3-yl)-2-oxoethyl]-3-phenyl-1,2-dihydropyridin-2-one 5-(5-{[(5-chlorothiophen-2-yl)methyl](methyl)amino}-1-(2,2-dimethylpropanoyl)-1H-pyrazol-3-yl)-1-[2-(furan-2-yl)-2-oxoethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-1-[2-oxo-2-(1,2-thiazol-3-yl)ethyl]-4-phenyl-1,2-dihydropyridin-2-one 5-(5-{[(5-chlorothiophen-2-yl)methyl](methyl)amino}-1-(2,2-dimethylpropanoyl)-1H-pyrazol-3-yl)-1-[2-oxo-2-(1,3-thiazol-2-yl)ethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-1-[2-oxo-2-(pyrazin-2-yl)ethyl]-6-phenyl-1,2-dihydropyridin-2-one 5-(5-{[(5-chlorothiophen-2-yl)methyl](methyl)amino}-1-(2,2-dimethylpropanoyl)-1H-pyrazol-3-yl)-1-[2-oxo-2-(pyrimidin-2-yl)ethyl]-4-(pyridin-3-yl)-1,2-dihydropyridin-2-one 5-(5-{[(5-chlorothiophen-2-yl)methyl](methyl)amino}-1-(2,2-dimethylpropanoyl)-1H-pyrazol-3-yl)-1-[2-oxo-2-(thiophen-2-yl)ethyl]-3-(pyridin-3-yl)-1,2-dihydropyridin-2-one 5-(5-{[(5-chlorothiophen-2-yl)methyl](methyl)amino}-1-(2,2-dimethylpropanoyl)-1H-pyrazol-3-yl)-2-oxo-1-[2-oxo-2-(1,3-thiazol-4-yl)ethyl]-1,2-dihydropyridine-4-carbonitrile 5-(5-{[(5-chlorothiophen-2-yl)methyl](methyl)amino}-1-(2,2-dimethylpropanoyl)-1H-pyrazol-3-yl)-2-oxo-1-[2-oxo-2-(piperidin-1-yl)ethyl]-1,2-dihydropyridine-3-carbonitrile 5-(5-{[(5-chlorothiophen-2-yl)methyl](methyl)amino}-1-(2,2-dimethylpropanoyl)-1H-pyrazol-3-yl)-3-(dimethylamino)-1-[2-(furan-2-yl)-2-oxoethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-3-ethenyl-1-[2-(1,3-oxazol-4-yl)-2-oxoethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-3-hydroxy-1-[2-oxo-2-(1,2-thiazol-4-yl)ethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-4-ethenyl-1-[2-(1,3-oxazol-2-yl)-2-oxoethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-4-hydroxy-1-[2-oxo-2-(1,3-thiazol-5-yl)ethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-6-(dimethylamino)-1-[2-(1,2-oxazol-3-yl)-2-oxoethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-6-ethenyl-1-[2-(1,3-oxazol-5-yl)-2-oxoethyl]-1,2-dihydropyridin-2-one 5-(5-{[(5-chlorothiophen-2-yl)methyl](methyl)amino}-1-(2,2-dimethylpropanoyl)-1H-pyrazol-3-yl)-6-hydroxy-1-[2-(1,3-oxazol-4-yl)-2-oxoethyl]-1,2-dihydropyridin-2-one 5-(5-{[(5-chlorothiophen-2-yl)methyl]amino}-1-(1,2-oxazole-3-carbonyl)-1H-pyrazol-3-yl)-4-(pyridin-4-yl)-1-[2-(pyrimidin-2-yl)ethyl]-1,2-dihydropyridin-2-one 5-(5-{[(5-chlorothiophen-2-yl)methyl]amino}-1-(1,2-oxazole-3-carbonyl)-1H-pyrazol-3-yl)-4-fluoro-1-[2-oxo-2-(thiophen-2-yl)ethyl]-1,2-dihydropyridin-2-one 5-(5-{[(5-chlorothiophen-2-yl)methyl]amino}-1-(1,2-oxazole-3-carbonyl)-1H-pyrazol-3-yl)-6-(2-phenylethynyl)-1-(pyridin-2-ylmethyl)-1,2-dihydropyridin-2-one 5-(5-{[(5-chlorothiophen-2-yl)methyl]amino}-1-(1,2-oxazole-3-carbonyl)-1H-pyrazol-3-yl)-6-methoxy-1-[2-oxo-2-(pyrimidin-2-yl)ethyl]-1,2-dihydropyridin-2-one 5-(5-{[(5-chlorothiophen-2-yl)methyl]amino}-1-(1,2-oxazole-4-carbonyl)-1H-pyrazol-3-yl)-1-[2-oxo-2-(pyrimidin-5-yl)ethyl]-6-(pyridin-3-yl)-1,2-dihydropyridin-2-one 5-(5-{[(5-chlorothiophen-2-yl)methyl]amino}-1-(1,2-oxazole-4-carbonyl)-1H-pyrazol-3-yl)-2-oxo-1-[2-oxo-2-(pyrazin-2-yl)ethyl]-1,2-dihydropyridine-4-carbonitrile 5-(5-{[(5-chlorothiophen-2-yl)methyl]amino}-1-(1,2-oxazole-4-carbonyl)-1H-pyrazol-3-yl)-3-(dimethylamino)-1-[2-oxo-2-(1,2-thiazol-3-yl)ethyl]-1,2-dihydropyridin-2-one APPENDIX A-continued Table B 5-(5-{[(5-chlorothiophen-2-yl)methyl]amino}-1-(1,2-oxazole-5-carbonyl)-1H-pyrazol-3-yl)-4-hydroxy-1-[2-(1,3-oxazol-5-yl)-2-oxoethyl]-1,2-dihydropyridin-2-one
5-(5-{[(5-chlorothiophen-2-yl)methyl]amino}-1-(1,2-oxazole-5-carbonyl)-1H-pyrazol-3-yl)-6-phenyl-1-[2-(pyrimidin-2-yl)ethyl]-1,2-dihydropyridin-2-one
5-(5-{[(5-chlorothiophen-2-yl)methyl]amino}-1-(1,2-thiazole-3-carbonyl)-1H-pyrazol-3-yl)-1-[2-(piperidin-1-yl)ethyl]-3-(pyridin-4-yl)-1,2-dihydropyridin-2-one
5-(5-{[(5-chlorothiophen-2-yl)methyl]amino}-1-(1,2-thiazole-3-carbonyl)-1H-pyrazol-3-yl)-3-(morpholin-4-yl)-1-[2-(1,3-oxazol-4-yl)-2-oxoethyl]-1,2-dihydropyridin-2-one
5-(5-{[(5-chlorothiophen-2-yl)methyl]amino}-1-(1,2-thiazole-3-carbonyl)-1H-pyrazol-3-yl)-4-ethenyl-1-[2-(1,3-oxazol-2-yl)-2-oxoethyl]-1,2-dihydropyridin-2-one
5-(5-{[(5-chlorothiophen-2-yl)methyl]amino}-1-(1,2-thiazole-4-carbonyl)-1H-pyrazol-3-yl)-1-[2-oxo-2-(pyrimidin-2-yl)ethyl]-4-(pyridin-2-yl)-1,2-dihydropyridin-2-one
5-(5-{[(5-chlorothiophen-2-yl)methyl]amino}-1-(1,2-thiazole-4-carbonyl)-1H-pyrazol-3-yl)-3-ethenyl-1-(1,2-oxazol-5-ylmethyl)-1,2-dihydropyridin-2-one
5-(5-{[(5-chlorothiophen-2-yl)methyl]amino}-1-(1,2-thiazole-4-carbonyl)-1H-pyrazol-3-yl)-3-methoxy-1-[2-oxo-2-(thiophen-2-yl)ethyl]-1,2-dihydropyridin-2-one
5-(5-{[(5-chlorothiophen-2-yl)methyl]amino}-1-(1,2-thiazole-5-carbonyl)-1H-pyrazol-3-yl)-1-[2-(1,2-oxazol-3-yl)-2-oxoethyl]-3-phenyl-1,2-dihydropyridin-2-one
5-(5-{[(5-chlorothiophen-2-yl)methyl]amino}-1-(1,2-thiazole-5-carbonyl)-1H-pyrazol-3-yl)-1-[2-(1,3-oxazol-2-yl)-2-oxoethyl]-6-oxo-1,6-dihydropyridine-2-carbonitrile
5-(5-{[(5-chlorothiophen-2-yl)methyl]amino}-1-(1,2-thiazole-5-carbonyl)-1H-pyrazol-3-yl)-1-[2-oxo-2-(1,2-thiazol-3-yl)ethyl]-4-(pyridin-4-yl)-1,2-dihydropyridin-2-one
5-(5-{[(5-chlorothiophen-2-yl)methyl]amino}-1-(1,2-thiazole-5-carbonyl)-1H-pyrazol-3-yl)-6-(dimethylamino)-1-[2-oxo-2-(pyrazin-2-yl)ethyl]-1,2-dihydropyridin-2-one
5-(5-{[(5-chlorothiophen-2-yl)methyl]amino}-1-(1,3-oxazole-2-carbonyl)-1H-pyrazol-3-yl)-1-[2-(1,2-oxazol-3-yl)-2-oxoethyl]-4-(pyridin-3-yl)-1,2-dihydropyridin-2-one
5-(5-{[(5-chlorothiophen-2-yl)methyl]amino}-1-(1,3-oxazole-2-carbonyl)-1H-pyrazol-3-yl)-1-[2-oxo-2-(1,2-thiazol-3-yl)ethyl]-6-phenyl-1,2-dihydropyridin-2-one
5-(5-{[(5-chlorothiophen-2-yl)methyl]amino}-1-(1,3-oxazole-2-carbonyl)-1H-pyrazol-3-yl)-3-phenyl-1-[2-(thiophen-2-yl)ethyl]-1,2-dihydropyridin-2-one
5-(5-{[(5-chlorothiophen-2-yl)methyl]amino}-1-(1,3-oxazole-4-carbonyl)-1H-pyrazol-3-yl)-1-[2-(1,3-oxazol-2-yl)ethyl]-4-(2-phenylethynyl)-1,2-dihydropyridin-2-one
5-(5-{[(5-chlorothiophen-2-yl)methyl]amino}-1-(1,3-oxazole-4-carbonyl)-1H-pyrazol-3-yl)-3-hydroxy-1-[2-oxo-2-(1,3-thiazol-5-yl)ethyl]-1,2-dihydropyridin-2-one
5-(5-{[(5-chlorothiophen-2-yl)methyl]amino}-1-(1,3-oxazole-4-carbonyl)-1H-pyrazol-3-yl)-6-(morpholin-4-yl)-1-[2-(1,3-oxazol-2-yl)-2-oxoethyl]-1,2-dihydropyridin-2-one
5-(5-{[(5-chlorothiophen-2-yl)methyl]amino}-1-(1,3-oxazole-5-carbonyl)-1H-pyrazol-3-yl)-1-[2-oxo-2-(1,3-thiazol-4-yl)ethyl]-6-(pyridin-2-yl)-1,2-dihydropyridin-2-one
5-(5-{[(5-chlorothiophen-2-yl)methyl]amino}-1-(1,3-oxazole-5-carbonyl)-1H-pyrazol-3-yl)-3-fluoro-1-[2-oxo-2-(pyrazin-2-yl)ethyl]-1,2-dihydropyridin-2-one
5-(5-{[(5-chlorothiophen-2-yl)methyl]amino}-1-(1,3-oxazole-5-carbonyl)-1H-pyrazol-3-yl)-4-methoxy-1-[2-oxo-2-(piperidin-1-yl)ethyl]-1,2-dihydropyridin-2-one
5-(5-{[(5-chlorothiophen-2-yl)methyl]amino}-1-(1,3-oxazole-5-carbonyl)-1H-pyrazol-3-yl)-6-oxo-1-(pyrimidin-2-ylmethyl)-1,6-dihydropyridine-2-carbonitrile
5-(5-{[(5-chlorothiophen-2-yl)methyl]amino}-1-(1,3-thiazole-2-carbonyl)-1H-pyrazol-3-yl)-1-[2-oxo-2-(1,3-thiazol-4-yl)ethyl]-4-(2-phenylethynyl)-1,2-dihydropyridin-2-one
5-(5-{[(5-chlorothiophen-2-yl)methyl]amino}-1-(1,3-thiazole-2-carbonyl)-1H-pyrazol-3-yl)-1-[2-oxo-2-(piperidin-1-yl)ethyl]-3-(pyridin-2-yl)-1,2-dihydropyridin-2-one
5-(5-{[(5-chlorothiophen-2-yl)methyl]amino}-1-(1,3-thiazole-2-carbonyl)-1H-pyrazol-3-yl)-6-ethenyl-1-(1,2-oxazol-4-ylmethyl)-1,2-dihydropyridin-2-one
5-(5-{[(5-chlorothiophen-2-yl)methyl]amino}-1-(1,3-thiazole-2-carbonyl)-1H-pyrazol-3-yl)-6-oxo-1-[2-(1,2-thiazol-3-yl)ethyl]-1,6-dihydropyridine-2-carbonitrile
5-(5-{[(5-chlorothiophen-2-yl)methyl]amino}-1-(1,3-thiazole-4-carbonyl)-1H-pyrazol-3-yl)-1-[2-(furan-2-yl)-2-oxoethyl]-3-(pyridin-4-yl)-1,2-dihydropyridin-2-one
5-(5-{[(5-chlorothiophen-2-yl)methyl]amino}-1-(1,3-thiazole-4-carbonyl)-1H-pyrazol-3-yl)-2-oxo-1-[2-(1,3-thiazol-4-yl)ethyl]-1,2-dihydropyridine-3-carbonitrile

APPENDIX A-continued

Table B 5-(5-{[(5-chlorothiophen-2-yl)methyl]amino}-1-(1,3-thiazole-4-carbonyl)-1H-pyrazol-3-yl)-6-oxo-1-[2-oxo-2-(1,2-thiazol-5-yl)ethyl]-1,6-dihydropyridine-3-carbonitrile 5-(5-{[(5-chlorothiophen-2-yl)methyl]amino}-1-(1,3-thiazole-5-carbonyl)-1H-pyrazol-3-yl)-3-(dimethylamino)-1-(morpholin-4-ylmethyl)-1,2-dihydropyridin-2-one 5-(5-{[(5-chlorothiophen-2-yl)methyl]amino}-1-(1,3-thiazole-5-carbonyl)-1H-pyrazol-3-yl)-3-ethenyl-1-[2-oxo-2-(1,2-thiazol-4-yl)ethyl]-1,2-dihydropyridin-2-one 5-(5-{[(5-chlorothiophen-2-yl)methyl]amino}-1-(1,3-thiazole-5-carbonyl)-1H-pyrazol-3-yl)-4-ethenyl-1-(pyrimidin-2-ylmethyl)-1,2-dihydropyridin-2-one 5-(5-{[(5-chlorothiophen-2-yl)methyl]amino}-1-(1,3-thiazole-5-carbonyl)-1H-pyrazol-3-yl)-6-hydroxy-1-[2-(1,3-oxazol-4-yl)-2-oxoethyl]-1,2-dihydropyridin-2-one 5-(5-{[(5-chlorothiophen-2-yl)methyl]amino}-1-(2,2-dimethylpropanoyl)-1H-pyrazol-3-yl)-1-(2-oxo-2-phenylethyl)-6-(pyridin-2-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(1,2-oxazol-3-yl)-2-oxoethyl]-4-(pyridine-3-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(1,2-oxazol-5-yl)-2-oxoethyl]-6-(pyridin-3-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-4-(pyridine-4-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(1,3-oxazol-4-yl)-2-oxoethyl]-3-(pyridine-4-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(1,3-oxazol-4-yl)-2-oxoethyl]-6-(3-phenylprop-2-ynoyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(1,3-oxazol-5-yl)-2-oxoethyl]-1,2-dihydropyridin-2-one 5-(5-{[(5-chlorothiophen-2-yl)methyl]amino}-1-(2,2-dimethylpropanoyl)-1H-pyrazol-3-yl)-1-[2-(1,3-oxazol-5-yl)-2-oxoethyl]-6-(pyridine-4-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-3-(pyridin-4-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-4-phenyl-1,2-dihydropyridin-2-one 5-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-6-(2-phenylethynyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(furan-2-yl)-2-oxoethyl]-4-(morpholine-4-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(furan-3-yl)-2-oxoethyl]-3-(2-phenylethynyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(1,2-thiazol-3-yl)ethyl]-6-(pyridine-3-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(1,2-thiazol-4-yl)ethyl]-3-(3-phenylprop-2-ynoyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(1,2-thiazol-4-yl)ethyl]-6-(pyridin-3-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(1,2-thiazol-5-yl)ethyl]-4-(pyridin-3-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(1,3-thiazol-2-yl)ethyl]-4-(pyridin-2-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(1,3-thiazol-4-yl)ethyl]-4-(pyridine-2-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(1,3-thiazol-4-yl)ethyl]-6-(prop-2-enoyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(1,3-thiazol-5-yl)ethyl]-4-(3-phenylprop-2-ynoyl)-1,2-dihydropyridin-2-one

APPENDIX A-continued

Table B 5-(5-{[(5-chlorothiophen-2-yl)methyl]amino}-1-(2,2-dimethylpropanoyl)-1H-pyrazol-3-yl)-1-[2-oxo-2-(piperidin-1-yl)ethyl]-3-(pyridine-2-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(piperidin-1-yl)ethyl]-4-(prop-2-enoyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-3-(prop-2-enoyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-6-(pyridin-4-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-3-phenyl-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-4-(2-phenylethynyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(pyridin-3-yl)ethyl]-4-(pyridin-4-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(pyridin-3-yl)ethyl]-6-phenyl-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(pyrimidin-4-yl)ethyl]-3-(pyridin-2-yl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(thiophen-2-yl)ethyl]-6-(pyridine-2-carbonyl)-1,2-dihydropyridin-2-one 5-(5-{[(5-chlorothiophen-2-yl)methyl]amino}-1-(2,2-dimethylpropanoyl)-1H-pyrazol-3-yl)-1-[2-oxo-2-(thiophen-3-yl)ethyl]-3-(pyridin-3-yl)-1,2-dihydropyridin-2-one 5-(5-{[(5-chlorothiophen-2-yl)methyl]amino}-1-(2,2-dimethylpropanoyl)-1H-pyrazol-3-yl)-2-oxo-1-(2-oxo-2-phenylethyl)-1,2-dihydropyridine-4-carboxylic acid 5-(5-{[(5-chlorothiophen-2-yl)methyl]amino}-1-(2,2-dimethylpropanoyl)-1H-pyrazol-3-yl)-2-oxo-1-(2-oxoethyl)-1,2-dihydropyridine-4-carbonitrile 5-(5-{[(5-chlorothiophen-2-yl)methyl]amino}-1-(2,2-dimethylpropanoyl)-1H-pyrazol-3-yl)-2-oxo-1-[2-oxo-2-(1,3-thiazol-2-yl)ethyl]-1,2-dihydropyridine-3-carboxylic acid 5-(5-{[(5-chlorothiophen-2-yl)methyl]amino}-1-(2,2-dimethylpropanoyl)-1H-pyrazol-3-yl)-2-oxo-1-[2-oxo-2-(pyridin-2-yl)ethyl]-1,2-dihydropyridine-3-carbonitrile 5-(5-{[(5-chlorothiophen-2-yl)methyl]amino}-1-(2,2-dimethylpropanoyl)-1H-pyrazol-3-yl)-2-oxo-1-[2-oxo-2-(pyridin-4-yl)ethyl]-1,2-dihydropyridine-4-carbonitrile 5-(5-{[(5-chlorothiophen-2-yl)methyl]amino}-1-(2,2-dimethylpropanoyl)-1H-pyrazol-3-yl)-3-(dimethylamino)-1-[2-oxo-2-(pyrimidin-2-yl)ethyl]-1,2-dihydropyridin-2-one 5-(5-{[(5-chlorothiophen-2-yl)methyl]amino}-1-(2,2-dimethylpropanoyl)-1H-pyrazol-3-yl)-3-(morpholin-4-yl)-1-[2-(1,2-oxazol-5-yl)-2-oxoethyl]-1,2-dihydropyridin-2-one 5-(5-{[(5-chlorothiophen-2-yl)methyl]amino}-1-(2,2-dimethylpropanoyl)-1H-pyrazol-3-yl)-3-(morpholine-4-carbonyl)-1-(2-oxo-2-phenylethyl)-1,2-dihydropyridin-2-one 5-(5-{[(5-chlorothiophen-2-yl)methyl]amino}-1-(2,2-dimethylpropanoyl)-1H-pyrazol-3-yl)-3-ethenyl-1-[2-(1,2-oxazol-4-yl)-2-oxoethyl]-1,2-dihydropyridin-2-one 5-(5-{[(5-chlorothiophen-2-yl)methyl]amino}-1-(2,2-dimethylpropanoyl)-1H-pyrazol-3-yl)-3-fluoro-1-[2-oxo-2-(pyrimidin-2-yl)ethyl]-1,2-dihydropyridin-2-one 5-(5-{[(5-chlorothiophen-2-yl)methyl]amino}-1-(2,2-dimethylpropanoyl)-1H-pyrazol-3-yl)-3-methoxy-1-[2-oxo-2-(pyrimidin-5-yl)ethyl]-1,2-dihydropyridin-2-one 5-(5-{[(5-chlorothiophen-2-yl)methyl]amino}-1-(2,2-dimethylpropanoyl)-1H-pyrazol-3-yl)-4-(dimethylamino)-1-[2-(furan-3-yl)-2-oxoethyl]-1,2-dihydropyridin-2-one 5-(5-{[(5-chlorothiophen-2-yl)methyl]amino}-1-(2,2-dimethylpropanoyl)-1H-pyrazol-3-yl)-4-(morpholin-4-yl)-1-[2-(1,2-oxazol-4-yl)-2-oxoethyl]-1,2-dihydropyridin-2-one 5-(5-{[(5-chlorothiophen-2-yl)methyl]amino}-1-(2,2-dimethylpropanoyl)-1H-pyrazol-3-yl)-4-ethenyl-1-[2-oxo-2-(pyrimidin-4-yl)ethyl]-1,2-dihydropyridin-2-one 5-(5-{[(5-chlorothiophen-2-yl)methyl]amino}-1-(2,2-dimethylpropanoyl)-1H-pyrazol-3-yl)-4-hydroxy-1-[2-(1,2-oxazol-5-yl)-2-oxoethyl]-1,2-dihydropyridin-2-one APPENDIX A-continued Table B 5-(5-{[(5-chlorothiophen-2-yl)methyl]amino}-1-(2,2-dimethylpropanoyl)-1H-pyrazol-3-yl)-4-methoxy-1-[2-oxo-2-(pyridin-2-yl)ethyl]-1,2-dihydropyridin-2-one
5-(5-{[(5-chlorothiophen-2-yl)methyl]amino}-1-(2,2-dimethylpropanoyl)-1H-pyrazol-3-yl)-6-(dimethylamino)-1-[2-oxo-2-(pyridazin-4-yl)ethyl]-1,2-dihydropyridin-2-one
5-(5-{[(5-chlorothiophen-2-yl)methyl]amino}-1-(2,2-dimethylpropanoyl)-1H-pyrazol-3-yl)-6-(morpholin-4-yl)-1-[2-oxo-2-(pyrimidin-4-yl)ethyl]-1,2-dihydropyridin-2-one
5-(5-{[(5-chlorothiophen-2-yl)methyl]amino}-1-(2,2-dimethylpropanoyl)-1H-pyrazol-3-yl)-6-ethenyl-1-[2-oxo-2-(1,3-thiazol-2-yl)ethyl]-1,2-dihydropyridin-2-one
5-(5-{[(5-chlorothiophen-2-yl)methyl]amino}-1-(2,2-dimethylpropanoyl)-1H-pyrazol-3-yl)-6-fluoro-1-[2-(1,2-oxazol-5-yl)-2-oxoethyl]-1,2-dihydropyridin-2-one
5-(5-{[(5-chlorothiophen-2-yl)methyl]amino}-1-(2,2-dimethylpropanoyl)-1H-pyrazol-3-yl)-6-hydroxy-1-[2-(1,2-oxazol-4-yl)-2-oxoethyl]-1,2-dihydropyridin-2-one
5-(5-{[(5-chlorothiophen-2-yl)methyl]amino}-1-(2,2-dimethylpropanoyl)-1H-pyrazol-3-yl)-6-methoxy-1-[2-oxo-2-(pyridin-4-yl)ethyl]-1,2-dihydropyridin-2-one
5-(5-{[(5-chlorothiophen-2-yl)methyl]amino}-1-(2,2-dimethylpropanoyl)-1H-pyrazol-3-yl)-6-oxo-1-[2-oxo-2-(pyrazin-2-yl)ethyl]-1,6-dihydropyridine-3-carbonitrile
5-(5-{[(5-chlorothiophen-2-yl)methyl]amino}-1-(2,2-dimethylpropanoyl)-1H-pyrazol-3-yl)-6-oxo-1-[2-oxo-2-(pyridin-2-yl)ethyl]-1,6-dihydropyridine-2-carbonitrile
5-(5-{[(5-chlorothiophen-2-yl)methyl]amino}-1-(2,2-dimethylpropanoyl)-1H-pyrazol-3-yl)-6-oxo-1-[2-oxo-2-(pyridin-2-yl)ethyl]-1,6-dihydropyridine-3-carboxylic acid
5-(5-{[(5-chlorothiophen-2-yl)methyl]amino}-1-(2,2-dimethylpropanoyl)-1H-pyrazol-3-yl)-6-oxo-1-[2-oxo-2-(thiophen-3-yl)ethyl]-1,6-dihydropyridine-2-carboxylic acid
5-(5-{[(5-chlorothiophen-2-yl)methyl]amino}-1-(2,2-dimethylpropanoyl)-1H-pyrazol-3-yl)-N,N-dimethyl-1-[2-(1,2-oxazol-4-yl)-2-oxoethyl]-6-oxo-1,6-dihydropyridine-3-carboxamide
5-(5-{[(5-chlorothiophen-2-yl)methyl]amino}-1-(2,2-dimethylpropanoyl)-1H-pyrazol-3-yl)-N,N-dimethyl-2-oxo-1-[2-oxo-2-(pyrazin-2-yl)ethyl]-1,2-dihydropyridine-4-carboxamide
5-(5-{[(5-chlorothiophen-2-yl)methyl]amino}-1-(2,2-dimethylpropanoyl)-1H-pyrazol-3-yl)-N,N-dimethyl-2-oxo-1-[2-oxo-2-(pyridin-3-yl)ethyl]-1,2-dihydropyridine-3-carboxamide
5-(5-{[(5-chlorothiophen-2-yl)methyl]amino}-1-(2,2-dimethylpropanoyl)-1H-pyrazol-3-yl)-N,N-dimethyl-6-oxo-1-[2-oxo-2-(1,3-thiazol-2-yl)ethyl]-1,6-dihydropyridine-2-carboxamide
5-(5-{[(5-chlorothiophen-2-yl)methyl]amino}-1-(2-fluorobenzoyl)-1H-pyrazol-3-yl)-3-hydroxy-1-[2-oxo-2-(pyridin-2-yl)ethyl]-1,2-dihydropyridin-2-one
5-(5-{[(5-chlorothiophen-2-yl)methyl]amino}-1-(2-fluorobenzoyl)-1H-pyrazol-3-yl)-4-(dimethylamino)-1-[2-(1,3-thiazol-4-yl)ethyl]-1,2-dihydropyridin-2-one
5-(5-{[(5-chlorothiophen-2-yl)methyl]amino}-1-(2-fluorobenzoyl)-1H-pyrazol-3-yl)-6-(morpholin-4-yl)-1-[2-oxo-2-(thiophen-3-yl)ethyl]-1,2-dihydropyridin-2-one
5-(5-{[(5-chlorothiophen-2-yl)methyl]amino}-1-(2-methoxybenzoyl)-1H-pyrazol-3-yl)-1-[2-(1,3-oxazol-4-yl)ethyl]-3-(pyridin-2-yl)-1,2-dihydropyridin-2-one
5-(5-{[(5-chlorothiophen-2-yl)methyl]amino}-1-(2-methoxybenzoyl)-1H-pyrazol-3-yl)-1-[2-(furan-3-yl)-2-oxoethyl]-4-methoxy-1,2-dihydropyridin-2-one
5-(5-{[(5-chlorothiophen-2-yl)methyl]amino}-1-(2-methoxybenzoyl)-1H-pyrazol-3-yl)-1-[2-oxo-2-(pyridazin-4-yl)ethyl]-6-(pyridin-2-yl)-1,2-dihydropyridin-2-one
5-(5-{[(5-chlorothiophen-2-yl)methyl]amino}-1-(3-hydroxy-2,2-dimethylpropanoyl)-1H-pyrazol-3-yl)-4-(morpholin-4-yl)-1-[2-oxo-2-(pyrimidin-5-yl)ethyl]-1,2-dihydropyridin-2-one
5-(5-{[(5-chlorothiophen-2-yl)methyl]amino}-1-(3-hydroxy-2,2-dimethylpropanoyl)-1H-pyrazol-3-yl)-4-(pyridin-3-yl)-1-[2-(thiophen-2-yl)ethyl]-1,2-dihydropyridin-2-one
5-(5-{[(5-chlorothiophen-2-yl)methyl]amino}-1-(3-hydroxy-2,2-dimethylpropanoyl)-1H-pyrazol-3-yl)-6-ethenyl-1-[2-oxo-2-(pyridin-2-yl)ethyl]-1,2-dihydropyridin-2-one
5-(5-{[(5-chlorothiophen-2-yl)methyl]amino}-1-(3-hydroxy-2,2-dimethylpropanoyl)-1H-pyrazol-3-yl)-6-methoxy-1-(pyrimidin-5-ylmethyl)-1,2-dihydropyridin-2-one
5-(5-{[(5-chlorothiophen-2-yl)methyl]amino}-1-(3-methoxy-2,2-dimethylpropanoyl)-1H-pyrazol-3-yl)-1-[2-(morpholin-4-yl)-2-oxoethyl]-3-(2-phenylethynyl)-1,2-dihydropyridin-2-one
5-(5-{[(5-chlorothiophen-2-yl)methyl]amino}-1-(3-methoxy-2,2-dimethylpropanoyl)-1H-pyrazol-3-yl)-4-fluoro-1-(pyrazin-2-ylmethyl)-1,2-dihydropyridin-2-one APPENDIX A-continued Table B 5-(5-{[(5-chlorothiophen-2-yl)methyl]amino}-1-(3-methoxy-2,2-
dimethylpropanoyl)-1H-pyrazol-3-yl)-6-fluoro-1-[2-(furan-3-yl)-2-oxoethyl]-1,2-
dihydropyridin-2-one
5-(5-{[(5-chlorothiophen-2-yl)methyl]amino}-1-(furan-2-carbonyl)-1H-pyrazol-
3-yl)-1-(1,3-oxazol-5-ylmethyl)-3-phenyl-1,2-dihydropyridin-2-one
5-(5-{[(5-chlorothiophen-2-yl)methyl]amino}-1-(furan-2-carbonyl)-1H-pyrazol-
3-yl)-1-[2-(morpholin-4-yl)ethyl]-4-(pyridin-2-yl)-1,2-dihydropyridin-2-one
5-(5-{[(5-chlorothiophen-2-yl)methyl]amino}-1-(furan-2-carbonyl)-1H-pyrazol-
3-yl)-3-(2-phenylethynyl)-1-(pyrimidin-5-ylmethyl)-1,2-dihydropyridin-2-one
5-(5-{[(5-chlorothiophen-2-yl)methyl]amino}-1-(furan-2-carbonyl)-1H-pyrazol-
3-yl)-3-fluoro-1-[2-(1,3-thiazol-5-yl)ethyl]-1,2-dihydropyridin-2-one
5-(5-{[(5-chlorothiophen-2-yl)methyl]amino}-1-(furan-2-carbonyl)-1H-pyrazol-
3-yl)-4-(morpholin-4-yl)-1-[2-oxo-2-(1,2-thiazol-4-yl)ethyl]-1,2-dihydropyridin-
2-one
5-(5-{[(5-chlorothiophen-2-yl)methyl]amino}-1-(furan-2-carbonyl)-1H-pyrazol-
3-yl)-4-fluoro-1-[2-(1,3-oxazol-5-yl)ethyl]-1,2-dihydropyridin-2-one
5-(5-{[(5-chlorothiophen-2-yl)methyl]amino}-1-(furan-2-carbonyl)-1H-pyrazol-
3-yl)-6-ethenyl-1-[2-oxo-2-(1,3-thiazol-5-yl)ethyl]-1,2-dihydropyridin-2-one
5-(5-{[(5-chlorothiophen-2-yl)methyl]amino}-1-(furan-3-carbonyl)-1H-pyrazol-
3-yl)-1-(2-oxo-2-phenylethyl)-3-(pyridin-3-yl)-1,2-dihydropyridin-2-one
5-(5-{[(5-chlorothiophen-2-yl)methyl]amino}-1-(furan-3-carbonyl)-1H-pyrazol-
3-yl)-1-(furan-3-ylmethyl)-4-phenyl-1,2-dihydropyridin-2-one
5-(5-{[(5-chlorothiophen-2-yl)methyl]amino}-1-(furan-3-carbonyl)-1H-pyrazol-
3-yl)-1-(pyridazin-4-ylmethyl)-6-(pyridin-4-yl)-1,2-dihydropyridin-2-one
5-(5-{[(5-chlorothiophen-2-yl)methyl]amino}-1-(furan-3-carbonyl)-1H-pyrazol-
3-yl)-1-[2-(1,3-oxazol-2-yl)ethyl]-6-(pyridin-2-yl)-1,2-dihydropyridin-2-one
5-(5-{[(5-chlorothiophen-2-yl)methyl]amino}-1-(furan-3-carbonyl)-1H-pyrazol-
3-yl)-1-[2-(furan-2-yl)-2-oxoethyl]-4-phenyl-1,2-dihydropyridin-2-one
5-(5-{[(5-chlorothiophen-2-yl)methyl]amino}-1-(furan-3-carbonyl)-1H-pyrazol-
3-yl)-4-(morpholin-4-yl)-1-(1,2-oxazol-5-ylmethyl)-1,2-dihydropyridin-2-one
5-(5-{[(5-chlorothiophen-2-yl)methyl]amino}-1-(thiophene-2-carbonyl)-1H-
pyrazol-3-yl)-1-(morpholin-4-ylmethyl)-4-(pyridin-4-yl)-1,2-dihydropyridin-2-
one
5-(5-{[(5-chlorothiophen-2-yl)methyl]amino}-1-(thiophene-2-carbonyl)-1H-
pyrazol-3-yl)-1-[2-(furan-2-yl)-2-oxoethyl]-6-(pyridin-3-yl)-1,2-dihydropyridin-
2-one
5-(5-{[(5-chlorothiophen-2-yl)methyl]amino}-1-(thiophene-2-carbonyl)-1H-
pyrazol-3-yl)-2-oxo-1-(2-oxo-2-phenylethyl)-1,2-dihydropyridine-4-carbonitrile
5-(5-{[(5-chlorothiophen-2-yl)methyl]amino}-1-(thiophene-2-carbonyl)-1H-
pyrazol-3-yl)-3-(dimethylamino)-1-[2-oxo-2-(1,3-thiazol-2-yl)ethyl]-1,2-
dihydropyridin-2-one
5-(5-{[(5-chlorothiophen-2-yl)methyl]amino}-1-(thiophene-2-carbonyl)-1H-
pyrazol-3-yl)-3-(morpholin-4-yl)-1-(thiophen-2-ylmethyl)-1,2-dihydropyridin-2-
one
5-(5-{[(5-chlorothiophen-2-yl)methyl]amino}-1-(thiophene-2-carbonyl)-1H-
pyrazol-3-yl)-4-hydroxy-1-[2-(pyrazin-2-yl)ethyl]-1,2-dihydropyridin-2-one
5-(5-{[(5-chlorothiophen-2-yl)methyl]amino}-1-(thiophene-2-carbonyl)-1H-
pyrazol-3-yl)-6-(dimethylamino)-1-ethyl-1,2-dihydropyridin-2-one
5-(5-{[(5-chlorothiophen-2-yl)methyl]amino}-1-(thiophene-3-carbonyl)-1H-
pyrazol-3-yl)-1-[2-oxo-2-(pyridin-3-yl)ethyl]-3-(2-phenylethynyl)-1,2-
dihydropyridin-2-one
5-(5-{[(5-chlorothiophen-2-yl)methyl]amino}-1-(thiophene-3-carbonyl)-1H-
pyrazol-3-yl)-3-methoxy-1-[2-(1,3-oxazol-5-yl)ethyl]-1,2-dihydropyridin-2-one
5-(5-{[(5-chlorothiophen-2-yl)methyl]amino}-1-(thiophene-3-carbonyl)-1H-
pyrazol-3-yl)-6-(morpholin-4-yl)-1-[2-(1,2-thiazol-3-yl)ethyl]-1,2-
dihydropyridin-2-one
5-(5-{[(5-chlorothiophen-2-yl)methyl]amino}-1-(thiophene-3-carbonyl)-1H-
pyrazol-3-yl)-6-fluoro-1-[2-oxo-2-(piperidin-1-yl)ethyl]-1,2-dihydropyridin-2-
one
5-(5-{[(5-chlorothiophen-2-yl)methyl]amino}-1-[2-(trifluoromethyl)benzoyl]-1H-
pyrazol-3-yl)-1-(furan-3-ylmethyl)-6-(pyridin-3-yl)-1,2-dihydropyridin-2-one
5-(5-{[(5-chlorothiophen-2-yl)methyl]amino}-1-[2-(trifluoromethyl)benzoyl]-1H-
pyrazol-3-yl)-1-[2-(furan-3-yl)-2-oxoethyl]-3-(pyridin-2-yl)-1,2-dihydropyridin-
2-one
5-(5-{[(5-chlorothiophen-2-yl)methyl]amino}-1-[2-(trifluoromethyl)benzoyl]-1H-
pyrazol-3-yl)-1-[2-oxo-2-(pyridazin-4-yl)ethyl]-4-(2-phenylethynyl)-1,2-
dihydropyridin-2-one
5-(5-{[(5-chlorothiophen-2-yl)methyl]amino}-1-[2-(trifluoromethyl)benzoyl]-1H-
pyrazol-3-yl)-3-methoxy-1-(pyrazin-2-ylmethyl)-1,2-dihydropyridin-2-one
5-(5-{[(5-chlorothiophen-2-yl)methyl]amino}-1-[3-(hydroxymethyl)benzoyl]-
1H-pyrazol-3-yl)-4-ethenyl-1-[2-(1,2-thiazol-3-yl)ethyl]-1,2-dihydropyridin-2-
one
5-(5-{[(5-chlorothiophen-2-yl)methyl]amino}-1-[3-(hydroxymethyl)benzoyl]-
1H-pyrazol-3-yl)-4-fluoro-1-[2-(4-methylpiperazin-1-yl)-2-oxoethyl]-1,2-
dihydropyridin-2-one
5-(5-{[(5-chlorothiophen-2-yl)methyl]amino}-1-[3-(hydroxymethyl)benzoyl]-
1H-pyrazol-3-yl)-4-hydroxy-1-methyl-1,2-dihydropyridin-2-one APPENDIX A-continued Table B 5-(5-{[(5-chlorothiophen-2-yl)methyl]amino}-1-[3-(hydroxymethyl)benzoyl]-1H-pyrazol-3-yl)-6-hydroxy-1-(pyrimidin-4-ylmethyl)-1,2-dihydropyridin-2-one
5-(5-{[(5-chlorothiophen-2-yl)methyl]amino}-1-[3-(hydroxymethyl)benzoyl]-1H-pyrazol-3-yl)-6-methoxy-1-[2-(morpholin-4-yl)ethyl]-1,2-dihydropyridin-2-one
5-(5-{[(5-chlorothiophen-2-yl)methyl]amino}-1-[3-(hydroxymethyl)benzoyl]-1H-pyrazol-3-yl)-6-methoxy-1-[2-oxo-2-(pyridin-3-yl)ethyl]-1,2-dihydropyridin-2-one
5-(5-{[(5-chlorothiophen-2-yl)methyl]amino}-1-[3-(hydroxymethyl)benzoyl]-1H-pyrazol-3-yl)-6-oxo-1-(2-phenylethyl)-1,6-dihydropyridine-3-carbonitrile
5-(5-{[(5-chlorothiophen-2-yl)methyl]amino}-1-[4-(hydroxymethyl)benzoyl]-1H-pyrazol-3-yl)-1-[2-oxo-2-(pyrazin-2-yl)ethyl]-6-(2-phenylethynyl)-1,2-dihydropyridin-2-one
5-(5-{[(5-chlorothiophen-2-yl)methyl]amino}-1-[4-(hydroxymethyl)benzoyl]-1H-pyrazol-3-yl)-1-[2-oxo-2-(pyridin-3-yl)ethyl]-4-(pyridin-2-yl)-1,2-dihydropyridin-2-one
5-(5-{[(5-chlorothiophen-2-yl)methyl]amino}-1-[4-(hydroxymethyl)benzoyl]-1H-pyrazol-3-yl)-3-methoxy-1-[2-(4-methylpiperazin-1-yl)-2-oxoethyl]-1,2-dihydropyridin-2-one
5-(5-{[(5-chlorothiophen-2-yl)methyl]amino}-1-[4-(hydroxymethyl)benzoyl]-4-methoxy-1H-pyrazol-3-yl)-4-fluoro-1-(1,2-thiazol-5-ylmethyl)-1,2-dihydropyridin-2-one
5-(5-{[(5-chlorothiophen-2-yl)methyl]amino}-4-fluoro-1-(1,2-oxazole-3-carbonyl)-1H-pyrazol-3-yl)-3-fluoro-1-(pyridin-2-ylmethyl)-1,2-dihydropyridin-2-one
5-(5-{[(5-chlorothiophen-2-yl)methyl]amino}-4-fluoro-1-(1,2-oxazole-3-carbonyl)-1H-pyrazol-3-yl)-6-phenyl-1-(pyridin-3-ylmethyl)-1,2-dihydropyridin-2-one
5-(5-{[(5-chlorothiophen-2-yl)methyl]amino}-4-fluoro-1-(1,2-thiazole-3-carbonyl)-1H-pyrazol-3-yl)-1-methyl-6-oxo-1,6-dihydropyridine-3-carbonitrile
5-(5-{[(5-chlorothiophen-2-yl)methyl]amino}-4-fluoro-1-(1,2-thiazole-3-carbonyl)-1H-pyrazol-3-yl)-3-(pyridin-2-yl)-1-(pyridin-4-ylmethyl)-1,2-dihydropyridin-2-one
5-(5-{[(5-chlorothiophen-2-yl)methyl]amino}-4-fluoro-1-(1,2-thiazole-3-carbonyl)-1H-pyrazol-3-yl)-4-(2-phenylethynyl)-1-(thiophen-3-ylmethyl)-1,2-dihydropyridin-2-one
5-(5-{[(5-chlorothiophen-2-yl)methyl]amino}-4-fluoro-1-(1,2-thiazole-5-carbonyl)-1H-pyrazol-3-yl)-6-(pyridin-2-yl)-1-(thiophen-3-ylmethyl)-1,2-dihydropyridin-2-one
5-(5-{[(5-chlorothiophen-2-yl)methyl]amino}-4-fluoro-1-(1,3-oxazole-2-carbonyl)-1H-pyrazol-3-yl)-4-methoxy-1-(pyridin-4-ylmethyl)-1,2-dihydropyridin-2-one
5-(5-{[(5-chlorothiophen-2-yl)methyl]amino}-4-fluoro-1-(1,3-thiazole-2-carbonyl)-1H-pyrazol-3-yl)-1-(furan-3-ylmethyl)-3-(pyridin-4-yl)-1,2-dihydropyridin-2-one
5-(5-{[(5-chlorothiophen-2-yl)methyl]amino}-4-fluoro-1-(furan-2-carbonyl)-1H-pyrazol-3-yl)-4-(dimethylamino)-1-(pyridazin-4-ylmethyl)-1,2-dihydropyridin-2-one
5-(5-{[(5-chlorothiophen-2-yl)methyl]amino}-4-fluoro-1-[4-(hydroxymethyl)benzoyl]-1H-pyrazol-3-yl)-2-oxo-1-(pyridazin-4-ylmethyl)-1,2-dihydropyridine-3-carbonitrile
5-(5-{[(5-chlorothiophen-2-yl)methyl]amino}-4-fluoro-1-[4-(hydroxymethyl)benzoyl]-1H-pyrazol-3-yl)-3-hydroxy-1-(1,2-oxazol-4-ylmethyl)-1,2-dihydropyridin-2-one
5-(5-{[(5-chlorothiophen-2-yl)methyl]amino}-4-methoxy-1-(1,2-oxazole-3-carbonyl)-1H-pyrazol-3-yl)-3-(morpholin-4-yl)-1-(pyrimidin-4-ylmethyl)-1,2-dihydropyridin-2-one
5-(5-{[(5-chlorothiophen-2-yl)methyl]amino}-4-methoxy-1-(1,2-thiazole-3-carbonyl)-1H-pyrazol-3-yl)-6-methoxy-1-(1,2-thiazol-4-ylmethyl)-1,2-dihydropyridin-2-one
5-(5-{[(5-chlorothiophen-2-yl)methyl]amino}-4-methoxy-1-(1,3-oxazole-4-carbonyl)-1H-pyrazol-3-yl)-3-methoxy-1-(1,2-thiazol-5-ylmethyl)-1,2-dihydropyridin-2-one
5-(5-{[(5-chlorothiophen-2-yl)methyl]amino}-4-methoxy-1-(1,3-oxazole-4-carbonyl)-1H-pyrazol-3-yl)-4-ethenyl-1-(1,3-thiazol-2-ylmethyl)-1,2-dihydropyridin-2-one
5-(5-{[(5-chlorothiophen-2-yl)methyl]amino}-4-methoxy-1-(1,3-thiazole-5-carbonyl)-1H-pyrazol-3-yl)-6-(dimethylamino)-1-(pyrazin-2-ylmethyl)-1,2-dihydropyridin-2-one
5-(5-{[(5-chlorothiophen-2-yl)methyl]amino}-4-methoxy-1-[2-(trifluoromethyl)benzoyl]-1H-pyrazol-3-yl)-6-oxo-1-(1,3-thiazol-2-ylmethyl)-1,6-dihydropyridine-2-carbonitrile
5-(5-{[(5-chlorothiophen-2-yl)methyl]sulfanyl}-1-(2,2-dimethylpropanoyl)-1H-pyrazol-3-yl)-1-(2-oxo-2-phenylethyl)-6-(pyridin-2-yl)-1,2-dihydropyridin-2-one
5-(5-{[(5-chlorothiophen-2-yl)methyl]sulfanyl}-1-(2,2-dimethylpropanoyl)-1H-pyrazol-3-yl)-1-[2-(1,3-oxazol-5-yl)-2-oxoethyl]-6-oxo-1,6-dihydropyridine-3-carbonitrile

APPENDIX A-continued

Table B 5-(5-{[(5-chlorothiophen-2-yl)methyl]sulfanyl}-1-(2,2-dimethylpropanoyl)-1H-pyrazol-3-yl)-1-[2-(4-methylpiperazin-1-yl)-2-oxoethyl]-3-(pyridin-4-yl)-1,2-dihydropyridin-2-one 5-(5-{[(5-chlorothiophen-2-yl)methyl]sulfanyl}-1-(2,2-dimethylpropanoyl)-1H-pyrazol-3-yl)-1-[2-(4-methylpiperazin-1-yl)-2-oxoethyl]-6-(2-phenylethynyl)-1,2-dihydropyridin-2-one 5-(5-{[(5-chlorothiophen-2-yl)methyl]sulfanyl}-1-(2,2-dimethylpropanoyl)-1H-pyrazol-3-yl)-1-[2-(furan-3-yl)-2-oxoethyl]-3-(2-phenylethynyl)-1,2-dihydropyridin-2-one 5-(5-{[(5-chlorothiophen-2-yl)methyl]sulfanyl}-1-(2,2-dimethylpropanoyl)-1H-pyrazol-3-yl)-1-[2-oxo-2-(1,3-thiazol-2-yl)ethyl]-4-(pyridin-2-yl)-1,2-dihydropyridin-2-one 5-(5-{[(5-chlorothiophen-2-yl)methyl]sulfanyl}-1-(2,2-dimethylpropanoyl)-1H-pyrazol-3-yl)-1-[2-oxo-2-(pyrazin-2-yl)ethyl]-6-(pyridin-4-yl)-1,2-dihydropyridin-2-one 5-(5-{[(5-chlorothiophen-2-yl)methyl]sulfanyl}-1-(2,2-dimethylpropanoyl)-1H-pyrazol-3-yl)-1-[2-oxo-2-(pyridazin-4-yl)ethyl]-4-(2-phenylethynyl)-1,2-dihydropyridin-2-one 5-(5-{[(5-chlorothiophen-2-yl)methyl]sulfanyl}-1-(2,2-dimethylpropanoyl)-1H-pyrazol-3-yl)-1-[2-oxo-2-(pyridin-3-yl)ethyl]-4-(pyridin-4-yl)-1,2-dihydropyridin-2-one 5-(5-{[(5-chlorothiophen-2-yl)methyl]sulfanyl}-1-(2,2-dimethylpropanoyl)-1H-pyrazol-3-yl)-1-[2-oxo-2-(pyrimidin-4-yl)ethyl]-3-(pyridin-2-yl)-1,2-dihydropyridin-2-one 5-(5-{[(5-chlorothiophen-2-yl)methyl]sulfanyl}-1-(2,2-dimethylpropanoyl)-1H-pyrazol-3-yl)-3-(morpholin-4-yl)-1-[2-(1,2-oxazol-5-yl)-2-oxoethyl]-1,2-dihydropyridin-2-one 5-(5-{[(5-chlorothiophen-2-yl)methyl]sulfanyl}-1-(2,2-dimethylpropanoyl)-1H-pyrazol-3-yl)-3-fluoro-1-[2-oxo-2-(pyrimidin-2-yl)ethyl]-1,2-dihydropyridin-2-one 5-(5-{[(5-chlorothiophen-2-yl)methyl]sulfanyl}-1-(2,2-dimethylpropanoyl)-1H-pyrazol-3-yl)-3-methoxy-1-[2-oxo-2-(pyrimidin-5-yl)ethyl]-1,2-dihydropyridin-2-one 5-(5-{[(5-chlorothiophen-2-yl)methyl]sulfanyl}-1-(2,2-dimethylpropanoyl)-1H-pyrazol-3-yl)-4-(morpholin-4-yl)-1-[2-(1,2-oxazol-4-yl)-2-oxoethyl]-1,2-dihydropyridin-2-one 5-(5-{[(5-chlorothiophen-2-yl)methyl]sulfanyl}-1-(2,2-dimethylpropanoyl)-1H-pyrazol-3-yl)-4-methoxy-1-[2-oxo-2-(pyridin-2-yl)ethyl]-1,2-dihydropyridin-2-one 5-(5-{[(5-chlorothiophen-2-yl)methyl]sulfanyl}-1-(2,2-dimethylpropanoyl)-1H-pyrazol-3-yl)-6-(morpholin-4-yl)-1-[2-oxo-2-(pyrimidin-4-yl)ethyl]-1,2-dihydropyridin-2-one 5-(5-{[(5-chlorothiophen-2-yl)methyl]sulfanyl}-1-(2,2-dimethylpropanoyl)-1H-pyrazol-3-yl)-6-fluoro-1-[2-(1,2-oxazol-5-yl)-2-oxoethyl]-1,2-dihydropyridin-2-one 5-(5-{[(5-chlorothiophen-2-yl)methyl]sulfanyl}-1-(2,2-dimethylpropanoyl)-1H-pyrazol-3-yl)-6-methoxy-1-[2-oxo-2-(pyridin-4-yl)ethyl]-1,2-dihydropyridin-2-one 5-[1-(2-aminobenzoyl)-5-{[(5-chlorothiophen-2-yl)methyl]amino}-1H-pyrazol-3-yl]-1-[2-(1,2-oxazol-5-yl)-2-oxoethyl]-3-(pyridin-4-yl)-1,2-dihydropyridin-2-one 5-[1-(2-aminobenzoyl)-5-{[(5-chlorothiophen-2-yl)methyl]amino}-1H-pyrazol-3-yl]-3-bromo-1-[2-(1,3-oxazol-2-yl)ethyl]-1,2-dihydropyridin-2-one 5-[1-(2-aminobenzoyl)-5-{[(5-chlorothiophen-2-yl)methyl]amino}-1H-pyrazol-3-yl]-4-(dimethylamino)-1-[2-(1,2-oxazol-4-yl)-2-oxoethyl]-1,2-dihydropyridin-2-one 5-[1-(2-aminobenzoyl)-5-{[(5-chlorothiophen-2-yl)methyl]amino}-1H-pyrazol-3-yl]-4-(pyridin-2-yl)-1-(pyrimidin-5-ylmethyl)-1,2-dihydropyridin-2-one 5-[1-(2-aminobenzoyl)-5-{[(5-chlorothiophen-2-yl)methyl]amino}-1H-pyrazol-3-yl]-6-chloro-1-methyl-1,2-dihydropyridin-2-one 5-[1-(2-aminobenzoyl)-5-{[(5-chlorothiophen-2-yl)methyl]amino}-1H-pyrazol-3-yl]-6-oxo-1-[2-oxo-2-(pyrazin-2-yl)ethyl]-1,6-dihydropyridine-3-carbonitrile 5-[1-(2-aminobenzoyl)-5-{[(5-chlorothiophen-2-yl)methyl]amino}-4-methoxy-1H-pyrazol-3-yl]-6-(2-phenylethynyl)-1-(1,3-thiazol-5-ylmethyl)-1,2-dihydropyridin-2-one 5-[1-(2-chlorobenzoyl)-5-{[(5-chlorothiophen-2-yl)methyl]amino}-1H-pyrazol-3-yl]-3-ethenyl-1-[2-oxo-2-(pyrimidin-5-yl)ethyl]-1,2-dihydropyridin-2-one 5-[1-(2-chlorobenzoyl)-5-{[(5-chlorothiophen-2-yl)methyl]amino}-1H-pyrazol-3-yl]-6-hydroxy-1-[2-oxo-2-(pyridin-4-yl)ethyl]-1,2-dihydropyridin-2-one 5-[1-(2-chlorobenzoyl)-5-{[(5-chlorothiophen-2-yl)methyl]amino}-4-fluoro-1H-pyrazol-3-yl]-6-(morpholin-4-yl)-1-(1,3-thiazol-2-ylmethyl)-1,2-dihydropyridin-2-one 5-[1-(2-chlorobenzoyl)-5-{[(5-chlorothiophen-2-yl)methyl]amino}-4-methoxy-1H-pyrazol-3-yl]-4-(pyridin-2-yl)-1-(1,2-thiazol-4-ylmethyl)-1,2-dihydropyridin-2-one 5-benzoyl-3-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-1,2-dihydropyridin-2-one

APPENDIX A-continued

Table B 5-benzoyl-4-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-1,2-dihydropyridin-2-one 5-benzoyl-6-(5-{[(5-chlorothiophen-2-yl)methyl]amino}-1-(2,2-dimethylpropanoyl)-1H-pyrazol-3-yl)-1-[2-oxo-2-(thiophen-3-yl)ethyl]-1,2-dihydropyridin-2-one 5-bromo-3-(5-{[(5-chlorothiophen-2-yl)methyl](methyl)amino}-1-(2,2-dimethylpropanoyl)-1H-pyrazol-3-yl)-1-[2-oxo-2-(pyridazin-4-yl)ethyl]-1,2-dihydropyridin-2-one 5-bromo-3-(5-{[(5-chlorothiophen-2-yl)methyl]amino}-1-(1,3-thiazole-2-carbonyl)-1H-pyrazol-3-yl)-1-(2-oxo-2-phenylethyl)-1,2-dihydropyridin-2-one 5-bromo-3-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-1,2-dihydropyridin-2-one 5-bromo-3-(5-{[(5-chlorothiophen-2-yl)methyl]amino}-1-(3-hydroxy-2,2-dimethylpropanoyl)-1H-pyrazol-3-yl)-1-[2-(pyrazin-2-yl)ethyl]-1,2-dihydropyridin-2-one 5-bromo-4-(5-{[(5-chlorothiophen-2-yl)methyl]amino}-1-(1,2-thiazole-3-carbonyl)-1H-pyrazol-3-yl)-1-[2-(morpholin-4-yl)ethyl]-1,2-dihydropyridin-2-one 5-bromo-4-(5-{[(5-chlorothiophen-2-yl)methyl]amino}-1-(1,3-oxazole-5-carbonyl)-1H-pyrazol-3-yl)-1-[2-oxo-2-(pyrimidin-2-yl)ethyl]-1,2-dihydropyridin-2-one 5-bromo-4-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-1,2-dihydropyridin-2-one 5-bromo-4-(5-{[(5-chlorothiophen-2-yl)methyl]amino}-1-(2-methoxybenzoyl)-1H-pyrazol-3-yl)-1-[2-oxo-2-(pyridin-3-yl)ethyl]-1,2-dihydropyridin-2-one 5-bromo-4-(5-{[(5-chlorothiophen-2-yl)methyl]amino}-4-fluoro-1-(1,3-thiazole-2-carbonyl)-1H-pyrazol-3-yl)-1-(1,2-thiazol-4-ylmethyl)-1,2-dihydropyridin-2-one 5-bromo-4-(5-{[(5-chlorothiophen-2-yl)methyl]sulfanyl}-1-(2,2-dimethylpropanoyl)-1H-pyrazol-3-yl)-1-[2-(4-methylpiperazin-1-yl)-2-oxoethyl]-1,2-dihydropyridin-2-one 5-bromo-6-(5-{[(5-chlorothiophen-2-yl)methyl]amino}-1-(1,3-thiazole-2-carbonyl)-1H-pyrazol-3-yl)-1-[2-(4-methylpiperazin-1-yl)-2-oxoethyl]-1,2-dihydropyridin-2-one 5-bromo-6-(5-{[(5-chlorothiophen-2-yl)methyl]amino}-1-(2,2-dimethylpropanoyl)-1H-pyrazol-3-yl)-1-[2-(1,3-oxazol-4-yl)-2-oxoethyl]-1,2-dihydropyridin-2-one 5-bromo-6-(5-{[(5-chlorothiophen-2-yl)methyl]amino}-1-[2-(trifluoromethyl)benzoyl]-1H-pyrazol-3-yl)-1-[2-(1,3-oxazol-5-yl)-2-oxoethyl]-1,2-dihydropyridin-2-one 5-bromo-6-(5-{[(5-chlorothiophen-2-yl)methyl]amino}-4-fluoro-1-(1,3-oxazole-5-carbonyl)-1H-pyrazol-3-yl)-1-(pyrazin-2-ylmethyl)-1,2-dihydropyridin-2-one 5-bromo-6-(5-{[(5-chlorothiophen-2-yl)methyl]sulfanyl}-1-(2,2-dimethylpropanoyl)-1H-pyrazol-3-yl)-1-[2-(1,3-oxazol-4-yl)-2-oxoethyl]-1,2-dihydropyridin-2-one 5-chloro-3-(5-{[(5-chlorothiophen-2-yl)methyl]amino}-1-(1,2-thiazole-3-carbonyl)-1H-pyrazol-3-yl)-1-[2-oxo-2-(pyrazin-2-yl)ethyl]-1,2-dihydropyridin-2-one 5-chloro-3-(5-{[(5-chlorothiophen-2-yl)methyl]amino}-1-(2,2-dimethylpropanoyl)-1H-pyrazol-3-yl)-1-[2-(1,2-oxazol-3-yl)-2-oxoethyl]-1,2-dihydropyridin-2-one 5-chloro-3-(5-{[(5-chlorothiophen-2-yl)methyl]amino}-1-(2,2-dimethylpropanoyl)-4-methoxy-1H-pyrazol-3-yl)-1-(pyridin-2-ylmethyl)-1,2-dihydropyridin-2-one 5-chloro-3-(5-{[(5-chlorothiophen-2-yl)methyl]sulfanyl}-1-(2,2-dimethylpropanoyl)-1H-pyrazol-3-yl)-1-[2-(1,3-oxazol-4-yl)-2-oxoethyl]-1,2-dihydropyridin-2-one 5-chloro-3-[1-(2-chlorobenzoyl)-5-{[(5-chlorothiophen-2-yl)methyl]amino}-1H-pyrazol-3-yl]-1-[2-(1,3-thiazol-5-yl)ethyl]-1,2-dihydropyridin-2-one 5-chloro-4-(5-{[(5-chlorothiophen-2-yl)methyl](methyl)amino}-1-(2,2-dimethylpropanoyl)-1H-pyrazol-3-yl)-1-[2-oxo-2-(thiophen-2-yl)ethyl]-1,2-dihydropyridin-2-one 5-chloro-4-(5-{[(5-chlorothiophen-2-yl)methyl]amino}-1-(1,3-oxazole-4-carbonyl)-1H-pyrazol-3-yl)-1-[2-(morpholin-4-yl)-2-oxoethyl]-1,2-dihydropyridin-2-one 5-chloro-4-(5-{[(5-chlorothiophen-2-yl)methyl]amino}-1-(1,3-thiazole-2-carbonyl)-1H-pyrazol-3-yl)-1-[2-(pyrimidin-5-yl)ethyl]-1,2-dihydropyridin-2-one 5-chloro-4-(5-{[(5-chlorothiophen-2-yl)methyl]amino}-1-(2,2-dimethylpropanoyl)-1H-pyrazol-3-yl)-1-[2-oxo-2-(thiophen-3-yl)ethyl]-1,2-dihydropyridin-2-one 5-chloro-4-(5-{[(5-chlorothiophen-2-yl)methyl]amino}-1-(2-fluorobenzoyl)-1H-pyrazol-3-yl)-1-[2-oxo-2-(1,2-thiazol-4-yl)ethyl]-1,2-dihydropyridin-2-one 5-chloro-4-(5-{[(5-chlorothiophen-2-yl)methyl]amino}-4-fluoro-1-(1,3-oxazole-5-carbonyl)-1H-pyrazol-3-yl)-1-(furan-2-ylmethyl)-1,2-dihydropyridin-2-one APPENDIX A-continued Table B 5-chloro-6-(5-{[(5-chlorothiophen-2-yl)methyl](methyl)amino}-1-(2,2-dimethylpropanoyl)-1H-pyrazol-3-yl)-1-[2-(furan-3-yl)-2-oxoethyl]-1,2-dihydropyridin-2-one
5-chloro-6-(5-{[(5-chlorothiophen-2-yl)methyl]amino}-1-(1,2-thiazole-3-carbonyl)-1H-pyrazol-3-yl)-1-[2-oxo-2-(1,2-thiazol-5-yl)ethyl]-1,2-dihydropyridin-2-one
5-chloro-6-(5-{[(5-chlorothiophen-2-yl)methyl]amino}-1-(1,3-thiazole-5-carbonyl)-1H-pyrazol-3-yl)-1-(2-phenylethyl)-1,2-dihydropyridin-2-one
5-chloro-6-(5-{[(5-chlorothiophen-2-yl)methyl]amino}-4-methoxy-1-(1,2-oxazole-4-carbonyl)-1H-pyrazol-3-yl)-1-methyl-1,2-dihydropyridin-2-one
5-{[(5-chlorothiophen-2-yl)methyl]amino}-1-(1,2-oxazole-4-carbonyl)-3-[6-oxo-5-(pyridin-2-yl)-1-(1,2-thiazol-5-ylmethyl)-1,6-dihydropyridin-2-yl]-1H-pyrazole-4-carbonitrile
5-{[(5-chlorothiophen-2-yl)methyl]amino}-1-(1,3-oxazole-4-carbonyl)-3-[6-oxo-4-phenyl-1-(piperidin-1-ylmethyl)-1,6-dihydropyridin-3-yl]-1H-pyrazole-4-carbonitrile
5-{[(5-chlorothiophen-2-yl)methyl]amino}-1-(2-fluorobenzoyl)-3-[1-(furan-2-ylmethyl)-4-(morpholin-4-yl)-6-oxo-1,6-dihydropyridin-3-yl]-1H-pyrazole-4-carbonitrile
5-{[(5-chlorothiophen-2-yl)methyl]amino}-1-(2-fluorobenzoyl)-3-[4-methoxy-6-oxo-1-(thiophen-3-ylmethyl)-1,6-dihydropyridin-2-yl]-1H-pyrazole-4-carbonitrile
5-{[(5-chlorothiophen-2-yl)methyl]amino}-1-(2-methoxybenzoyl)-3-[6-oxo-1-(pyrazin-2-ylmethyl)-5-(pyridin-3-yl)-1,6-dihydropyridin-3-yl]-1H-pyrazole-4-carbonitrile
5-{[(5-chlorothiophen-2-yl)methyl]amino}-1-(3-hydroxy-2,2-dimethylpropanoyl)-3-[2-oxo-5-(pyridin-4-yl)-1-(1,3-thiazol-2-ylmethyl)-1,2-dihydropyridin-3-yl]-1H-pyrazole-4-carbonitrile
5-{[(5-chlorothiophen-2-yl)methyl]amino}-1-(3-hydroxy-2,2-dimethylpropanoyl)-3-[6-oxo-4-phenyl-1-(pyridazin-4-ylmethyl)-1,6-dihydropyridin-2-yl]-1H-pyrazole-4-carbonitrile
5-{[(5-chlorothiophen-2-yl)methyl]amino}-1-(furan-3-carbonyl)-3-[1-(furan-3-ylmethyl)-6-oxo-3-(pyridin-3-yl)-1,6-dihydropyridin-2-yl]-1H-pyrazole-4-carbonitrile
5-{[(5-chlorothiophen-2-yl)methyl]amino}-1-(furan-3-carbonyl)-3-[2-oxo-3-phenyl-1-(1,3-thiazol-4-ylmethyl)-1,2-dihydropyridin-4-yl]-1H-pyrazole-4-carbonitrile
5-{[(5-chlorothiophen-2-yl)methyl]amino}-1-(furan-3-carbonyl)-3-[5-hydroxy-2-oxo-1-(1,2-thiazol-5-ylmethyl)-1,2-dihydropyridin-3-yl]-1H-pyrazole-4-carbonitrile
5-{[(5-chlorothiophen-2-yl)methyl]amino}-1-(furan-3-carbonyl)-3-[6-oxo-1-(piperidin-1-ylmethyl)-2-(pyridin-3-yl)-1,6-dihydropyridin-3-yl]-1H-pyrazole-4-carbonitrile
5-{[(5-chlorothiophen-2-yl)methyl]amino}-1-[3-(hydroxymethyl)benzoyl]-3-[4-(morpholin-4-yl)-2-oxo-1-(pyridin-2-ylmethyl)-1,2-dihydropyridin-3-yl]-1H-pyrazole-4-carbonitrile
5-{[(5-chlorothiophen-2-yl)methyl]amino}-3-[1-(1,2-oxazol-4-ylmethyl)-2-oxo-4-phenyl-1,2-dihydropyridin-3-yl]-1-(1,3-oxazole-5-carbonyl)-1H-pyrazole-4-carbonitrile
5-{[(5-chlorothiophen-2-yl)methyl]amino}-3-[1-(1,3-oxazol-5-ylmethyl)-2-oxo-5-(pyridin-2-yl)-1,2-dihydropyridin-4-yl]-1-(1,3-thiazole-2-carbonyl)-1H-pyrazole-4-carbonitrile
5-{[(5-chlorothiophen-2-yl)methyl]amino}-3-[1-methyl-2-oxo-6-(pyridin-3-yl)-1,2-dihydropyridin-4-yl]-1-(1,2-oxazole-4-carbonyl)-1H-pyrazole-4-carbonitrile
5-{[(5-chlorothiophen-2-yl)methyl]amino}-3-[2-fluoro-1-(1,3-oxazol-4-ylmethyl)-6-oxo-1,6-dihydropyridin-3-yl]-1-(thiophene-3-carbonyl)-1H-pyrazole-4-carbonitrile
5-{[(5-chlorothiophen-2-yl)methyl]amino}-3-[2-hydroxy-1-(1,2-oxazol-3-ylmethyl)-6-oxo-1,6-dihydropyridin-3-yl]-1-(1,2-oxazole-5-carbonyl)-1H-pyrazole-4-carbonitrile
5-{[(5-chlorothiophen-2-yl)methyl]amino}-3-[2-oxo-5-(pyridin-3-yl)-1-(pyrimidin-4-ylmethyl)-1,2-dihydropyridin-3-yl]-1-(thiophene-2-carbonyl)-1H-pyrazole-4-carbonitrile
5-{[(5-chlorothiophen-2-yl)methyl]amino}-3-[2-oxo-5-(pyridin-4-yl)-1-(thiophen-2-ylmethyl)-1,2-dihydropyridin-4-yl]-1-(1,2-thiazole-3-carbonyl)-1H-pyrazole-4-carbonitrile
5-{[(5-chlorothiophen-2-yl)methyl]amino}-3-[3-(dimethylamino)-2-oxo-1-(thiophen-2-ylmethyl)-1,2-dihydropyridin-4-yl]-1-[3-(hydroxymethyl)benzoyl]-1H-pyrazole-4-carbonitrile
5-{[(5-chlorothiophen-2-yl)methyl]amino}-3-[3-ethenyl-1-(1,2-oxazol-4-ylmethyl)-6-oxo-1,6-dihydropyridin-2-yl]-1-[2-(trifluoromethyl)benzoyl]-1H-pyrazole-4-carbonitrile
5-{[(5-chlorothiophen-2-yl)methyl]amino}-3-[3-fluoro-6-oxo-1-(pyridin-4-ylmethyl)-1,6-dihydropyridin-2-yl]-1-[2-(trifluoromethyl)benzoyl]-1H-pyrazole-4-carbonitrile
5-{[(5-chlorothiophen-2-yl)methyl]amino}-3-[3-hydroxy-6-oxo-1-(pyrimidin-4-ylmethyl)-1,6-dihydropyridin-2-yl]-1-(1,3-thiazole-4-carbonyl)-1H-pyrazole-4-carbonitrile APPENDIX A-continued Table B 5-{[(5-chlorothiophen-2-yl)methyl]amino}-3-[3-methoxy-1-(1,3-oxazol-2-ylmethyl)-2-oxo-1,2-dihydropyridin-4-yl]-1-(thiophene-3-carbonyl)-1H-pyrazole-4-carbonitrile
5-{[(5-chlorothiophen-2-yl)methyl]amino}-3-[4-(dimethylamino)-1-[(4-methylpiperazin-1-yl)methyl]-6-oxo-1,6-dihydropyridin-2-yl]-1-[4-(hydroxymethyl)benzoyl]-1H-pyrazole-4-carbonitrile
5-{[(5-chlorothiophen-2-yl)methyl]amino}-3-[5-(dimethylamino)-6-oxo-1-(pyridin-3-ylmethyl)-1,6-dihydropyridin-3-yl]-1-(furan-2-carbonyl)-1H-pyrazole-4-carbonitrile
5-{[(5-chlorothiophen-2-yl)methyl]amino}-3-[5-ethenyl-1-(furan-2-ylmethyl)-6-oxo-1,6-dihydropyridin-3-yl]-1-(1,3-thiazole-4-carbonyl)-1H-pyrazole-4-carbonitrile
5-{[(5-chlorothiophen-2-yl)methyl]amino}-3-[5-ethenyl-2-oxo-1-(thiophen-3-ylmethyl)-1,2-dihydropyridin-3-yl]-1-[3-(hydroxymethyl)benzoyl]-1H-pyrazole-4-carbonitrile
5-{[(5-chlorothiophen-2-yl)methyl]amino}-3-[5-hydroxy-6-oxo-1-(1,3-thiazol-2-ylmethyl)-1,6-dihydropyridin-2-yl]-1-[2-(trifluoromethyl)benzoyl]-1H-pyrazole-4-carbonitrile
5-{[(5-chlorothiophen-2-yl)methyl]amino}-3-[6-(dimethylamino)-1-(furan-2-ylmethyl)-2-oxo-1,2-dihydropyridin-3-yl]-1-(1,3-oxazole-4-carbonyl)-1H-pyrazole-4-carbonitrile
5-{[(5-chlorothiophen-2-yl)methyl]amino}-3-[6-(dimethylamino)-2-oxo-1-(pyrimidin-2-ylmethyl)-1,2-dihydropyridin-4-yl]-1-(2-fluorobenzoyl)-1H-pyrazole-4-carbonitrile
5-{[(5-chlorothiophen-2-yl)methyl]amino}-3-[6-ethenyl-2-oxo-1-(pyrimidin-5-ylmethyl)-1,2-dihydropyridin-4-yl]-1-(1,2-thiazole-5-carbonyl)-1H-pyrazole-4-carbonitrile
5-{[(5-chlorothiophen-2-yl)methyl]amino}-3-[6-oxo-5-(2-phenylethynyl)-1-(1,2-thiazol-4-ylmethyl)-1,6-dihydropyridin-3-yl]-1-(thiophene-3-carbonyl)-1H-pyrazole-4-carbonitrile
5-{[(5-chlorothiophen-2-yl)methyl]amino}-3-{5-fluoro-1-[(4-methylpiperazin-1-yl)methyl]-2-oxo-1,2-dihydropyridin-3-yl}-1-(1,2-oxazole-3-carbonyl)-1H-pyrazole-4-carbonitrile
6-(1-benzoyl-5-{[(5-chlorothiophen-2-yl)methyl]amino}-1H-pyrazol-3-yl)-1-[2-oxo-2-(1,3-thiazol-4-yl)ethyl]-5-(pyridin-4-yl)-1,2-dihydropyridin-2-one
6-(1-benzoyl-5-{[(5-chlorothiophen-2-yl)methyl]amino}-1H-pyrazol-3-yl)-2-oxo-1-[2-oxo-2-(pyrimidin-2-yl)ethyl]-1,2-dihydropyridine-3-carbonitrile
6-(1-benzoyl-5-{[(5-chlorothiophen-2-yl)methyl]amino}-1H-pyrazol-3-yl)-4-(dimethylamino)-1-[2-oxo-2-(thiophen-2-yl)ethyl]-1,2-dihydropyridin-2-one
6-(1-benzoyl-5-{[(5-chlorothiophen-2-yl)methyl]amino}-1H-pyrazol-3-yl)-4-bromo-1-(1,2-oxazol-3-ylmethyl)-1,2-dihydropyridin-2-one
6-(1-benzoyl-5-{[(5-chlorothiophen-2-yl)methyl]amino}-1H-pyrazol-3-yl)-5-hydroxy-1-(thiophen-2-ylmethyl)-1,2-dihydropyridin-2-one
6-(1-benzoyl-5-{[(5-chlorothiophen-2-yl)methyl]amino}-4-methoxy-1H-pyrazol-3-yl)-3-ethenyl-1-(pyrimidin-4-ylmethyl)-1,2-dihydropyridin-2-one
6-(5-{[(5-chlorothiophen-2-yl)methyl](methyl)amino}-1-(2,2-dimethylpropanoyl)-1H-pyrazol-3-yl)-1-(2-oxo-2-phenylethyl)-5-phenyl-1,2-dihydropyridin-2-one
6-(5-{[(5-chlorothiophen-2-yl)methyl](methyl)amino}-1-(2,2-dimethylpropanoyl)-1H-pyrazol-3-yl)-1-[2-(1,2-oxazol-4-yl)-2-oxoethyl]-1,2-dihydropyridin-2-one
6-(5-{[(5-chlorothiophen-2-yl)methyl](methyl)amino}-1-(2,2-dimethylpropanoyl)-1H-pyrazol-3-yl)-1-[2-(1,2-oxazol-5-yl)-2-oxoethyl]-1,2-dihydropyridin-2-one
6-(5-{[(5-chlorothiophen-2-yl)methyl](methyl)amino}-1-(2,2-dimethylpropanoyl)-1H-pyrazol-3-yl)-1-[2-(furan-2-yl)-2-oxoethyl]-4-phenyl-1,2-dihydropyridin-2-one
6-(5-{[(5-chlorothiophen-2-yl)methyl](methyl)amino}-1-(2,2-dimethylpropanoyl)-1H-pyrazol-3-yl)-1-[2-oxo-2-(1,3-thiazol-4-yl)ethyl]-3-(pyridin-3-yl)-1,2-dihydropyridin-2-one
6-(5-{[(5-chlorothiophen-2-yl)methyl](methyl)amino}-1-(2,2-dimethylpropanoyl)-1H-pyrazol-3-yl)-1-[2-oxo-2-(piperidin-1-yl)ethyl]-4-(pyridin-3-yl)-1,2-dihydropyridin-2-one
6-(5-{[(5-chlorothiophen-2-yl)methyl](methyl)amino}-1-(2,2-dimethylpropanoyl)-1H-pyrazol-3-yl)-1-[2-oxo-2-(pyrazin-2-yl)ethyl]-5-(pyridin-3-yl)-1,2-dihydropyridin-2-one
6-(5-{[(5-chlorothiophen-2-yl)methyl](methyl)amino}-1-(2,2-dimethylpropanoyl)-1H-pyrazol-3-yl)-1-[2-oxo-2-(pyrimidin-4-yl)ethyl]-1,2-dihydropyridin-2-one
6-(5-{[(5-chlorothiophen-2-yl)methyl](methyl)amino}-1-(2,2-dimethylpropanoyl)-1H-pyrazol-3-yl)-2-oxo-1-[2-oxo-2-(pyrazin-2-yl)ethyl]-1,2-dihydropyridine-3-carbonitrile
6-(5-{[(5-chlorothiophen-2-yl)methyl](methyl)amino}-1-(2,2-dimethylpropanoyl)-1H-pyrazol-3-yl)-2-oxo-1-[2-oxo-2-(pyridin-3-yl)ethyl]-1,2-dihydropyridine-4-carbonitrile
6-(5-{[(5-chlorothiophen-2-yl)methyl](methyl)amino}-1-(2,2-dimethylpropanoyl)-1H-pyrazol-3-yl)-3-(dimethylamino)-1-(2-oxo-2-phenylethyl)-1,2-dihydropyridin-2-one

APPENDIX A-continued

Table B 6-(5-{[(5-chlorothiophen-2-yl)methyl](methyl)amino}-1-(2,2-dimethylpropanoyl)-1H-pyrazol-3-yl)-3-ethenyl-1-[2-oxo-2-(1,3-thiazol-5-yl)ethyl]-1,2-dihydropyridin-2-one 6-(5-{[(5-chlorothiophen-2-yl)methyl](methyl)amino}-1-(2,2-dimethylpropanoyl)-1H-pyrazol-3-yl)-3-hydroxy-1-[2-oxo-2-(1,2-thiazol-5-yl)ethyl]-1,2-dihydropyridin-2-one 6-(5-{[(5-chlorothiophen-2-yl)methyl](methyl)amino}-1-(2,2-dimethylpropanoyl)-1H-pyrazol-3-yl)-4-(dimethylamino)-1-[2-oxo-2-(1,3-thiazol-2-yl)ethyl]-1,2-dihydropyridin-2-one 6-(5-{[(5-chlorothiophen-2-yl)methyl](methyl)amino}-1-(2,2-dimethylpropanoyl)-1H-pyrazol-3-yl)-4-ethenyl-1-[2-oxo-2-(1,2-thiazol-4-yl)ethyl]-1,2-dihydropyridin-2-one 6-(5-{[(5-chlorothiophen-2-yl)methyl](methyl)amino}-1-(2,2-dimethylpropanoyl)-1H-pyrazol-3-yl)-4-hydroxy-1-[2-oxo-2-(thiophen-3-yl)ethyl]-1,2-dihydropyridin-2-one 6-(5-{[(5-chlorothiophen-2-yl)methyl](methyl)amino}-1-(2,2-dimethylpropanoyl)-1H-pyrazol-3-yl)-5-(dimethylamino)-1-[2-oxo-2-(pyrimidin-4-yl)ethyl]-1,2-dihydropyridin-2-one 6-(5-{[(5-chlorothiophen-2-yl)methyl](methyl)amino}-1-(2,2-dimethylpropanoyl)-1H-pyrazol-3-yl)-5-ethenyl-1-[2-oxo-2-(1,2-thiazol-5-yl)ethyl]-1,2-dihydropyridin-2-one 6-(5-{[(5-chlorothiophen-2-yl)methyl](methyl)amino}-1-(2,2-dimethylpropanoyl)-1H-pyrazol-3-yl)-5-hydroxy-1-[2-oxo-2-(pyridin-4-yl)ethyl]-1,2-dihydropyridin-2-one 6-(5-{[(5-chlorothiophen-2-yl)methyl]amino}-1-(1,2-oxazole-3-carbonyl)-1H-pyrazol-3-yl)-1-[2-oxo-2-(piperidin-1-yl)ethyl]-3-(2-phenylethynyl)-1,2-dihydropyridin-2-one 6-(5-{[(5-chlorothiophen-2-yl)methyl]amino}-1-(1,2-oxazole-3-carbonyl)-1H-pyrazol-3-yl)-1-[2-oxo-2-(pyrazin-2-yl)ethyl]-4-(pyridin-2-yl)-1,2-dihydropyridin-2-one 6-(5-{[(5-chlorothiophen-2-yl)methyl]amino}-1-(1,2-oxazole-3-carbonyl)-1H-pyrazol-3-yl)-3-fluoro-1-(1,2-thiazol-3-ylmethyl)-1,2-dihydropyridin-2-one 6-(5-{[(5-chlorothiophen-2-yl)methyl]amino}-1-(1,2-oxazole-3-carbonyl)-1H-pyrazol-3-yl)-5-methoxy-1-[2-oxo-2-(pyridin-3-yl)ethyl]-1,2-dihydropyridin-2-one 6-(5-{[(5-chlorothiophen-2-yl)methyl]amino}-1-(1,2-oxazole-4-carbonyl)-1H-pyrazol-3-yl)-1-[2-(1,2-oxazol-3-yl)-2-oxoethyl]-3-(pyridin-4-yl)-1,2-dihydropyridin-2-one 6-(5-{[(5-chlorothiophen-2-yl)methyl]amino}-1-(1,2-oxazole-4-carbonyl)-1H-pyrazol-3-yl)-1-[2-(furan-2-yl)-2-oxoethyl]-5-(pyridin-3-yl)-1,2-dihydropyridin-2-one 6-(5-{[(5-chlorothiophen-2-yl)methyl]amino}-1-(1,2-oxazole-5-carbonyl)-1H-pyrazol-3-yl)-3-ethenyl-1-[2-(1,3-oxazol-4-yl)-2-oxoethyl]-1,2-dihydropyridin-2-one 6-(5-{[(5-chlorothiophen-2-yl)methyl]amino}-1-(1,2-oxazole-5-carbonyl)-1H-pyrazol-3-yl)-4-(morpholin-4-yl)-1-[2-oxo-2-(1,3-thiazol-5-yl)ethyl]-1,2-dihydropyridin-2-one 6-(5-{[(5-chlorothiophen-2-yl)methyl]amino}-1-(1,2-thiazole-3-carbonyl)-1H-pyrazol-3-yl)-4-hydroxy-1-[2-oxo-2-(1,2-thiazol-4-yl)ethyl]-1,2-dihydropyridin-2-one 6-(5-{[(5-chlorothiophen-2-yl)methyl]amino}-1-(1,2-thiazole-4-carbonyl)-1H-pyrazol-3-yl)-1-(1,3-oxazol-4-ylmethyl)-5-(pyridin-3-yl)-1,2-dihydropyridin-2-one 6-(5-{[(5-chlorothiophen-2-yl)methyl]amino}-1-(1,2-thiazole-4-carbonyl)-1H-pyrazol-3-yl)-1-[2-oxo-2-(pyrazin-2-yl)ethyl]-5-(2-phenylethynyl)-1,2-dihydropyridin-2-one 6-(5-{[(5-chlorothiophen-2-yl)methyl]amino}-1-(1,2-thiazole-4-carbonyl)-1H-pyrazol-3-yl)-3-fluoro-1-[2-oxo-2-(1,3-thiazol-4-yl)ethyl]-1,2-dihydropyridin-2-one 6-(5-{[(5-chlorothiophen-2-yl)methyl]amino}-1-(1,2-thiazole-5-carbonyl)-1H-pyrazol-3-yl)-1-(morpholin-4-ylmethyl)-2-oxo-1,2-dihydropyridine-3-carbonitrile 6-(5-{[(5-chlorothiophen-2-yl)methyl]amino}-1-(1,2-thiazole-5-carbonyl)-1H-pyrazol-3-yl)-1-[2-(1,3-oxazol-4-yl)ethyl]-3-(2-phenylethynyl)-1,2-dihydropyridin-2-one 6-(5-{[(5-chlorothiophen-2-yl)methyl]amino}-1-(1,2-thiazole-5-carbonyl)-1H-pyrazol-3-yl)-1-[2-(furan-2-yl)-2-oxoethyl]-2-oxo-1,2-dihydropyridine-4-carbonitrile 6-(5-{[(5-chlorothiophen-2-yl)methyl]amino}-1-(1,2-thiazole-5-carbonyl)-1H-pyrazol-3-yl)-5-(dimethylamino)-1-(2-oxo-2-phenylethyl)-1,2-dihydropyridin-2-one 6-(5-{[(5-chlorothiophen-2-yl)methyl]amino}-1-(1,3-oxazole-2-carbonyl)-1H-pyrazol-3-yl)-1-(2-oxo-2-phenylethyl)-4-(pyridin-4-yl)-1,2-dihydropyridin-2-one 6-(5-{[(5-chlorothiophen-2-yl)methyl]amino}-1-(1,3-oxazole-2-carbonyl)-1H-pyrazol-3-yl)-1-[2-oxo-2-(1,3-thiazol-2-yl)ethyl]-5-phenyl-1,2-dihydropyridin-2-one APPENDIX A-continued Table B 6-(5-{[(5-chlorothiophen-2-yl)methyl]amino}-1-(1,3-oxazole-2-carbonyl)-1H-pyrazol-3-yl)-3-(dimethylamino)-1-[2-(furan-2-yl)-2-oxoethyl]-1,2-dihydropyridin-2-one
6-(5-{[(5-chlorothiophen-2-yl)methyl]amino}-1-(1,3-oxazole-2-carbonyl)-1H-pyrazol-3-yl)-5-ethenyl-1-(1,3-thiazol-4-ylmethyl)-1,2-dihydropyridin-2-one
6-(5-{[(5-chlorothiophen-2-yl)methyl]amino}-1-(1,3-oxazole-4-carbonyl)-1H-pyrazol-3-yl)-4-ethenyl-1-[2-oxo-2-(1,2-thiazol-5-yl)ethyl]-1,2-dihydropyridin-2-one
6-(5-{[(5-chlorothiophen-2-yl)methyl]amino}-1-(1,3-oxazole-4-carbonyl)-1H-pyrazol-3-yl)-5-(morpholin-4-yl)-1-[2-oxo-2-(thiophen-3-yl)ethyl]-1,2-dihydropyridin-2-one
6-(5-{[(5-chlorothiophen-2-yl)methyl]amino}-1-(1,3-oxazole-5-carbonyl)-1H-pyrazol-3-yl)-1-[2-(4-methylpiperazin-1-yl)-2-oxoethyl]-4-(2-phenylethynyl)-1,2-dihydropyridin-2-one
6-(5-{[(5-chlorothiophen-2-yl)methyl]amino}-1-(1,3-oxazole-5-carbonyl)-1H-pyrazol-3-yl)-1-[2-oxo-2-(pyridazin-4-yl)ethyl]-5-(pyridin-2-yl)-1,2-dihydropyridin-2-one
6-(5-{[(5-chlorothiophen-2-yl)methyl]amino}-1-(1,3-oxazole-5-carbonyl)-1H-pyrazol-3-yl)-3-methoxy-1-[2-(1,3-thiazol-5-yl)ethyl]-1,2-dihydropyridin-2-one
6-(5-{[(5-chlorothiophen-2-yl)methyl]amino}-1-(1,3-thiazole-2-carbonyl)-1H-pyrazol-3-yl)-1-(1,3-oxazol-5-ylmethyl)-3-(pyridin-4-yl)-1,2-dihydropyridin-2-one
6-(5-{[(5-chlorothiophen-2-yl)methyl]amino}-1-(1,3-thiazole-2-carbonyl)-1H-pyrazol-3-yl)-3-methoxy-1-[2-oxo-2-(pyrazin-2-yl)ethyl]-1,2-dihydropyridin-2-one
6-(5-{[(5-chlorothiophen-2-yl)methyl]amino}-1-(1,3-thiazole-2-carbonyl)-1H-pyrazol-3-yl)-4-fluoro-1-[2-oxo-2-(pyridin-3-yl)ethyl]-1,2-dihydropyridin-2-one
6-(5-{[(5-chlorothiophen-2-yl)methyl]amino}-1-(1,3-thiazole-2-carbonyl)-1H-pyrazol-3-yl)-5-(2-phenylethynyl)-1-[2-(1,3-thiazol-5-yl)ethyl]-1,2-dihydropyridin-2-one
6-(5-{[(5-chlorothiophen-2-yl)methyl]amino}-1-(1,3-thiazole-4-carbonyl)-1H-pyrazol-3-yl)-1-(2-oxo-2-phenylethyl)-3-phenyl-1,2-dihydropyridin-2-one
6-(5-{[(5-chlorothiophen-2-yl)methyl]amino}-1-(1,3-thiazole-4-carbonyl)-1H-pyrazol-3-yl)-1-[2-oxo-2-(1,3-thiazol-2-yl)ethyl]-4-(pyridin-3-yl)-1,2-dihydropyridin-2-one
6-(5-{[(5-chlorothiophen-2-yl)methyl]amino}-1-(1,3-thiazole-4-carbonyl)-1H-pyrazol-3-yl)-5-phenyl-1-[2-(pyridin-3-yl)ethyl]-1,2-dihydropyridin-2-one
6-(5-{[(5-chlorothiophen-2-yl)methyl]amino}-1-(1,3-thiazole-5-carbonyl)-1H-pyrazol-3-yl)-3-(morpholin-4-yl)-1-[2-oxo-2-(1,2-thiazol-5-yl)ethyl]-1,2-dihydropyridin-2-one
6-(5-{[(5-chlorothiophen-2-yl)methyl]amino}-1-(1,3-thiazole-5-carbonyl)-1H-pyrazol-3-yl)-4-methoxy-1-(1,2-thiazol-3-ylmethyl)-1,2-dihydropyridin-2-one
6-(5-{[(5-chlorothiophen-2-yl)methyl]amino}-1-(1,3-thiazole-5-carbonyl)-1H-pyrazol-3-yl)-5-hydroxy-1-[2-oxo-2-(pyridin-4-yl)ethyl]-1,2-dihydropyridin-2-one
6-(5-{[(5-chlorothiophen-2-yl)methyl]amino}-1-(2,2-dimethylpropanoyl)-1H-pyrazol-3-yl)-1-(1,2-oxazol-3-ylmethyl)-3-(2-phenylethynyl)-1,2-dihydropyridin-2-one
6-(5-{[(5-chlorothiophen-2-yl)methyl]amino}-1-(2,2-dimethylpropanoyl)-1H-pyrazol-3-yl)-1-(2-oxo-2-phenylethyl)-4-(pyridine-3-carbonyl)-1,2-dihydropyridin-2-one
6-(5-{[(5-chlorothiophen-2-yl)methyl]amino}-1-(2,2-dimethylpropanoyl)-1H-pyrazol-3-yl)-1-[2-(1,2-oxazol-4-yl)-2-oxoethyl]-2-oxo-1,2-dihydropyridine-4-carboxylic acid
6-(5-{[(5-chlorothiophen-2-yl)methyl]amino}-1-(2,2-dimethylpropanoyl)-1H-pyrazol-3-yl)-1-[2-(1,2-oxazol-4-yl)-2-oxoethyl]-3-(pyridin-2-yl)-1,2-dihydropyridin-2-one
6-(5-{[(5-chlorothiophen-2-yl)methyl]amino}-1-(2,2-dimethylpropanoyl)-1H-pyrazol-3-yl)-1-[2-(1,2-oxazol-5-yl)-2-oxoethyl]-4-(pyridin-2-yl)-1,2-dihydropyridin-2-one
6-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-1,2-dihydropyridin-2-one
6-(5-{[(5-chlorothiophen-2-yl)methyl]amino}-1-(2,2-dimethylpropanoyl)-1H-pyrazol-3-yl)-1-[2-(1,3-oxazol-4-yl)-2-oxoethyl]-1,2-dihydropyridin-2-one
6-(5-{[(5-chlorothiophen-2-yl)methyl]amino}-1-(2,2-dimethylpropanoyl)-1H-pyrazol-3-yl)-1-[2-(1,3-oxazol-5-yl)-2-oxoethyl]-5-(2-phenylethynyl)-1,2-dihydropyridin-2-one
6-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-4-(prop-2-enoyl)-1,2-dihydropyridin-2-one
6-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-5-(pyridine-2-carbonyl)-1,2-dihydropyridin-2-one
6-(5-{[(5-chlorothiophen-2-yl)methyl]amino}-1-(2,2-dimethylpropanoyl)-1H-pyrazol-3-yl)-1-[2-(furan-2-yl)-2-oxoethyl]-3-(pyridine-3-carbonyl)-1,2-dihydropyridin-2-one
6-(5-{[(5-chlorothiophen-2-yl)methyl]amino}-1-(2,2-dimethylpropanoyl)-1H-pyrazol-3-yl)-1-[2-(furan-3-yl)-2-oxoethyl]-3-phenyl-1,2-dihydropyridin-2-one

APPENDIX A-continued

Table B 6-(5-{[(5-chlorothiophen-2-yl)methyl]amino}-1-(2,2-dimethylpropanoyl)-1H-pyrazol-3-yl)-1-[2-(furan-3-yl)-2-oxoethyl]-4-(pyridin-4-yl)-1,2-dihydropyridin-2-one 6-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-4-(2-phenylethynyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-5-phenyl-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(1,2-thiazol-4-yl)ethyl]-4-(pyridine-4-carbonyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(1,2-thiazol-5-yl)ethyl]-3-(3-phenylprop-2-ynoyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(1,2-thiazol-5-yl)ethyl]-5-(pyridine-4-carbonyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(1,3-thiazol-2-yl)ethyl]-5-(pyridine-3-carbonyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(1,3-thiazol-4-yl)ethyl]-4-phenyl-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(1,3-thiazol-5-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(1,3-thiazol-5-yl)ethyl]-3-(pyridine-4-carbonyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(piperidin-1-yl)ethyl]-5-(pyridin-3-yl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-3-(pyridine-2-carbonyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-3-(pyridin-4-yl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyridazin-4-yl)ethyl]-5-(prop-2-enoyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyridin-2-yl)ethyl]-4-(pyridin-3-yl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyridin-3-yl)ethyl]-3-(prop-2-enoyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyridin-3-yl)ethyl]-4-(pyridine-2-carbonyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyridin-4-yl)ethyl]-3-(pyridin-3-yl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyridin-4-yl)ethyl]-5-(3-phenylprop-2-ynoyl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(pyrimidin-5-yl)ethyl]-5-(pyridin-3-yl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(thiophen-2-yl)ethyl]-3-(pyridin-4-yl)-1,2-dihydropyridin-2-one 6-(5-{[(5-chlorothiophen-2-yl)methyl]amino}-1-(2,2-dimethylpropanoyl)-1H-pyrazol-3-yl)-1-[2-oxo-2-(thiophen-3-yl)ethyl]-4-(3-phenylprop-2-ynoyl)-1,2-dihydropyridin-2-one 6-(5-{[(5-chlorothiophen-2-yl)methyl]amino}-1-(2,2-dimethylpropanoyl)-1H-pyrazol-3-yl)-2-oxo-1-[2-oxo-2-(pyrazin-2-yl)ethyl]-1,2-dihydropyridine-4-carbonitrile 6-(5-{[(5-chlorothiophen-2-yl)methyl]amino}-1-(2,2-dimethylpropanoyl)-1H-pyrazol-3-yl)-2-oxo-1-[2-oxo-2-(pyrimidin-4-yl)ethyl]-1,2-dihydropyridine-3-carboxylic acid 6-(5-{[(5-chlorothiophen-2-yl)methyl]amino}-1-(2,2-dimethylpropanoyl)-1H-pyrazol-3-yl)-2-oxo-1-[2-oxo-2-(pyrimidin-5-yl)ethyl]-1,2-dihydropyridine-3-carbonitrile 6-(5-{[(5-chlorothiophen-2-yl)methyl]amino}-1-(2,2-dimethylpropanoyl)-1H-pyrazol-3-yl)-3-(dimethylamino)-1-[2-(morpholin-4-yl)-2-oxoethyl]-1,2-dihydropyridin-2-one

APPENDIX A-continued

Table B 6-(5-{[(5-chlorothiophen-2-yl)methyl]amino}-1-(2,2-dimethylpropanoyl)-1H-pyrazol-3-yl)-3-(morpholine-4-carbonyl)-1-[2-oxo-2-(1,3-thiazol-2-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-3-ethenyl-1-[2-(1,2-oxazol-5-yl)-2-oxoethyl]-1,2-dihydropyridin-2-one 6-(5-{[(5-chlorothiophen-2-yl)methyl]amino}-1-(2,2-dimethylpropanoyl)-1H-pyrazol-3-yl)-3-fluoro-1-[2-oxo-2-(thiophen-2-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-3-hydroxy-1-[2-oxo-2-(pyrimidin-2-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-3-methoxy-1-[2-oxo-2-(pyrazin-2-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-4-(dimethylamino)-1-[2-(1,3-oxazol-5-yl)-2-oxoethyl]-1,2-dihydropyridin-2-one 6-(5-{[(5-chlorothiophen-2-yl)methyl]amino}-1-(2,2-dimethylpropanoyl)-1H-pyrazol-3-yl)-4-(morpholin-4-yl)-1-[2-oxo-2-(pyrimidin-2-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-4-(morpholine-4-carbonyl)-1-[2-oxo-2-(pyrimidin-4-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-4-fluoro-1-[2-oxo-2-(1,3-thiazol-4-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-4-hydroxy-1-[2-oxo-2-(thiophen-2-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-4-methoxy-1-[2-oxo-2-(1,2-thiazol-3-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-5-(dimethylamino)-1-[2-(1,3-oxazol-2-yl)-2-oxoethyl]-1,2-dihydropyridin-2-one 6-(5-{[(5-chlorothiophen-2-yl)methyl]amino}-1-(2,2-dimethylpropanoyl)-1H-pyrazol-3-yl)-5-(morpholin-4-yl)-1-[2-oxo-2-(thiophen-2-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-5-(morpholine-4-carbonyl)-1-[2-(1,2-oxazol-4-yl)-2-oxoethyl]-1,2-dihydropyridin-2-one 6-(5-{[(5-chlorothiophen-2-yl)methyl]amino}-1-(2,2-dimethylpropanoyl)-1H-pyrazol-3-yl)-5-ethenyl-1-[2-oxo-2-(pyrimidin-2-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-5-fluoro-1-[2-oxo-2-(piperidin-1-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-5-hydroxy-1-[2-oxo-2-(1,3-thiazol-4-yl)ethyl]-1,2-dihydropyridin-2-one 6-(5-{[(5-chlorothiophen-2-yl)methyl]amino}-1-(2,2-dimethylpropanoyl)-1H-pyrazol-3-yl)-5-methoxy-1-[2-(1,2-oxazol-3-yl)-2-oxoethyl]-1,2-dihydropyridin-2-one 6-(5-{[(5-chlorothiophen-2-yl)methyl]amino}-1-(2,2-dimethylpropanoyl)-1H-pyrazol-3-yl)-N,N-dimethyl-1-[2-(4-methylpiperazin-1-yl)-2-oxoethyl]-2-oxo-1,2-dihydropyridine-3-carboxamide 6-(5-{[(5-chlorothiophen-2-yl)methyl]amino}-1-(2,2-dimethylpropanoyl)-1H-pyrazol-3-yl)-N,N-dimethyl-2-oxo-1-[2-oxo-2-(pyridazin-4-yl)ethyl]-1,2-dihydropyridine-4-carboxamide 6-(5-{[(5-chlorothiophen-2-yl)methyl]amino}-1-(2,2-dimethylpropanoyl)-4-fluoro-1H-pyrazol-3-yl)-5-(pyridin-2-yl)-1-(1,2-thiazol-3-ylmethyl)-1,2-dihydropyridin-2-one 6-(5-{[(5-chlorothiophen-2-yl)methyl]amino}-1-(2-fluorobenzoyl)-1H-pyrazol-3-yl)-4-ethenyl-1-(2-phenylethyl)-1,2-dihydropyridin-2-one 6-(5-{[(5-chlorothiophen-2-yl)methyl]amino}-1-(2-fluorobenzoyl)-1H-pyrazol-3-yl)-4-ethenyl-1-[2-oxo-2-(pyrazin-2-yl)ethyl]-1,2-dihydropyridin-2-one 6-(5-{[(5-chlorothiophen-2-yl)methyl]amino}-1-(2-fluorobenzoyl)-1H-pyrazol-3-yl)-5-(morpholin-4-yl)-1-[2-oxo-2-(1,2-thiazol-3-yl)ethyl]-1,2-dihydropyridin-2-one 6-(5-{[(5-chlorothiophen-2-yl)methyl]amino}-1-(2-fluorobenzoyl)-4-methoxy-1H-pyrazol-3-yl)-5-(2-phenylethynyl)-1-(pyridin-2-ylmethyl)-1,2-dihydropyridin-2-one 6-(5-{[(5-chlorothiophen-2-yl)methyl]amino}-1-(2-methoxybenzoyl)-1H-pyrazol-3-yl)-1-[2-(1,3-oxazol-2-yl)-2-oxoethyl]-5-(pyridin-2-yl)-1,2-dihydropyridin-2-one APPENDIX A-continued Table B 6-(5-{[(5-chlorothiophen-2-yl)methyl]amino}-1-(2-methoxybenzoyl)-1H-pyrazol-3-yl)-1-[2-(1,3-oxazol-5-yl)-2-oxoethyl]-4-(2-phenylethynyl)-1,2-dihydropyridin-2-one
6-(5-{[(5-chlorothiophen-2-yl)methyl]amino}-1-(3-hydroxy-2,2-dimethylpropanoyl)-1H-pyrazol-3-yl)-1-(pyrazin-2-ylmethyl)-3-(pyridin-2-yl)-1,2-dihydropyridin-2-one
6-(5-{[(5-chlorothiophen-2-yl)methyl]amino}-1-(3-hydroxy-2,2-dimethylpropanoyl)-1H-pyrazol-3-yl)-3-ethenyl-1-(thiophen-2-ylmethyl)-1,2-dihydropyridin-2-one
6-(5-{[(5-chlorothiophen-2-yl)methyl]amino}-1-(3-hydroxy-2,2-dimethylpropanoyl)-1H-pyrazol-3-yl)-3-hydroxy-1-[2-oxo-2-(1,2-thiazol-3-yl)ethyl]-1,2-dihydropyridin-2-one
6-(5-{[(5-chlorothiophen-2-yl)methyl]amino}-1-(3-hydroxy-2,2-dimethylpropanoyl)-1H-pyrazol-3-yl)-4-(2-phenylethynyl)-1-[2-(1,2-thiazol-5-yl)ethyl]-1,2-dihydropyridin-2-one
6-(5-{[(5-chlorothiophen-2-yl)methyl]amino}-1-(3-methoxy-2,2-dimethylpropanoyl)-1H-pyrazol-3-yl)-1-[2-(1,3-oxazol-5-yl)-2-oxoethyl]-3-(pyridin-2-yl)-1,2-dihydropyridin-2-one
6-(5-{[(5-chlorothiophen-2-yl)methyl]amino}-1-(3-methoxy-2,2-dimethylpropanoyl)-1H-pyrazol-3-yl)-3-ethenyl-1-[2-(1,2-oxazol-3-yl)ethyl]-1,2-dihydropyridin-2-one
6-(5-{[(5-chlorothiophen-2-yl)methyl]amino}-1-(3-methoxy-2,2-dimethylpropanoyl)-1H-pyrazol-3-yl)-4-methoxy-1-[2-(1,3-oxazol-2-yl)-2-oxoethyl]-1,2-dihydropyridin-2-one
6-(5-{[(5-chlorothiophen-2-yl)methyl]amino}-1-(3-methoxy-2,2-dimethylpropanoyl)-1H-pyrazol-3-yl)-5-fluoro-1-[2-(1,3-oxazol-4-yl)-2-oxoethyl]-1,2-dihydropyridin-2-one
6-(5-{[(5-chlorothiophen-2-yl)methyl]amino}-1-(furan-2-carbonyl)-1H-pyrazol-3-yl)-1-[2-(pyrazin-2-yl)ethyl]-4-(pyridin-4-yl)-1,2-dihydropyridin-2-one
6-(5-{[(5-chlorothiophen-2-yl)methyl]amino}-1-(furan-2-carbonyl)-1H-pyrazol-3-yl)-3-hydroxy-1-[2-oxo-2-(thiophen-3-yl)ethyl]-1,2-dihydropyridin-2-one
6-(5-{[(5-chlorothiophen-2-yl)methyl]amino}-1-(furan-2-carbonyl)-1H-pyrazol-3-yl)-5-(dimethylamino)-1-[2-(pyrazin-2-yl)ethyl]-1,2-dihydropyridin-2-one
6-(5-{[(5-chlorothiophen-2-yl)methyl]amino}-1-(furan-2-carbonyl)-1H-pyrazol-3-yl)-5-ethenyl-1-[2-oxo-2-(pyridin-2-yl)ethyl]-1,2-dihydropyridin-2-one
6-(5-{[(5-chlorothiophen-2-yl)methyl]amino}-1-(furan-3-carbonyl)-1H-pyrazol-3-yl)-1-[2-(1,2-oxazol-4-yl)-2-oxoethyl]-5-(pyridin-4-yl)-1,2-dihydropyridin-2-one
6-(5-{[(5-chlorothiophen-2-yl)methyl]amino}-1-(furan-3-carbonyl)-1H-pyrazol-3-yl)-2-oxo-1-[2-oxo-2-(1,3-thiazol-2-yl)ethyl]-1,2-dihydropyridine-3-carbonitrile
6-(5-{[(5-chlorothiophen-2-yl)methyl]amino}-1-(furan-3-carbonyl)-1H-pyrazol-3-yl)-4-(dimethylamino)-1-[2-oxo-2-(pyrimidin-4-yl)ethyl]-1,2-dihydropyridin-2-one
6-(5-{[(5-chlorothiophen-2-yl)methyl]amino}-1-(furan-3-carbonyl)-1H-pyrazol-3-yl)-5-(dimethylamino)-1-(1,3-thiazol-5-ylmethyl)-1,2-dihydropyridin-2-one
6-(5-{[(5-chlorothiophen-2-yl)methyl]amino}-1-(furan-3-carbonyl)-1H-pyrazol-3-yl)-5-(pyridin-2-yl)-1-[2-(thiophen-3-yl)ethyl]-1,2-dihydropyridin-2-one
6-(5-{[(5-chlorothiophen-2-yl)methyl]amino}-1-(furan-3-carbonyl)-4-methoxy-1H-pyrazol-3-yl)-1-(pyridazin-4-ylmethyl)-3-(pyridin-3-yl)-1,2-dihydropyridin-2-one
6-(5-{[(5-chlorothiophen-2-yl)methyl]amino}-1-(furan-3-carbonyl)-4-methoxy-1H-pyrazol-3-yl)-4-hydroxy-1-(1,2-oxazol-5-ylmethyl)-1,2-dihydropyridin-2-one
6-(5-{[(5-chlorothiophen-2-yl)methyl]amino}-1-(thiophene-2-carbonyl)-1H-pyrazol-3-yl)-1-[2-(1,2-oxazol-4-yl)-2-oxoethyl]-4-phenyl-1,2-dihydropyridin-2-one
6-(5-{[(5-chlorothiophen-2-yl)methyl]amino}-1-(thiophene-2-carbonyl)-1H-pyrazol-3-yl)-1-[2-(1,2-oxazol-5-yl)-2-oxoethyl]-5-(pyridin-3-yl)-1,2-dihydropyridin-2-one
6-(5-{[(5-chlorothiophen-2-yl)methyl]amino}-1-(thiophene-2-carbonyl)-1H-pyrazol-3-yl)-1-[2-oxo-2-(pyrimidin-4-yl)ethyl]-3-(pyridin-4-yl)-1,2-dihydropyridin-2-one
6-(5-{[(5-chlorothiophen-2-yl)methyl]amino}-1-(thiophene-2-carbonyl)-1H-pyrazol-3-yl)-5-methoxy-1-[2-(1,2-thiazol-4-yl)ethyl]-1,2-dihydropyridin-2-one
6-(5-{[(5-chlorothiophen-2-yl)methyl]amino}-1-(thiophene-3-carbonyl)-1H-pyrazol-3-yl)-1-(furan-2-ylmethyl)-5-methoxy-1,2-dihydropyridin-2-one
6-(5-{[(5-chlorothiophen-2-yl)methyl]amino}-1-(thiophene-3-carbonyl)-1H-pyrazol-3-yl)-1-[2-(4-methylpiperazin-1-yl)-2-oxoethyl]-3-(pyridin-2-yl)-1,2-dihydropyridin-2-one
6-(5-{[(5-chlorothiophen-2-yl)methyl]amino}-1-(thiophene-3-carbonyl)-1H-pyrazol-3-yl)-4-methoxy-1-[2-oxo-2-(pyridazin-4-yl)ethyl]-1,2-dihydropyridin-2-one
6-(5-{[(5-chlorothiophen-2-yl)methyl]amino}-1-(thiophene-3-carbonyl)-1H-pyrazol-3-yl)-5-fluoro-1-[2-(furan-3-yl)-2-oxoethyl]-1,2-dihydropyridin-2-one
6-(5-{[(5-chlorothiophen-2-yl)methyl]amino}-1-[2-(trifluoromethyl)benzoyl]-1H-pyrazol-3-yl)-1-(1,3-oxazol-2-ylmethyl)-3-(pyridin-3-yl)-1,2-dihydropyridin-2-one APPENDIX A-continued Table B 6-(5-{[(5-chlorothiophen-2-yl)methyl]amino}-1-[2-(trifluoromethyl)benzoyl]-1H-pyrazol-3-yl)-3-hydroxy-1-(pyrimidin-2-ylmethyl)-1,2-dihydropyridin-2-one
6-(5-{[(5-chlorothiophen-2-yl)methyl]amino}-1-[2-(trifluoromethyl)benzoyl]-1H-pyrazol-3-yl)-3-phenyl-1-[2-(pyrazin-2-yl)ethyl]-1,2-dihydropyridin-2-one
6-(5-{[(5-chlorothiophen-2-yl)methyl]amino}-1-[2-(trifluoromethyl)benzoyl]-1H-pyrazol-3-yl)-4-fluoro-1-[2-(morpholin-4-yl)-2-oxoethyl]-1,2-dihydropyridin-2-one
6-(5-{[(5-chlorothiophen-2-yl)methyl]amino}-1-[2-(trifluoromethyl)benzoyl]-1H-pyrazol-3-yl)-5-(morpholin-4-yl)-1-[2-(1,3-thiazol-2-yl)ethyl]-1,2-dihydropyridin-2-one
6-(5-{[(5-chlorothiophen-2-yl)methyl]amino}-1-[3-(hydroxymethyl)benzoyl]-1H-pyrazol-3-yl)-1-(1,3-oxazol-2-ylmethyl)-4-phenyl-1,2-dihydropyridin-2-one
6-(5-{[(5-chlorothiophen-2-yl)methyl]amino}-1-[3-(hydroxymethyl)benzoyl]-1H-pyrazol-3-yl)-1-[2-(furan-3-yl)-2-oxoethyl]-3-(2-phenylethynyl)-1,2-dihydropyridin-2-one
6-(5-{[(5-chlorothiophen-2-yl)methyl]amino}-1-[3-(hydroxymethyl)benzoyl]-1H-pyrazol-3-yl)-5-methoxy-1-[2-(morpholin-4-yl)-2-oxoethyl]-1,2-dihydropyridin-2-one
6-(5-{[(5-chlorothiophen-2-yl)methyl]amino}-1-[3-(hydroxymethyl)benzoyl]-4-methoxy-1H-pyrazol-3-yl)-3-fluoro-1-(thiophen-3-ylmethyl)-1,2-dihydropyridin-2-one
6-(5-{[(5-chlorothiophen-2-yl)methyl]amino}-1-[4-(hydroxymethyl)benzoyl]-1H-pyrazol-3-yl)-1-(1,3-oxazol-2-ylmethyl)-5-(pyridin-4-yl)-1,2-dihydropyridin-2-one
6-(5-{[(5-chlorothiophen-2-yl)methyl]amino}-1-[4-(hydroxymethyl)benzoyl]-1H-pyrazol-3-yl)-3-fluoro-1-[2-oxo-2-(pyridazin-4-yl)ethyl]-1,2-dihydropyridin-2-one
6-(5-{[(5-chlorothiophen-2-yl)methyl]amino}-1-[4-(hydroxymethyl)benzoyl]-1H-pyrazol-3-yl)-4-(pyridin-2-yl)-1-[2-(1,3-thiazol-5-yl)ethyl]-1,2-dihydropyridin-2-one
6-(5-{[(5-chlorothiophen-2-yl)methyl]amino}-1-[4-(hydroxymethyl)benzoyl]-1H-pyrazol-3-yl)-4-fluoro-1-[2-(1,2-thiazol-4-yl)ethyl]-1,2-dihydropyridin-2-one
6-(5-{[(5-chlorothiophen-2-yl)methyl]amino}-1-[4-(hydroxymethyl)benzoyl]-1H-pyrazol-3-yl)-5-fluoro-1-(1,2-oxazol-3-ylmethyl)-1,2-dihydropyridin-2-one
6-(5-{[(5-chlorothiophen-2-yl)methyl]amino}-4-cyano-1-(1,3-oxazole-5-carbonyl)-1H-pyrazol-3-yl)-2-oxo-1-(pyridin-3-ylmethyl)-1,2-dihydropyridine-3-carbonitrile
6-(5-{[(5-chlorothiophen-2-yl)methyl]amino}-4-fluoro-1-(1,2-oxazole-4-carbonyl)-1H-pyrazol-3-yl)-4-fluoro-1-(pyrimidin-5-ylmethyl)-1,2-dihydropyridin-2-one
6-(5-{[(5-chlorothiophen-2-yl)methyl]amino}-4-fluoro-1-(1,2-thiazole-4-carbonyl)-1H-pyrazol-3-yl)-1-(morpholin-4-ylmethyl)-4-(pyridin-3-yl)-1,2-dihydropyridin-2-one
6-(5-{[(5-chlorothiophen-2-yl)methyl]amino}-4-fluoro-1-(1,2-thiazole-5-carbonyl)-1H-pyrazol-3-yl)-1-(morpholin-4-ylmethyl)-5-phenyl-1,2-dihydropyridin-2-one
6-(5-{[(5-chlorothiophen-2-yl)methyl]amino}-4-fluoro-1-(1,3-oxazole-4-carbonyl)-1H-pyrazol-3-yl)-3-methoxy-1-(pyridin-2-ylmethyl)-1,2-dihydropyridin-2-one
6-(5-{[(5-chlorothiophen-2-yl)methyl]amino}-4-fluoro-1-(furan-2-carbonyl)-1H-pyrazol-3-yl)-3-(dimethylamino)-1-(furan-3-ylmethyl)-1,2-dihydropyridin-2-one
6-(5-{[(5-chlorothiophen-2-yl)methyl]amino}-4-fluoro-1-(furan-2-carbonyl)-1H-pyrazol-3-yl)-4-ethenyl-1-methyl-1,2-dihydropyridin-2-one
6-(5-{[(5-chlorothiophen-2-yl)methyl]amino}-4-fluoro-1-(thiophene-2-carbonyl)-1H-pyrazol-3-yl)-4-(2-phenylethynyl)-1-(pyrazin-2-ylmethyl)-1,2-dihydropyridin-2-one
6-(5-{[(5-chlorothiophen-2-yl)methyl]amino}-4-fluoro-1-(thiophene-2-carbonyl)-1H-pyrazol-3-yl)-5-(morpholin-4-yl)-1-(pyrimidin-2-ylmethyl)-1,2-dihydropyridin-2-one
6-(5-{[(5-chlorothiophen-2-yl)methyl]amino}-4-methoxy-1-(1,2-oxazole-5-carbonyl)-1H-pyrazol-3-yl)-4-(morpholin-4-yl)-1-(1,2-oxazol-4-ylmethyl)-1,2-dihydropyridin-2-one
6-(5-{[(5-chlorothiophen-2-yl)methyl]amino}-4-methoxy-1-(1,3-thiazole-2-carbonyl)-1H-pyrazol-3-yl)-1-(furan-3-ylmethyl)-2-oxo-1,2-dihydropyridine-4-carbonitrile
6-(5-{[(5-chlorothiophen-2-yl)methyl]amino}-4-methoxy-1-(1,3-thiazole-2-carbonyl)-1H-pyrazol-3-yl)-5-methoxy-1-(pyrimidin-5-ylmethyl)-1,2-dihydropyridin-2-one
6-(5-{[(5-chlorothiophen-2-yl)methyl]amino}-4-methoxy-1-(thiophene-3-carbonyl)-1H-pyrazol-3-yl)-4-(pyridin-2-yl)-1-(pyridin-2-ylmethyl)-1,2-dihydropyridin-2-one
6-(5-{[(5-chlorothiophen-2-yl)methyl]sulfanyl}-1-(2,2-dimethylpropanoyl)-1H-pyrazol-3-yl)-1-[2-(1,2-oxazol-4-yl)-2-oxoethyl]-3-(pyridin-2-yl)-1,2-dihydropyridin-2-one
6-(5-{[(5-chlorothiophen-2-yl)methyl]sulfanyl}-1-(2,2-dimethylpropanoyl)-1H-pyrazol-3-yl)-1-[2-(1,2-oxazol-5-yl)-2-oxoethyl]-4-(pyridin-2-yl)-1,2-dihydropyridin-2-one

APPENDIX A-continued

Table B 6-(5-{[(5-chlorothiophen-2-yl)methyl]sulfanyl}-1-(2,2-dimethylpropanoyl)-1H-pyrazol-3-yl)-1-[2-(1,3-oxazol-5-yl)-2-oxoethyl]-5-(2-phenylethynyl)-1,2-dihydropyridin-2-one 6-(5-{[(5-chlorothiophen-2-yl)methyl]sulfanyl}-1-(2,2-dimethylpropanoyl)-1H-pyrazol-3-yl)-1-[2-(furan-3-yl)-2-oxoethyl]-4-(pyridin-4-yl)-1,2-dihydropyridin-2-one 6-(5-{[(5-chlorothiophen-2-yl)methyl]sulfanyl}-1-(2,2-dimethylpropanoyl)-1H-pyrazol-3-yl)-1-[2-(morpholin-4-yl)-2-oxoethyl]-4-(2-phenylethynyl)-1,2-dihydropyridin-2-one 6-(5-{[(5-chlorothiophen-2-yl)methyl]sulfanyl}-1-(2,2-dimethylpropanoyl)-1H-pyrazol-3-yl)-1-[2-oxo-2-(pyridazin-4-yl)ethyl]-3-(pyridin-4-yl)-1,2-dihydropyridin-2-one 6-(5-{[(5-chlorothiophen-2-yl)methyl]sulfanyl}-1-(2,2-dimethylpropanoyl)-1H-pyrazol-3-yl)-3-fluoro-1-[2-oxo-2-(thiophen-2-yl)ethyl]-1,2-dihydropyridin-2-one 6-(5-{[(5-chlorothiophen-2-yl)methyl]sulfanyl}-1-(2,2-dimethylpropanoyl)-1H-pyrazol-3-yl)-3-methoxy-1-[2-oxo-2-(pyrazin-2-yl)ethyl]-1,2-dihydropyridin-2-one 6-(5-{[(5-chlorothiophen-2-yl)methyl]sulfanyl}-1-(2,2-dimethylpropanoyl)-1H-pyrazol-3-yl)-4-(morpholin-4-yl)-1-[2-oxo-2-(pyrimidin-2-yl)ethyl]-1,2-dihydropyridin-2-one 6-(5-{[(5-chlorothiophen-2-yl)methyl]sulfanyl}-1-(2,2-dimethylpropanoyl)-1H-pyrazol-3-yl)-4-fluoro-1-[2-oxo-2-(1,3-thiazol-4-yl)ethyl]-1,2-dihydropyridin-2-one 6-(5-{[(5-chlorothiophen-2-yl)methyl]sulfanyl}-1-(2,2-dimethylpropanoyl)-1H-pyrazol-3-yl)-4-methoxy-1-[2-oxo-2-(1,2-thiazol-3-yl)ethyl]-1,2-dihydropyridin-2-one 6-(5-{[(5-chlorothiophen-2-yl)methyl]sulfanyl}-1-(2,2-dimethylpropanoyl)-1H-pyrazol-3-yl)-5-(morpholin-4-yl)-1-[2-oxo-2-(thiophen-2-yl)ethyl]-1,2-dihydropyridin-2-one 6-(5-{[(5-chlorothiophen-2-yl)methyl]sulfanyl}-1-(2,2-dimethylpropanoyl)-1H-pyrazol-3-yl)-5-fluoro-1-[2-oxo-2-(piperidin-1-yl)ethyl]-1,2-dihydropyridin-2-one 6-(5-{[(5-chlorothiophen-2-yl)methyl]sulfanyl}-1-(2,2-dimethylpropanoyl)-1H-pyrazol-3-yl)-5-methoxy-1-[2-(1,2-oxazol-3-yl)-2-oxoethyl]-1,2-dihydropyridin-2-one 6-[1-(2-aminobenzoyl)-5-{[(5-chlorothiophen-2-yl)methyl]amino}-1H-pyrazol-3-yl]-1-[2-oxo-2-(pyrimidin-2-yl)ethyl]-4-(pyridin-3-yl)-1,2-dihydropyridin-2-one 6-[1-(2-aminobenzoyl)-5-{[(5-chlorothiophen-2-yl)methyl]amino}-1H-pyrazol-3-yl]-3-(dimethylamino)-1-[2-(piperidin-1-yl)ethyl]-1,2-dihydropyridin-2-one 6-[1-(2-chlorobenzoyl)-5-{[(5-chlorothiophen-2-yl)methyl]amino}-1H-pyrazol-3-yl]-1-(1,3-oxazol-4-ylmethyl)-2-oxo-1,2-dihydropyridine-4-carbonitrile 6-[1-(2-chlorobenzoyl)-5-{[(5-chlorothiophen-2-yl)methyl]amino}-1H-pyrazol-3-yl]-3-(morpholin-4-yl)-1-[2-oxo-2-(pyrazin-2-yl)ethyl]-1,2-dihydropyridin-2-one 6-[1-(2-chlorobenzoyl)-5-{[(5-chlorothiophen-2-yl)methyl]amino}-1H-pyrazol-3-yl]-5-hydroxy-1-[2-(1,2-oxazol-3-yl)-2-oxoethyl]-1,2-dihydropyridin-2-one 6-benzoyl-3-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-1,2-dihydropyridin-2-one 6-benzoyl-5-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-1,2-dihydropyridin-2-one 6-bromo-3-(5-{[(5-chlorothiophen-2-yl)methyl](methyl)amino}-1-(2,2-dimethylpropanoyl)-1H-pyrazol-3-yl)-1-[2-oxo-2-(pyridin-3-yl)ethyl]-1,2-dihydropyridin-2-one 6-bromo-3-(5-{[(5-chlorothiophen-2-yl)methyl]amino}-1-(1,2-thiazole-3-carbonyl)-1H-pyrazol-3-yl)-1-[2-(pyrimidin-2-yl)ethyl]-1,2-dihydropyridin-2-one 6-bromo-3-(5-{[(5-chlorothiophen-2-yl)methyl]amino}-1-(1,2-thiazole-4-carbonyl)-1H-pyrazol-3-yl)-1-[2-oxo-2-(1,2-thiazol-3-yl)ethyl]-1,2-dihydropyridin-2-one 6-bromo-3-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-1,2-dihydropyridin-2-one 6-bromo-3-(5-{[(5-chlorothiophen-2-yl)methyl]amino}-1-(2-methoxybenzoyl)-1H-pyrazol-3-yl)-1-(morpholin-4-ylmethyl)-1,2-dihydropyridin-2-one 6-bromo-3-(5-{[(5-chlorothiophen-2-yl)methyl]amino}-1-[4-(hydroxymethyl)benzoyl]-1H-pyrazol-3-yl)-1-[2-oxo-2-(1,3-thiazol-2-yl)ethyl]-1,2-dihydropyridin-2-one 6-bromo-3-(5-{[(5-chlorothiophen-2-yl)methyl]amino}-4-methoxy-1-(1,3-thiazole-5-carbonyl)-1H-pyrazol-3-yl)-1-(pyridin-3-ylmethyl)-1,2-dihydropyridin-2-one 6-bromo-4-(5-{[(5-chlorothiophen-2-yl)methyl]amino}-1-(1,2-oxazole-3-carbonyl)-1H-pyrazol-3-yl)-1-[2-(1,2-oxazol-4-yl)-2-oxoethyl]-1,2-dihydropyridin-2-one 6-bromo-4-(5-{[(5-chlorothiophen-2-yl)methyl]amino}-1-(1,2-oxazole-5-carbonyl)-1H-pyrazol-3-yl)-1-[2-(pyridazin-4-yl)ethyl]-1,2-dihydropyridin-2-one APPENDIX A-continued Table B 6-bromo-4-(5-{[(5-chlorothiophen-2-yl)methyl]amino}-1-(2,2-dimethylpropanoyl)-1H-pyrazol-3-yl)-1-[2-oxo-2-(pyridin-3-yl)ethyl]-1,2-dihydropyridin-2-one
6-bromo-4-(5-{[(5-chlorothiophen-2-yl)methyl]amino}-1-[3-(hydroxymethyl)benzoyl]-1H-pyrazol-3-yl)-1-[2-oxo-2-(1,3-thiazol-4-yl)ethyl]-1,2-dihydropyridin-2-one
6-bromo-4-(5-{[(5-chlorothiophen-2-yl)methyl]amino}-1-[4-(hydroxymethyl)benzoyl]-4-methoxy-1H-pyrazol-3-yl)-1-(1,3-oxazol-2-ylmethyl)-1,2-dihydropyridin-2-one
6-bromo-4-(5-{[(5-chlorothiophen-2-yl)methyl]sulfanyl}-1-(2,2-dimethylpropanoyl)-1H-pyrazol-3-yl)-1-[2-oxo-2-(pyridin-3-yl)ethyl]-1,2-dihydropyridin-2-one
6-bromo-4-[1-(2-chlorobenzoyl)-5-{[(5-chlorothiophen-2-yl)methyl]amino}-1H-pyrazol-3-yl]-1-(thiophen-3-ylmethyl)-1,2-dihydropyridin-2-one
6-bromo-5-(5-{[(5-chlorothiophen-2-yl)methyl]amino}-1-(1,3-thiazole-2-carbonyl)-1H-pyrazol-3-yl)-1-[2-oxo-2-(thiophen-2-yl)ethyl]-1,2-dihydropyridin-2-one
6-bromo-5-(5-{[(5-chlorothiophen-2-yl)methyl]amino}-1-(2,2-dimethylpropanoyl)-1H-pyrazol-3-yl)-1-[2-(furan-3-yl)-2-oxoethyl]-1,2-dihydropyridin-2-one
6-bromo-5-(5-{[(5-chlorothiophen-2-yl)methyl]amino}-1-[2-(trifluoromethyl)benzoyl]-1H-pyrazol-3-yl)-1-[2-(4-methylpiperazin-1-yl)-2-oxoethyl]-1,2-dihydropyridin-2-one
6-bromo-5-(5-{[(5-chlorothiophen-2-yl)methyl]amino}-4-fluoro-1-(1,2-thiazole-3-carbonyl)-1H-pyrazol-3-yl)-1-(1,2-thiazol-5-ylmethyl)-1,2-dihydropyridin-2-one
6-bromo-5-(5-{[(5-chlorothiophen-2-yl)methyl]sulfanyl}-1-(2,2-dimethylpropanoyl)-1H-pyrazol-3-yl)-1-[2-(furan-3-yl)-2-oxoethyl]-1,2-dihydropyridin-2-one
6-chloro-3-(5-{[(5-chlorothiophen-2-yl)methyl]amino}-1-(2,2-dimethylpropanoyl)-1H-pyrazol-3-yl)-1-[2-oxo-2-(pyrazin-2-yl)ethyl]-1,2-dihydropyridin-2-one
6-chloro-3-(5-{[(5-chlorothiophen-2-yl)methyl]amino}-1-(3-hydroxy-2,2-dimethylpropanoyl)-1H-pyrazol-3-yl)-1-(pyrimidin-5-ylmethyl)-1,2-dihydropyridin-2-one
6-chloro-3-(5-{[(5-chlorothiophen-2-yl)methyl]amino}-1-(3-hydroxy-2,2-dimethylpropanoyl)-1H-pyrazol-3-yl)-1-[2-(morpholin-4-yl)-2-oxoethyl]-1,2-dihydropyridin-2-one
6-chloro-3-(5-{[(5-chlorothiophen-2-yl)methyl]amino}-1-(furan-2-carbonyl)-1H-pyrazol-3-yl)-1-[2-oxo-2-(pyridin-3-yl)ethyl]-1,2-dihydropyridin-2-one
6-chloro-3-(5-{[(5-chlorothiophen-2-yl)methyl]sulfanyl}-1-(2,2-dimethylpropanoyl)-1H-pyrazol-3-yl)-1-[2-(1,3-oxazol-5-yl)-2-oxoethyl]-1,2-dihydropyridin-2-one
6-chloro-4-(5-{[(5-chlorothiophen-2-yl)methyl](methyl)amino}-1-(2,2-dimethylpropanoyl)-1H-pyrazol-3-yl)-1-[2-oxo-2-(pyrimidin-2-yl)ethyl]-1,2-dihydropyridin-2-one
6-chloro-4-(5-{[(5-chlorothiophen-2-yl)methyl]amino}-1-(1,2-oxazole-5-carbonyl)-1H-pyrazol-3-yl)-1-[2-oxo-2-(pyridazin-4-yl)ethyl]-1,2-dihydropyridin-2-one
6-chloro-4-(5-{[(5-chlorothiophen-2-yl)methyl]amino}-1-(2,2-dimethylpropanoyl)-1H-pyrazol-3-yl)-1-[2-oxo-2-(1,2-thiazol-5-yl)ethyl]-1,2-dihydropyridin-2-one
6-chloro-4-(5-{[(5-chlorothiophen-2-yl)methyl]amino}-1-(3-hydroxy-2,2-dimethylpropanoyl)-1H-pyrazol-3-yl)-1-(1,3-thiazol-2-ylmethyl)-1,2-dihydropyridin-2-one
6-chloro-4-(5-{[(5-chlorothiophen-2-yl)methyl]amino}-4-methoxy-1-(1,2-thiazole-5-carbonyl)-1H-pyrazol-3-yl)-1-(1,2-thiazol-3-ylmethyl)-1,2-dihydropyridin-2-one
6-chloro-5-(5-{[(5-chlorothiophen-2-yl)methyl](methyl)amino}-1-(2,2-dimethylpropanoyl)-1H-pyrazol-3-yl)-1-[2-oxo-2-(piperidin-1-yl)ethyl]-1,2-dihydropyridin-2-one
6-chloro-5-(5-{[(5-chlorothiophen-2-yl)methyl]amino}-1-(1,2-thiazole-3-carbonyl)-1H-pyrazol-3-yl)-1-[2-(1,3-oxazol-5-yl)-2-oxoethyl]-1,2-dihydropyridin-2-one
6-chloro-5-(5-{[(5-chlorothiophen-2-yl)methyl]amino}-1-(2,2-dimethylpropanoyl)-1H-pyrazol-3-yl)-1-[2-oxo-2-(pyridin-2-yl)ethyl]-1,2-dihydropyridin-2-one
6-chloro-5-(5-{[(5-chlorothiophen-2-yl)methyl]amino}-1-[3-(hydroxymethyl)benzoyl]-1H-pyrazol-3-yl)-1-[2-(pyrazin-2-yl)ethyl]-1,2-dihydropyridin-2-one
methyl 1-benzyl-4-(5-{[(5-chlorothiophen-2-yl)methyl]amino}-1-(1,3-oxazole-5-carbonyl)-1H-pyrazol-3-yl)-6-oxo-1,6-dihydropyridine-2-carboxylate
methyl 1-benzyl-5-(5-{[(5-chlorothiophen-2-yl)methyl]amino}-1H-pyrazol-3-yl)-4-cyano-1-(1,2-thiazole-3-carbonyl)-1H-pyrazol-3-yl)-2-oxo-1,2-dihydropyridine-3-carboxylate
methyl 2-(5-{[(5-chlorothiophen-2-yl)methyl]amino}-1-(1,2-oxazole-5-carbonyl)-1H-pyrazol-3-yl)-6-oxo-1-[2-oxo-2-(1,2-thiazol-4-yl)ethyl]-1,6-dihydropyridine-3-carboxylate APPENDIX A-continued Table B methyl 2-(5-{[(5-chlorothiophen-2-yl)methyl]amino}-1-(1,3-thiazole-2-carbonyl)-1H-pyrazol-3-yl)-6-oxo-1-(piperidin-1-ylmethyl)-1,6-dihydropyridine-3-carboxylate methyl 2-(5-{[(5-chlorothiophen-2-yl)methyl]amino}-1-(2,2-dimethylpropanoyl)-1H-pyrazol-3-yl)-6-oxo-1-[2-oxo-2-(pyrazin-2-yl)ethyl]-1,6-dihydropyridine-3-carboxylate methyl 2-(5-{[(5-chlorothiophen-2-yl)methyl]amino}-1-(2,2-dimethylpropanoyl)-1H-pyrazol-3-yl)-6-oxo-1-[2-oxo-2-(pyridin-2-yl)ethyl]-1,6-dihydropyridine-3-carboxylate methyl 2-(5-{[(5-chlorothiophen-2-yl)methyl]amino}-4-methoxy-1-(1,2-thiazole-5-carbonyl)-1H-pyrazol-3-yl)-1-(1,2-oxazol-5-ylmethyl)-6-oxo-1,6-dihydropyridine-3-carboxylate methyl 2-(5-{[(5-chlorothiophen-2-yl)methyl]sulfanyl}-1-(2,2-dimethylpropanoyl)-1H-pyrazol-3-yl)-6-oxo-1-[2-oxo-2-(pyrazin-2-yl)ethyl]-1,6-dihydropyridine-3-carboxylate methyl 2-[1-(2-chlorobenzoyl)-5-{[(5-chlorothiophen-2-yl)methyl]amino}-1H-pyrazol-3-yl]-1-[2-(furan-2-yl)ethyl]-6-oxo-1,6-dihydropyridine-3-carboxylate methyl 2-[1-(4-carbamoylbenzoyl)-5-{[(5-chlorothiophen-2-yl)methyl]amino}-1H-pyrazol-3-yl]-6-oxo-1-[2-oxo-2-(pyrimidin-5-yl)ethyl]-1,6-dihydropyridine-3-carboxylate methyl 2-[2-(5-{[(5-chlorothiophen-2-yl)methyl]amino}-1-(2,2-dimethylpropanoyl)-1H-pyrazol-3-yl)-6-oxo-1-[2-oxo-2-(pyrimidin-4-yl)ethyl]-1,6-dihydropyridin-3-yl]-2-oxoacetate methyl 2-[3-(5-{[(5-chlorothiophen-2-yl)methyl]amino}-1-(2,2-dimethylpropanoyl)-1H-pyrazol-3-yl)-1-[2-(1,2-oxazol-3-yl)-2-oxoethyl]-6-oxo-1,6-dihydropyridin-2-yl]-2-oxoacetate methyl 2-[3-(5-{[(5-chlorothiophen-2-yl)methyl]amino}-1-(2,2-dimethylpropanoyl)-1H-pyrazol-3-yl)-2-oxo-1-[2-oxo-2-(pyridin-2-yl)ethyl]-1,2-dihydropyridin-4-yl]-2-oxoacetate methyl 2-[3-(5-{[(5-chlorothiophen-2-yl)methyl]amino}-1-[2-(trifluoromethyl)benzoyl]-1H-pyrazol-3-yl)-6-methoxy-2-oxo-1,2-dihydropyridin-1-yl]acetate methyl 2-[3-(5-{[(5-chlorothiophen-2-yl)methyl]amino}-4-methoxy-1-(1,3-thiazole-5-carbonyl)-1H-pyrazol-3-yl)-2-oxo-4-(pyridin-2-yl)-1,2-dihydropyridin-1-yl]acetate methyl 2-[4-(5-{[(5-chlorothiophen-2-yl)methyl]amino}-1-(2,2-dimethylpropanoyl)-1H-pyrazol-3-yl)-2-oxo-1-[2-oxo-2-(1,2-thiazol-3-yl)ethyl]-1,2-dihydropyridin-3-yl]-2-oxoacetate methyl 2-[4-(5-{[(5-chlorothiophen-2-yl)methyl]amino}-1-(2,2-dimethylpropanoyl)-1H-pyrazol-3-yl)-6-oxo-1-[2-oxo-2-(pyrazin-2-yl)ethyl]-1,6-dihydropyridin-3-yl]-2-oxoacetate methyl 2-[4-(5-{[(5-chlorothiophen-2-yl)methyl]amino}-1-(2,2-dimethylpropanoyl)-1H-pyrazol-3-yl)-6-oxo-1-[2-oxo-2-(pyrimidin-5-yl)ethyl]-1,6-dihydropyridin-2-yl]-2-oxoacetate methyl 2-[5-(5-{[(5-chlorothiophen-2-yl)methyl]amino}-1-(1,3-oxazole-5-carbonyl)-1H-pyrazol-3-yl)-2-oxo-3-(pyridin-3-yl)-1,2-dihydropyridin-1-yl]acetate methyl 2-[5-(5-{[(5-chlorothiophen-2-yl)methyl]amino}-1-(1,3-thiazole-4-carbonyl)-1H-pyrazol-3-yl)-4-cyano-2-oxo-1,2-dihydropyridin-1-yl]acetate methyl 2-[5-(5-{[(5-chlorothiophen-2-yl)methyl]amino}-1-(2,2-dimethylpropanoyl)-1H-pyrazol-3-yl)-1-[2-(furan-2-yl)-2-oxoethyl]-2-oxo-1,2-dihydropyridin-3-yl]-2-oxoacetate methyl 2-[5-(5-{[(5-chlorothiophen-2-yl)methyl]amino}-1-(2,2-dimethylpropanoyl)-1H-pyrazol-3-yl)-6-oxo-1-[2-oxo-2-(1,2-thiazol-4-yl)ethyl]-1,6-dihydropyridin-2-yl]-2-oxoacetate methyl 2-[5-(5-{[(5-chlorothiophen-2-yl)methyl]amino}-1-(2,2-dimethylpropanoyl)-1H-pyrazol-3-yl)-6-oxo-1-[2-oxo-2-(thiophen-3-yl)ethyl]-1,6-dihydropyridin-3-yl]-2-oxoacetate methyl 2-[5-(5-{[(5-chlorothiophen-2-yl)methyl]amino}-1-(thiophene-3-carbonyl)-1H-pyrazol-3-yl)-6-(dimethylamino)-2-oxo-1,2-dihydropyridin-1-yl]acetate methyl 2-[5-bromo-3-(5-{[(5-chlorothiophen-2-yl)methyl]amino}-4-fluoro-1-(2-methoxybenzoyl)-1H-pyrazol-3-yl)-2-oxo-1,2-dihydropyridin-1-yl]acetate methyl 2-[6-(5-{[(5-chlorothiophen-2-yl)methyl]amino}-1-(2,2-dimethylpropanoyl)-1H-pyrazol-3-yl)-2-oxo-1-(2-oxo-2-phenylethyl)-1,2-dihydropyridin-3-yl]-2-oxoacetate methyl 2-[6-(5-{[(5-chlorothiophen-2-yl)methyl]amino}-1-(2,2-dimethylpropanoyl)-1H-pyrazol-3-yl)-2-oxo-1-[2-oxo-2-(1,3-thiazol-2-yl)ethyl]-1,2-dihydropyridin-4-yl]-2-oxoacetate methyl 2-[6-(5-{[(5-chlorothiophen-2-yl)methyl]amino}-4-fluoro-1-(1,2-thiazole-4-carbonyl)-1H-pyrazol-3-yl)-2-oxo-3-phenyl-1,2-dihydropyridin-1-yl]acetate methyl 2-[6-(5-{[(5-chlorothiophen-2-yl)methyl]amino}-4-fluoro-1-(2-methoxybenzoyl)-1H-pyrazol-3-yl)-2-oxo-4-(pyridin-4-yl)-1,2-dihydropyridin-1-yl]acetate methyl 2-[6-(5-{[(5-chlorothiophen-2-yl)methyl]amino}-4-methoxy-1-(1,3-thiazole-4-carbonyl)-1H-pyrazol-3-yl)-5-(dimethylamino)-2-oxo-1,2-dihydropyridin-1-yl]acetate APPENDIX A-continued Table B methyl 3-(1-benzoyl-5-{[(5-chlorothiophen-2-yl)methyl]amino}-4-methoxy-1H-pyrazol-3-yl)-1-(furan-2-ylmethyl)-6-oxo-1,6-dihydropyridine-2-carboxylate
methyl 3-(5-{[(5-chlorothiophen-2-yl)methyl](methyl)amino}-1-(2,2-dimethylpropanoyl)-1H-pyrazol-3-yl)-2-oxo-1-[2-oxo-2-(thiophen-3-yl)ethyl]-1,2-dihydropyridine-4-carboxylate
methyl 3-(5-{[(5-chlorothiophen-2-yl)methyl]amino}-1-(1,2-oxazole-5-carbonyl)-1H-pyrazol-3-yl)-1-[2-(morpholin-4-yl)-2-oxoethyl]-6-oxo-1,6-dihydropyridine-2-carboxylate
methyl 3-(5-{[(5-chlorothiophen-2-yl)methyl]amino}-1-(1,2-oxazole-5-carbonyl)-1H-pyrazol-3-yl)-2-oxo-1-[2-(thiophen-3-yl)ethyl]-1,2-dihydropyridine-4-carboxylate
methyl 3-(5-{[(5-chlorothiophen-2-yl)methyl]amino}-1-(1,3-oxazole-4-carbonyl)-1H-pyrazol-3-yl)-2-oxo-1-[2-oxo-2-(pyridazin-4-yl)ethyl]-1,2-dihydropyridine-4-carboxylate
methyl 3-(5-{[(5-chlorothiophen-2-yl)methyl]amino}-1-(1,3-thiazole-2-carbonyl)-1H-pyrazol-3-yl)-1-(1,2-oxazol-5-ylmethyl)-6-oxo-1,6-dihydropyridine-2-carboxylate
methyl 3-(5-{[(5-chlorothiophen-2-yl)methyl]amino}-1-(1,3-thiazole-4-carbonyl)-1H-pyrazol-3-yl)-6-oxo-1-[2-(pyrimidin-5-yl)ethyl]-1,6-dihydropyridine-2-carboxylate
methyl 3-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-2-oxo-1,2-dihydropyridine-4-carboxylate
methyl 3-(5-{[(5-chlorothiophen-2-yl)methyl]amino}-1-(2,2-dimethylpropanoyl)-1H-pyrazol-3-yl)-2-oxo-1-[2-oxo-2-(1,2-thiazol-3-yl)ethyl]-1,2-dihydropyridine-4-carboxylate
methyl 3-(5-{[(5-chlorothiophen-2-yl)methyl]amino}-1-(2,2-dimethylpropanoyl)-1H-pyrazol-3-yl)-6-oxo-1-[2-oxo-2-(1,2-thiazol-5-yl)ethyl]-1,6-dihydropyridine-2-carboxylate
methyl 3-(5-{[(5-chlorothiophen-2-yl)methyl]amino}-1-(2,2-dimethylpropanoyl)-1H-pyrazol-3-yl)-6-oxo-1-[2-oxo-2-(1,3-thiazol-5-yl)ethyl]-1,6-dihydropyridine-2-carboxylate
methyl 3-(5-{[(5-chlorothiophen-2-yl)methyl]amino}-1-(2-fluorobenzoyl)-1H-pyrazol-3-yl)-1-[2-(1,3-oxazol-2-yl)-2-oxoethyl]-2-oxo-1,2-dihydropyridine-4-carboxylate
methyl 3-(5-{[(5-chlorothiophen-2-yl)methyl]amino}-4-fluoro-1-(1,2-oxazole-5-carbonyl)-1H-pyrazol-3-yl)-2-oxo-1-(1,2-thiazol-3-ylmethyl)-1,2-dihydropyridine-4-carboxylate
methyl 3-(5-{[(5-chlorothiophen-2-yl)methyl]sulfanyl}-1-(2,2-dimethylpropanoyl)-1H-pyrazol-3-yl)-6-oxo-1-[2-oxo-2-(1,2-thiazol-5-yl)ethyl]-1,6-dihydropyridine-2-carboxylate
methyl 3-[1-(4-carbamoylbenzoyl)-5-{[(5-chlorothiophen-2-yl)methyl]amino}-1H-pyrazol-3-yl]-6-oxo-1-[2-oxo-2-(1,2-thiazol-4-yl)ethyl]-1,6-dihydropyridine-2-carboxylate
methyl 3-[3-(5-{[(5-chlorothiophen-2-yl)methyl]amino}-1-(2,2-dimethylpropanoyl)-1H-pyrazol-3-yl)-2-oxo-4-(3-phenylprop-2-ynoyl)-1,2-dihydropyridin-1-yl]-2-oxopropanoate
methyl 3-[3-(5-{[(5-chlorothiophen-2-yl)methyl]amino}-1-(2,2-dimethylpropanoyl)-1H-pyrazol-3-yl)-2-oxo-5-phenyl-1,2-dihydropyridin-1-yl]-2-oxopropanoate
methyl 3-[3-(5-{[(5-chlorothiophen-2-yl)methyl]amino}-1-(2,2-dimethylpropanoyl)-1H-pyrazol-3-yl)-6-(dimethylamino)-2-oxo-1,2-dihydropyridin-1-yl]-2-oxopropanoate
methyl 3-[3-(5-{[(5-chlorothiophen-2-yl)methyl]amino}-1-(furan-2-carbonyl)-1H-pyrazol-3-yl)-4-(morpholin-4-yl)-2-oxo-1,2-dihydropyridin-1-yl]-2-oxopropanoate
methyl 3-[3-(5-{[(5-chlorothiophen-2-yl)methyl]sulfanyl}-1-(2,2-dimethylpropanoyl)-1H-pyrazol-3-yl)-2-oxo-5-(pyridin-3-yl)-1,2-dihydropyridin-1-yl]-2-oxopropanoate
methyl 3-[3-(5-{[(5-chlorothiophen-2-yl)methyl]sulfanyl}-1-(2,2-dimethylpropanoyl)-1H-pyrazol-3-yl)-6-cyano-2-oxo-1,2-dihydropyridin-1-yl]-2-oxopropanoate
methyl 3-[4-(5-{[(5-chlorothiophen-2-yl)methyl(methyl)amino}-1-(2,2-dimethylpropanoyl)-1H-pyrazol-3-yl)-5-ethenyl-2-oxo-1,2-dihydropyridin-1-yl]-2-oxopropanoate
methyl 3-[4-(5-{[(5-chlorothiophen-2-yl)methyl]amino}-1-(1,2-oxazole-5-carbonyl)-1H-pyrazol-3-yl)-3-(morpholin-4-yl)-2-oxo-1,2-dihydropyridin-1-yl]-2-oxopropanoate
methyl 3-[4-(5-{[(5-chlorothiophen-2-yl)methyl]amino}-1-(1,3-oxazole-4-carbonyl)-1H-pyrazol-3-yl)-2-oxo-3-(pyridin-2-yl)-1,2-dihydropyridin-1-yl]propanoate
methyl 3-[4-(5-{[(5-chlorothiophen-2-yl)methyl]amino}-1-(1,3-oxazole-4-carbonyl)-1H-pyrazol-3-yl)-6-hydroxy-2-oxo-1,2-dihydropyridin-1-yl]-2-oxopropanoate
methyl 3-[4-(5-{[(5-chlorothiophen-2-yl)methyl]amino}-1-(2,2-dimethylpropanoyl)-1H-pyrazol-3-yl)-2-oxo-5-(pyridine-4-carbonyl)-1,2-dihydropyridin-1-yl]-2-oxopropanoate APPENDIX A-continued Table B methyl 3-[4-(5-{[(5-chlorothiophen-2-yl)methyl]amino}-1-(2-fluorobenzoyl)-1H-pyrazol-3-yl)-6-fluoro-2-oxo-1,2-dihydropyridin-1-yl]propanoate
methyl 3-[4-bromo-3-(5-{[(5-chlorothiophen-2-yl)methyl](methyl)amino}-1-(2,2-dimethylpropanoyl)-1H-pyrazol-3-yl)-2-oxo-1,2-dihydropyridin-1-yl]-2-oxopropanoate
methyl 3-[4-bromo-5-(5-{[(5-chlorothiophen-2-yl)methyl]amino}-1-(2,2-dimethylpropanoyl)-1H-pyrazol-3-yl)-2-oxo-1,2-dihydropyridin-1-yl]-2-oxopropanoate
methyl 3-[4-bromo-5-(5-{[(5-chlorothiophen-2-yl)methyl]amino}-1-(3-methoxy-2,2-dimethylpropanoyl)-1H-pyrazol-3-yl)-2-oxo-1,2-dihydropyridin-1-yl]-2-oxopropanoate
methyl 3-[4-bromo-5-(5-{[(5-chlorothiophen-2-yl)methyl]sulfanyl}-1-(2,2-dimethylpropanoyl)-1H-pyrazol-3-yl)-2-oxo-1,2-dihydropyridin-1-yl]-2-oxopropanoate
methyl 3-[5-(5-{[(5-chlorothiophen-2-yl)methyl]amino}-1-(2,2-dimethylpropanoyl)-1H-pyrazol-3-yl)-2-oxo-1,2-dihydropyridin-1-yl]-2-oxopropanoate
methyl 3-[5-(5-{[(5-chlorothiophen-2-yl)methyl]amino}-1-(2,2-dimethylpropanoyl)-1H-pyrazol-3-yl)-3-(dimethylamino)-2-oxo-1,2-dihydropyridin-1-yl]-2-oxopropanoate
methyl 3-[5-(5-{[(5-chlorothiophen-2-yl)methyl]amino}-1-(2-methoxybenzoyl)-1H-pyrazol-3-yl)-3-fluoro-2-oxo-1,2-dihydropyridin-1-yl]-2-oxopropanoate
methyl 3-[6-(5-{[(5-chlorothiophen-2-yl)methyl]amino}-1-(2,2-dimethylpropanoyl)-1H-pyrazol-3-yl)-2-oxo-3-(2-phenylethynyl)-1,2-dihydropyridin-1-yl]-2-oxopropanoate
methyl 3-[6-(5-{[(5-chlorothiophen-2-yl)methyl]amino}-1-(2,2-dimethylpropanoyl)-1H-pyrazol-3-yl)-2-oxo-4-phenyl-1,2-dihydropyridin-1-yl]-2-oxopropanoate
methyl 3-[6-(5-{[(5-chlorothiophen-2-yl)methyl]amino}-1-(2,2-dimethylpropanoyl)-1H-pyrazol-3-yl)-2-oxo-5-(pyridin-4-yl)-1,2-dihydropyridin-1-yl]-2-oxopropanoate
methyl 3-[6-(5-{[(5-chlorothiophen-2-yl)methyl]amino}-1-[2-(trifluoromethyl)benzoyl]-1H-pyrazol-3-yl)-3-methoxy-2-oxo-1,2-dihydropyridin-1-yl]-2-oxopropanoate
methyl 3-[6-(5-{[(5-chlorothiophen-2-yl)methyl]amino}-1-[3-(hydroxymethyl)benzoyl]-1H-pyrazol-3-yl)-2-oxo-4-(pyridin-2-yl)-1,2-dihydropyridin-1-yl]-2-oxopropanoate
methyl 3-[6-(5-{[(5-chlorothiophen-2-yl)methyl]amino}-1-[4-(hydroxymethyl)benzoyl]-1H-pyrazol-3-yl)-2-oxo-5-(2-phenylethynyl)-1,2-dihydropyridin-1-yl]-2-oxopropanoate
methyl 3-[6-(5-{[(5-chlorothiophen-2-yl)methyl]sulfanyl}-1-(2,2-dimethylpropanoyl)-1H-pyrazol-3-yl)-2-oxo-3-(2-phenylethynyl)-1,2-dihydropyridin-1-yl]-2-oxopropanoate
methyl 3-[6-(5-{[(5-chlorothiophen-2-yl)methyl]sulfanyl}-1-(2,2-dimethylpropanoyl)-1H-pyrazol-3-yl)-2-oxo-5-(pyridin-4-yl)-1,2-dihydropyridin-1-yl]-2-oxopropanoate
methyl 3-[6-benzoyl-4-(5-{[(5-chlorothiophen-2-yl)methyl]amino}-1-(2,2-dimethylpropanoyl)-1H-pyrazol-3-yl)-2-oxo-1,2-dihydropyridin-1-yl]-2-oxopropanoate
methyl 3-{3-[1-(3-carbamoylbenzoyl)-5-{[(5-chlorothiophen-2-yl)methyl]amino}-1H-pyrazol-3-yl]-5-chloro-2-oxo-1,2-dihydropyridin-1-yl}-2-oxopropanoate
methyl 3-{4-[1-(3-carbamoylbenzoyl)-5-{[(5-chlorothiophen-2-yl)methyl]amino}-1H-pyrazol-3-yl]-5-methoxy-2-oxo-1,2-dihydropyridin-1-yl}propanoate
methyl 3-{5-[1-(2-aminobenzoyl)-5-{[(5-chlorothiophen-2-yl)methyl]amino}-1H-pyrazol-3-yl]-2-oxo-6-(2-phenylethynyl)-1,2-dihydropyridin-1-yl}propanoate
methyl 4-(5-{[(5-chlorothiophen-2-yl)methyl]amino}-1-(1,2-oxazole-4-carbonyl)-1H-pyrazol-3-yl)-6-oxo-1-[2-(pyridin-2-yl)ethyl]-1,6-dihydropyridine-3-carboxylate
methyl 4-(5-{[(5-chlorothiophen-2-yl)methyl]amino}-1-(1,2-thiazole-3-carbonyl)-1H-pyrazol-3-yl)-1-(3-methoxy-2,3-dioxopropyl)-6-oxo-1,6-dihydropyridine-3-carboxylate
methyl 4-(5-{[(5-chlorothiophen-2-yl)methyl]amino}-1-(1,3-thiazole-5-carbonyl)-1H-pyrazol-3-yl)-1-[2-(1,3-oxazol-2-yl)-2-oxoethyl]-2-oxo-1,2-dihydropyridine-3-carboxylate
methyl 4-(5-{[(5-chlorothiophen-2-yl)methyl]amino}-1-(1,3-thiazole-5-carbonyl)-1H-pyrazol-3-yl)-2-oxo-1-(1,3-thiazol-2-ylmethyl)-1,2-dihydropyridine-3-carboxylate
methyl 4-(5-{[(5-chlorothiophen-2-yl)methyl]amino}-1-(2,2-dimethylpropanoyl)-1H-pyrazol-3-yl)-1-[2-(1,3-oxazol-2-yl)-2-oxoethyl]-6-oxo-1,6-dihydropyridine-3-carboxylate
methyl 4-(5-{[(5-chlorothiophen-2-yl)methyl]amino}-1-(2,2-dimethylpropanoyl)-1H-pyrazol-3-yl)-1-[2-(1,3-oxazol-4-yl)-2-oxoethyl]-2-oxo-1,2-dihydropyridine-3-carboxylate APPENDIX A-continued Table B methyl 4-(5-{[(5-chlorothiophen-2-yl)methyl]amino}-1-(2,2-dimethylpropanoyl)-1H-pyrazol-3-yl)-1-[2-(1,3-oxazol-4-yl)-2-oxoethyl]-6-oxo-1,6-dihydropyridine-2-carboxylate
methyl 4-(5-{[(5-chlorothiophen-2-yl)methyl]amino}-1-(2,2-dimethylpropanoyl)-1H-pyrazol-3-yl)-1-[2-(1,3-oxazol-5-yl)-2-oxoethyl]-6-oxo-1,6-dihydropyridine-2-carboxylate
methyl 4-(5-{[(5-chlorothiophen-2-yl)methyl]amino}-1-(2,2-dimethylpropanoyl)-1H-pyrazol-3-yl)-2-oxo-1-[2-oxo-2-(1,2-thiazol-4-yl)ethyl]-1,2-dihydropyridine-3-carboxylate
methyl 4-(5-{[(5-chlorothiophen-2-yl)methyl]amino}-1-(2,2-dimethylpropanoyl)-1H-pyrazol-3-yl)-6-oxo-1-[2-oxo-2-(1,3-thiazol-5-yl)ethyl]-1,6-dihydropyridine-3-carboxylate
methyl 4-(5-{[(5-chlorothiophen-2-yl)methyl]amino}-1-(3-hydroxy-2,2-dimethylpropanoyl)-1H-pyrazol-3-yl)-6-oxo-1-[2-oxo-2-(1,2-thiazol-5-yl)ethyl]-1,6-dihydropyridine-2-carboxylate
methyl 4-(5-{[(5-chlorothiophen-2-yl)methyl]amino}-1-(furan-2-carbonyl)-1H-pyrazol-3-yl)-1-[2-(1,3-oxazol-5-yl)-2-oxoethyl]-6-oxo-1,6-dihydropyridine-2-carboxylate
methyl 4-(5-{[(5-chlorothiophen-2-yl)methyl]amino}-4-cyano-1-(1,2-thiazole-3-carbonyl)-1H-pyrazol-3-yl)-6-oxo-1-(pyrazin-2-ylmethyl)-1,6-dihydropyridine-2-carboxylate
methyl 4-(5-{[(5-chlorothiophen-2-yl)methyl]amino}-4-cyano-1-(furan-2-carbonyl)-1H-pyrazol-3-yl)-2-oxo-1-(1,2-thiazol-3-ylmethyl)-1,2-dihydropyridine-3-carboxylate
methyl 4-(5-{[(5-chlorothiophen-2-yl)methyl]sulfanyl}-1-(2,2-dimethylpropanoyl)-1H-pyrazol-3-yl)-1-[2-(1,3-oxazol-4-yl)-2-oxoethyl]-6-oxo-1,6-dihydropyridine-2-carboxylate
methyl 4-(5-{[(5-chlorothiophen-2-yl)methyl]sulfanyl}-1-(2,2-dimethylpropanoyl)-1H-pyrazol-3-yl)-2-oxo-1-[2-oxo-2-(1,2-thiazol-4-yl)ethyl]-1,2-dihydropyridine-3-carboxylate
methyl 4-(5-{[(5-chlorothiophen-2-yl)methyl]sulfanyl}-1-(2,2-dimethylpropanoyl)-1H-pyrazol-3-yl)-6-oxo-1-[2-oxo-2-(1,3-thiazol-5-yl)ethyl]-1,6-dihydropyridine-3-carboxylate
methyl 4-[1-(2-aminobenzoyl)-5-{[(5-chlorothiophen-2-yl)methyl]amino}-1H-pyrazol-3-yl]-1-(1,2-oxazol-4-ylmethyl)-6-oxo-1,6-dihydropyridine-3-carboxylate
methyl 4-[1-(2-chlorobenzoyl)-5-{[(5-chlorothiophen-2-yl)methyl]amino}-1H-pyrazol-3-yl]-2-oxo-1-[2-oxo-2-(thiophen-3-yl)ethyl]-1,2-dihydropyridine-3-carboxylate
methyl 4-[1-(3-carbamoylbenzoyl)-5-{[(5-chlorothiophen-2-yl)methyl]amino}-1H-pyrazol-3-yl]-6-oxo-1-[2-oxo-2-(1,3-thiazol-5-yl)ethyl]-1,6-dihydropyridine-3-carboxylate
methyl 5-(5-{[(5-chlorothiophen-2-yl)methyl](methyl)amino}-1-(2,2-dimethylpropanoyl)-1H-pyrazol-3-yl)-1-[2-(1,3-oxazol-4-yl)-2-oxoethyl]-6-oxo-1,6-dihydropyridine-2-carboxylate
methyl 5-(5-{[(5-chlorothiophen-2-yl)methyl](methyl)amino}-1-(2,2-dimethylpropanoyl)-1H-pyrazol-3-yl)-6-oxo-1-[2-oxo-2-(1,2-thiazol-4-yl)ethyl]-1,6-dihydropyridine-3-carboxylate
methyl 5-(5-{[(5-chlorothiophen-2-yl)methyl]amino}-1-(1,2-oxazole-4-carbonyl)-1H-pyrazol-3-yl)-6-oxo-1-(pyridin-2-ylmethyl)-1,6-dihydropyridine-2-carboxylate
methyl 5-(5-{[(5-chlorothiophen-2-yl)methyl]amino}-1-(1,2-oxazole-5-carbonyl)-1H-pyrazol-3-yl)-6-oxo-1-[2-oxo-2-(piperidin-1-yl)ethyl]-1,6-dihydropyridine-3-carboxylate
methyl 5-(5-{[(5-chlorothiophen-2-yl)methyl]amino}-1-(1,3-oxazole-4-carbonyl)-1H-pyrazol-3-yl)-1-[2-(1,3-oxazol-4-yl)-2-oxoethyl]-2-oxo-1,2-dihydropyridine-4-carboxylate
methyl 5-(5-{[(5-chlorothiophen-2-yl)methyl]amino}-1-(1,3-thiazole-5-carbonyl)-1H-pyrazol-3-yl)-6-oxo-1-[2-oxo-2-(pyrazin-2-yl)ethyl]-1,6-dihydropyridine-2-carboxylate
methyl 5-(5-{[(5-chlorothiophen-2-yl)methyl]amino}-1-(2,2-dimethylpropanoyl)-1H-pyrazol-3-yl)-1-[2-(4-methylpiperazin-1-yl)-2-oxoethyl]-6-oxo-1,6-dihydropyridine-2-carboxylate
methyl 5-(5-{[(5-chlorothiophen-2-yl)methyl]amino}-1-(2,2-dimethylpropanoyl)-1H-pyrazol-3-yl)-1-[2-(furan-3-yl)-2-oxoethyl]-6-oxo-1,6-dihydropyridine-3-carboxylate
methyl 5-(5-{[(5-chlorothiophen-2-yl)methyl]amino}-1-(2,2-dimethylpropanoyl)-1H-pyrazol-3-yl)-2-oxo-1-[2-oxo-2-(1,2-thiazol-4-yl)ethyl]-1,2-dihydropyridine-4-carboxylate
methyl 5-(5-{[(5-chlorothiophen-2-yl)methyl]amino}-1-(2,2-dimethylpropanoyl)-1H-pyrazol-3-yl)-2-oxo-1-[2-oxo-2-(1,2-thiazol-5-yl)ethyl]-1,2-dihydropyridine-3-carboxylate
methyl 5-(5-{[(5-chlorothiophen-2-yl)methyl]amino}-1-(2,2-dimethylpropanoyl)-1H-pyrazol-3-yl)-2-oxo-1-[2-oxo-2-(pyridin-4-yl)ethyl]-1,2-dihydropyridine-3-carboxylate
methyl 5-(5-{[(5-chlorothiophen-2-yl)methyl]amino}-1-(2,2-dimethylpropanoyl)-1H-pyrazol-3-yl)-2-oxo-1-[2-oxo-2-(thiophen-3-yl)ethyl]-1,2-dihydropyridine-4-carboxylate

APPENDIX A-continued

Table B methyl 5-(5-{[(5-chlorothiophen-2-yl)methyl]amino}-1-(2,2-dimethylpropanoyl)-1H-pyrazol-3-yl)-6-oxo-1-[2-oxo-2-(pyridin-4-yl)ethyl]-1,6-dihydropyridine-2-carboxylate methyl 5-(5-{[(5-chlorothiophen-2-yl)methyl]amino}-1-(2,2-dimethylpropanoyl)-1H-pyrazol-3-yl)-6-oxo-1-[2-oxo-2-(pyrimidin-5-yl)ethyl]-1,6-dihydropyridine-3-carboxylate methyl 5-(5-{[(5-chlorothiophen-2-yl)methyl]amino}-1-(2-fluorobenzoyl)-1H-pyrazol-3-yl)-2-oxo-1-[2-oxo-2-(pyridin-4-yl)ethyl]-1,2-dihydropyridine-4-carboxylate methyl 5-(5-{[(5-chlorothiophen-2-yl)methyl]amino}-1-(2-methoxybenzoyl)-1H-pyrazol-3-yl)-1-methyl-2-oxo-1,2-dihydropyridine-3-carboxylate methyl 5-(5-{[(5-chlorothiophen-2-yl)methyl]amino}-1-(3-hydroxy-2,2-dimethylpropanoyl)-1H-pyrazol-3-yl)-2-oxo-1-[2-oxo-2-(pyrazin-2-yl)ethyl]-1,2-dihydropyridine-3-carboxylate methyl 5-(5-{[(5-chlorothiophen-2-yl)methyl]amino}-1-(furan-2-carbonyl)-1H-pyrazol-3-yl)-2-oxo-1-[2-oxo-2-(1,2-thiazol-5-yl)ethyl]-1,2-dihydropyridine-3-carboxylate methyl 5-(5-{[(5-chlorothiophen-2-yl)methyl]amino}-1-[3-(hydroxymethyl)benzoyl]-1H-pyrazol-3-yl)-1-[2-(1,3-oxazol-4-yl)ethyl]-6-oxo-1,6-dihydropyridine-3-carboxylate methyl 5-(5-{[(5-chlorothiophen-2-yl)methyl]amino}-4-cyano-1-(1,2-oxazole-5-carbonyl)-1H-pyrazol-3-yl)-6-oxo-1-(1,3-thiazol-5-ylmethyl)-1,6-dihydropyridine-2-carboxylate methyl 5-(5-{[(5-chlorothiophen-2-yl)methyl]sulfanyl}-1-(2,2-dimethylpropanoyl)-1H-pyrazol-3-yl)-2-oxo-1-[2-oxo-2-(pyridin-4-yl)ethyl]-1,2-dihydropyridine-3-carboxylate methyl 5-(5-{[(5-chlorothiophen-2-yl)methyl]sulfanyl}-1-(2,2-dimethylpropanoyl)-1H-pyrazol-3-yl)-2-oxo-1-[2-oxo-2-(thiophen-3-yl)ethyl]-1,2-dihydropyridine-4-carboxylate methyl 5-[1-(2-chlorobenzoyl)-5-{[(5-chlorothiophen-2-yl)methyl]amino}-1H-pyrazol-3-yl]-1-(3-methoxy-2,3-dioxopropyl)-6-oxo-1,6-dihydropyridine-2-carboxylate methyl 5-[1-(4-carbamoylbenzoyl)-5-{[(5-chlorothiophen-2-yl)methyl]amino}-1H-pyrazol-3-yl]-1-[2-(furan-3-yl)-2-oxoethyl]-6-oxo-1,6-dihydropyridine-3-carboxylate methyl 6-(5-{[(5-chlorothiophen-2-yl)methyl]amino}-1-(1,2-thiazole-3-carbonyl)-1H-pyrazol-3-yl)-2-oxo-1-[2-oxo-2-(1,3-thiazol-5-yl)ethyl]-1,2-dihydropyridine-3-carboxylate methyl 6-(5-{[(5-chlorothiophen-2-yl)methyl]amino}-1-(1,3-oxazole-2-carbonyl)-1H-pyrazol-3-yl)-2-oxo-1-(pyrimidin-2-ylmethyl)-1,2-dihydropyridine-4-carboxylate methyl 6-(5-{[(5-chlorothiophen-2-yl)methyl]amino}-1-(1,3-thiazole-5-carbonyl)-1H-pyrazol-3-yl)-2-oxo-1-[2-oxo-2-(thiophen-3-yl)ethyl]-1,2-dihydropyridine-4-carboxylate methyl 6-(5-{[(5-chlorothiophen-2-yl)methyl]amino}-1-(2,2-dimethylpropanoyl)-1H-pyrazol-3-yl)-2-oxo-1-[2-oxo-2-(pyridin-2-yl)ethyl]-1,2-dihydropyridine-3-carboxylate methyl 6-(5-{[(5-chlorothiophen-2-yl)methyl]amino}-1-(2,2-dimethylpropanoyl)-1H-pyrazol-3-yl)-2-oxo-1-[2-oxo-2-(pyridin-4-yl)ethyl]-1,2-dihydropyridine-4-carboxylate methyl 6-(5-{[(5-chlorothiophen-2-yl)methyl]amino}-1-(2,2-dimethylpropanoyl)-1H-pyrazol-3-yl)-2-oxo-1-[2-oxo-2-(pyrimidin-5-yl)ethyl]-1,2-dihydropyridine-4-carboxylate methyl 6-(5-{[(5-chlorothiophen-2-yl)methyl]amino}-1-(2,2-dimethylpropanoyl)-1H-pyrazol-3-yl)-2-oxo-1-[2-oxo-2-(thiophen-3-yl)ethyl]-1,2-dihydropyridine-3-carboxylate methyl 6-(5-{[(5-chlorothiophen-2-yl)methyl]amino}-1-(3-hydroxy-2,2-dimethylpropanoyl)-1H-pyrazol-3-yl)-2-oxo-1-(1,3-thiazol-4-ylmethyl)-1,2-dihydropyridine-3-carboxylate methyl 6-(5-{[(5-chlorothiophen-2-yl)methyl]amino}-4-cyano-1-(furan-2-carbonyl)-1H-pyrazol-3-yl)-2-oxo-1-(1,3-thiazol-2-ylmethyl)-1,2-dihydropyridine-4-carboxylate methyl 6-(5-{[(5-chlorothiophen-2-yl)methyl]amino}-4-methoxy-1-(1,2-oxazole-5-carbonyl)-1H-pyrazol-3-yl)-1-(1,2-oxazol-4-ylmethyl)-2-oxo-1,2-dihydropyridine-3-carboxylate methyl 6-(5-{[(5-chlorothiophen-2-yl)methyl]sulfanyl}-1-(2,2-dimethylpropanoyl)-1H-pyrazol-3-yl)-2-oxo-1-[2-oxo-2-(pyridin-2-yl)ethyl]-1,2-dihydropyridine-3-carboxylate methyl 6-(5-{[(5-chlorothiophen-2-yl)methyl]sulfanyl}-1-(2,2-dimethylpropanoyl)-1H-pyrazol-3-yl)-2-oxo-1-[2-oxo-2-(pyrimidin-5-yl)ethyl]-1,2-dihydropyridine-4-carboxylate methyl 6-[1-(2-chlorobenzoyl)-5-{[(5-chlorothiophen-2-yl)methyl]amino}-1H-pyrazol-3-yl]-2-oxo-1-[2-oxo-2-(1,2-thiazol-3-yl)ethyl]-1,2-dihydropyridine-4-carboxylate methyl 6-[1-(3-carbamoylbenzoyl)-5-{[(5-chlorothiophen-2-yl)methyl]amino}-1H-pyrazol-3-yl]-2-oxo-1-[2-oxo-2-(pyridin-2-yl)ethyl]-1,2-dihydropyridine-3-carboxylate

What is claimed is:

1. A compound comprising a substituted or unsubstituted pyridone ring attached to a substituted or unsubstituted pyrazole ring with structure of Formula (I):

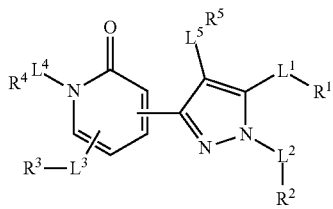

or pharmaceutically acceptable salt thereof;
wherein
$L^1$ is $NR^6$—;
$L^2$ is $C(=O)$—;
$L^4$ is a bond, substituted or unsubstituted alkylene, substituted or unsubstituted heteroalkylene, —S—, —SO—, or —SO$_2$—;
$L^3$ and $L^5$ are independently a bond, substituted or unsubstituted alkylene, substituted or unsubstituted heteroalkylene, or —O—;
$R^1$ is halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl;
$R^2$ is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl;
$R^4$ is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl;
$R^3$ and $R^5$ are independently hydrogen, halogen, substituted or unsubstituted alkyl, substituted or unsubstituted heteroalkyl, substituted or unsubstituted aryl, or substituted or unsubstituted heteroaryl; and
$R^6$ is hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted heterocycloalkyl, substituted or unsubstituted aryl, or substituted or unsubstituted heteroaryl;
provided that if the compound has a structure according to Formula (IIa), as follows, either $L^3$ is not a bond or $R^3$ is not hydrogen:

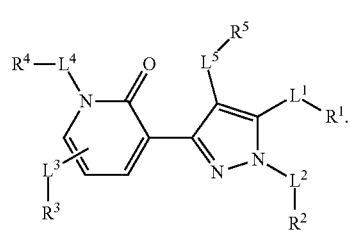

2. The compound according to claim 1, with structure of Formula (IIa), Formula (IIIa), Formula (IVa), or Formula (Va):

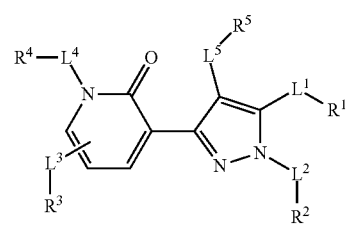

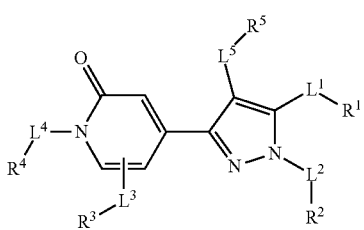

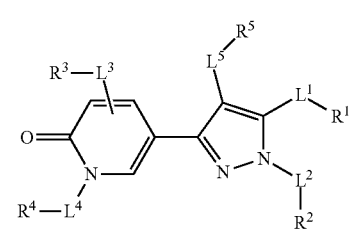

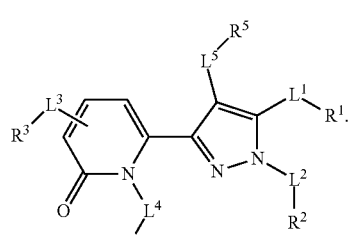

3. The compound according to claim 2, wherein $R^2$ is hydrogen.

4. The compound according to any of Formula (IIIa), Formula (IVa), or Formula (Va) as set forth in claim 2, wherein $L^3$ is a bond, and $R^3$ is hydrogen.

5. The compound according to claim 2, wherein $L^4$ is a bond and $R^4$ is hydrogen.

6. The compound according to claim 2, wherein $L^5$ is a bond, and $R^5$ is hydrogen.

7. The compound according to claim 2, wherein $L^2$ is —C(O)—, and $R^2$ is substituted or unsubstituted alkyl, substituted or unsubstituted cycloalkyl, substituted or unsubstituted cycloalkenyl, substituted or unsubstituted heteroalkyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl.

8. The compound according to claim 7, wherein $R^2$ is substituted or unsubstituted aryl or substituted or unsubstituted heteroaryl.

9. The compound according to claim 8, wherein $R^2$ is substituted or unsubstituted aryl or substituted or unsubstituted heteroaryl selected from the group consisting of phenyl, 2-chlorophenyl, 2-methoxyphenyl, phenyl-3-carboxylic acid, phenyl-3-carboxamide, 3-(hydroxymethyl)phenyl, phenyl-4-carboxylic acid, phenyl-4-carboxamide, 4-(hydroxymethyl)phenyl, 2-thienyl, 3-thienyl, 2-furyl, 3-furyl, 1,3-thiazol-2-yl, 1,3-thiazol-4-yl, 1,3-thiazol-5-yl, 1,3-oxazol-2-yl, 1,3-oxazol-4-yl, and 1,3-oxazol-5-yl.

10. The compound according to claim 7, wherein $R^2$ is substituted or unsubstituted alkyl.

11. The compound according to claim 10, wherein $R^2$ is tert-butyl, 1,1-dimethyl-2-hydroxy-ethyl, 1,1-dimethyl-2-methoxy-ethyl, or 1,1-dimethyl-2-cyclopropoxy-ethyl.

12. The compound according to claim 2, wherein $R^1$ is substituted alkyl.

13. The compound according to claim 12, wherein $R^1$ is substituted alkyl, wherein said $R^1$ substituted alkyl has a substituted or unsubstituted aryl or substituted or unsubstituted heteroaryl substituent group selected from the group consisting of phenyl, 4-fluorophenyl, 4-chlorophenyl, 2-thienyl, or 5-chloro-thien-2-yl, 1,3-thiazol-2-yl, 1,3-thiazol-4-yl, 2-chloro-1,3-thiazol-5-yl, and 5-chloro-1,3-thiazol-2-yl.

14. The compound according to claim 2, wherein $L^4$ is a bond or substituted or unsubstituted alkylene, and $R^4$ is substituted or unsubstituted aryl, substituted or unsubstituted fused ring aryl, or substituted or unsubstituted heteroaryl.

15. The compound according to claim 14, wherein $R^4$ is substituted or unsubstituted heteroaryl selected from the group consisting of substituted or unsubstituted pyridyl, substituted or unsubstituted pyridazinyl, substituted or unsubstituted pyrimidinyl, substituted or unsubstituted thienyl, and substituted or unsubstituted furyl.

16. The compound according to claim 2, wherein $L^4$ is substituted or unsubstituted alkylene, and $R^4$ is substituted or unsubstituted heterocycloalkyl.

17. The compound according to claim 16, wherein $R^4$ is substituted or unsubstituted heterocycloalkyl selected from the group consisting of substituted or unsubstituted morpholinyl, substituted or unsubstituted oxanyl, and substituted or unsubstituted oxetanyl.

18. The compound according to claim 2, wherein $L^4$ is a bond, and $R^4$ is substituted or unsubstituted alkyl or substituted or unsubstituted heteroalkyl.

19. The compound according to claim 2, wherein $L^3$ is bond, and $R^3$ is halogen, substituted or unsubstituted alkyl, substituted or unsubstituted heteroalkyl, substituted or unsubstituted aryl, or substituted or unsubstituted heteroaryl.

20. The compound according to claim 19, wherein $R^3$ is substituted or unsubstituted aryl or substituted or unsubstituted heteroaryl selected from the group consisting of substituted or unsubstituted phenyl, substituted or unsubstituted pyridyl, substituted or unsubstituted pyridazinyl, substituted or unsubstituted pyrimidinyl, substituted or unsubstituted thienyl, and substituted or unsubstituted furyl.

21. The compound according to claim 19, wherein $R^3$ is substituted or unsubstituted alkyl or substituted or unsubstituted heteroalkyl selected from the group consisting of methyl and cyano.

22. The compound according to claim 1, wherein $L^5$ is bond, and $R^5$ is hydrogen, halogen, substituted or unsubstituted alkyl, substituted or unsubstituted heteroalkyl, substituted or unsubstituted aryl, or substituted or unsubstituted heteroaryl.

23. The compound according to claim 1, wherein the compound is selected from the group consisting of:
Compound 1, 3-(5-{[(5-chlorothiophen-2-yl)methyl]amino}-1-(2,2-dimethylpropanoyl)-1H-pyrazol-3-yl)-5-(morpholin-4-yl)-1,2-dihydropyridin-2-one;
Compound 2, 3-(5-{[(5-chlorothiophen-2-yl)methyl]amino}-1-(2,2-dimethylpropanoyl)-1H-pyrazol-3-yl)-5-phenyl-1,2-dihydropyridin-2-one;
Compound 3, 3-(5-{[(5-chlorothiophen-2-yl)methyl]amino}-1-(2-methoxybenzoyl)-1H-pyrazol-3-yl)-5-(pyridin-3-yl)-1,2-dihydropyridin-2-one;
Compound 4, 3-(5-{[(5-chlorothiophen-2-yl)methyl]amino}-1-(furan-3-carbonyl)-1H-pyrazol-3-yl)-5-methyl-1,2-dihydropyridin-2-one;
Compound 5, 3-bromo-5-(5-{[(5-chlorothiophen-2-yl)methyl]amino}-1-(2-methoxybenzoyl)-1H-pyrazol-3-yl)-1,2-dihydropyridin-2-one;
Compound 7, 3-bromo-6-(5-{[(5-chlorothiophen-2-yl)methyl]amino}-1-(furan-3-carbonyl)-1H-pyrazol-3-yl)-1,2-dihydropyridin-2-one;
Compound 8, 4-(5-{[(5-chlorothiophen-2-yl)methyl]amino}-1-(2,2-dimethylpropanoyl)-1H-pyrazol-3-yl)-1,2-dihydropyridin-2-one;
Compound 9, 4-(5-{[(5-chlorothiophen-2-yl)methyl]amino}-1-(2,2-dimethylpropanoyl)-1H-pyrazol-3-yl)-1-(2-methoxyethyl)-1,2-dihydropyridin-2-one;
Compound 10, 4-(5-{[(5-chlorothiophen-2-yl)methyl]amino}-1-(2,2-dimethylpropanoyl)-1H-pyrazol-3-yl)-1-(pyridin-2-ylmethyl)-1,2-dihydropyridin-2-one;
Compound 11, 4-(5-{[(5-chlorothiophen-2-yl)methyl]amino}-1-(2,2-dimethylpropanoyl)-1H-pyrazol-3-yl)-1-(pyridin-3-ylmethyl)-1,2-dihydropyridin-2-one;
Compound 12, 4-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-1,2-dihydropyridin-2-one;
Compound 13, 4-(5-{[(5-chlorothiophen-2-yl)methyl]amino}-1-(2,2-dimethylpropanoyl)-1H-pyrazol-3-yl)-6-(morpholin-4-yl)-1,2-dihydropyridin-2-one;
Compound 14, 4-(5-{[(5-chlorothiophen-2-yl)methyl]amino}-1-(2-methoxybenzoyl)-1H-pyrazol-3-yl)-6-ethenyl-1,2-dihydropyridin-2-one;
Compound 15, 4-(5-{[(5-chlorothiophen-2-yl)methyl]amino}-1-(furan-2-carbonyl)-1H-pyrazol-3-yl)-6-(pyridin-3-yl)-1,2-dihydropyridin-2-one;
Compound 16, 4-(5-{[(5-chlorothiophen-2-yl)methyl]amino}-1-(furan-3-carbonyl)-1H-pyrazol-3-yl)-1,2-dihydropyridin-2-one;
Compound 17, 4-(5-{[(5-chlorothiophen-2-yl)methyl]amino}-1-(furan-3-carbonyl)-1H-pyrazol-3-yl)-1-(2-methoxyethyl)-1,2-dihydropyridin-2-one;
Compound 18, 4-(5-{[(5-chlorothiophen-2-yl)methyl]amino}-1-(furan-3-carbonyl)-1H-pyrazol-3-yl)-1-(pyridin-2-ylmethyl)-1,2-dihydropyridin-2-one;
Compound 19, 4-(5-{[(5-chlorothiophen-2-yl)methyl]amino}-1-(furan-3-carbonyl)-1H-pyrazol-3-yl)-1-(pyridin-3-ylmethyl)-1,2-dihydropyridin-2-one;

Compound 20, 4-(5-{[(5-chlorothiophen-2-yl)methyl]amino}-1-(furan-3-carbonyl)-1H-pyrazol-3-yl)-1-[2-(morpholin-4-yl)-2-oxoethyl]-1,2-dihydropyridin-2-one;
Compound 21, 4-(5-{[(5-chlorothiophen-2-yl)methyl]amino}-1-(furan-3-carbonyl)-1H-pyrazol-3-yl)-1-[2-(morpholin-4-yl)ethyl]-1,2-dihydropyridin-2-one;
Compound 22, 4-(5-{[(5-chlorothiophen-2-yl)methyl]amino}-1-(thiophene-3-carbonyl)-1H-pyrazol-3-yl)-1,2-dihydropyridin-2-one;
Compound 23, 4-(5-{[(5-chlorothiophen-2-yl)methyl]amino}-1-(thiophene-3-carbonyl)-1H-pyrazol-3-yl)-1-(2-methoxyethyl)-1,2-dihydropyridin-2-one;
Compound 24, 4-(5-{[(5-chlorothiophen-2-yl)methyl]amino}-1-(thiophene-3-carbonyl)-1H-pyrazol-3-yl)-1-(pyridin-2-ylmethyl)-1,2-dihydropyridin-2-one;
Compound 25, 4-(5-{[(5-chlorothiophen-2-yl)methyl]amino}-1-(thiophene-3-carbonyl)-1H-pyrazol-3-yl)-1-(pyridin-3-ylmethyl)-1,2-dihydropyridin-2-one;
Compound 26, 4-(5-{[(5-chlorothiophen-2-yl)methyl]amino}-1-(thiophene-3-carbonyl)-1H-pyrazol-3-yl)-1-[2-(morpholin-4-yl)-2-oxoethyl]-1,2-dihydropyridin-2-one;
Compound 27, 4-(5-{[(5-chlorothiophen-2-yl)methyl]amino}-1-(thiophene-3-carbonyl)-1H-pyrazol-3-yl)-1-[2-(morpholin-4-yl)ethyl]-1,2-dihydropyridin-2-one;
Compound 28, 4-(5-{[(5-chlorothiophen-2-yl)methyl]amino}-1-(thiophene-3-carbonyl)-1H-pyrazol-3-yl)-6-phenyl-1,2-dihydropyridin-2-one;
Compound 31, 5-(5-{[(5-chlorothiophen-2-yl)methyl]amino}-1-(2,2-dimethylpropanoyl)-1H-pyrazol-3-yl)-1,2-dihydropyridin-2-one;
Compound 32, 5-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-1,2-dihydropyridin-2-one;
Compound 33, 5-(5-{[(5-chlorothiophen-2-yl)methyl]amino}-1-(2,2-dimethylpropanoyl)-1H-pyrazol-3-yl)-3-(pyridin-3-yl)-1,2-dihydropyridin-2-one;
Compound 34, 5-(5-{[(5-chlorothiophen-2-yl)methyl]amino}-1-(2,2-dimethylpropanoyl)-1H-pyrazol-3-yl)-3-methyl-1,2-dihydropyridin-2-one;
Compound 35, 5-(5-{[(5-chlorothiophen-2-yl)methyl]amino}-1-(2,2-dimethylpropanoyl)-1H-pyrazol-3-yl)-3-phenyl-1,2-dihydropyridin-2-one;
Compound 36, 5-(5-{[(5-chlorothiophen-2-yl)methyl]amino}-1-(2-methoxybenzoyl)-1H-pyrazol-3-yl)-6-oxo-1,6-dihydropyridine-3-carbonitrile;
Compound 37, 5-(5-{[(5-chlorothiophen-2-yl)methyl]amino}-1-(thiophene-3-carbonyl)-1H-pyrazol-3-yl)-1,2-dihydropyridin-2-one;
Compound 39, 5-bromo-3-(5-{[(5-chlorothiophen-2-yl)methyl]amino}-1-(2,2-dimethylpropanoyl)-1H-pyrazol-3-yl)-1,2-dihydropyridin-2-one;
Compound 40, 5-bromo-3-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-1,2-dihydropyridin-2-one;
Compound 41, 5-bromo-3-(5-{[(5-chlorothiophen-2-yl)methyl]amino}-1-(thiophene-3-carbonyl)-1H-pyrazol-3-yl)-1,2-dihydropyridin-2-one;
Compound 43, 6-(5-{[(5-chlorothiophen-2-yl)methyl]amino}-1-(2,2-dimethylpropanoyl)-1H-pyrazol-3-yl)-1,2-dihydropyridin-2-one;
Compound 44, 6-(5-{[(5-chlorothiophen-2-yl)methyl]amino}-1-(2,2-dimethylpropanoyl)-1H-pyrazol-3-yl)-1-(pyridin-2-ylmethyl)-1,2-dihydropyridin-2-one;
Compound 45, 6-(5-{[(5-chlorothiophen-2-yl)methyl]amino}-1-(2,2-dimethylpropanoyl)-1H-pyrazol-3-yl)-1-[2-(morpholin-4-yl)-2-oxoethyl]-1,2-dihydropyridin-2-one;
Compound 46, 6-(5-{[(5-chlorothiophen-2-yl)methyl]amino}-1-(2,2-dimethylpropanoyl)-1H-pyrazol-3-yl)-3-ethenyl-1,2-dihydropyridin-2-one; and
Compound 48, 6-bromo-4-(5-{[(5-chlorothiophen-2-yl)methyl]amino}-1-(2,2-dimethylpropanoyl)-1H-pyrazol-3-yl)-1,2-dihydropyridin-2-one.

24. A pharmaceutical composition comprising a compound according to claim 1, and a pharmaceutically acceptable excipient.

25. A method for treating a disease or disorder in a subject, comprising administering a compound according to claim 1 or a pharmaceutical composition comprising a compound according to claim 1, to a subject in need thereof in an amount effective to treat said disease or disorder, wherein said disease or disorder is selected from the group consisting of: a thrombotic disorder selected from the group consisting of acute coronary syndrome thromboembolism, and thrombosis; a disease or disorder involving a blood clot thrombus; a fibrinolytic disease; fibrosis, multiple sclerosis; neuropathic pain; Type I diabetes mellitus; chronic liver injury; ischemia reperfusion injury; a type of cancer selected from the group consisting of cervical-, testicular-, and non-small cell lung adenocarcinoma, limited small lung cancer, glioma, malignant breast cancer, micrometastasis, lung metastasis, and prostatic cancer; an inflammatory condition selected from the group consisting of sepsis, inflammatory bowel disease, systemic inflammatory response syndrome, hereditary angioedema, and rheumatoid arthritis; a dermatological condition selected from the group consisting of atopic dermatitis, psoriasis, and Netherton Syndrome; and an ophthalmic disease selected from the group consisting of diabetic macular edema, age-related macular degeneration, and diabetic retinopathy.

26. The method according to claim 25, wherein said disease or disorder is at least one of a thrombotic disorder selected from the group consisting of acute coronary syndrome, thromboembolism, and thrombosis, or a disease or disorder involving a blood clot thrombus.

27. The method according to claim 26, wherein said thrombotic disorder comprises at least one of acute coronary syndrome, thromboembolism, and thrombosis.

28. The method according to claim 26, wherein said compound acts by inhibiting thrombin.

29. The method according to claim 25, wherein said disease or disorder is one or more selected from the group consisting of a fibrinolytic disease, a type of cancer selected from the group consisting of cervical-, testicular-, and non-small-cell lung adenocarcinoma, an inflammatory condition selected from the group consisting of sepsis, inflammatory bowel disease, systemic inflammatory response syndrome, hereditary angioedema, and rheumatoid arthritis, a dermatological condition selected from the group consisting of atopic dermatitis, psoriasis, and Netherton Syndrome, and an ophthalmic disease selected from the group consisting of diabetic macular edema, age-related macular degeneration, and diabetic retinopathy.

30. The method according to claim 29, wherein said disease or disorder is an ophthalmic disease selected from the group consisting of diabetic macular edema, age-related macular degeneration, and diabetic retinopathy.

31. The method according to claim 29, wherein said disease or disorder is an inflammatory condition selected from the group consisting of sepsis, inflammatory bowel disease, systemic inflammatory response syndrome, hereditary angioedema, and rheumatoid arthritis.

32. The method according to claim 25, wherein said compound acts by inhibiting at least one of plasma kallikrein and tissue kallikrein.

33. The method according to claim 25, wherein said disease or disorder is selected from the group consisting of fibrosis, multiple sclerosis, a type of cancer selected from the group consisting of limited small lung cancer, glioma, malignant breast cancer, micrometastasis, lung metastatis, and prostatic cancer, and Type I diabetes mellitus.

34. The method according to claim 27, wherein said thromboembolism comprises at least one of venous thromboembolism, arterial thromboembolism, and cardiogenic thromboembolism.

35. The method according to claim 34, wherein said venous thromboembolism comprises at least one of deep vein thrombosis and pulmonary embolism.

36. The method according to claim 35, wherein said at least one deep vein thrombosis and pulmonary embolism occurs following a medical procedure.

37. The method according to claim 27, wherein said thrombotic disorder involves dysfunctional coagulation or disseminated intravascular coagulation.

38. The method according to claim 37, wherein the subject is undergoing percutaneous coronary intervention (PCI).

39. The method according to claim 26, wherein said thrombotic disorder involves a blood clot thrombus and further involves at least one of stroke and one or more transient ischemic attacks (TIA).

40. The method according to claim 39, wherein said thrombotic disorder involving a blood clot thrombus further involves stroke and wherein the subject has non-valvular atrial fibrillation.

41. The method according to claim 26, wherein said thrombotic disorder involves a blood clot thrombus and further involves pulmonary hypertension.

42. The method according to claim 41, wherein said pulmonary hypertension is caused by at least one of left heart disorder and chronic thromboembolic disease.

43. The method according to claim 41, wherein said pulmonary hypertension is associated with at least one or more lung diseases.

44. The method according to claim 43, wherein said one or more lung diseases are selected from the group consisting of idiopathic pulmonary fibrosis, non-idiopathic pulmonary fibrosis, and hypoxia.

45. The method according to claim 25, wherein said disease or disorder involves recurrent cardiac events after myocardial infarction.

46. The method according to claim 34, wherein said venous thromboembolism is associated with at least one of formation of a thrombus within a vein that is associated with one or more acquired or inherited risk factors and embolism of peripheral veins caused by a detached thrombus.

47. The method according to claim 46, wherein said one or more risk factors comprise a previous venous thromboembolism.

48. The method according to claim 34, wherein said cardiogenic thromboembolism is due to formation of a thrombus in the heart associated with at least one of cardiac arrhythmia, a heart valve defect, prosthetic heart valves or heart disease, and embolism of peripheral arteries caused by a detached thrombus.

49. The method according to claim 48, wherein said detached thrombus is in the brain (ischemic stroke).

50. The method according to claim 49, wherein said detached thrombus causes a transient ischemic attack (TIA).

51. The method according to claim 48, wherein said cardiogenic thromboembolism is due to non-valvular atrial fibrillation.

52. The method according to claim 27, wherein said thrombosis is arterial thrombosis.

53. The method according to claim 52, wherein said arterial thrombosis is due to one or more underlying atherosclerotic processes in the arteries.

54. The method according to claim 53, wherein said one or more underlying atherosclerotic processes in the arteries cause at least one of obstruction or occlusion of an artery, myocardial ischemia (angina pectoris, acute coronary syndrome), myocardial infarction, obstruction or occlusion of a peripheral artery (ischemic peripheral artery disease), and obstruction or occlusion of the artery after a procedure on a blood vessel (reocclusion or restenosis after transluminal coronary angioplasty, reocclusion or restenosis after percutaneous transluminal angioplasty of peripheral arteries).

55. The method according to claim 25, wherein the subject has had at least one myocardial infarction.

56. The method according to claim 25, wherein the subject has at least one of unstable angina pectoris, thrombosis, and heparin-induced thrombocytopenia.

57. The method according to claim 25, wherein the subject has non-valvular atrial fibrillation.

58. The method according to claim 25, wherein said disease or disorder is neuropathic pain.

59. The method according to claim 33, wherein the micrometastatis is of the blood or liver.

60. The method according to claim 25, wherein said disease or disorder is selected from the group consisting of chronic liver injury and ischemia reperfusion injury.

61. The method according to claim 29, wherein said disease or disorder is a dermatological condition selected from the group consisting of atopic dermatitis, psoriasis, and Netherton Syndrome.

62. The method according to claim 29, wherein said disease or disorder is an ophthalmic disease selected from the group consisting of diabetic macular edema, age-related macular degeneration, and diabetic retinopathy, and wherein said compound or pharmaceutical composition is administered orally, in the form of an ophthalmic composition applied topically to the eye, or in the form of an ophthalmic composition via intravitreal injection.

63. The method according to claim 62, wherein said ophthalmic composition is in the form of eye drops.

64. The method according to claim 25, wherein said compound acts by reducing retinal vascular permeability.

65. The method according to claim 25, wherein said disease or disorder is an inflammatory condition selected from the group consisting of sepsis, inflammatory bowel disease, systemic inflammatory response syndrome, hereditary angioedema, and rheumatoid arthritis, and wherein said compound is administered orally.

66. The method according to claim 25, wherein said compound inhibits blood coagulation.

* * * * *